(12) United States Patent
Mickle et al.

(10) Patent No.: US 7,375,083 B2
(45) Date of Patent: May 20, 2008

(54) PHARMACEUTICAL COMPOSITIONS FOR PREVENTION OF OVERDOSE OR ABUSE

(75) Inventors: Travis Mickle, Charlottesville, VA (US); Suma Krishnan, Blacksburg, VA (US); James Scott Moncrief, Christiansburg, VA (US); Christopher Lauderback, Blacksburg, VA (US); Christal Mickle, Charlottesville, VA (US)

(73) Assignee: Shire LLC, Florence, KY (US)

( * ) Notice: Subject to any disclaimer, the term of this patent is extended or adjusted under 35 U.S.C. 154(b) by 323 days.

(21) Appl. No.: 10/953,119

(22) Filed: Sep. 30, 2004

(65) Prior Publication Data

US 2005/0176646 A1    Aug. 11, 2005

Related U.S. Application Data

(60) Provisional application No. 60/567,800, filed on May 5, 2004, provisional application No. 60/567,802, filed on May 5, 2004, provisional application No. 60/568,011, filed on May 5, 2004, provisional application No. 60/507,012, filed on Sep. 30, 2003.

(51) Int. Cl.
*A61K 38/00* (2006.01)
*A61K 38/04* (2006.01)
*A61K 38/06* (2006.01)
*A61K 31/00* (2006.01)

(52) U.S. Cl. ............... 514/12; 514/14; 514/17; 530/330; 530/331; 424/78.13

(58) Field of Classification Search ............ 514/9
See application file for complete search history.

(56) References Cited

U.S. PATENT DOCUMENTS

| | | | |
|---|---|---|---|
| 3,843,696 A | 10/1974 | Wagner et al. |
| 3,846,399 A | 11/1974 | Hirschmann et al. |
| 3,878,187 A | 4/1975 | Schneider et al. |
| 3,884,898 A | 5/1975 | Schneider |
| 3,975,342 A | 8/1976 | Gross |
| 3,998,799 A | 12/1976 | Bodor et al. |
| 4,025,501 A | 5/1977 | Leute |
| 4,040,907 A | 8/1977 | Ullman et al. |
| 4,346,166 A | 8/1982 | Montag et al. |
| 4,356,166 A | 10/1982 | Peterson et al. |
| 4,399,121 A | 8/1983 | Albarella et al. |
| 4,427,660 A | 1/1984 | Schiffman et al. |
| 4,457,907 A | 7/1984 | Porter |
| 4,552,864 A | 11/1985 | Antoni et al. |
| 4,650,675 A | 3/1987 | Borel et al. |
| 4,801,575 A | 1/1989 | Pardridge |
| 4,863,735 A | 9/1989 | Kohn et al. |
| 4,902,505 A | 2/1990 | Pardridge et al. |
| 4,960,790 A | 10/1990 | Stella et al. |
| 4,976,962 A | 12/1990 | Bichon et al. |
| 5,026,827 A | 6/1991 | Miyazaki |
| 5,073,641 A | 12/1991 | Bundgaard et al. |
| 5,087,616 A | 2/1992 | Myers et al. |
| 5,169,933 A | 12/1992 | Anderson et al. |
| 5,183,883 A | 2/1993 | Tanaka et al. |
| 5,219,564 A | 6/1993 | Zalipsky et al. |
| 5,238,714 A | 8/1993 | Wallace et al. |
| 5,362,831 A | 11/1994 | Mongelli et al. |
| 5,534,496 A | 7/1996 | Lee et al. |
| 5,670,477 A | 9/1997 | Poduslo et al. |
| 5,762,909 A | 6/1998 | Uzgiris |
| 5,767,227 A | 6/1998 | Latham et al. |
| 5,846,743 A | 12/1998 | Janmey et al. |
| 5,851,536 A | 12/1998 | Yager et al. |
| 5,882,645 A | 3/1999 | Toth et al. |
| 5,891,459 A | 4/1999 | Cooke et al. |
| 5,898,033 A | 4/1999 | Swadesh et al. |
| 5,910,569 A | 6/1999 | Latham et al. |
| 5,948,750 A | 9/1999 | Garsky et al. |
| 5,952,294 A | 9/1999 | Lazo et al. |
| 5,977,163 A | 11/1999 | Li et al. |
| 6,005,004 A | 12/1999 | Katz et al. |
| 6,030,941 A | 2/2000 | Summerton et al. |
| 6,043,230 A | 3/2000 | Arimilli et al. |
| 6,048,736 A | 4/2000 | Kosak |
| 6,074,659 A | 6/2000 | Kunz et al. |
| 6,075,120 A | 6/2000 | Cheronis et al. |

(Continued)

FOREIGN PATENT DOCUMENTS

AU    54168165    1/1965

(Continued)

OTHER PUBLICATIONS

Aggarwal, et al., "Synthesis and Biological Evaluation of Prodrugs of Zidovudine," *J. Med. Chem.*, 33(5):1505-1511 (1990).

(Continued)

*Primary Examiner*—Cecilia J. Tsang
*Assistant Examiner*—Maury Audet
(74) *Attorney, Agent, or Firm*—Darby & Darby

(57) ABSTRACT

The invention relates to pharmaceutical compositions comprised of a chemical moiety attached to an active agent in a manner that substantially decreases the potential of the active agent to cause overdose or to be abused. When delivered at the proper dosage the pharmaceutical composition provides therapeutic activity similar to that of the parent active agent.

10 Claims, 195 Drawing Sheets

U.S. PATENT DOCUMENTS

| | | | |
|---|---|---|---|
| 6,093,391 | A | 7/2000 | Kabanov et al. |
| 6,235,718 | B1 | 5/2001 | Balasubramanium |
| 6,255,285 | B1 | 7/2001 | Kotake |
| 6,306,993 | B1 | 10/2001 | Rothbard et al. |
| 6,309,633 | B1 | 10/2001 | Ekwuribe et al. |
| 6,458,842 | B1 | 10/2002 | Dickinson et al. |
| 6,716,452 | B1 | 4/2004 | Piccariello et al. |
| 6,740,641 | B2 | 5/2004 | Gao |
| 6,784,186 | B1 | 8/2004 | Jackson |
| 7,060,708 | B2 | 6/2006 | Piccariello et al. |
| 2001/0031873 | A1 | 10/2001 | Greenwald et al. |
| 2002/0059013 | A1 | 5/2002 | Rajala et al. |
| 2002/0098999 | A1 | 7/2002 | Gallop et al. |
| 2002/0099013 | A1 | 7/2002 | Piccariello et al. |
| 2002/0151526 | A1 | 10/2002 | Gallop et al. |
| 2002/0151529 | A1 | 10/2002 | Cundy et al. |
| 2004/0204434 | A1 | 10/2004 | Shafer |
| 2005/0038121 | A1 | 2/2005 | Mickle et al. |
| 2005/0054561 | A1 | 3/2005 | Mickle et al. |
| 2005/0065086 | A1 | 3/2005 | Mickle et al. |
| 2005/0069550 | A1 | 3/2005 | Mickle et al. |
| 2005/0080012 | A1 | 4/2005 | Mickle et al. |
| 2005/0176644 | A1* | 8/2005 | Mickle et al. ............ 514/15 |
| 2005/0176645 | A1 | 8/2005 | Mickle et al. |
| 2005/0176646 | A1 | 8/2005 | Mickle et al. |
| 2005/0266070 | A1 | 12/2005 | Mickle et al. |
| 2006/0014697 | A1 | 1/2006 | Mickle et al. |

FOREIGN PATENT DOCUMENTS

| | | |
|---|---|---|
| EP | 0 187 547 A2 | 7/1987 |
| FR | 1421130 | 1/1965 |
| GB | 1092089 | 11/1967 |
| GB | 1112347 | 5/1968 |
| WO | WO 94/11021 A | 5/1994 |
| WO | WO 95/12605 | 5/1995 |
| WO | WO 95/14033 | 5/1995 |
| WO | WO 97/36616 | 10/1997 |
| WO | WO 08/04277 | 2/1998 |
| WO | WO 00/37103 A | 6/2000 |
| WO | WO 02/34237 A1 | 5/2002 |

OTHER PUBLICATIONS

Amidon, G., et al., "A Theoretical Basis for a Biopharmaceutic Drug Classification: The Correlation of in Vitro Drug Product Dissolution and in Vivo Bioavailability," *Pharmaceutical Research*, vol. 12, No. 3 (1995).

Amidon, G.L., et al., "5'-Amino Acid Esters of Antiviral Nucleosides, Acyclovir, and AZT are Absorbed by the Intestinal PEPT1 Peptide Transporter," *Pharm Res*, 16(2):175 (1999), Abstract.

Balimane, P., et al., "Effect of Ionization on the Variable Uptake of Valacyclovir via Human Intestinal Peptide Transporter (hPepT1) in CHP cells," *Biopharm Drug Dispos*, 21(5):165-174 (2000), Abstract.

Balimane, P.V., et al., "Direct Evidence for Peptide Transporter (PepT1)-Mediated Uptake of a Nonpeptide Prodrug, Valacyclovir," *Biochem Biophys Res Commun*, 250(2):246-251 (1998), Abstract.

Bunevicius, R., "Effects of Thyroxine as Compared with Thyroxine Plus Triiodothyronine in Patients with Hypothyroidism," *The New England Journal of Medicine*, vol. 340, No. 6 (1999).

Burnette, Thimysta C., et al., "Metabolic Disposition of the Acyclovir Prodrug Valaciclovir in the Rat," *Drug Metabolism and Disposition*, 22(1):60-64 (1994).

Canaris, G., "The Colorado Thyroid Disease Prevalence Study," *Archives Internal Medicine Articles and Abstracts*, vol. 160, No. 4, (2000).

De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2):1166-1170 (1988).

Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.

Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 289(1):448-454 (1999), Abstract.

Han H., et al., "5'-Amino Acid Esters of Antiviral Nucleosides, Acyclovir, and AZT and Absorbed by the Intestinal PEPT1 Peotide Transporter," *Pharm Res*, 15(8):1154-1159 (1998), Abstract.

Han, H.K., et al., "Cellular Uptake Mechanism of Amino Acid Ester prodrugs in Caco-2hPEPT1 Cells Overexpressing a Human Peptide Transporter," *Pharm Res*, 15(9):1382-1386 (1998), Abstract.

Han, Hyo-Kyung, et al., "Targeted Prodrug Design to Optimize Drug Delivery," *AAPS PharmSci*, 2(1): Article 6 (2000).

Havranova, Marie et al., "A High-Molecular Mass Derivative of Trypsin-Kallikrein Inhibitor for Potential Medical Use, II," *Hoppe-Seylers's Z. Physiol. Chem.*, 363:295-303 (1982).

Herrera-Ruiz, D., et al., "Spatial Expression Patterns of Peptide Transporters in the Human and Rat Gastrointestinal Tracts, Caco-2 in vitro Cell Culture Model, and Multiple Human Tissues," *AAPS PharmSci*, 3(1):E9 (2001), Abstract.

Hosztafi, S. et al. "Synthesis and Analgetic Activity of Nicotinic Esters of Morphine Derivatives," Arzneim.-Forsch./Drug Res. 43(II), Nr. 11 (1993).

International Search Report, dated Oct. 9, 2003, for PCT/US03/05525.

International Search Report, dated Sep. 3, 2003.

Knutter, I. et al., "A Novel Inhibitor of the Mammalian Peptide Transporter PEPT1," *Biochemistry*, 40(14):4454-4458 (2001), Abstract.

Kovacs, J., et al., "Glutamic and Aspartic Anhydrides. Rearrangement of N-Carboxyglutamic 1,5-Anhydride to the Leuchs' Anhydride and Conversion of the Latter to Pyroglutamic Acid,".

Kramer, Werner et al., "Intestinal Absorption of Peptides by Coupling to Bile Acids," *The Journal of Biochemistry*, 269(14):10621-10627 (1994).

Leibach, F.H, et al., "Peptide Transporters in the Intestine and the Kidney," *Annu Rev Nutri*, 16:99-119 (1996), Abstract.

Li, Chun, et al., "Complete Regression of Well-Established Tumors Using a Novel Water-Soluble Poly(L-Glutamic Acid)-Paclitaxel Conjugate," *Cancer Res*, 58:2404-2409 (1998).

Marriq, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).

Negishi, Naoki, et al., "Coupling of Naltrexone to Biodegradable Poly (α-Amino Acids)," *Pharmaceutical Research*, 4(4):305-310 (1987).

Nishida, Koyo, et al., "Pharmacokinetic Analysis of in Vivo Metabolism of Amino Acid or Dipeptide Conjugates of Salicylic Acid in Rabbit Intestinal Microorganisms," *Pharmaceutical Research*, 11(1):160-164 (1994).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Oh, DM, et al., "Drug Transport and Targeting, Intestinal Transport," *Pharma Biotechnol*, 12:59-88 (1999), Abstract.

Okada, Masahiko, et al., "Synthesis of Glycopeptide-conjugates via Ring-Opening Polymerization of Sugar-Substituted α-Amino Acid N-Carboxyanhydrides (GlycoNCAs)," *Proc. Japan Acad.*, 73:205-209 (1997).

Orten, James M. et al., "Thyroxine," *Human Biochemistry*, 9th Ed., C.V. Mosby Company, St. Louis,pp. 401-405 (1975).

Pade, V., et al., " Link Between Drug Absorption Solubility and Permeability Measurements in Caco-2 Cells," *Journal of Pharmaceutical Sciences*, vol. 87, No. 12 (1998).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423-429 (1984).

Ryser, Hugues J.P., et al., "Conjugation of Methotrexate to Poly (L-lysine) Increases Drug Transport and Overcomes Drug Resistance in Cultured Cells," *Proc. Natl. Acad. Sci. USA,* 75(8):3867-3870 (1978).

Sawada, Kyoko, et al., "Recognition of L-Amino Acid Ester Compounds by Rat Peptide Transporters PEPT1 and PEPT2," *Journal of Pharmacology and Experimental Therapeutics,* 291(2):705-709 (1999).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry,* 37(22):3812-3817 (1994).

Shen, H., et al., "Developmental Expression of PEPT1 and PEPT2 in Rat Small Intestine, Colon, and Kidney," *Pediatr Res,* 49(6):789-795 (2001), Abstract.

Shiraga, T., et al., "Cellular and Molecular Mechanisms of Dietary Regulation on Rat Intestinal H+/Peptide Transporter PepT1," *Gastroenterology,* 116(2):354-362 (1999), Abstract.

Tamai, I., et al., "Improvemant of L-dopa Absorption by Dipeptidyl Derivation, Utilizing Peptide Transporter PepT1," *J. Pharma. Sci.,* 87(12):1542-1546 (1988), Abstract.

Toft, A., "Thyroid Hormone Replacement—One Hormone or Two?," *The New England Journal of Medicine,* vol. 340, No. 6, (1999).

Toth, Istvan, "A Novel Chemical Approach to Drug Delivery: Lipidic Amino Acid Conjugates," *Journal of Drug Targeting,* 2:217-239 (1994).

Zunino, Franco, et al., "Anti-Tumor Activity of Daunorubicin Linked to Poly-L-Aspartic Acid," *International Journal of Cancer,* 30:465-470 (1982).

Zunino, Franco, et al., "Comparison of Antitumor Effects of Daunorubicin Covalently Linked to Poly-L-Amino Acid Carriers," *European Journal of Cancer & Clinical Oncology,* 20(3):121-125 (1984).

Thomson Derwent World Patents Index.

Supplementary European Search Report for EP 01273387 dated Sep. 28, 2004.

U.S. Appl. No. 10/923,088, Entitled "Active Agent Delivery Systems And Methods For Protecting And Administering Active Agents", Mickle et al., filed Aug. 23, 2004.

U.S. Appl. No. 10/953,111, Entitled "Compounds and Compositions for the Prevention of Overdose of Oxycodone", Mickle et al., filed Aug. 23, 2004.

U.S. Appl. No. 11/179,801, Entitled "Carbohydrate Conjugates to Prevent Abuse of Controlled Substances", Mickle et al., filed Jul. 13, 2005.

U.S. Appl. No. 11/392,878, Entitled "Pharmaceutical Compositions for Prevention of Overdose or Abuse", Mickle et al., filed Apr. 4, 2006.

U.S. Appl. No. 11/400,304, Entitled "Abuse Resistant Amphetamine Prodrugs", Mickle et al., filed Apr. 10, 2006.

* cited by examiner

Step 1: Coupling

Step 2: Deprotection

Oral Formulation: Solution, 0 2 mg/mL in water

Representative Nucleosides

Site of Conjugation for Hydrocodone

Figure 128

Niacin

Biotin

```
                           SEQUENCE LISTING

<160> NUMBER OF SEQ ID NOS: 26

<210> SEQ ID NO 1
<211> LENGTH: 4
<212> TYPE: PRT
<213> ORGANISM: artificial
<220> FEATURE:
<223> OTHER INFORMATION: synthetic peptide

<400> SEQUENCE: 1

Gly Gly Gly Leu
1

<210> SEQ ID NO 2
<211> LENGTH: 6
<212> TYPE: PRT
<213> ORGANISM: artificial
<220> FEATURE:
<223> OTHER INFORMATION: synthetic peptide

<400> SEQUENCE: 2

Glu Glu Phe Phe Phe Ile
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Glu Glu Phe Phe Phe
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Gly Gly Lys Gly Gly
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Glu Glu Phe Phe Ile
1               5

<210> SEQ ID NO 6
<211> LENGTH: 5
```

```
<212> TYPE: PRT
<213> ORGANISM: Artificial
<220> FEATURE:
<223> OTHER INFORMATION: synthetic peptide

<400> SEQUENCE: 6

Glu Glu Phe Phe Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Glu Glu Phe Phe Phe
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Tyr Tyr Phe Phe Ile
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Tyr Tyr Lys Tyr Tyr
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Phe Lys Phe Phe
1               5

<210> SEQ ID NO 11
<211> LENGTH: 4
<212> TYPE: PRT
<213> ORGANISM: Artificial
<220> FEATURE:
<223> OTHER INFORMATION: synthetic peptide

<400> SEQUENCE: 11

Lys Lys Gly Gly
1

<210> SEQ ID NO 12
<211> LENGTH: 5
<212> TYPE: PRT
```

```
<213> ORGANISM: Artificial
<220> FEATURE:
<223> OTHER INFORMATION: synthetic peptide

<400> SEQUENCE: 12

Tyr Tyr Phe Pro Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Glu Glu Glu Glu Glu
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Glu Glu Gly Gly Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Glu Glu Gly Gly Leu
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Gly Gly Gly Gly Ile
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Lys Lys Gly Gly Ile
1               5

<210> SEQ ID NO 18
<211> LENGTH: 5
<212> TYPE: PRT
<213> ORGANISM: Artificial
```

```
<220> FEATURE:
<223> OTHER INFORMATION: synthetic peptide

<400> SEQUENCE: 18

Lys Lys Pro Pro Ile
1               5

<210> SEQ ID NO 19
<211> LENGTH: 5
<212> TYPE: PRT
<213> ORGANISM: Artificial
<220> FEATURE:
<223> OTHER INFORMATION: synthetic peptide

<400> SEQUENCE: 19

Tyr Tyr Gly Gly Ile
1               5

<210> SEQ ID NO 20
<211> LENGTH: 5
<212> TYPE: PRT
<213> ORGANISM: Artificial
<220> FEATURE:
<223> OTHER INFORMATION: synthetic peptide

<400> SEQUENCE: 20

Gly Gly Pro Pro Ile
1               5

<210> SEQ ID NO 21
<211> LENGTH: 5
<212> TYPE: PRT
<213> ORGANISM: Artificial
<220> FEATURE:
<223> OTHER INFORMATION: synthetic peptide

<400> SEQUENCE: 21

Asp Asp Phe Phe Ile
1               5

<210> SEQ ID NO 22
<211> LENGTH: 5
<212> TYPE: PRT
<213> ORGANISM: Artificial
<220> FEATURE:
<223> OTHER INFORMATION: synthetic peptide

<400> SEQUENCE: 22

Glu Glu Asp Asp Ile
1               5

<210> SEQ ID NO 23
<211> LENGTH: 5
<212> TYPE: PRT
<213> ORGANISM: Artificial
<220> FEATURE:
<223> OTHER INFORMATION: synthetic peptide

<400> SEQUENCE: 23

Lys Lys Asp Asp Ile
1               5

<210> SEQ ID NO 24
<211> LENGTH: 5
<212> TYPE: PRT
<213> ORGANISM: Artificial
<220> FEATURE:
```

```
<223> OTHER INFORMATION: synthetic peptide

<400> SEQUENCE: 24

Tyr Tyr Glu Glu Ile
1               5

<210> SEQ ID NO 25
<211> LENGTH: 5
<212> TYPE: PRT
<213> ORGANISM: Artificial
<220> FEATURE:
<223> OTHER INFORMATION: synthetic peptide

<400> SEQUENCE: 25

Asp Asp Asp Asp Ile
1               5

<210> SEQ ID NO 26
<211> LENGTH: 5
<212> TYPE: PRT
<213> ORGANISM: Artificial
<220> FEATURE:
<223> OTHER INFORMATION: synthetic peptide

<400> SEQUENCE: 26

Lys Lys Glu Glu Ile
1               5
```

PHARMACEUTICAL COMPOSITIONS FOR PREVENTION OF OVERDOSE OR ABUSE

CROSS REFERENCE RELATED APPLICATIONS

This application claims benefit under 35 U.S.C. 119(e) to U.S. Provisional application No. 60/567,800 filed May 5, 2004; U.S. Provisional application No. 60/507,012 filed Sep. 30, 2003; U.S. Provisional application No. 60/567,802 filed May 5, 2004; and U.S. Provisional application No. 60/568,011 filed on May 5, 2004, all of which are hereby incorporated by reference in their entirety.

FIELD OF INVENTION

Accidental and intentional overdose with prescription and over the counter drugs is a serious health problem with thousands of fatalities occurring each year as a result. The present invention relates to pharmaceutical compositions comprised of a chemical moiety attached to an active agent in a manner that substantially decreases the potential of the active agent to cause overdose or to be abused. When delivered at the proper dosage the pharmaceutical composition provides therapeutic activity similar to that of the parent active agent. However, when the composition is delivered at higher doses the potential for overdose or abuse is reduced due to the limited bioavailability of the active agent as compared to the active agent delivered as free drug.

BACKGROUND

Drug overdose is a significant and growing problem. It can occur accidentally, as when a child swallows pills without understanding the consequences, or intentionally as with suicide attempts. In addition, accidental overdose due to an unusually potent batch of a street drug in illicit drug users is quite common. Common examples of drugs that are seen in overdose cases include the ubiquitous over-the-counter analgesics acetaminophen (paracetamol) and aspirin. While the former is the preferred drug among adolescents in cases of deliberate self poisonings (Lifshitz et al., Isr. Med. Assoc. J., 4(4): 252-4 (2002), aspirin is perhaps more dangerous because there is no antidote (Jones, Am. J. Ther. 9(3):245-57 (2002).

In the elderly population, drugs most often implicated in poisonings include psychotherapeutic drugs, cardiovascular drugs, analgesics and anti-inflammatory drugs, oral hypoglycemics and theophylline (Klein-Schwartz et al., Drugs Aging 1(1):67-89 (1991). It is important-to realize that in many cases where death due to overdose is averted, there appears to be extensive morbidity associated with overdoses (Warner-Smith et al., Addition 97(8):963-7 (2002).

The Drug Abuse Warning Network (DAWN) reported in June 2003 on the most recent trends in emergency department (ED) visits related to drug abuse. Data was presented for 8-year trends from 1994 to 2001. The following summaries were provided:

In 2001, there were over 638,000 ED visits related to drug abuse in the conterminous U.S. This translates to 252 visits per 100,000 populations or 0.6 percent of all ED visits.

Seven categories of drugs accounted for 85% of the ED mentions in 2001. The ED visits related to drug abuse most frequently involved alcohol, (34% of mentions), marijuana (17%), benzodiazepines (16%), narcotic analgesic combinations (16%), heroin (15%), other analgesics/combinations (12%), and antidepressants (10%).

ED mentions of benzodiazepines increased 14 percent from 2000 to 2001 (from 91,078 to 103,972), as did the top 2 benzodiazapines, alprazolam (up 16%) and benzodiazepines-NOS (up 35%). The latter includes benzodiazepines not identified by name.

ED mentions of narcotic analgesics/combinations rose 21 percent (from 82,373 to 99,317) from 2000 to 2001.

Narcotic analgesics not identified by name were mentioned most frequently (narcotic analgesics-NOS, 32,196 mentions, up 24% from 2000 to 2001), followed by those containing hydrocodone (21,567), oxycodone (18,409, up 70%), and methadone (10,725, up 37%). Narcotic analgesics/combinations containing propoxyphene (5,361), codeine (3,720, down 30%), and morphine (3,403) were much less frequent and not increasing.

Emergency department reporting for a number of drugs rose substantially from 1994 to 2000. These include: amphetamines (10,118 to 18,555, up 83.4%), anticonvulsants, including carbamazepine (9,358 to 14,642, up 56.5%), muscle relaxants, including carisoprodol (12,223 to 19,001, up 55.5%), psychotherapeutic drugs, including SSRI antidepressants, tricyclic antidepressants, and other antidepressants (190,467 to 220,289, up 15.7%). Anxiolytics, sedatives, and hypnotics, including benzodiazepines (74,637 to 103,972, up 27.7%) and narcotic analgesics including codeine, hydrocodone, methadone, oxycodone, propoxyphene and others (44,518 to 99,317, up 123.1%).

Other drugs for which the number of ED mentions did not rise but were still responsible for over 10,000 visits include respiratory agents, including antihistamines (12,238), antipsychotics including risperidone (20,182), nonsteroidal anti-inflammatory agents, including ibuprofen and naproxen (22,663) and acetaminophen (42,044). Aspirin and salicylates-NOS accounted for 8,499 ED visits in 2001.

The commercial drugs benzodiazapines (16%), narcotic analgesics other than heroin (16%), non-narcotic analgesics (12%), and antidepressants (10%) accounted for 54% of ED visits in 2001.

Amphetamine is commonly administered as the sulfate salt in single oral doses of 5-15 mg. When abused amphetamine is typically either orally or intravenously used in amounts up to 2000 mg per day by addicts. A normal dosage of amphetamine typically provides blood concentrations which peak at 35 ng/mL, 2 hours following a single oral dose of 10 mg (half-life 11-13 hours). Following the oral administration of 30 mg of amphetamine, an average peak plasma level of about 111 ng/mL may be observed at 2.5 hours. After 4.5 hours, the level may drop to about 84 ng/mL. After oral ingestion of amphetamine, absorption is complete in 4-6 hours. Concentration in blood or plasma following a therapeutic dose is low because of the large volume of distribution. Contrarily, a steady-state blood level of 2000-3000 ng/mL has been observed in addicts who orally consume an average of 1000 mg per day of amphetamine. While peripheral effects such as increased heart rate start at blood levels of 20 ng/mL, rapid tolerance from intravenous use develops.

Similarly, methamphetamine used in the treatment of obesity in single oral doses of 2.5-15 mg. After the administration of a single dose of 10 mg of methamphetamine, a maximum blood concentration of 30 ng/mL may be observed at one hour. A 12.5 mg dose may produced an average peak blood level of about 20 ng/mL at 2.5 hours, about 16 ng/mL at 6 hours, and about 10 ng/mL at 24 hours.

Methamphetamine urine concentrations after the administration of 10 mg are typically 500-4,000 ng/mL during the first 24 hours. It has been reported that the methamphetamine concentration of methamphetamine abusers is 2,400-33,300 ng/mL (average 14,200 ng/mL) and amphetamine concentrations of 1,000-9,000 ng/mL. (average 1,800 ng/mL). The estimated lethal dose is 100 mg in children and 1 g in adults.

Oxycodone is an ingredient of Percodan, Percocet, Roxicet, and Tylox. It is a semisynthetic narcotic analgesic that is derived from thebaine. Available in oral formulations often in combination with aspirin, phenacetin and caffeine. Typical adult dose is 2.5-5 mg as the hydrochloride or terephthalate salt every 6 hours. Although it is typically used for the relief of moderate to moderately severe pain, it can also produce drug dependence of the morphine type. Therapeutic plasma concentration is 10-100 ng/mL and the toxic plasma concentration is greater than 200 ng/mL.

Hydrocodone is an opioid analgesic and antitussive and occurs as fine, white crystals or as crystalline powder. Hydrocodone is a semisynthetic narcotic analgesic prepared from codeine with multiple actions qualitatively similar to those of codeine. It is mainly used as an antitussive in cough syrups and tablets in sub-analgesic doses (2.5-5 mg). Additionally, it is used for the relief of moderate to moderately severe pain. Hydromorphone is administered orally in 5-10 mg doses four times daily. Therapeutic plasma concentration is 1-30 ng/mL and the toxic plasma concentration is greater than 100 ng/mL.

Others have sought to prevent the potential harmful effects of overdose through various formulations. For example, opioids have been combined with antagonists in particular formulations designed to counteract the opioid if the formulation is disrupted before oral administration or is given parenterally. Extended release Concerta (methylphenidate) has been formulated in a paste to preclude administration by snorting or injection. Compositions have been coated with emetics in a quantity that if administered in moderation as intended no emesis occurs, however, if excessive amounts are consumed emesis is induced therefore preventing overdose. These methods, as well as conventional control release formulations, are insufficient and can be easily circumvented. Consequently, improved methods are needed to make drugs with reduced potential for overdose that are resistant to manipulation.

Figure 120:
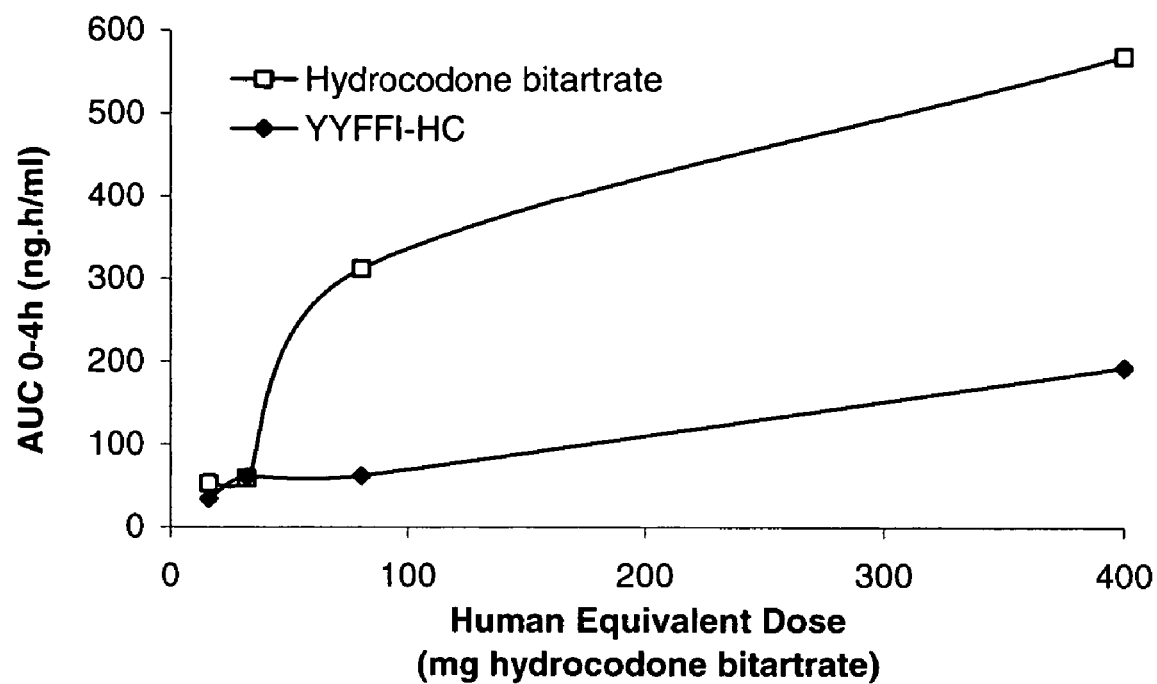

FIG. 120. Oral bioavailability (AUC0-4h) of hydrocodone plus hydromorphone in proportion to human equivalent doses (HED) following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 121:
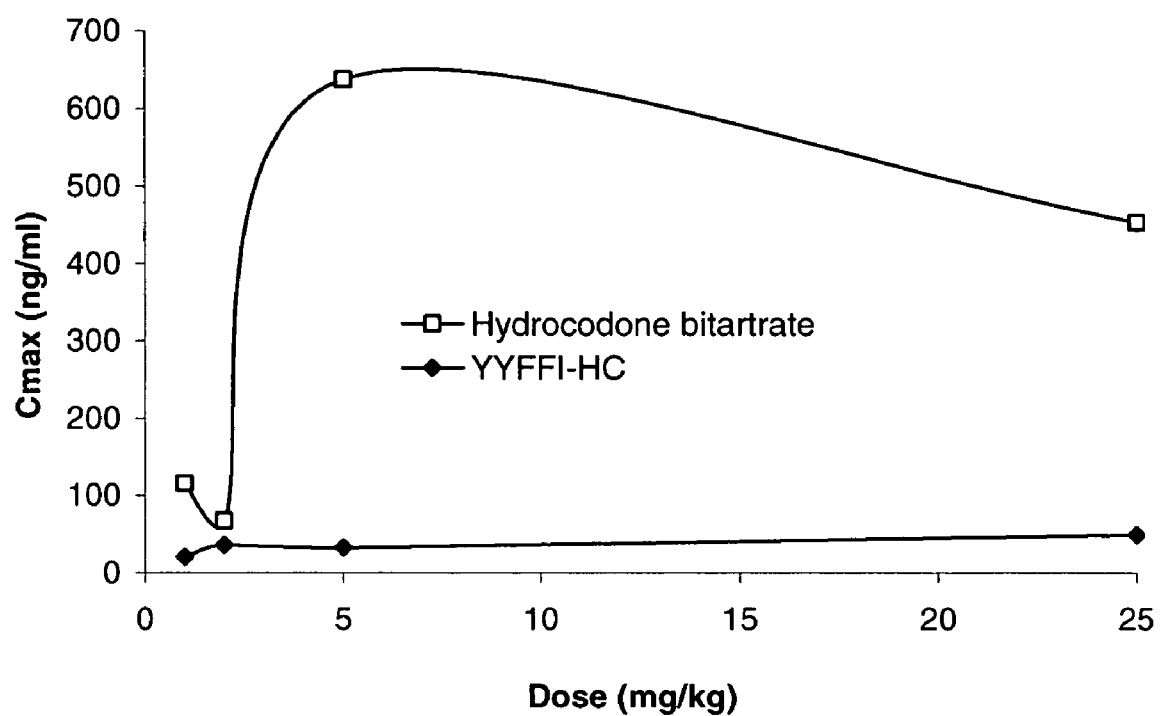

FIG. 121. Oral bioavailability (Cmax) of hydrocodone plus hydromorphone (concentration vs. dose) in proportion to dose following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 122:
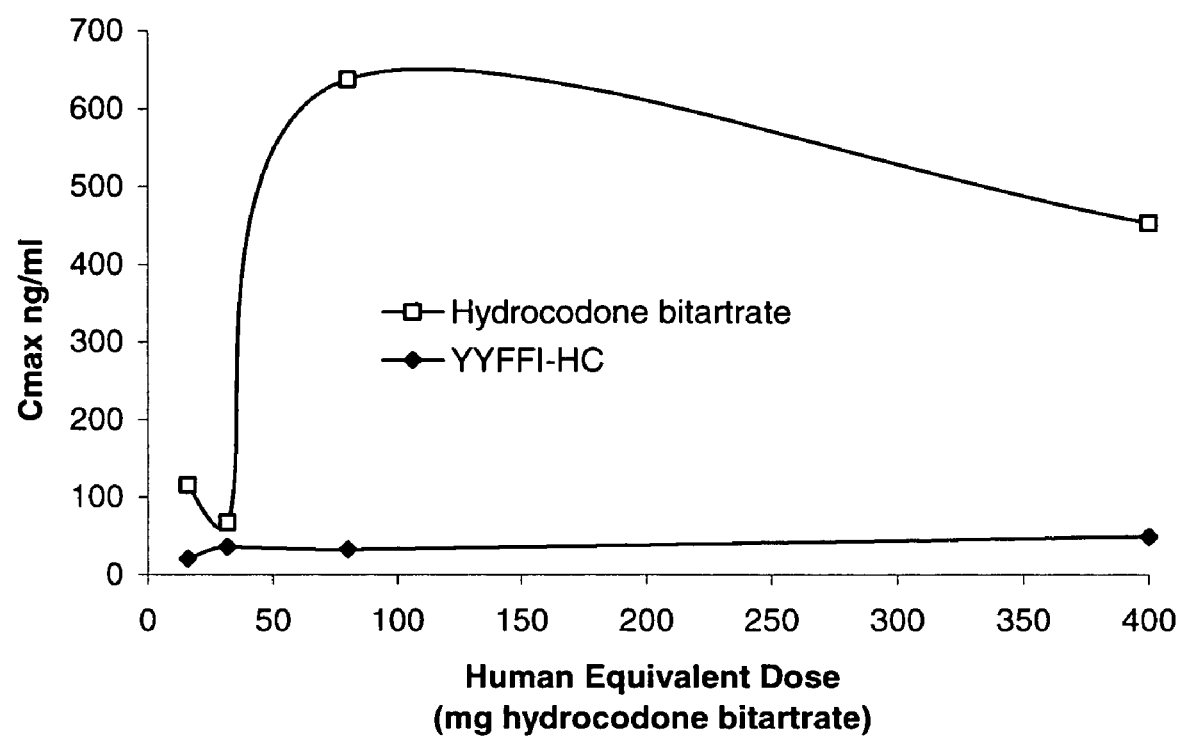

FIG. 122. Oral bioavailability (Cmax) of hydrocodone plus hydromorphone in proportion to human equivalent doses (HED) following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 123:
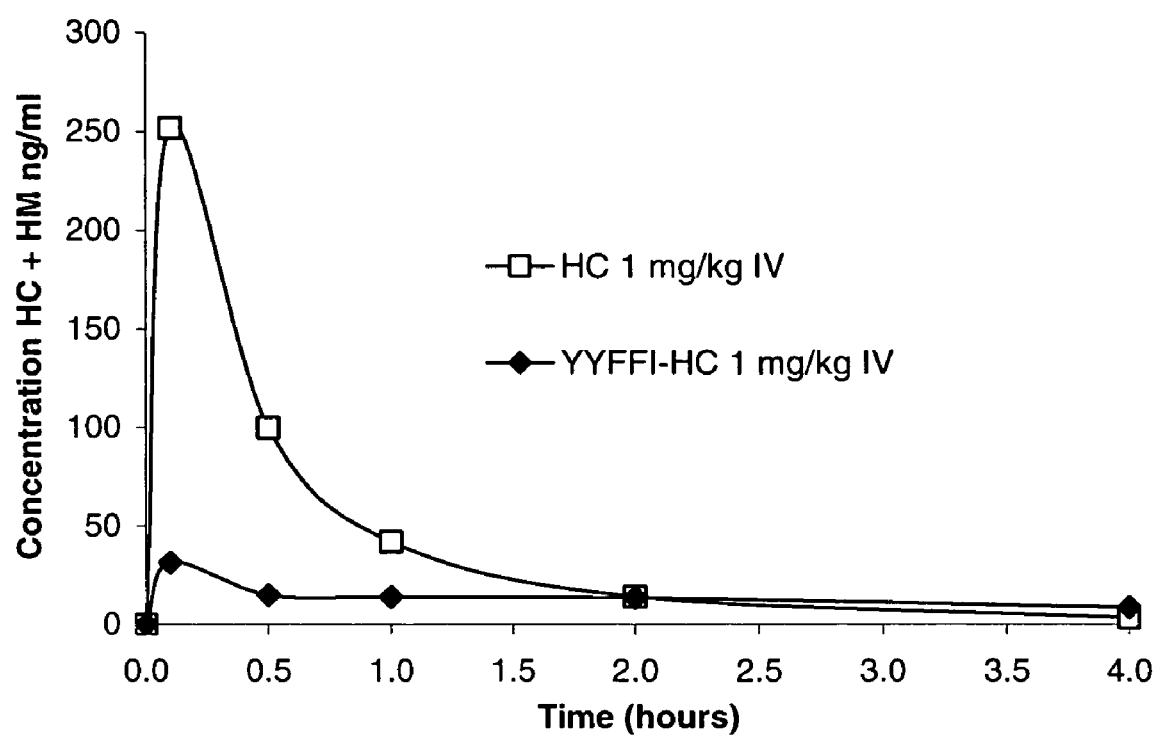

FIG. 123. Intravenous bioavailability of hydrocodone plus hydromorphone and YYFFI[SEQ ID NO: 8]-HC (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 124:
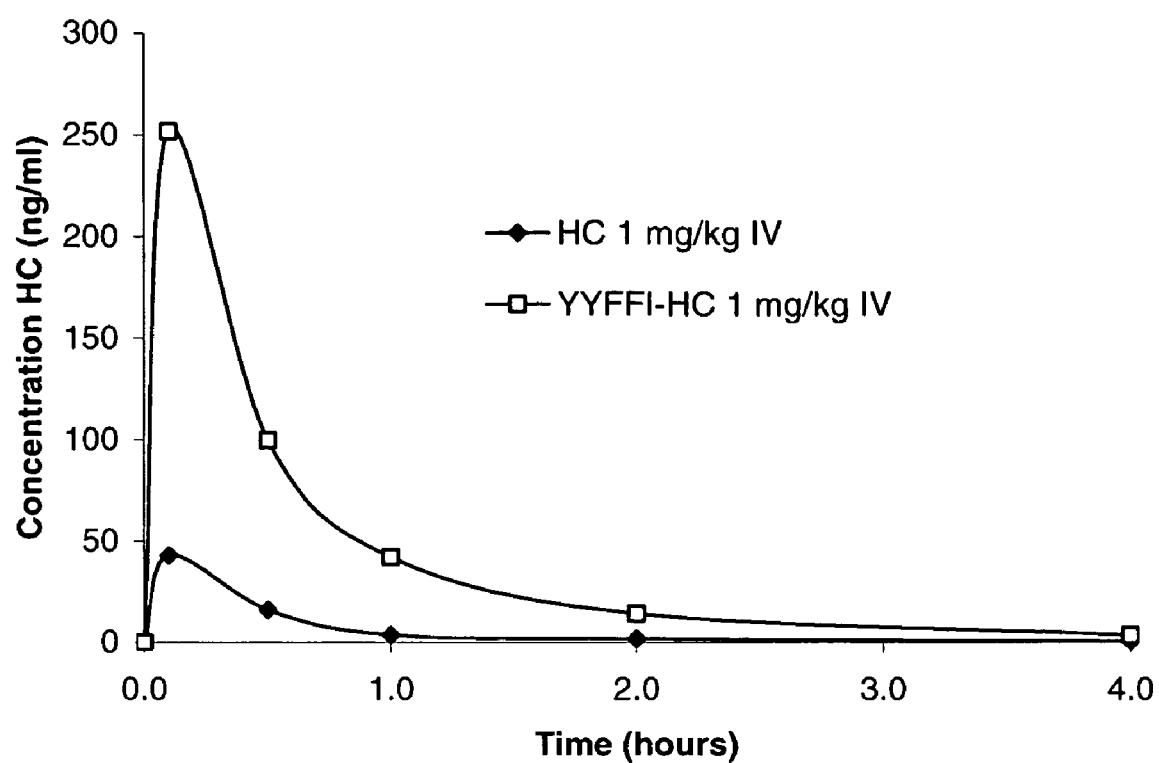

FIG. 124. Intravenous bioavailability of hydrocodone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 125:
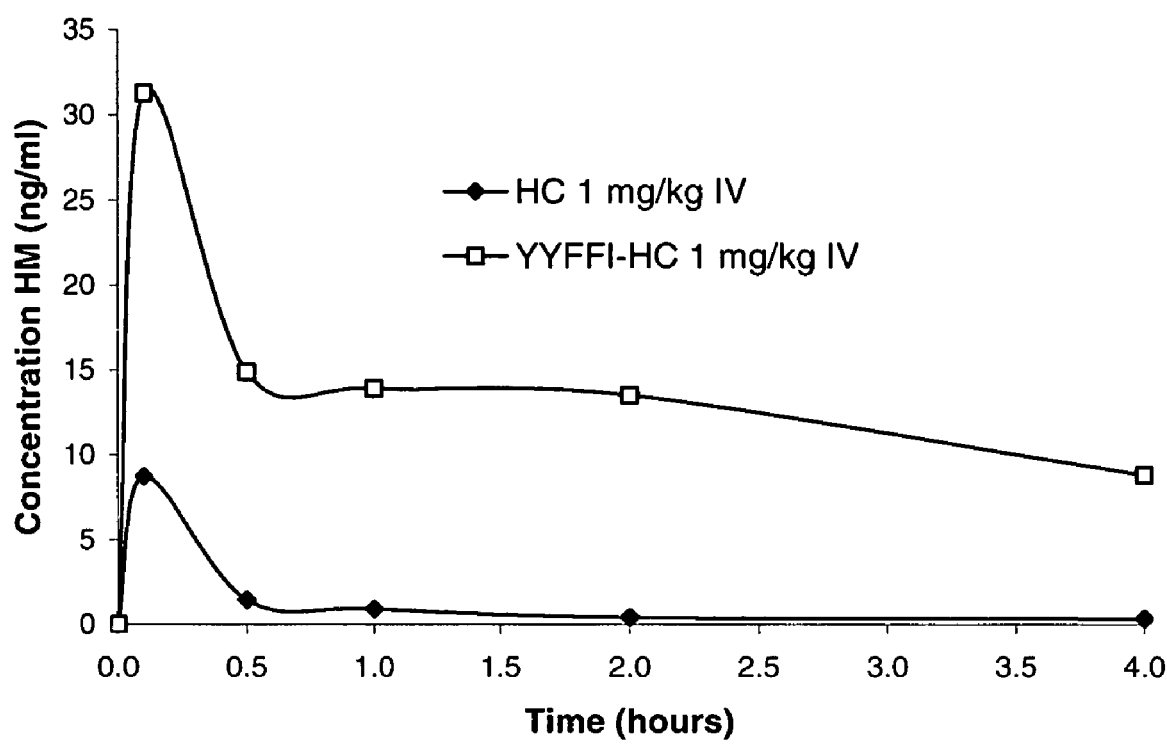

FIG. 125. Intravenous bioavailability of hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 126:
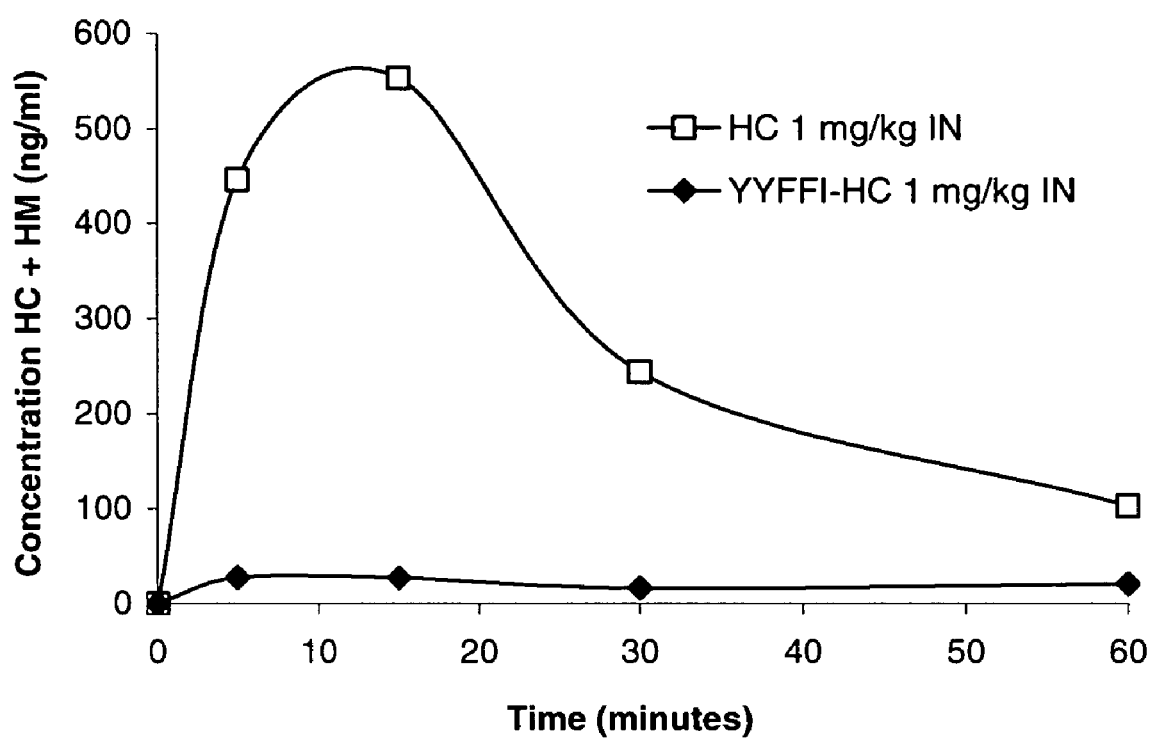

FIG. 126. Intranasal bioavailability of hydrocodone plus hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 127:
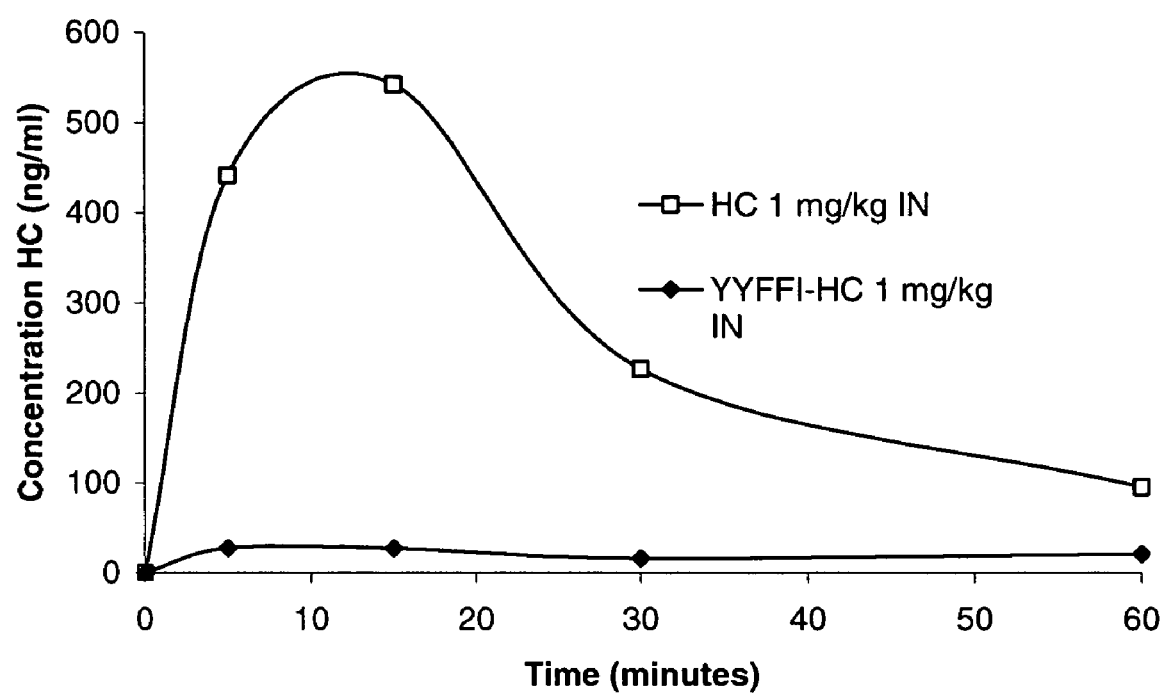

FIG. 127. Intranasal bioavailability of hydrocodone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 128:
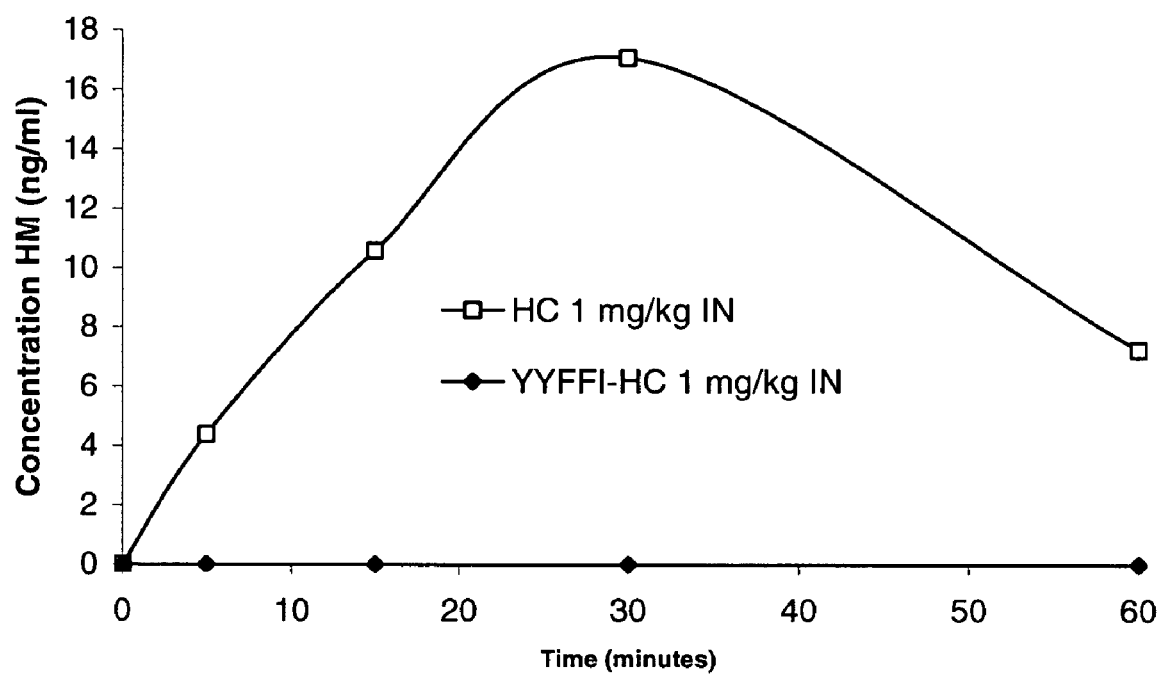

FIG. 128. Intranasal bioavailability of hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 129:
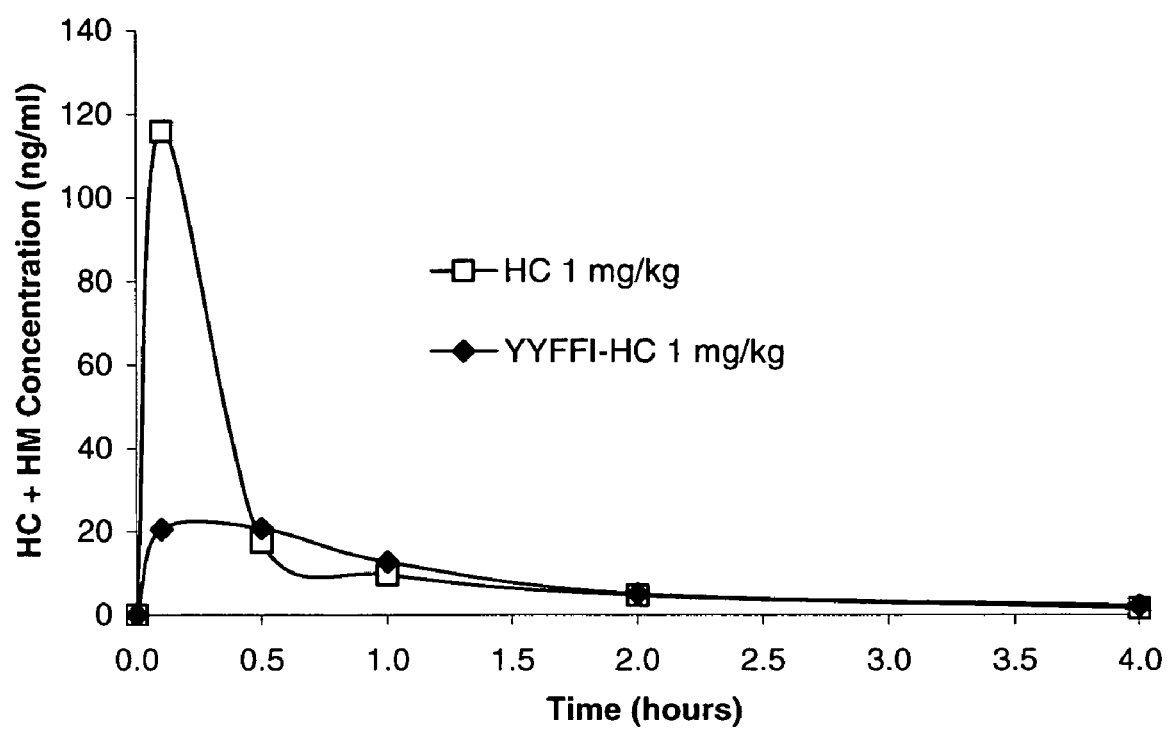

FIG. 129. Oral bioavailability of hydrocodone plus hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 130:
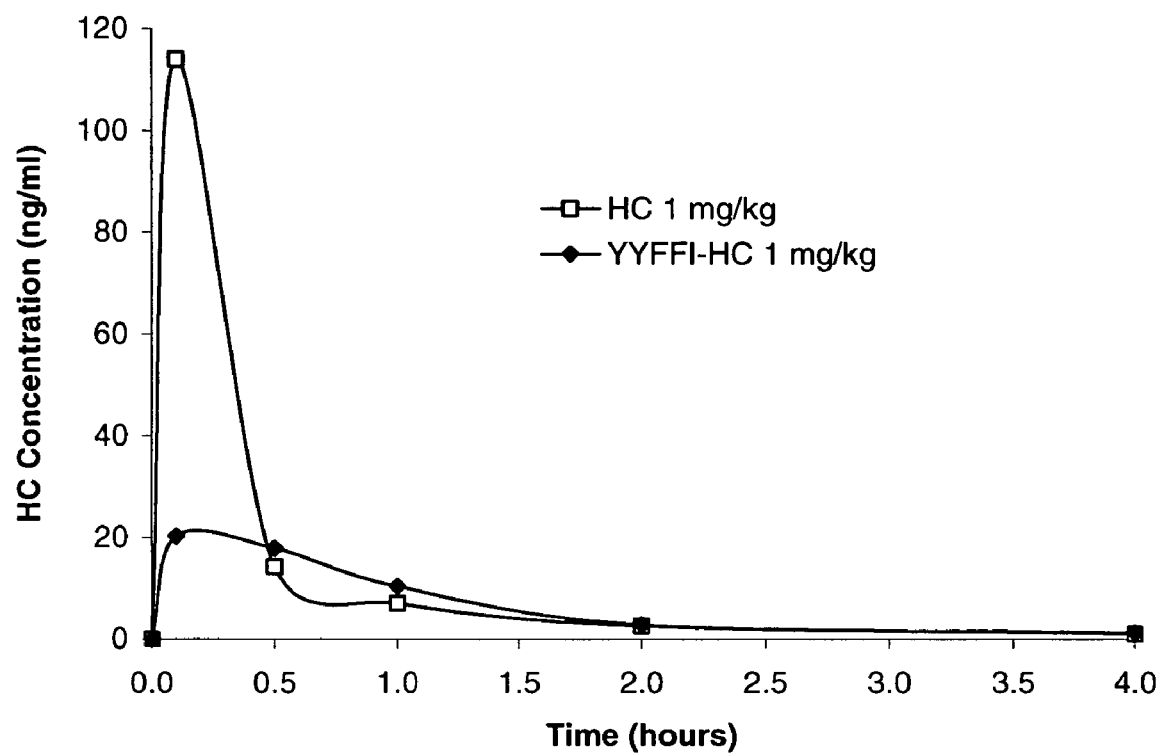

FIG. 130. Oral bioavailability of hydrocodone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 131:
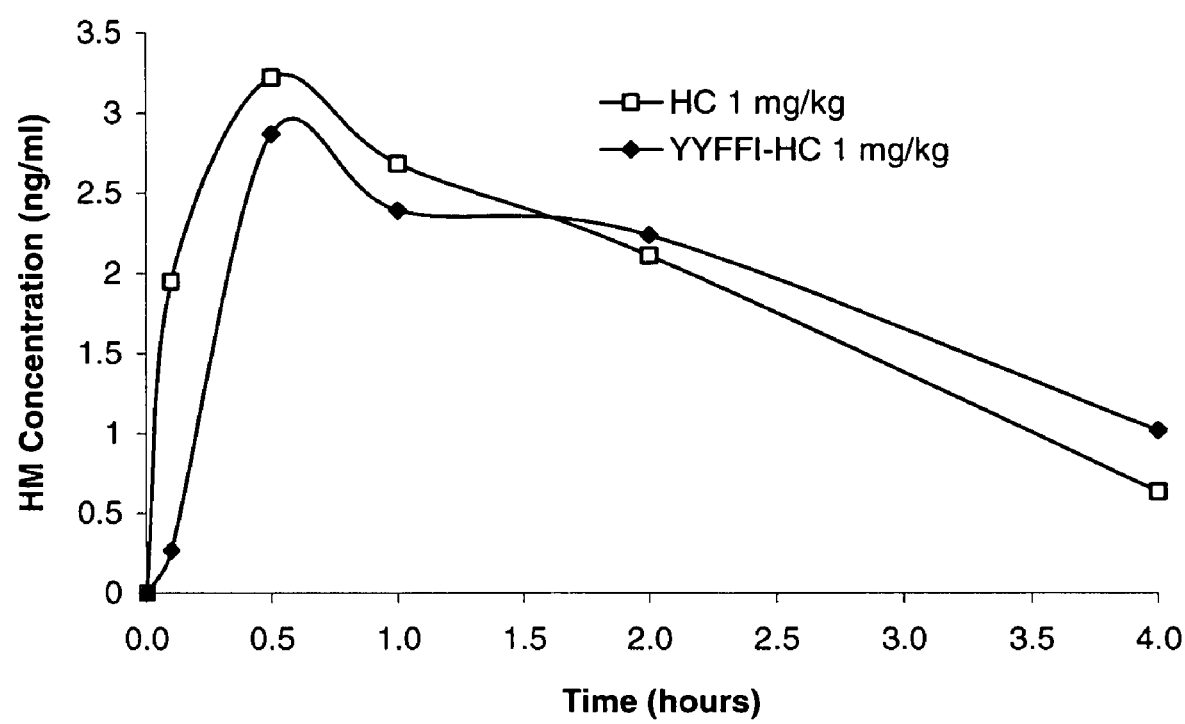

FIG. 131. Oral bioavailability of hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 132:
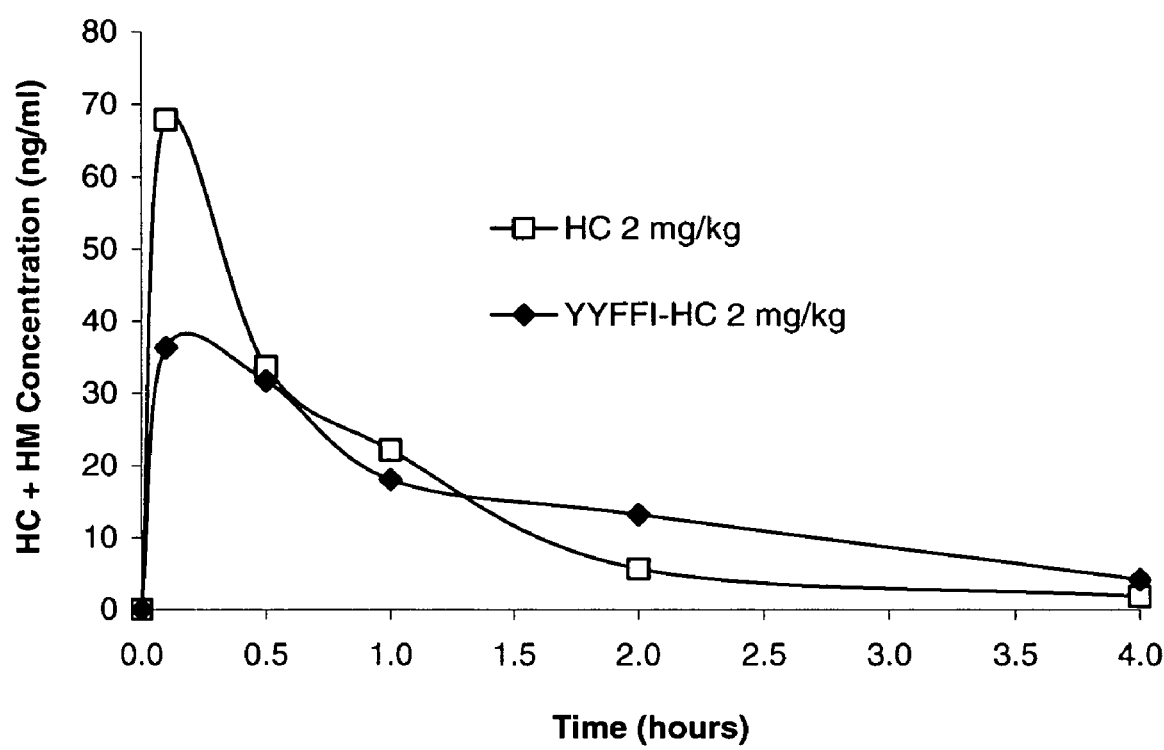

FIG. 132. Oral bioavailability of hydrocodone plus hydromorphone (concentration vs. time) following administration of hydrocodone bitratrate or YYFFI[SEQ ID NO: 8]-HC at 2 mg/kg (equimolar doses with equivalent content of hydrocodone base) in rats, measured as free hydrocodone.

Figure 133:
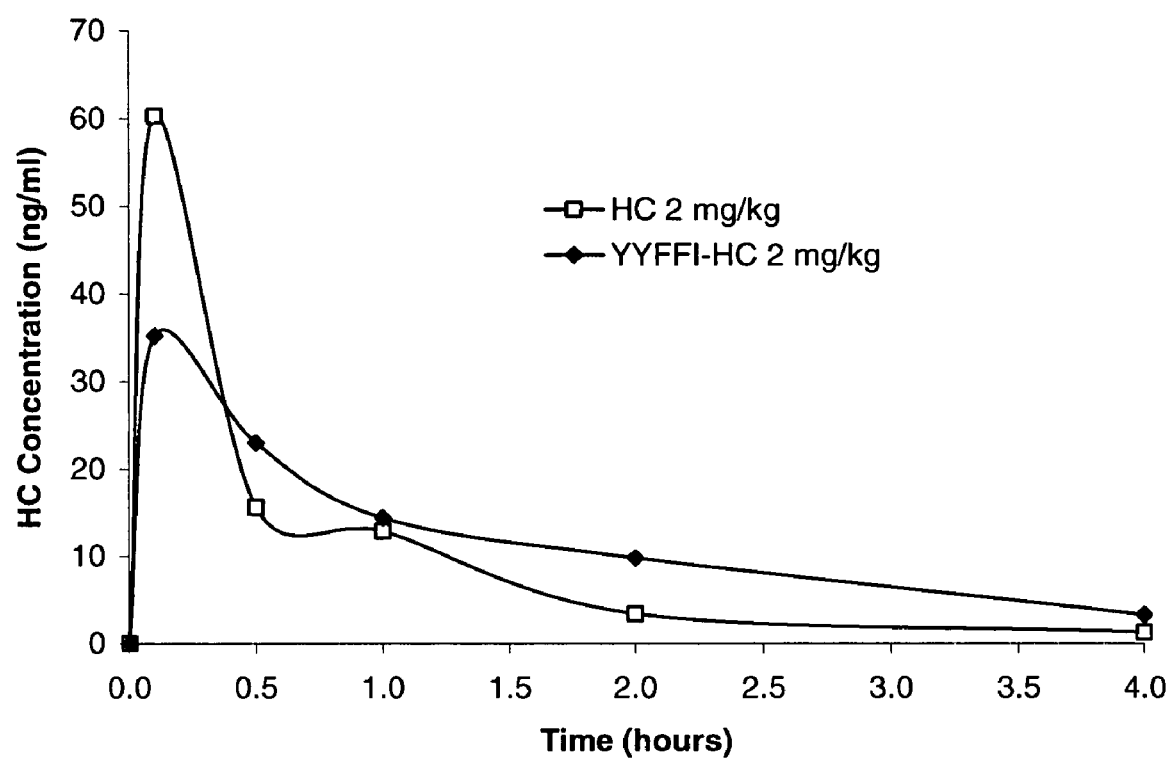

FIG. 133. Oral bioavailability of hydrocodone (concentration vs. time) following administration of hydrocodone bitratrate or YYFFI[SEQ ID NO: 8]-HC at 2 mg/kg (equimolar doses with equivalent content of hydrocodone base) in rats, measured as free hydrocodone.

Figure 134:
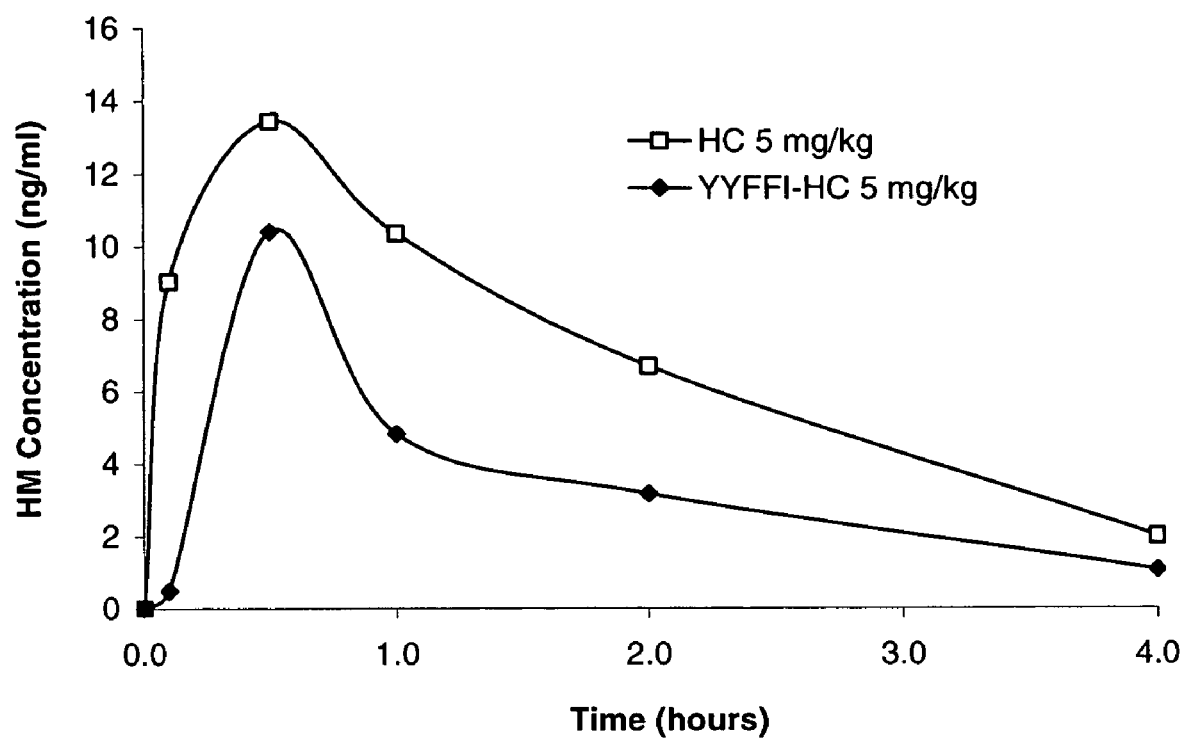

FIG. 134. Oral bioavailability of hydromorphone (concentration vs. time) following administration of hydrocodone bitratrate or YYFFI[SEQ ID NO: 8]-HC at 2 mg/kg (equimolar doses with equivalent content of hydrocodone base) in rats, measured as free hydrocodone.

Figure 135:
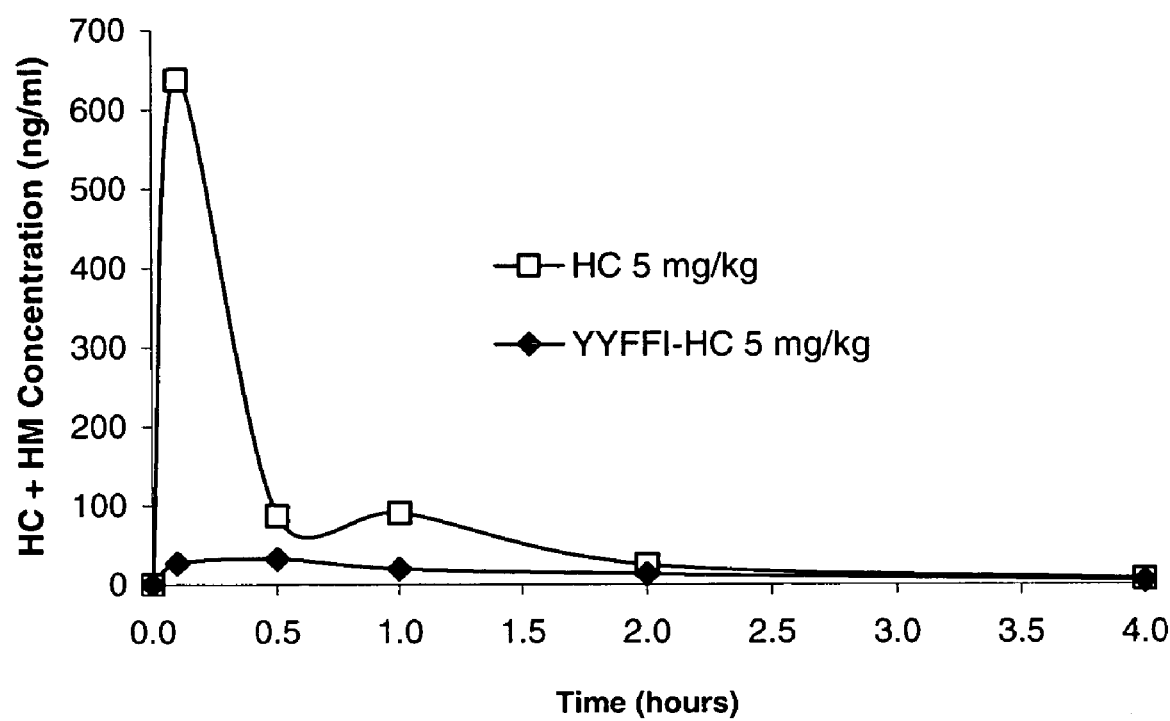

FIG. 135. Oral bioavailability of hydrocodone plus hydromorphone (concentration vs. time) following administration of hydrocodone bitratrate or YYFFI[SEQ ID NO: 8]-HC at 5 mg/kg (equimolar doses with equivalent content of hydrocodone base) in rats, measured as free hydrocodone.

Figure 136:
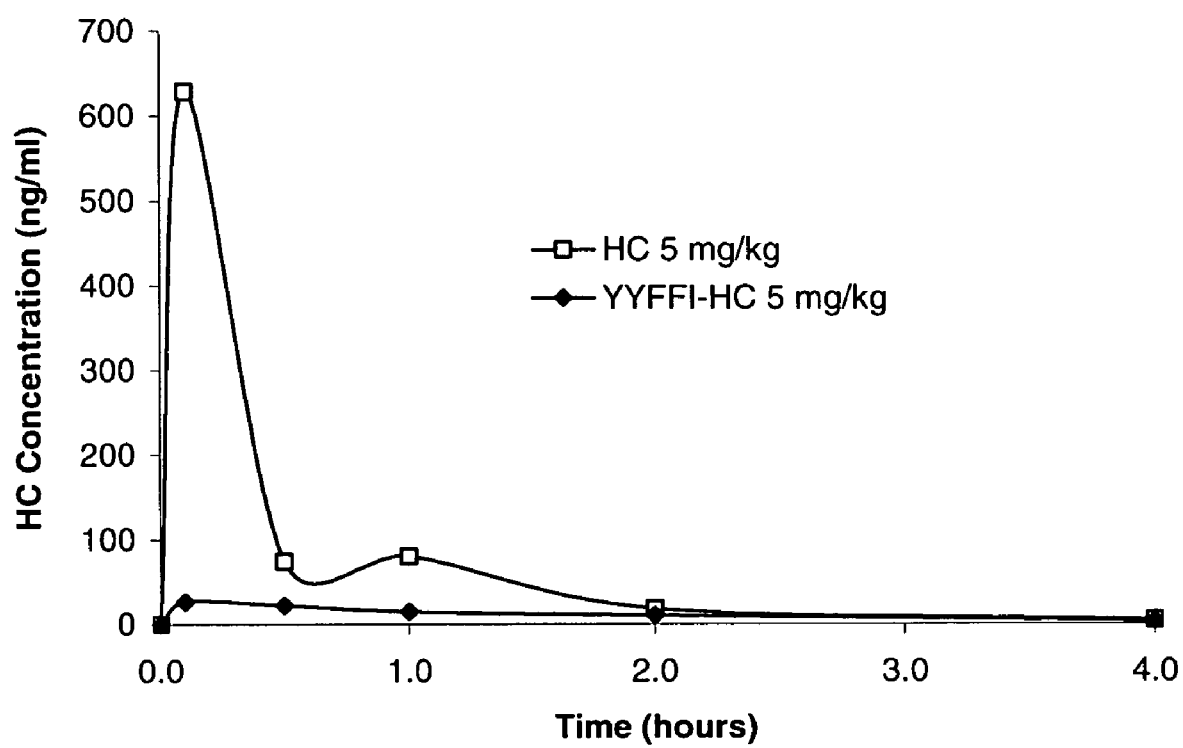

FIG. 136. Oral bioavailability of hydrocodone (concentration vs. time) following administration of hydrocodone bitratrate or YYFFI[SEQ ID NO: 8]-HC at 5 mg/kg (equimolar doses with equivalent content of hydrocodone base) in rats, measured as free hydrocodone.

Figure 137:
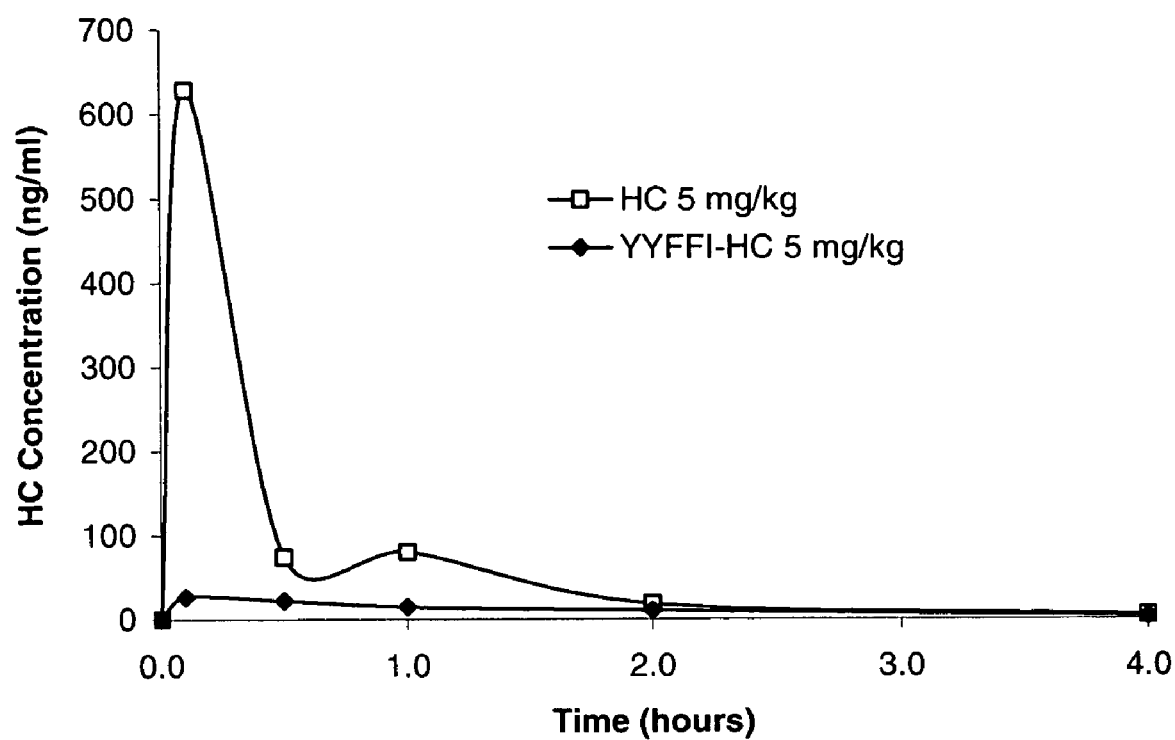

FIG. 137. Oral bioavailability of hydromorphone (concentration vs. time) following administration of hydrocodone bitratrate or YYFFI[SEQ ID NO: 8]-HC at 5 mg/kg (equimolar doses with equivalent content of hydrocodone base) in rats, measured as free hydrocodone.

Figure 138:
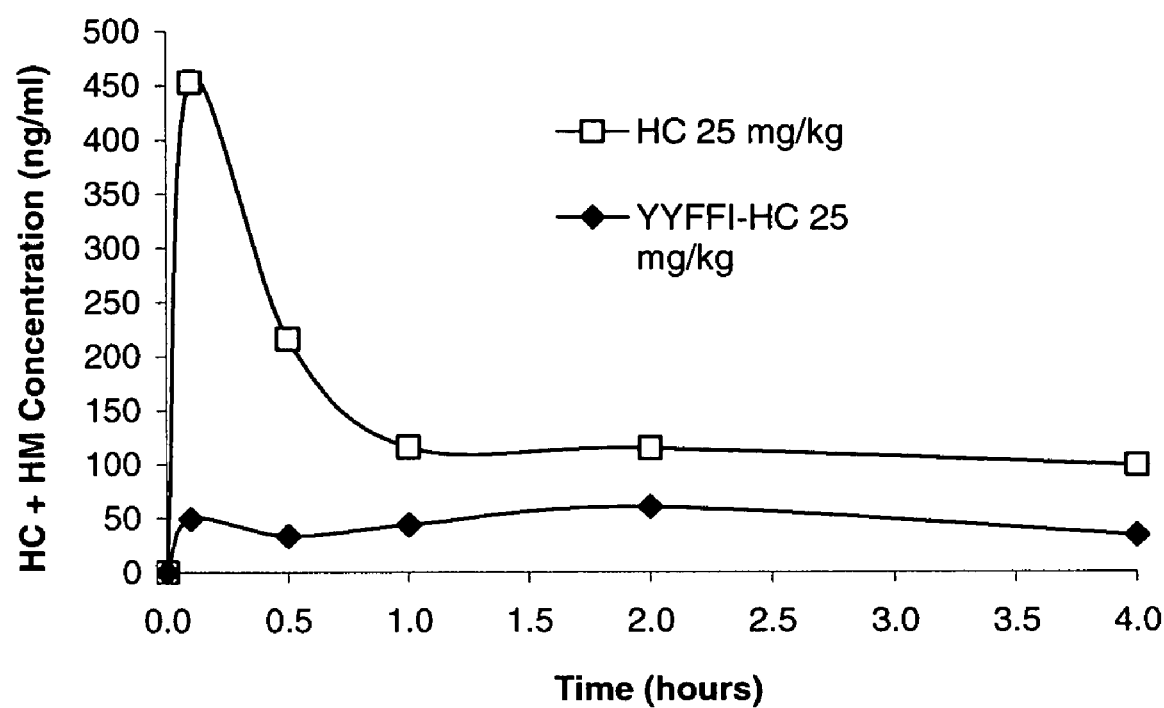

FIG. 138. Oral bioavailability of hydrocodone plus hydromorphone (concentration vs. time) following administration of hydrocodone bitratrate or YYFFI[SEQ ID NO: 8]-HC at 25 mg/kg (equimolar doses with equivalent content of hydrocodone base) in rats, measured as free hydrocodone.

Figure 139:
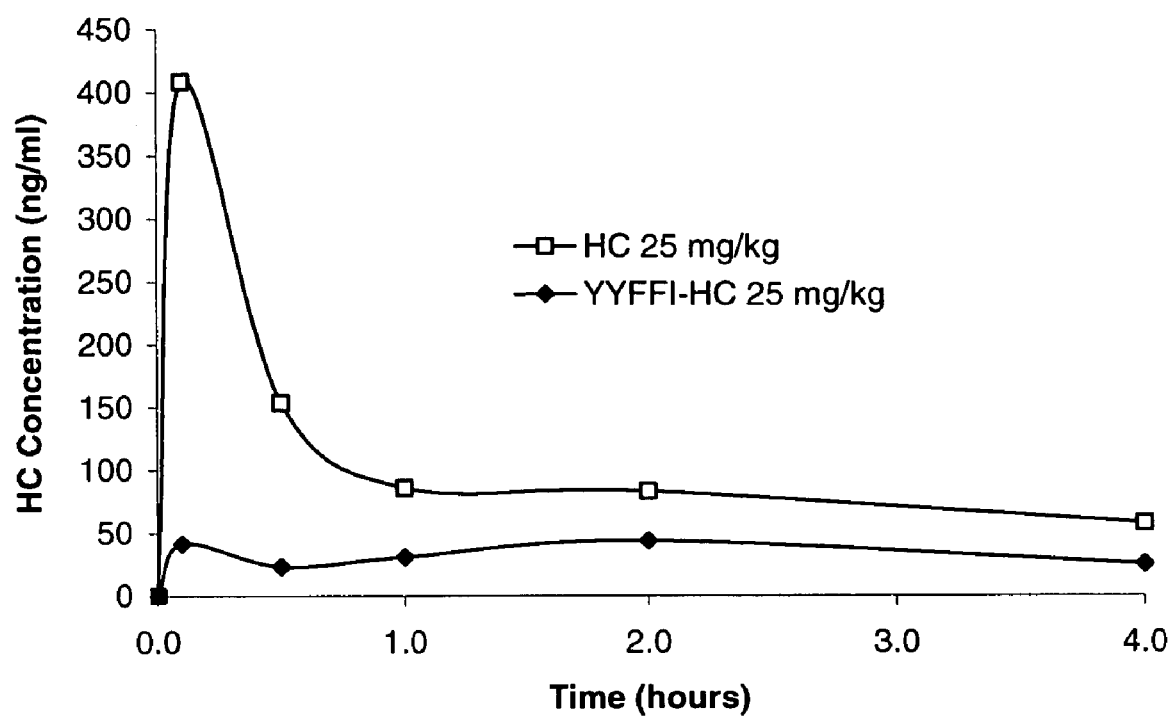

FIG. 139. Oral bioavailability of hydrocodone (concentration vs. time) following administration of hydrocodone bitratrate or YYFFI[SEQ ID NO: 8]-HC at 25 mg/kg (equimolar doses with equivalent content of hydrocodone base) in rats, measured as free hydrocodone.

Figure 140:
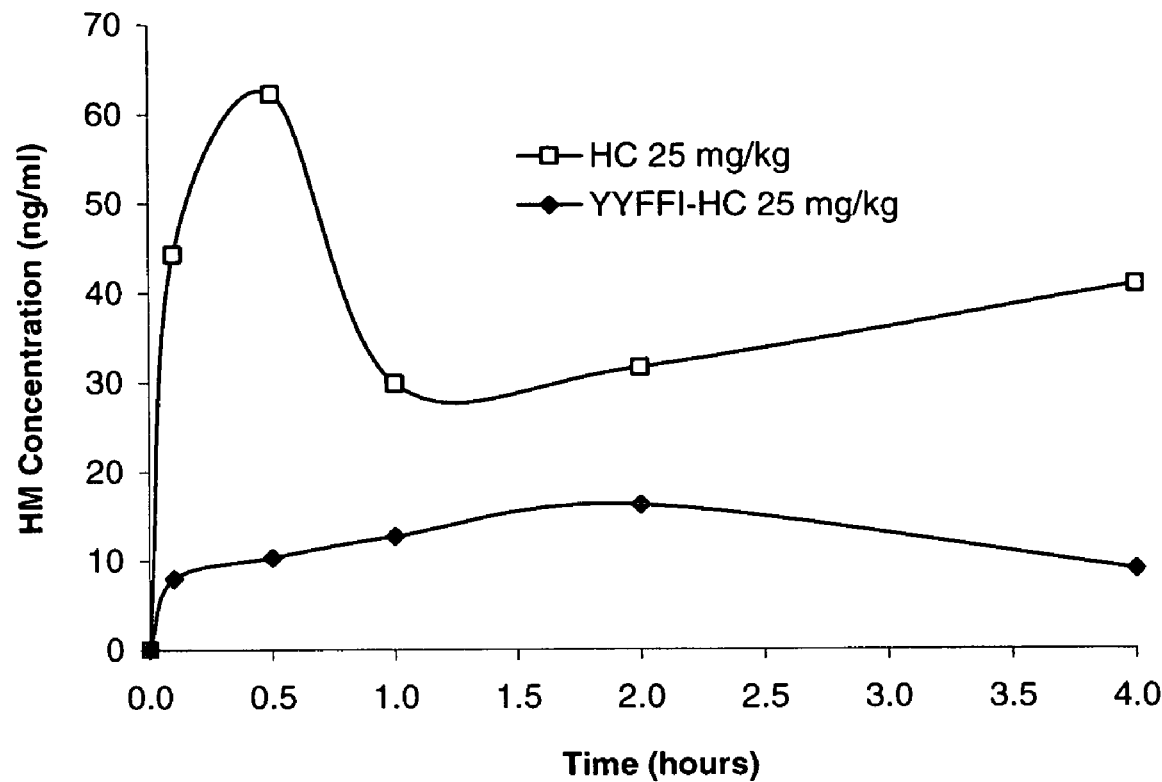

FIG. 140. Oral bioavailability of hydromorphone (concentration vs. time) following administration of hydrocodone bitratrate or YYFFI[SEQ ID NO: 8]-HC at 25 mg/kg (equimolar doses with equivalent content of hydrocodone base) in rats, measured as free hydrocodone.

Figure 141:
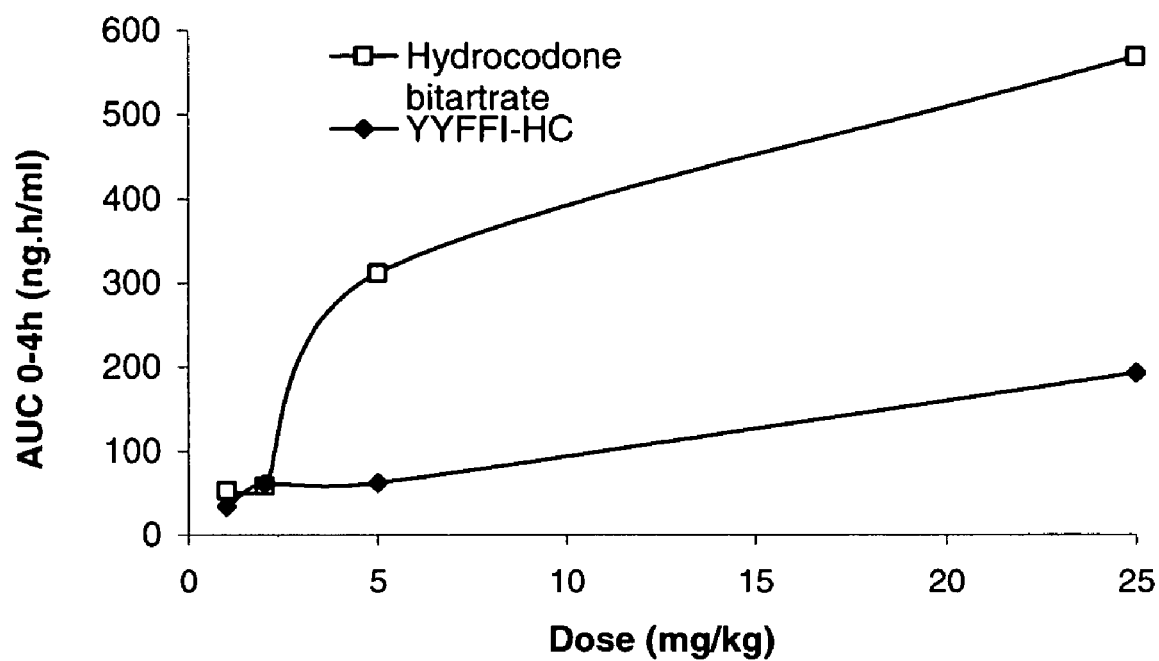

FIG. 141. Oral bioavailability (AUC0-4) of hydrocodone plus hydromorphone (concentration vs. dose) in proportion to dose following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 142:
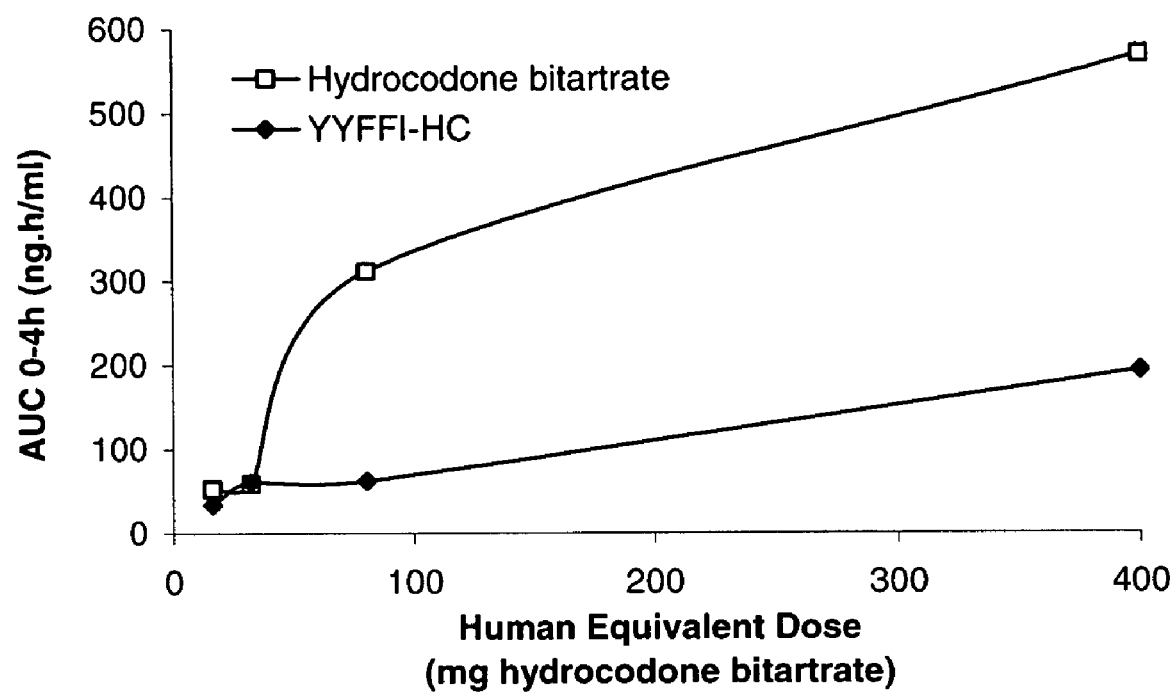

FIG. 142. Oral bioavailability (AUC0-4) of hydrocodone plus hydromorphone in proportion to human equivalent doses (HED) following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 143:
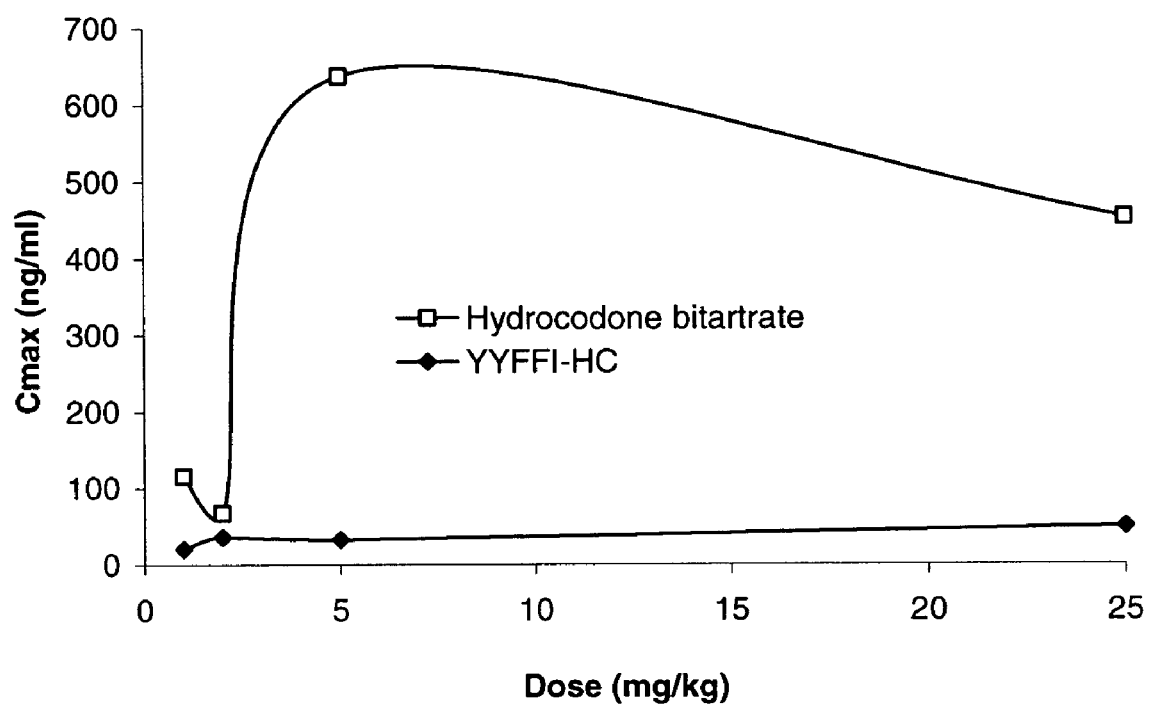

FIG. 143. Oral bioavailability (Cmax) of hydrocodone plus hydromorphone (concentration vs. dose) in proportion to dose following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 144:
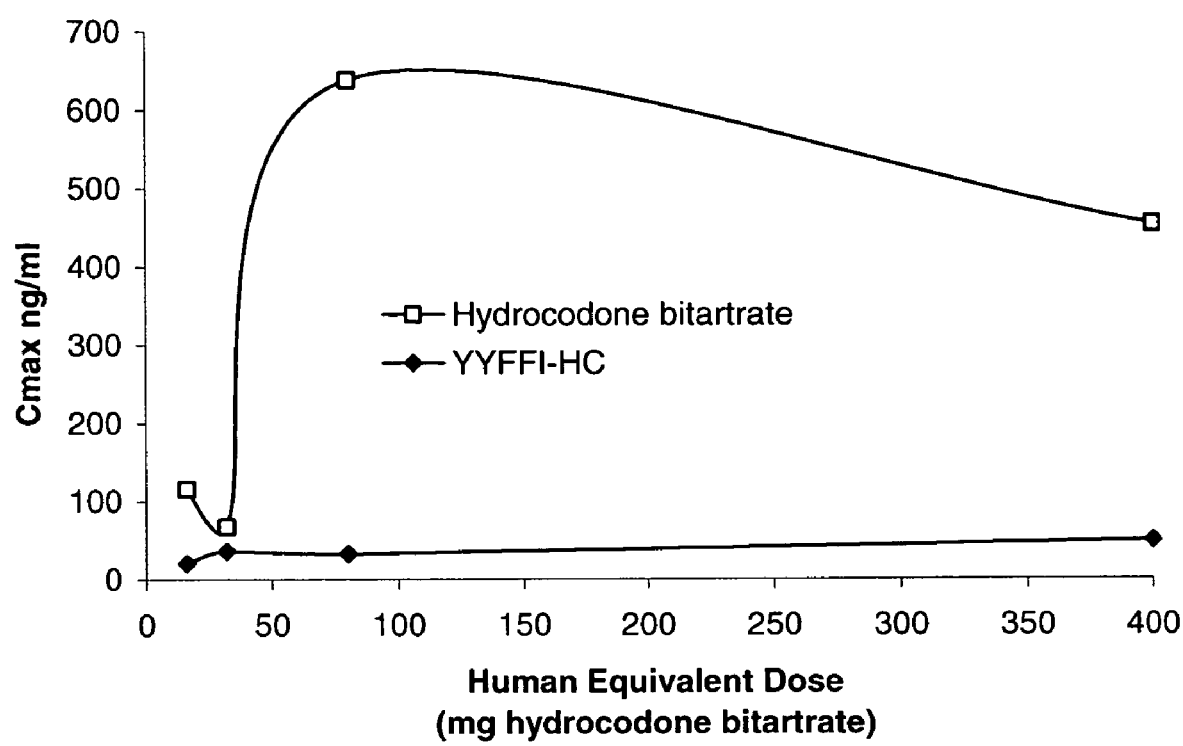

FIG. 144. Oral bioavailability (Cmax) of hydrocodone plus hydromorphone in proportion to human equivalent doses (HED) following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

Figure 145:
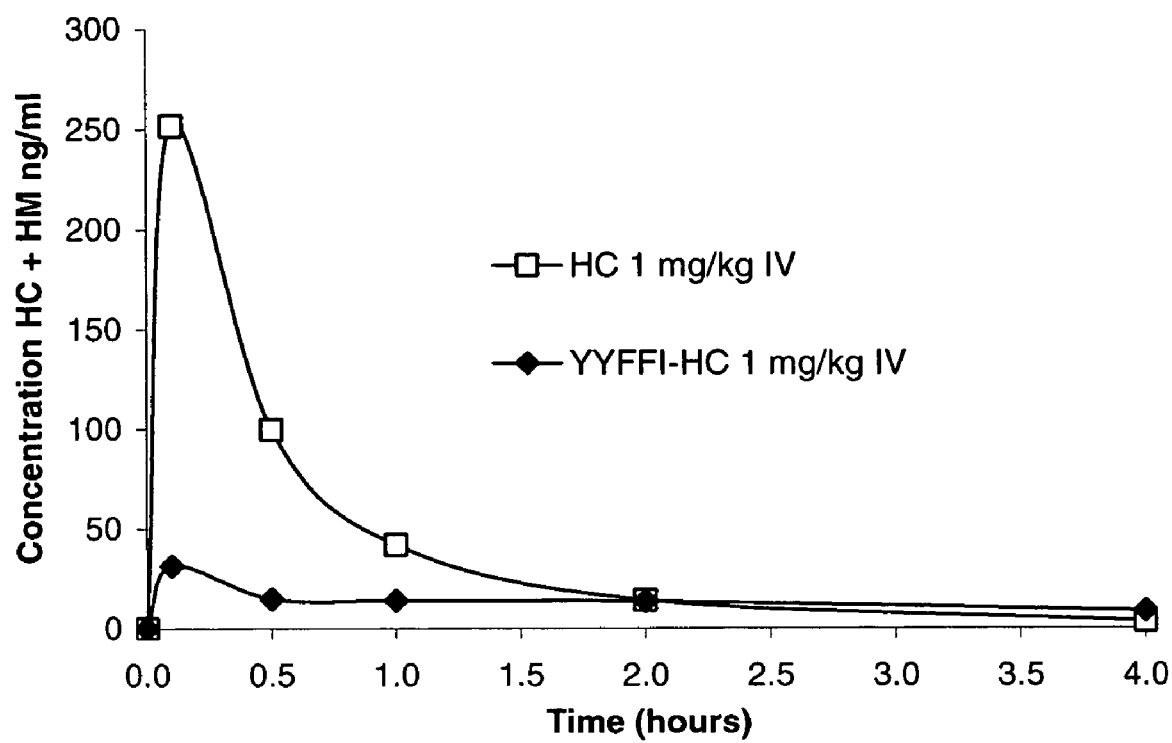

FIG. 145. Intravenous bioavailability of hydrocodone plus hydromorphone and YYFFI[SEQ ID NO: 8]-HC (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 146:
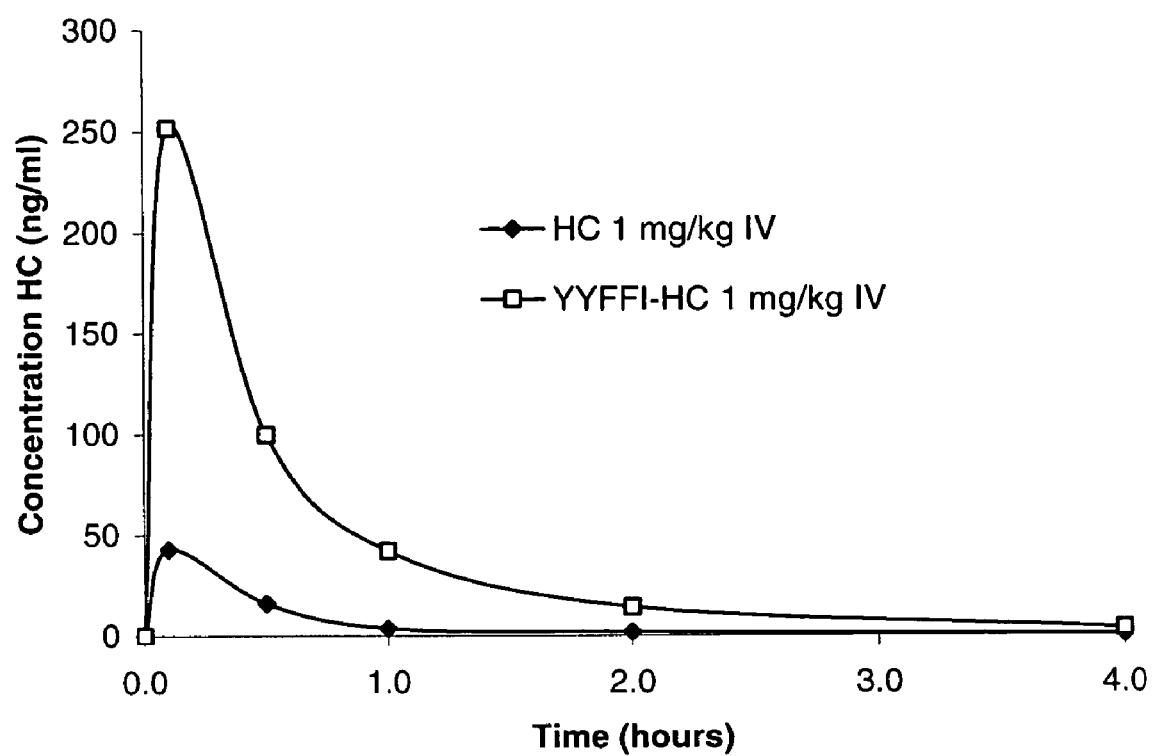

FIG. 146. Intravenous bioavailability of hydrocodone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 147:
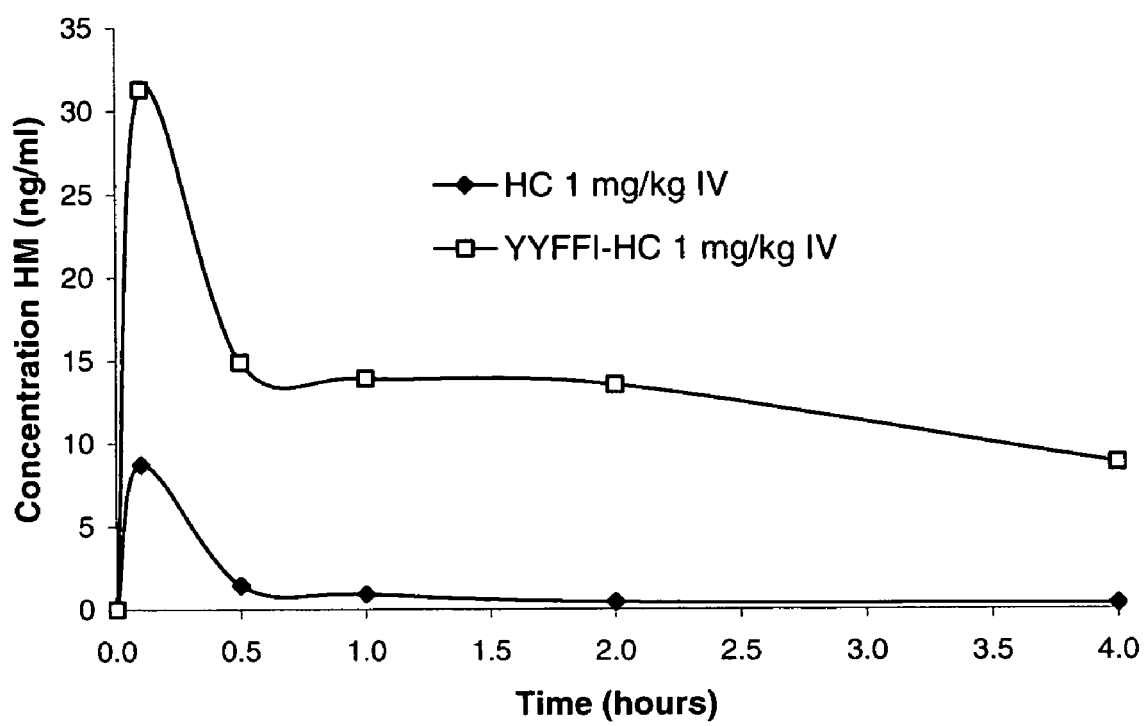

FIG. 147. Intravenous bioavailability of hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 148:
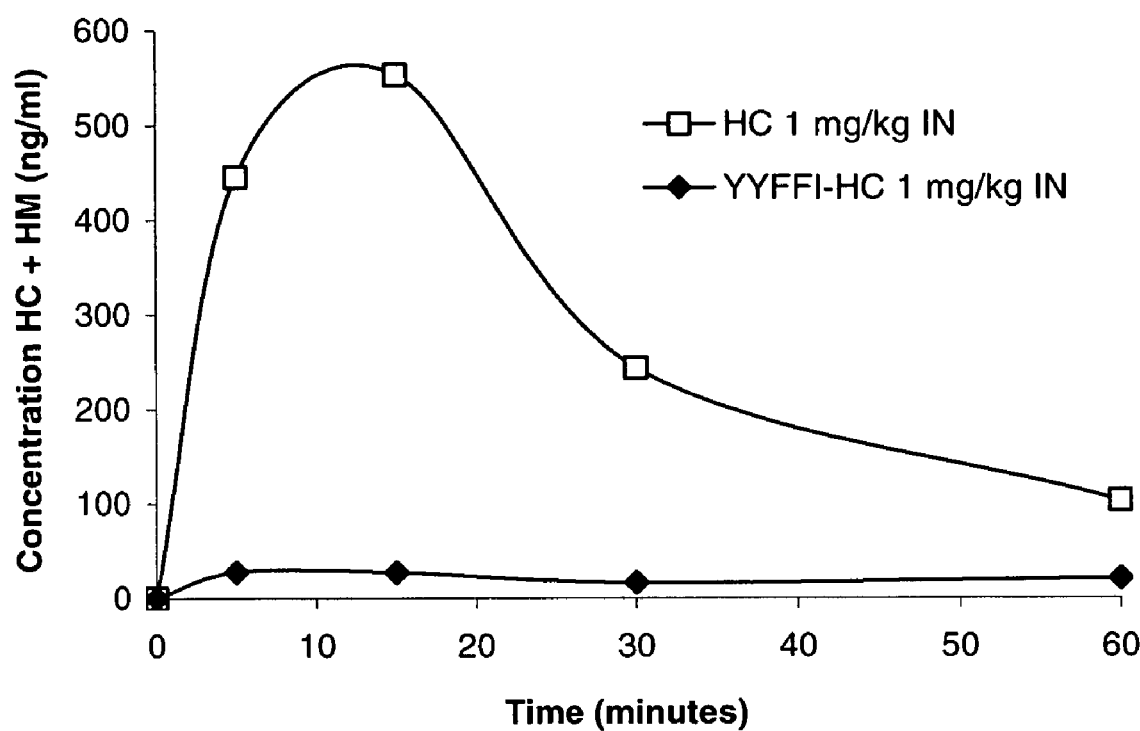

FIG. 148. Intranasal bioavailability of hydrocodone plus hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 149:
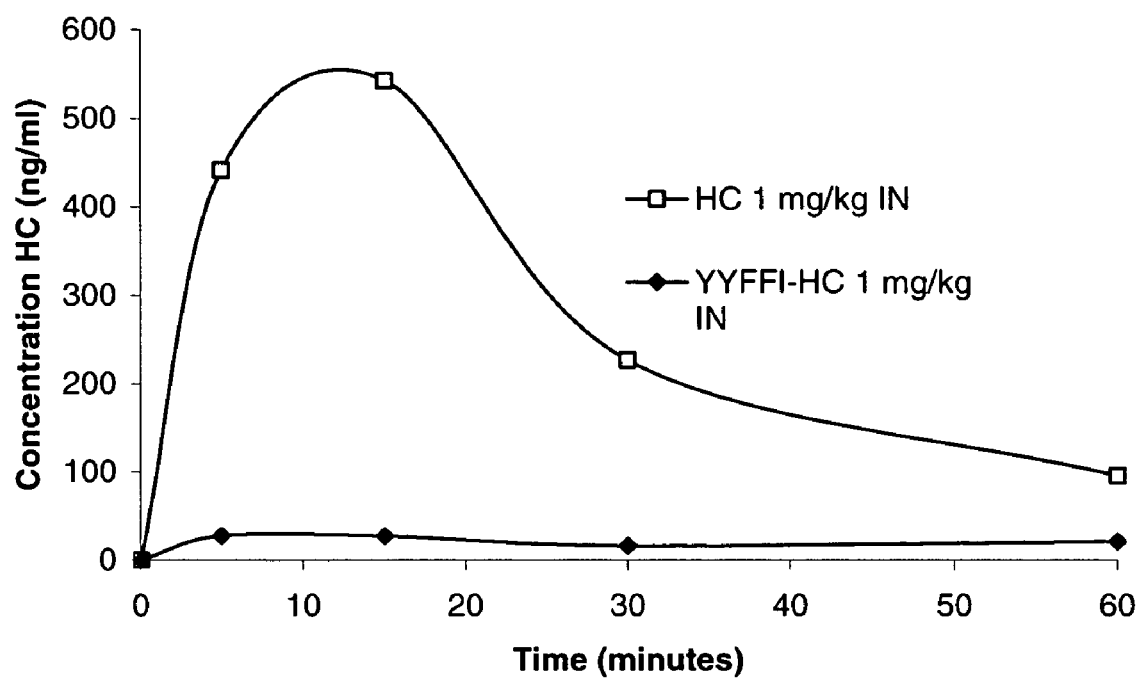

FIG. 149. Intranasal bioavailability of hydrocodone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 150:
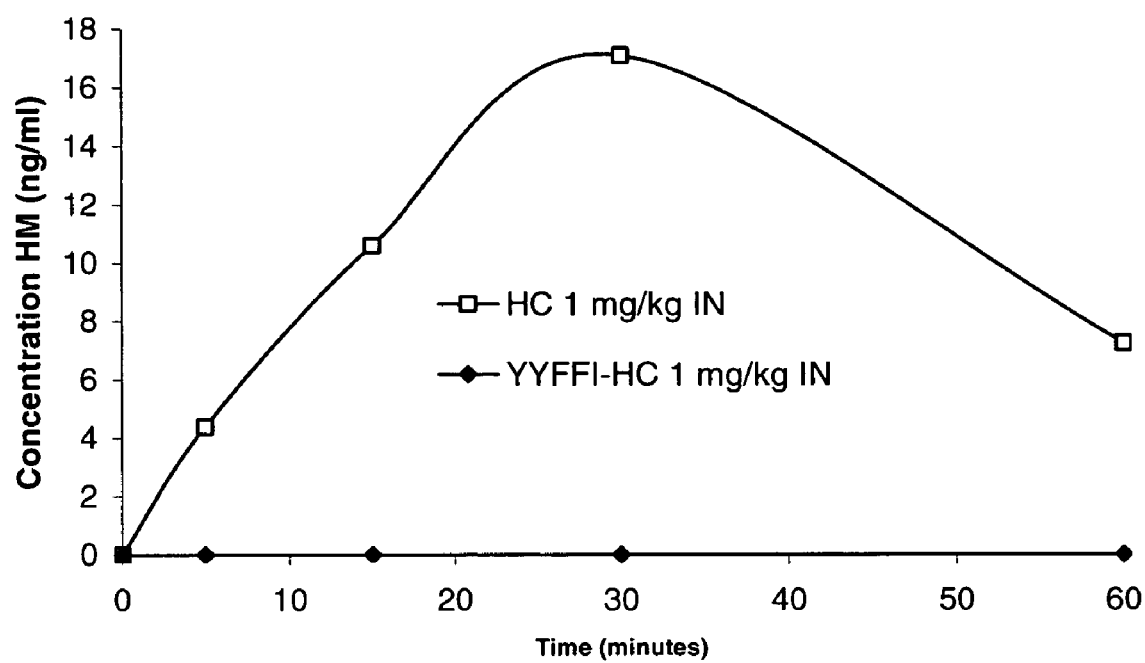

FIG. 150. Intranasal bioavailability of hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.

Figure 151:
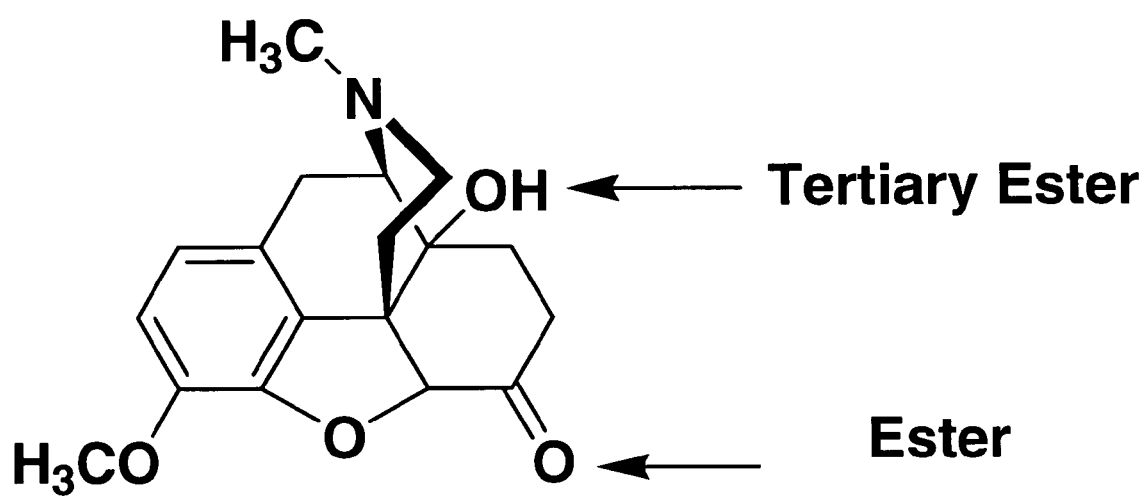

FIG. 151. depicts oxycodone.

Figure 152:
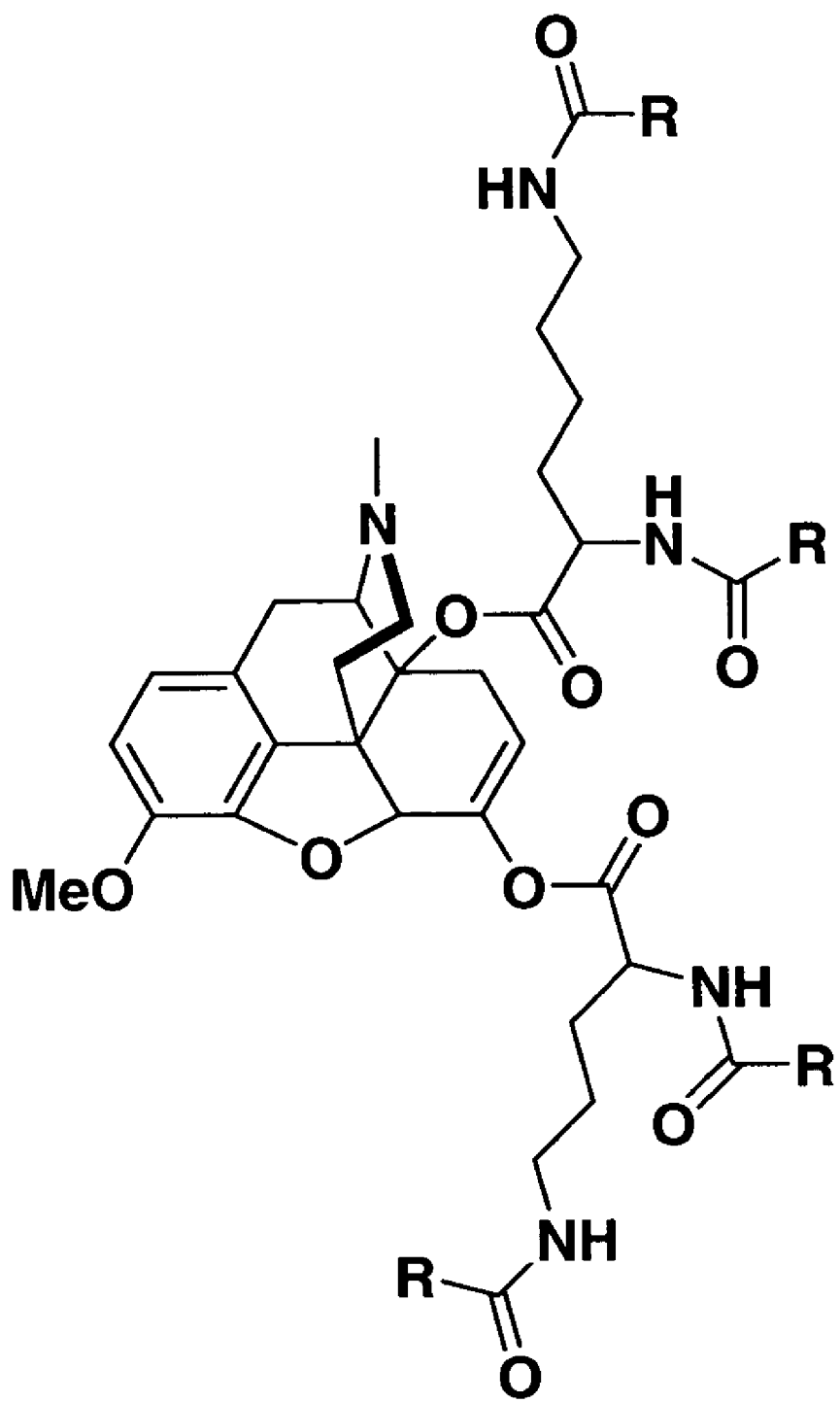

FIG. 152. depicts oxycodone with lysine branched peptides.

Figure 153:
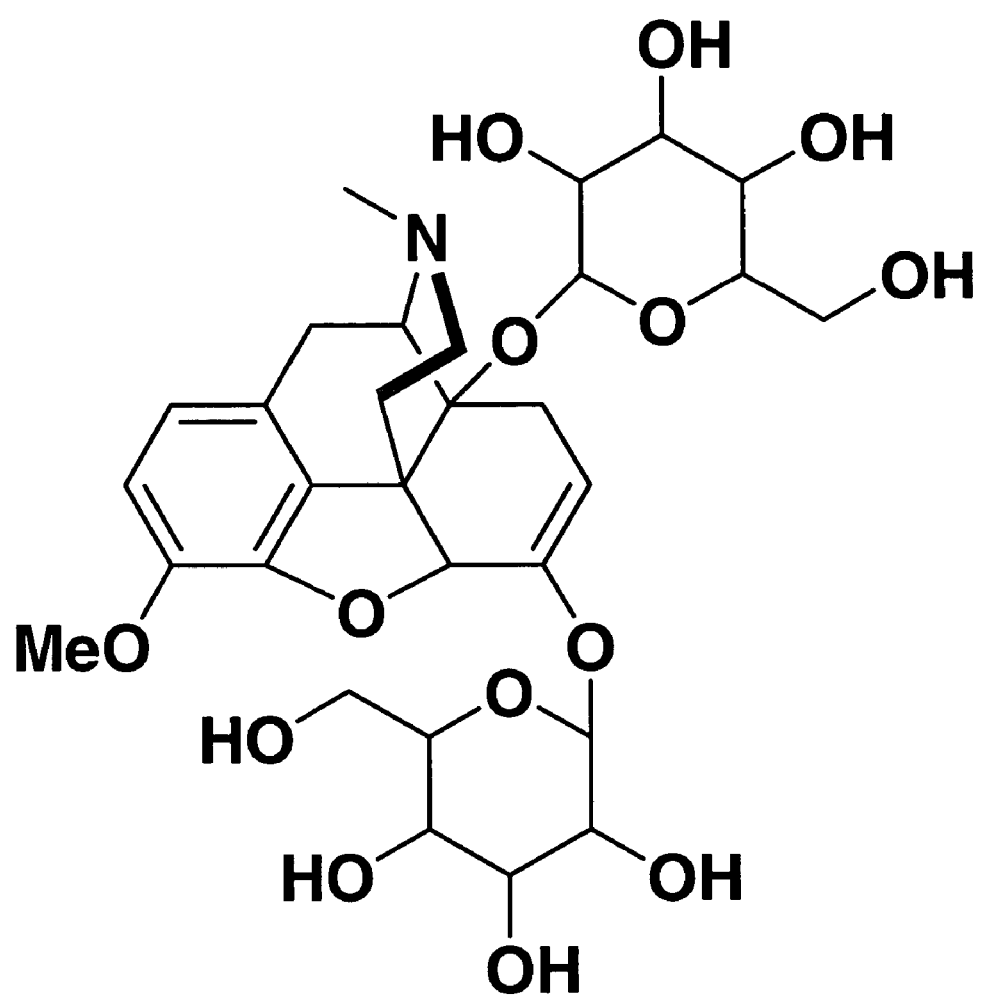

FIG. 153. depicts a glycosylated oxycodone.

Figure 154:
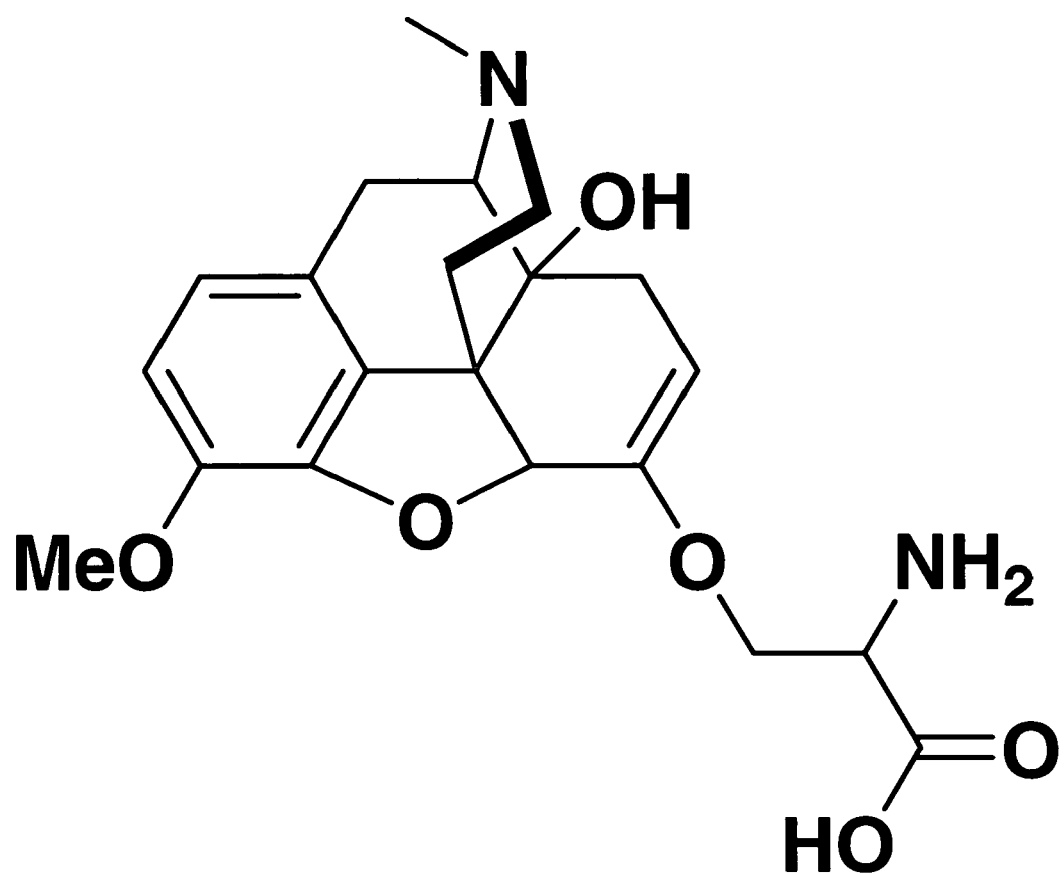

FIG. 154. depicts formation of an enol ether with serine.

Figure 155:
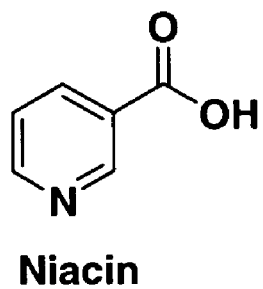
Figure 155:
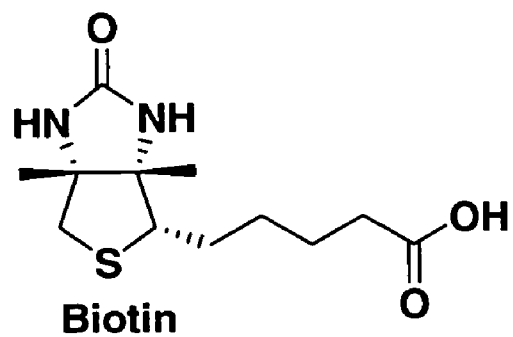

FIG. 155. depicts niacin and biotin.

Figure 156:
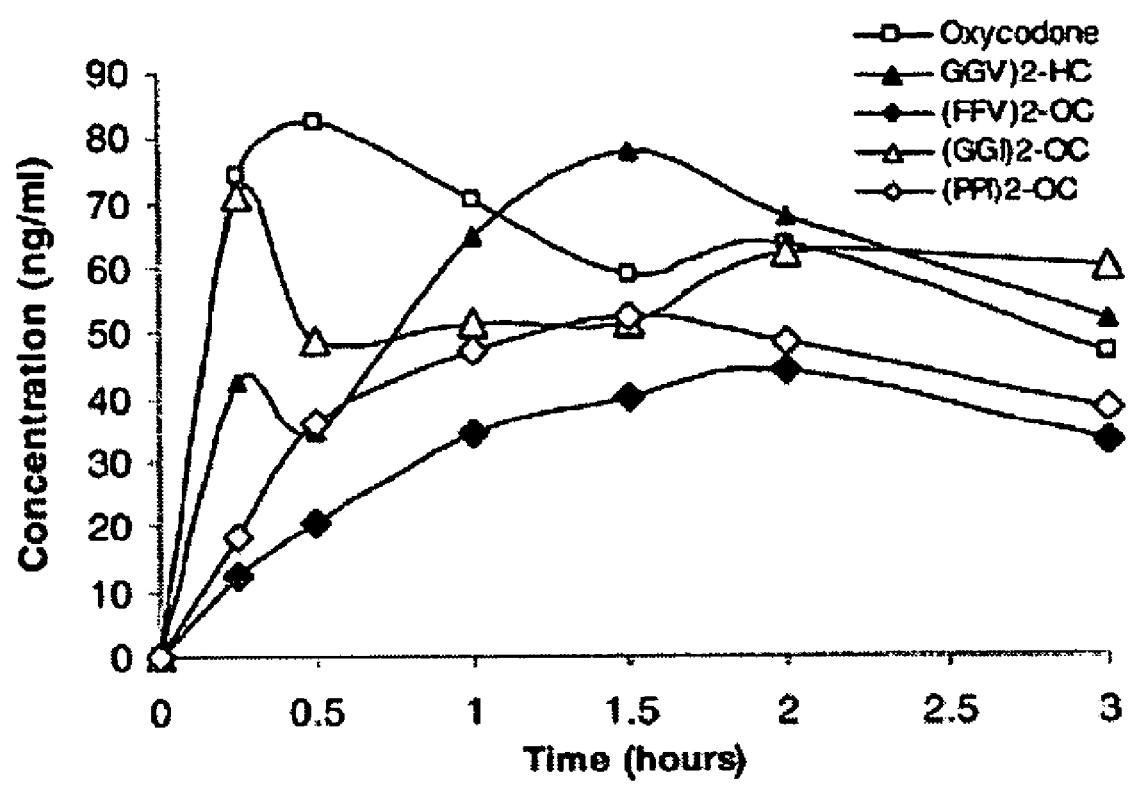

FIG. 156. Oral bioavailability of abuse-resistant oxycodone disubstituted tripeptide conjugates, measured as free oxycodone.

Figure 157:
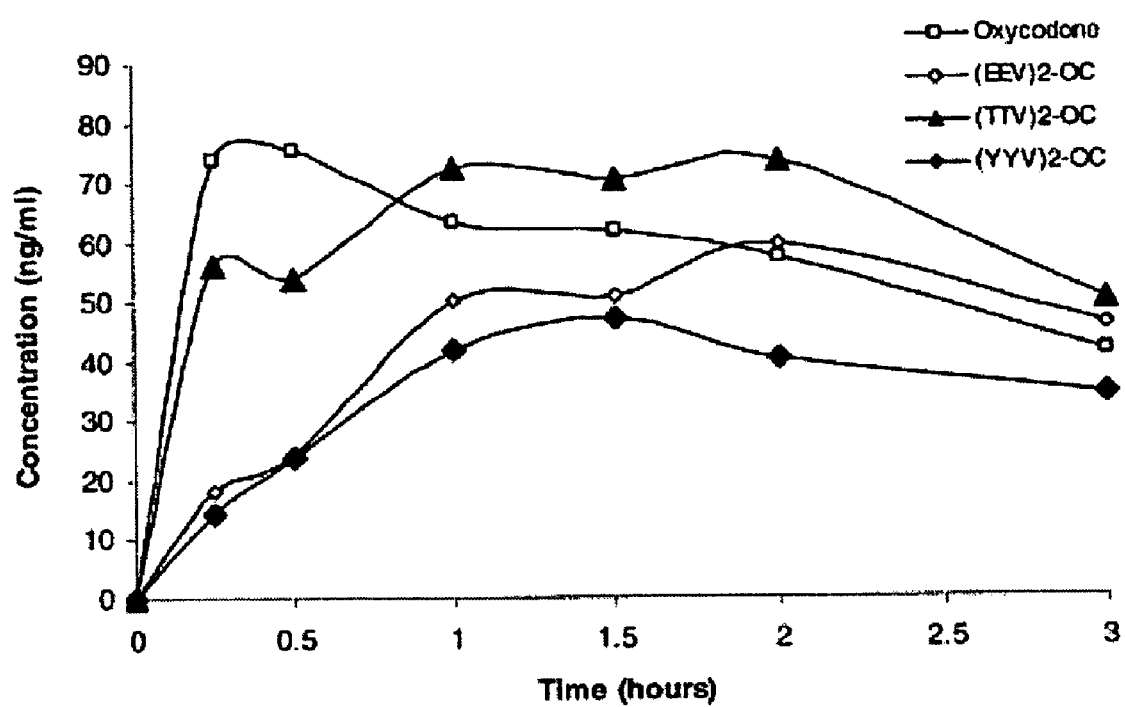

FIG. 157. Oral bioavailability of abuse-resistant oxycodone disubstituted tripeptide conjugates, measured as free oxycodone.

Figure 158:
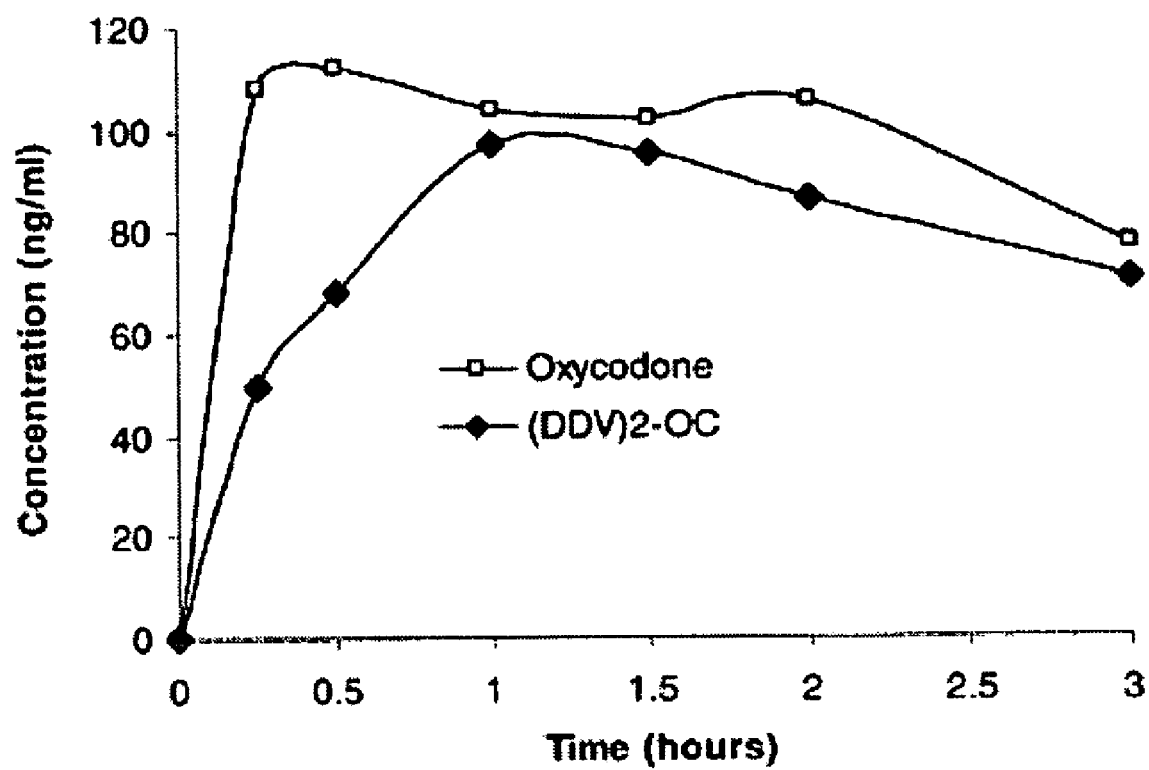

FIG. 158. Oral bioavailability of abuse-resistant oxycodone disubstituted tripeptide conjugates, measured as free oxycodone.

Figure 159:
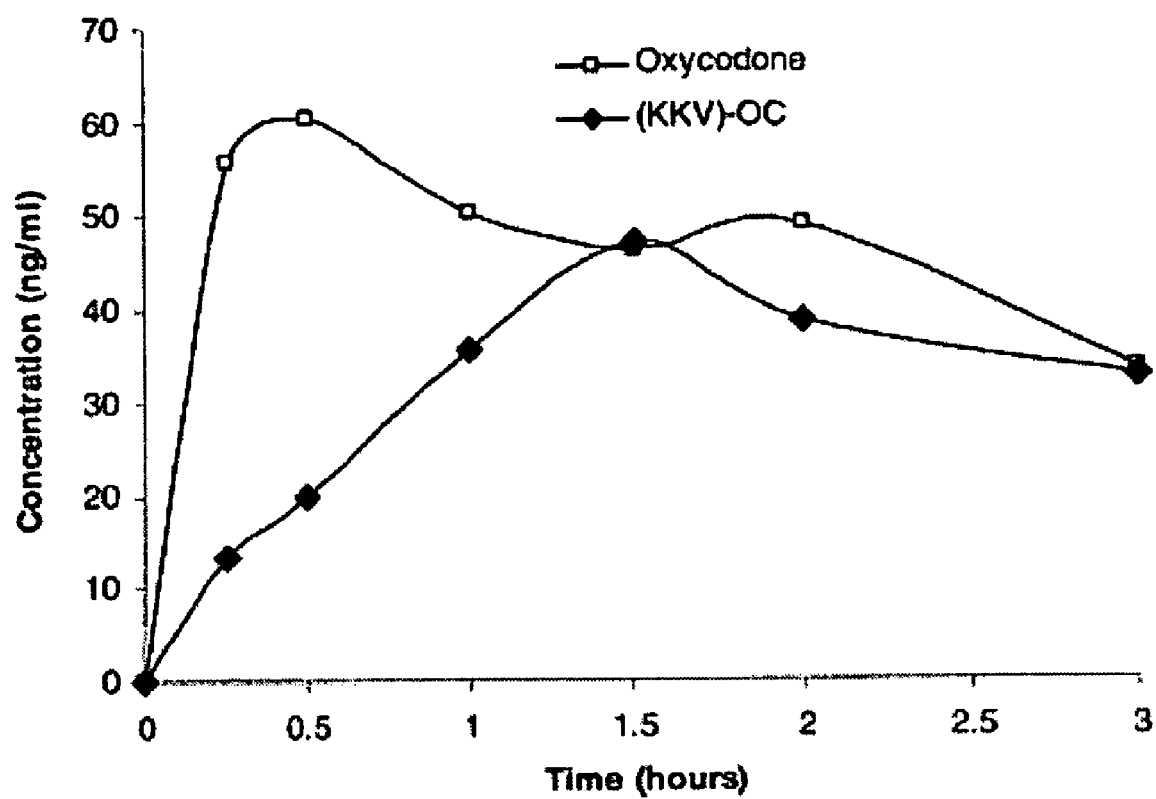

FIG. 159. Oral bioavailability of abuse-resistant oxycodone disubstituted tripeptide conjugates, measured as free oxycodone.

Figure 160:
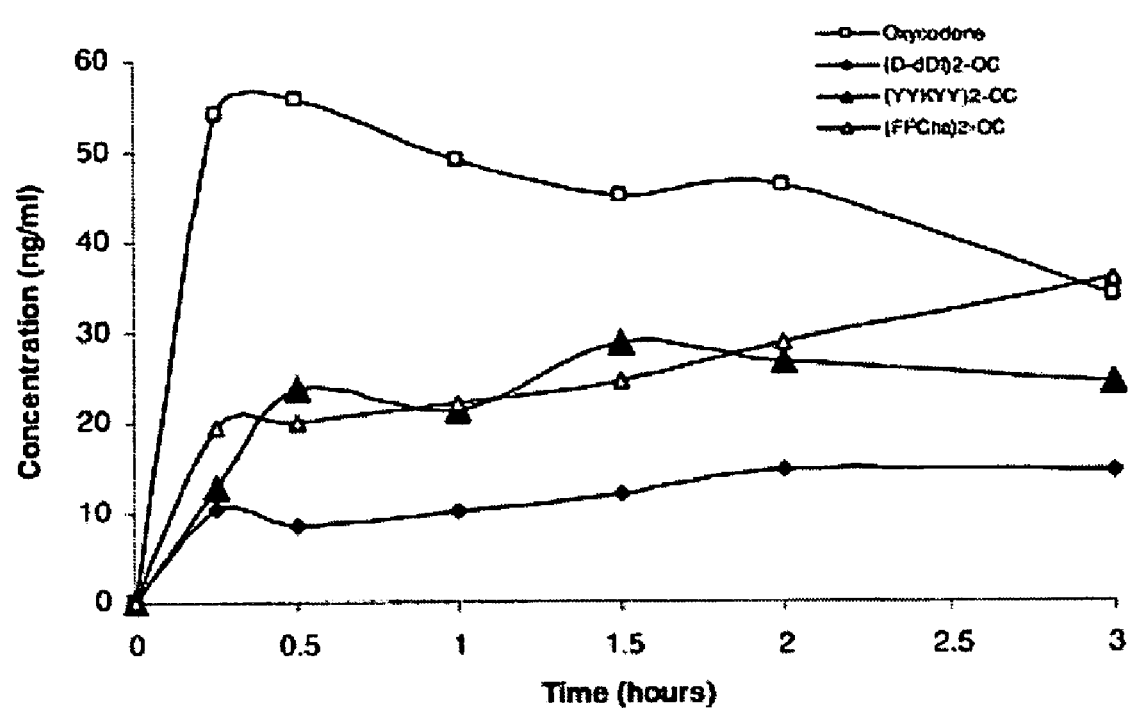

FIG. 160. Oral bioavailability of abuse-resistant oxycodone disubstituted tripeptide conjugates, measured as free oxycodone.

Figure 161:
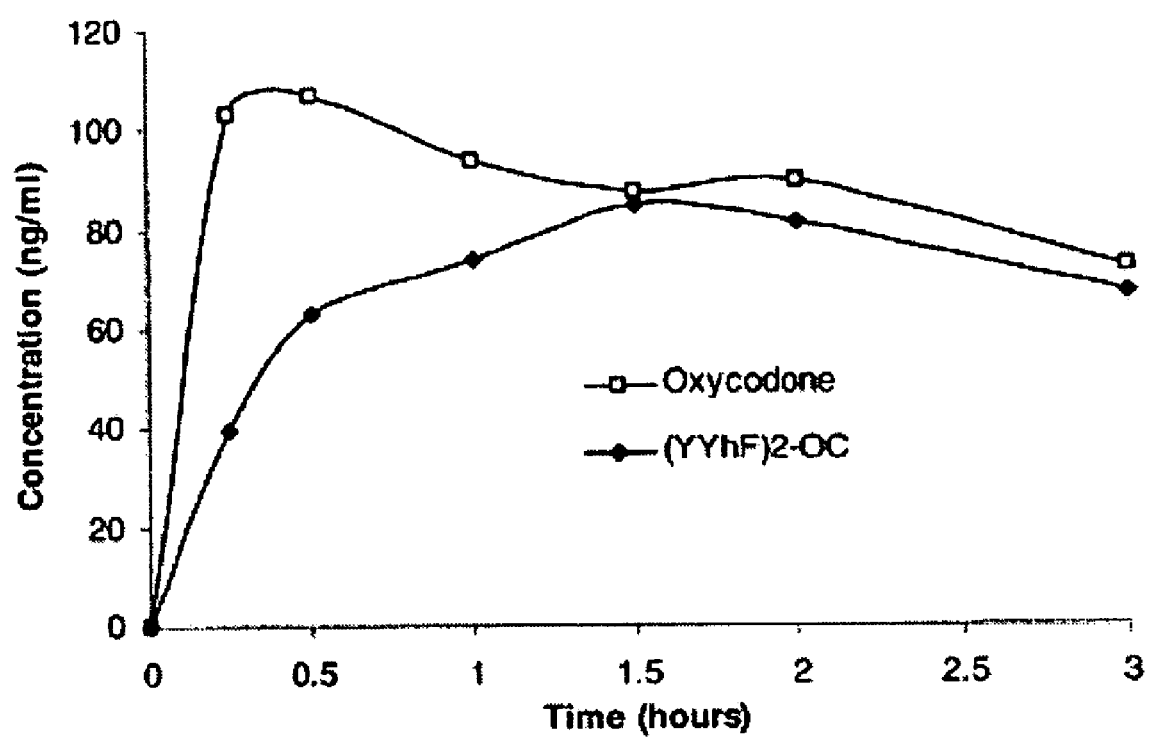

FIG. 161. Oral bioavailability of abuse-resistant oxycodone disubstituted tripeptide conjugates, measured as free oxycodone.

Figure 162:
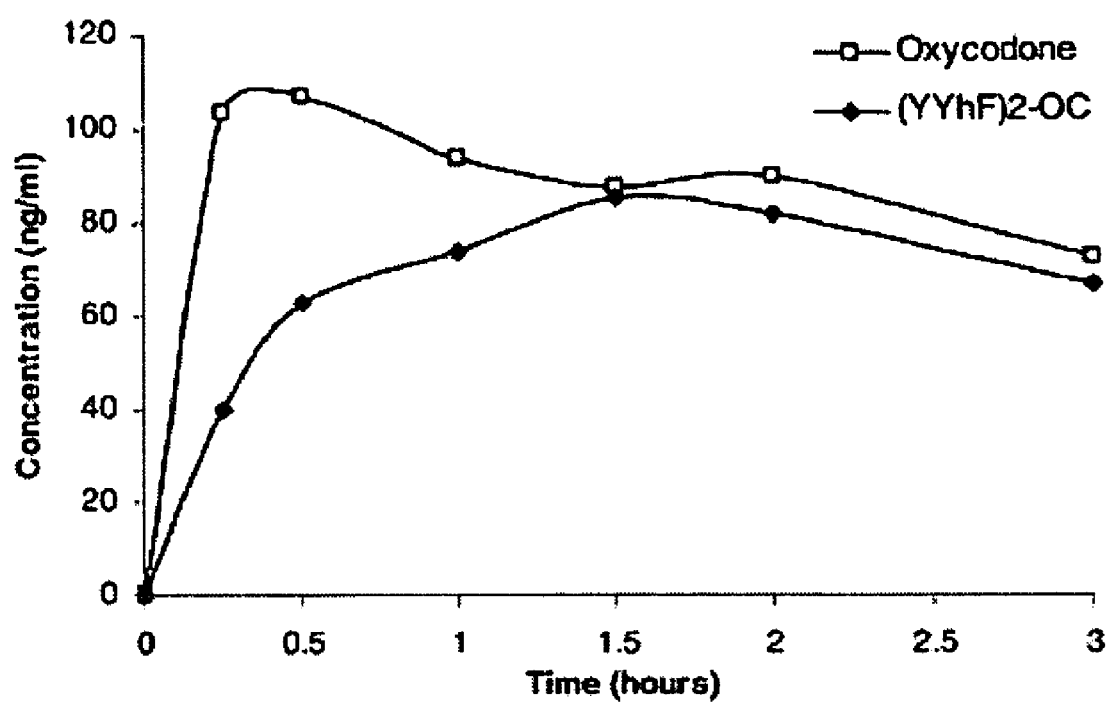

FIG. 162. Oral bioavailability of abuse-resistant oxycodone disubstituted tripeptide conjugates, measured as free oxycodone.

Figure 163:
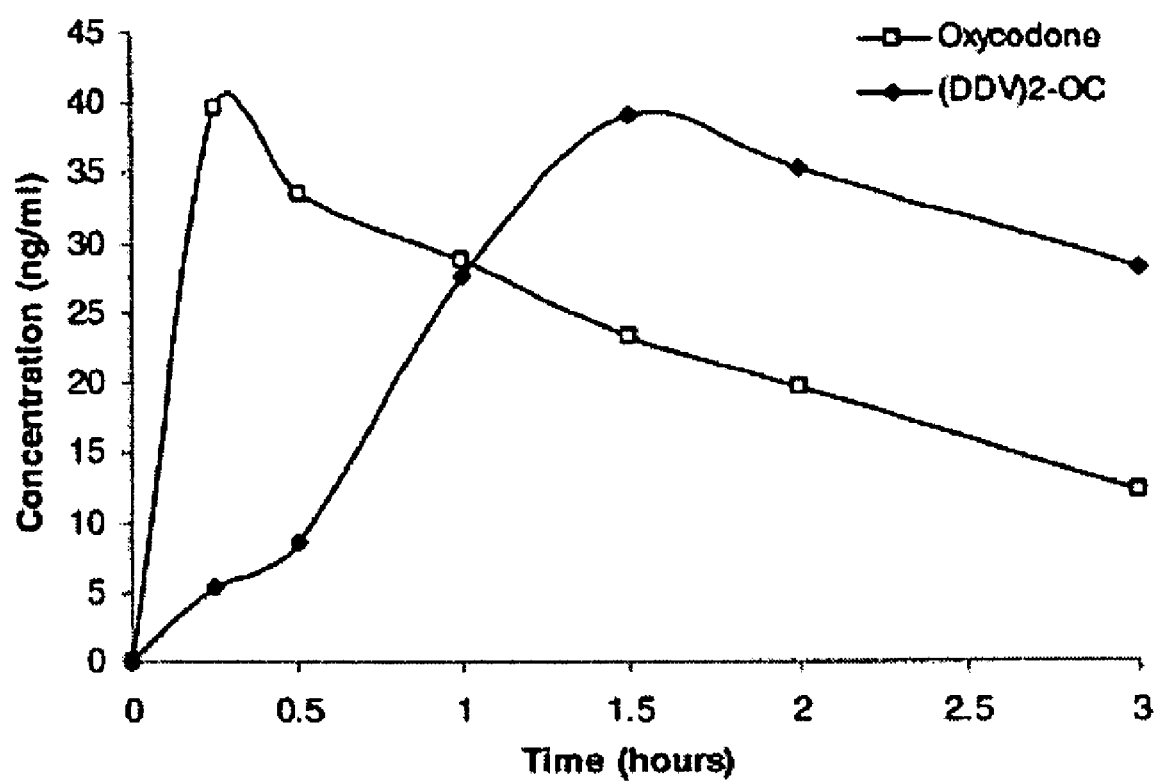

FIG. 163. Oral bioavailability of abuse-resistant oxycodone disubstituted tripeptide conjugates, measured as free oxycodone.

Figure 164:
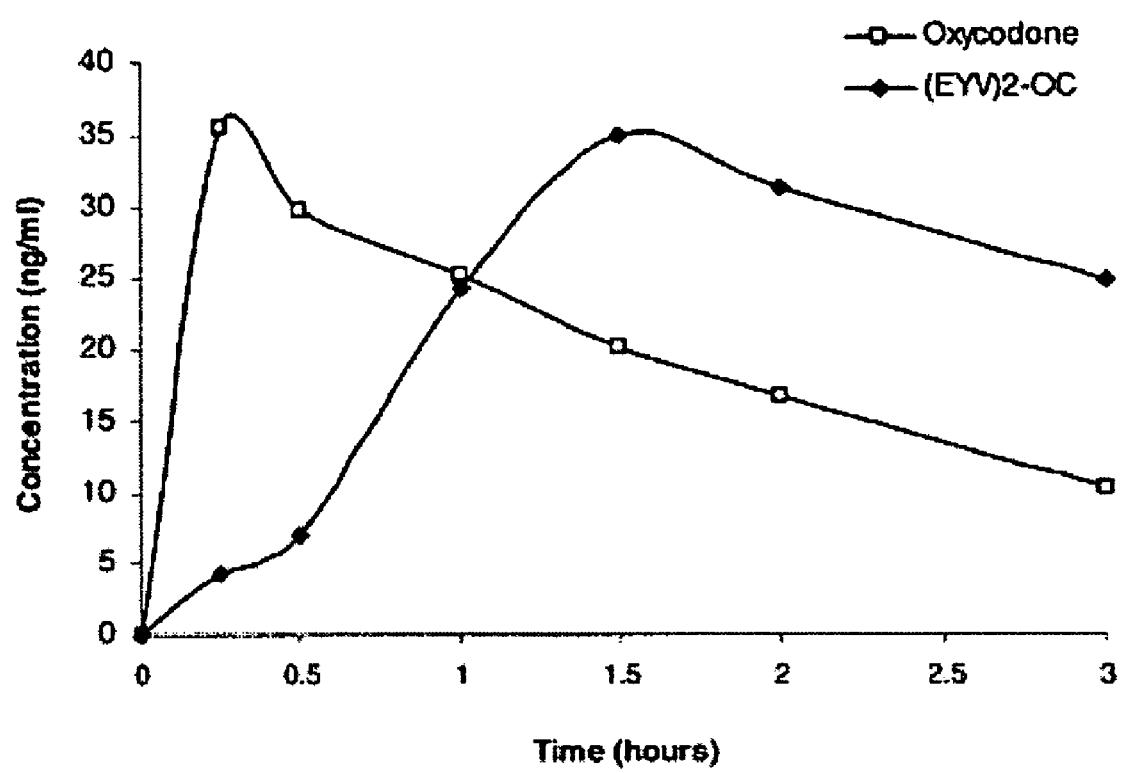

FIG. 164. Oral bioavailability of abuse-resistant oxycodone disubstituted tripeptide conjugates, measured as free oxycodone.

Figure 165:
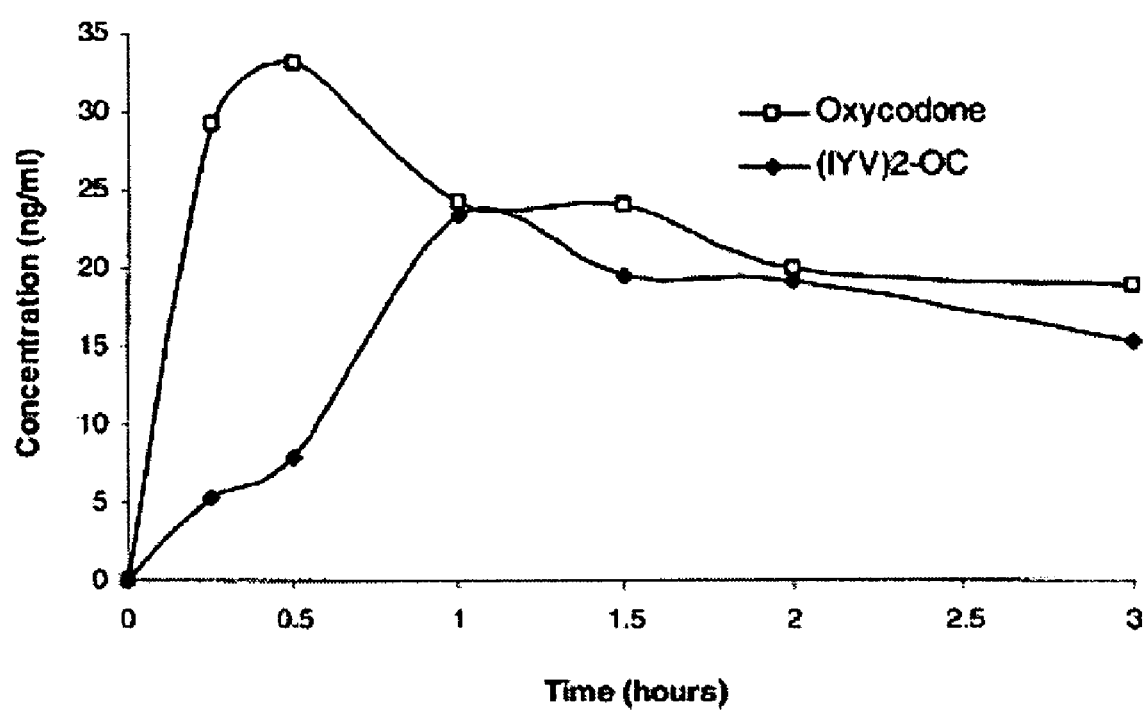

FIG. 165. Oral bioavailability of abuse-resistant oxycodone disubstituted tripeptide conjugates, measured as free oxycodone.

Figure 166:
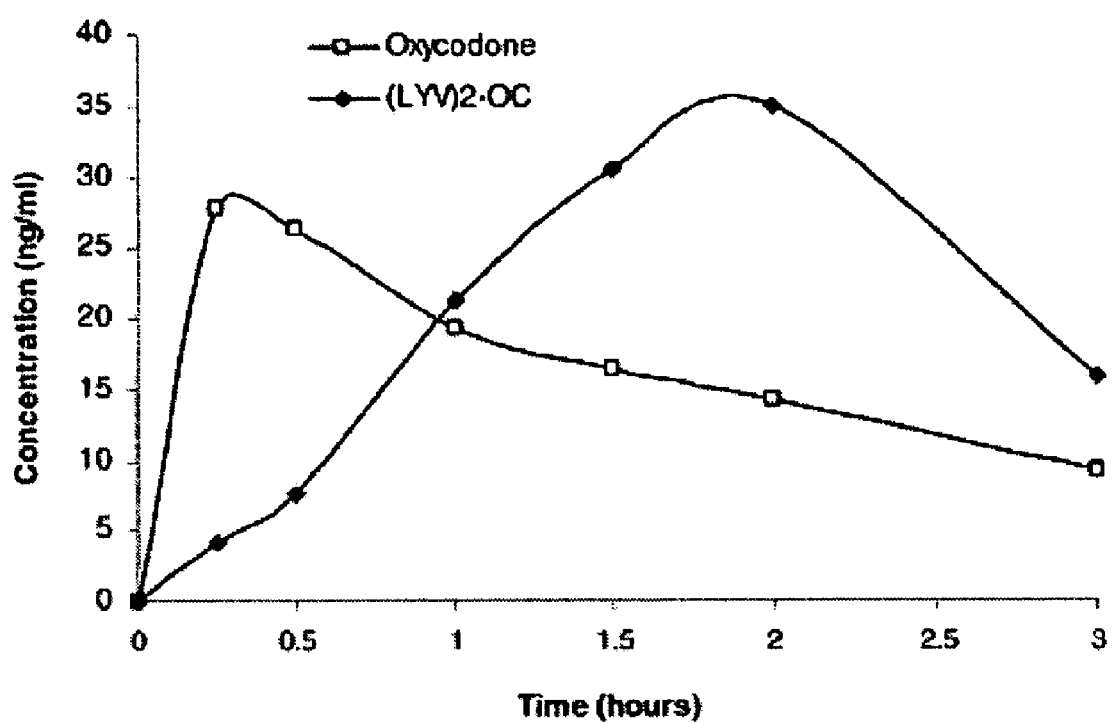

FIG. 166. Oral bioavailability of abuse-resistant oxycodone disubstituted tripeptide conjugates, measured as free oxycodone.

Figure 167:
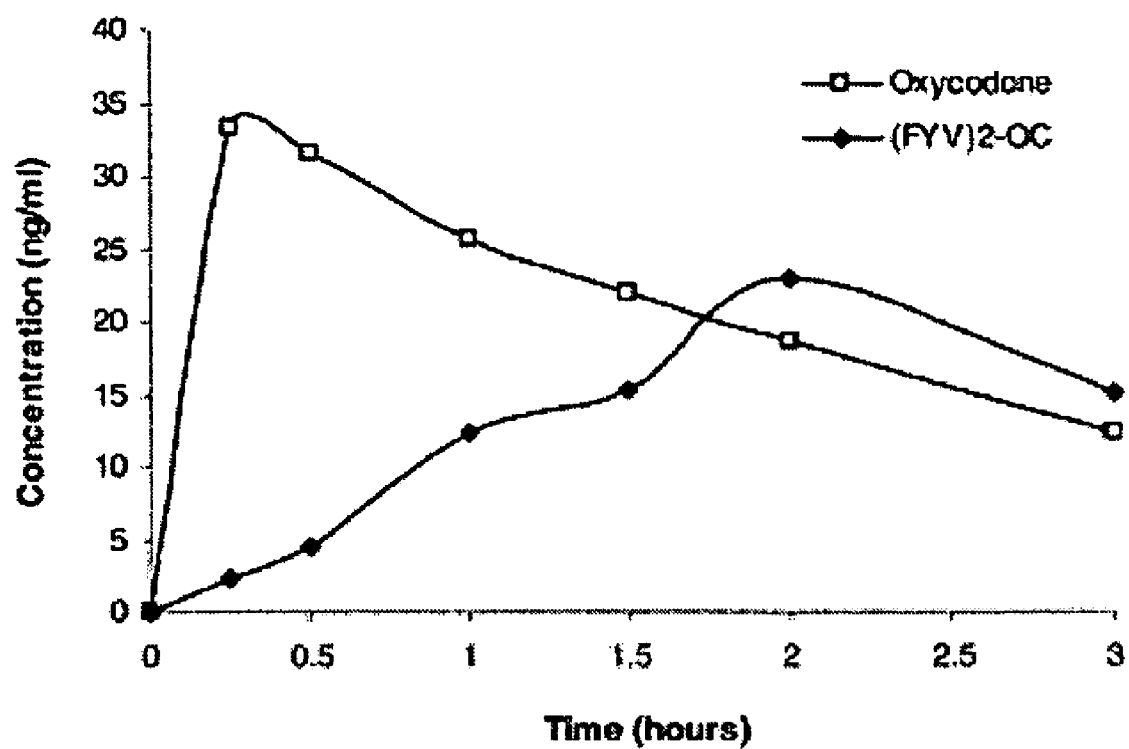

FIG. 167. Oral bioavailability of abuse-resistant oxycodone disubstituted tripeptide conjugates, measured as free oxycodone.

Figure 168:
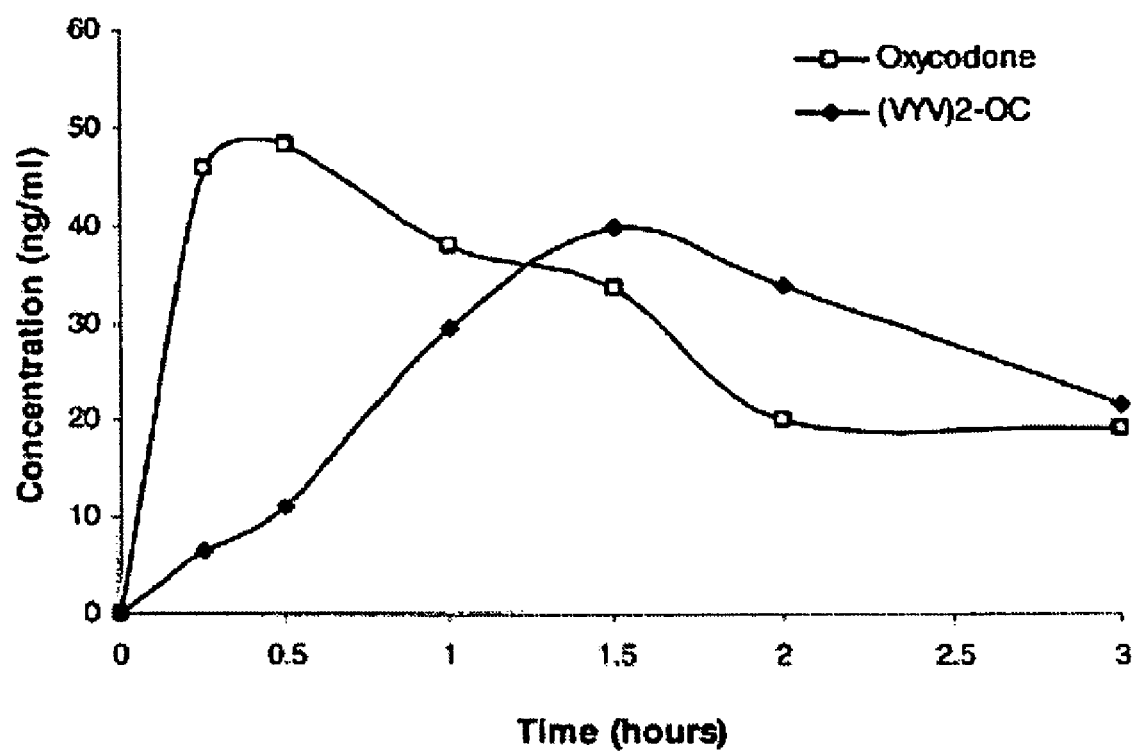

FIG. 168. Oral bioavailability of abuse-resistant oxycodone disubstituted tripeptide conjugates, measured as free oxycodone.

Figure 169:
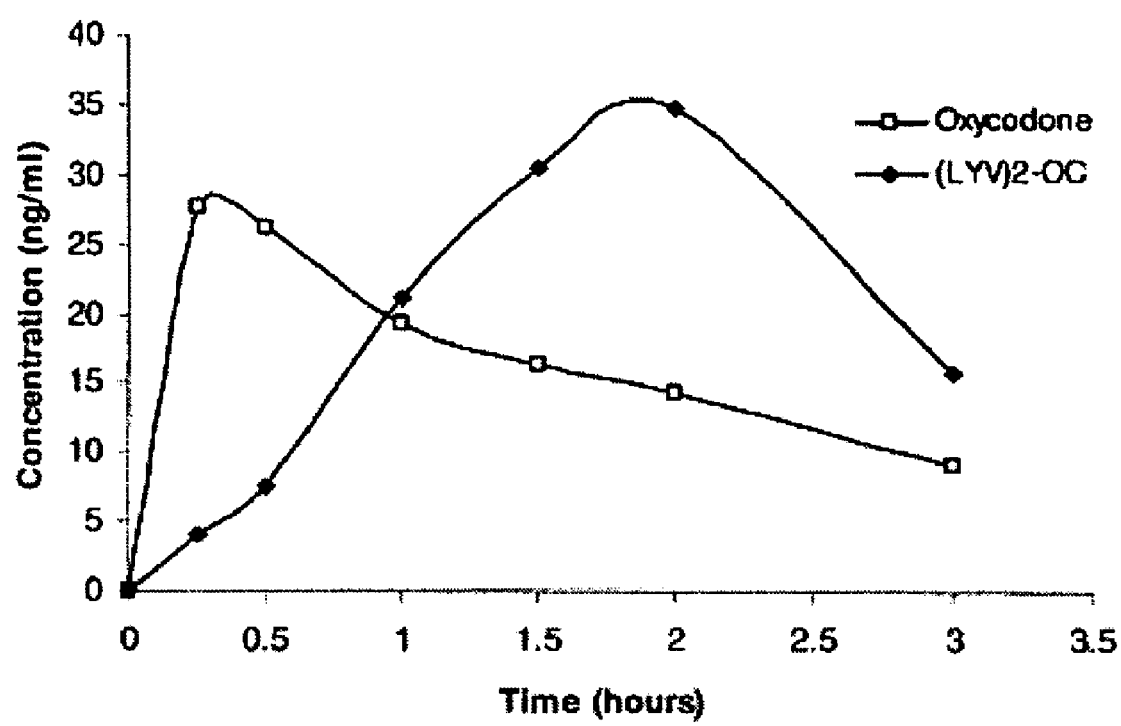

FIG. 169. Oral bioavailability of abuse-resistant oxycodone disubstituted tripeptide conjugates, measured as free oxycodone.

Figure 170:
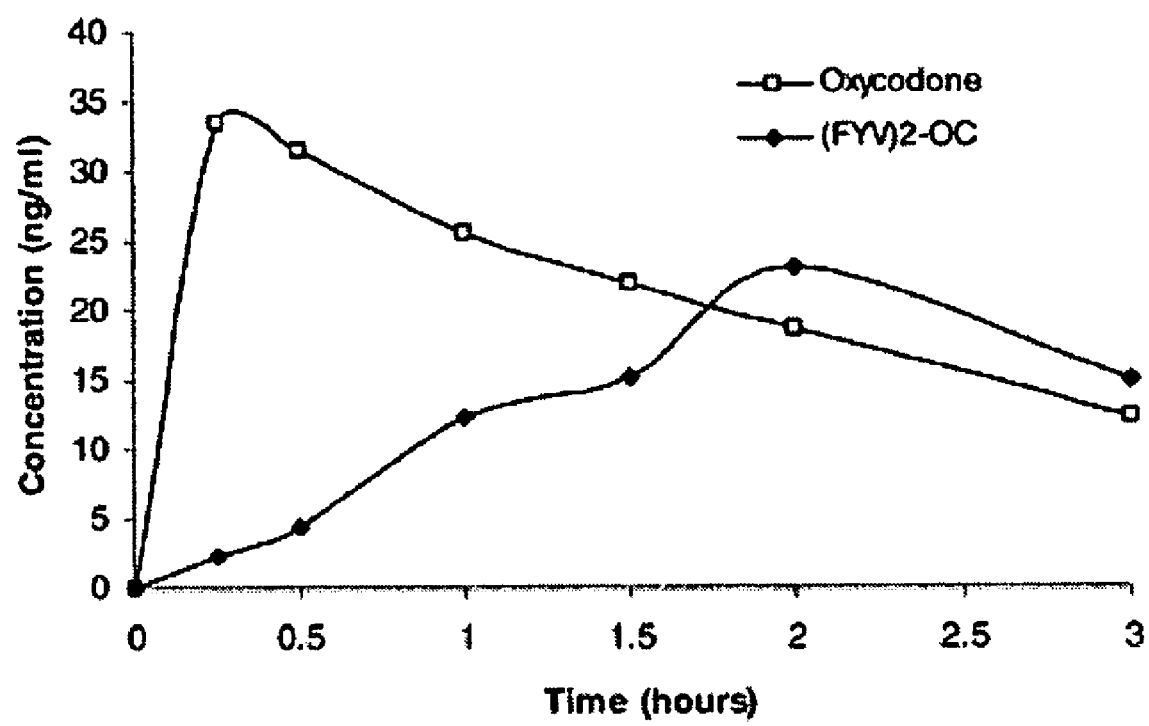

FIG. 170. Oral bioavailability of abuse-resistant oxycodone disubstituted tripeptide conjugates, measured as free oxycodone.

Figure 171:
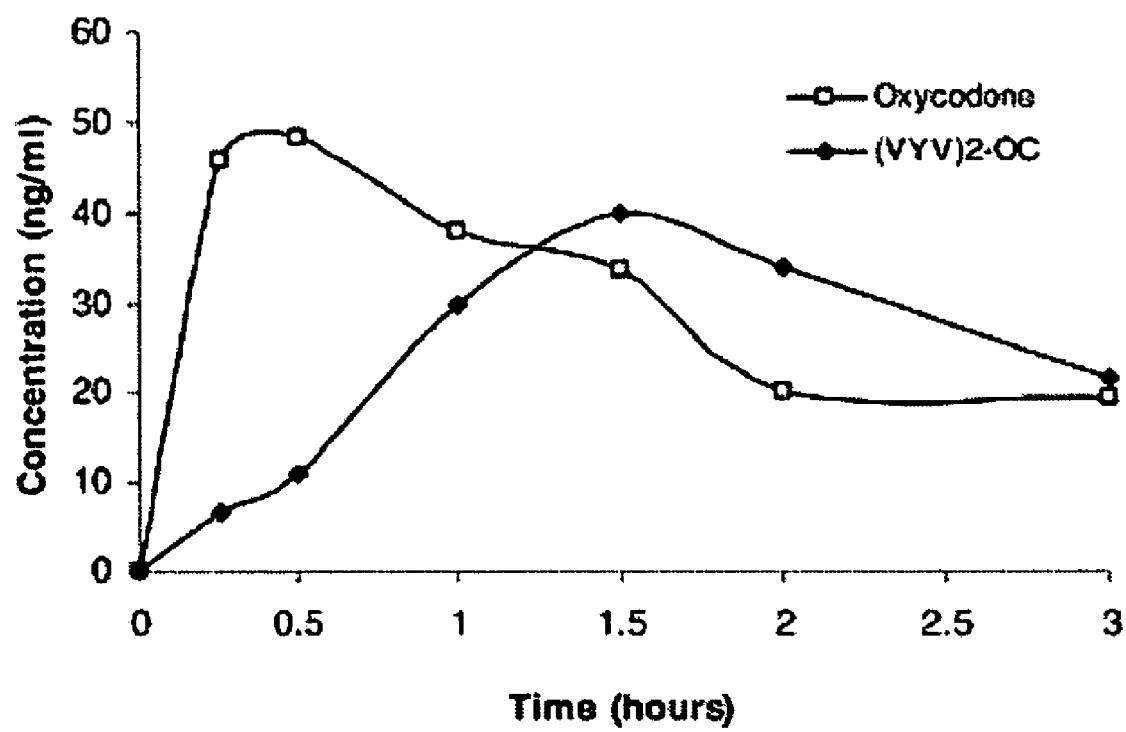

FIG. 171. Oral bioavailability of abuse-resistant oxycodone disubstituted tripeptide conjugates, measured as free oxycodone.

Figure 172:
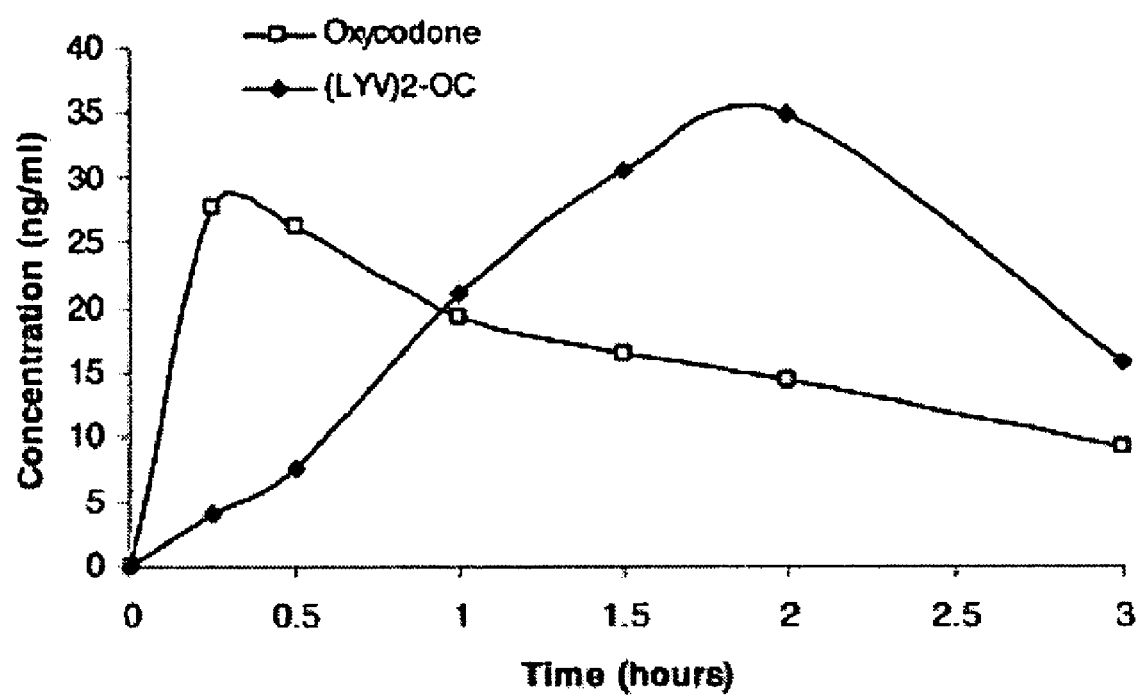

FIG. 172. Oral bioavailability of abuse-resistant oxycodone disubstituted tripeptide conjugates, measured as free oxycodone.

Figure 173:
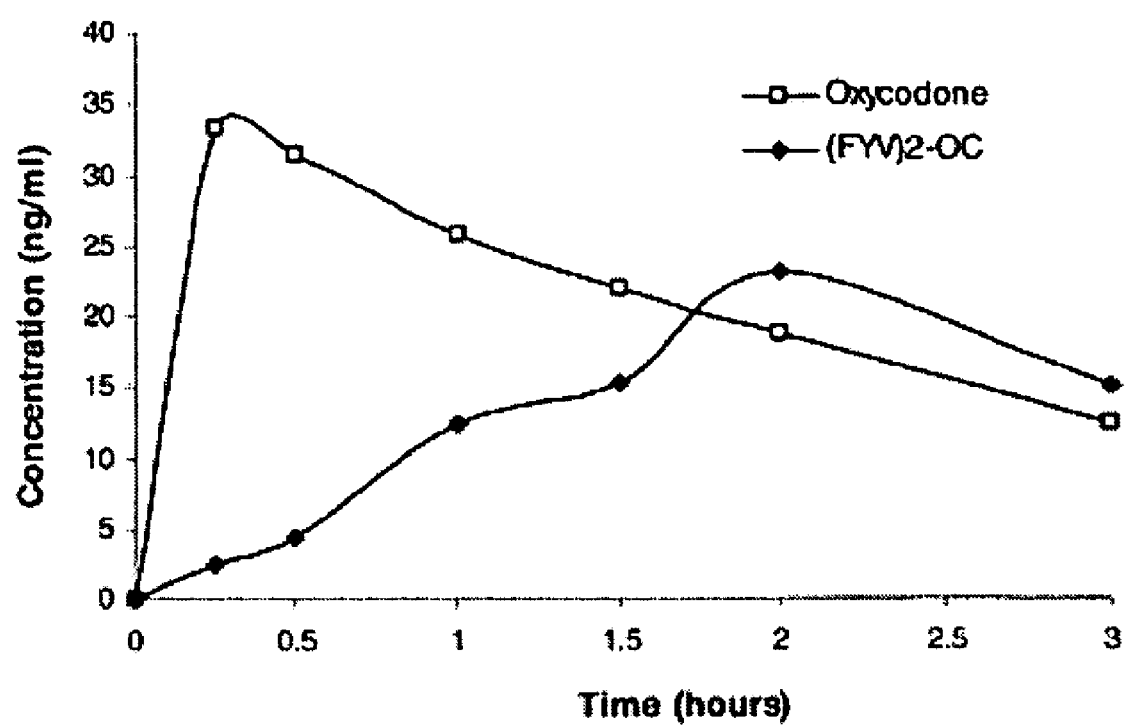

FIG. 173. Oral bioavailability of abuse-resistant oxycodone disubstituted tripeptide conjugates, measured as free oxycodone.

Figure 174:
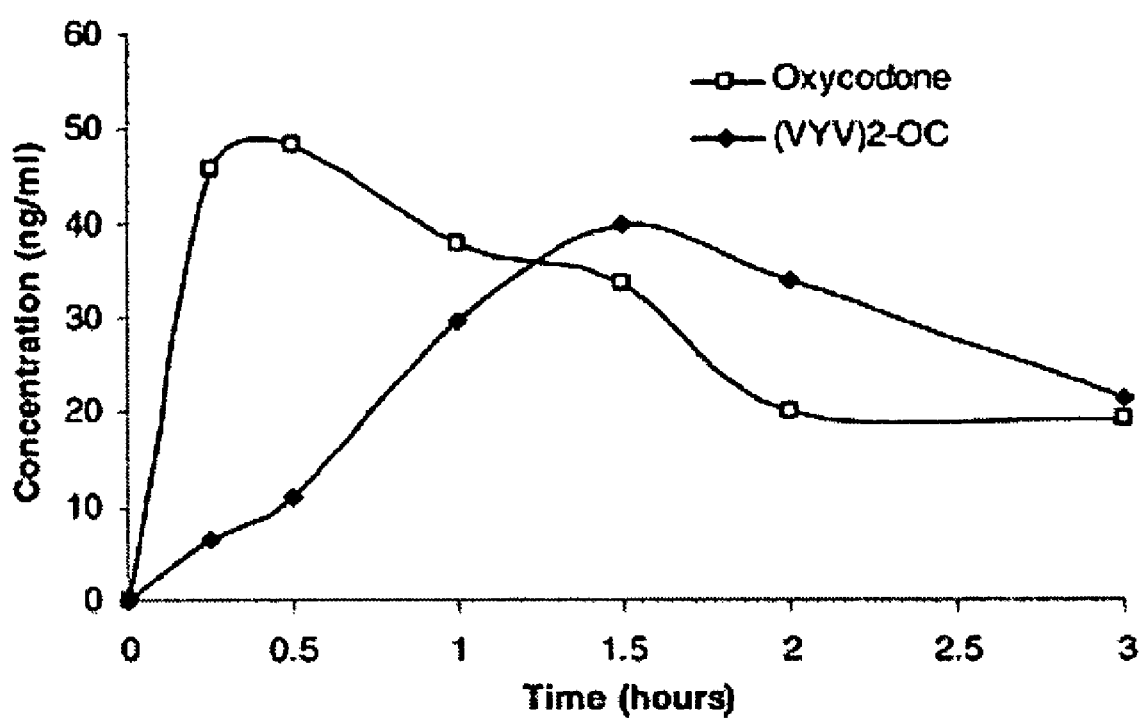

FIG. 174. Oral bioavailability of abuse-resistant oxycodone disubstituted-tripeptide conjugates, measured as free oxycodone.

Figure 175:
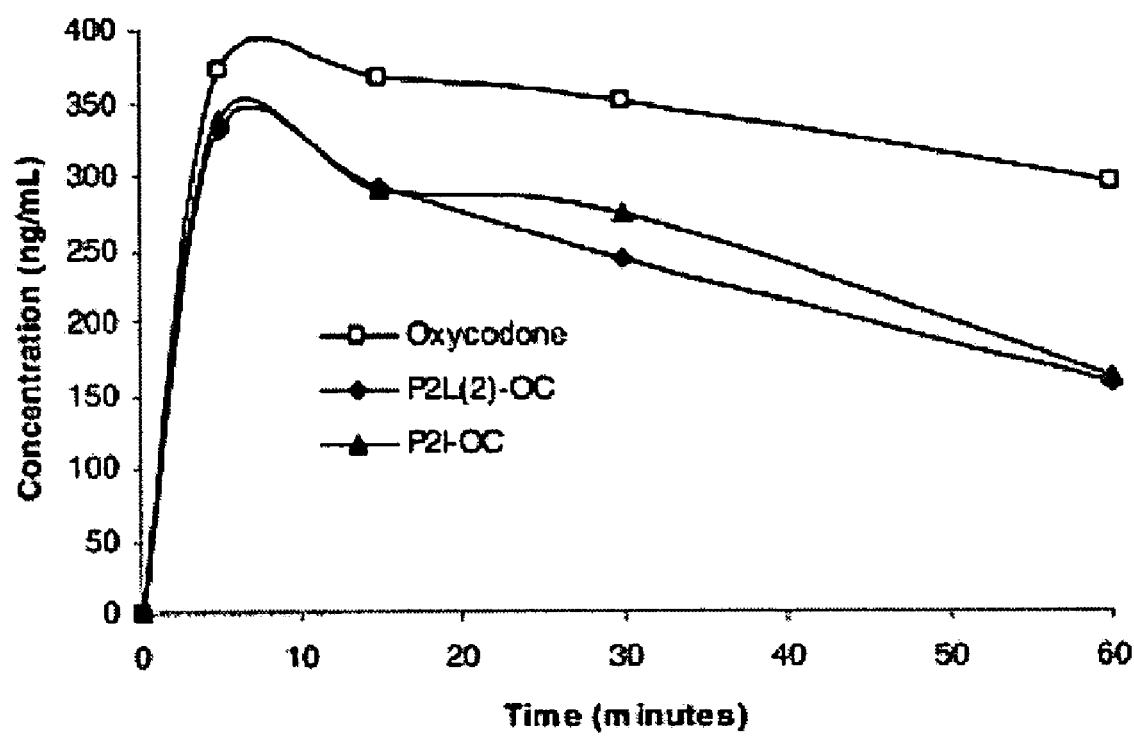

FIG. 175. Intranasal bioavailability of abuse-resistant oxycodone disubstituted tripeptide conjugates, measured as free oxycodone.

Figure 176:
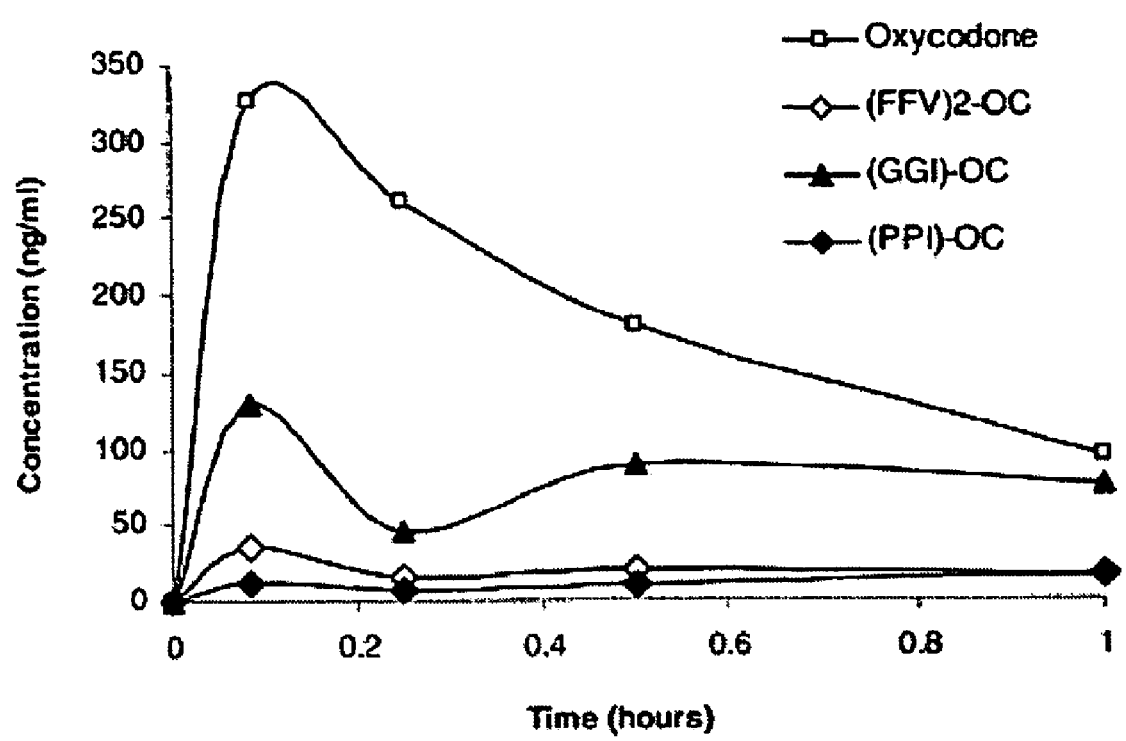

FIG. 176. Intranasal bioavailability of abuse-resistant oxycodone disubstituted tripeptide conjugates, measured as free oxycodone.

Figure 177:
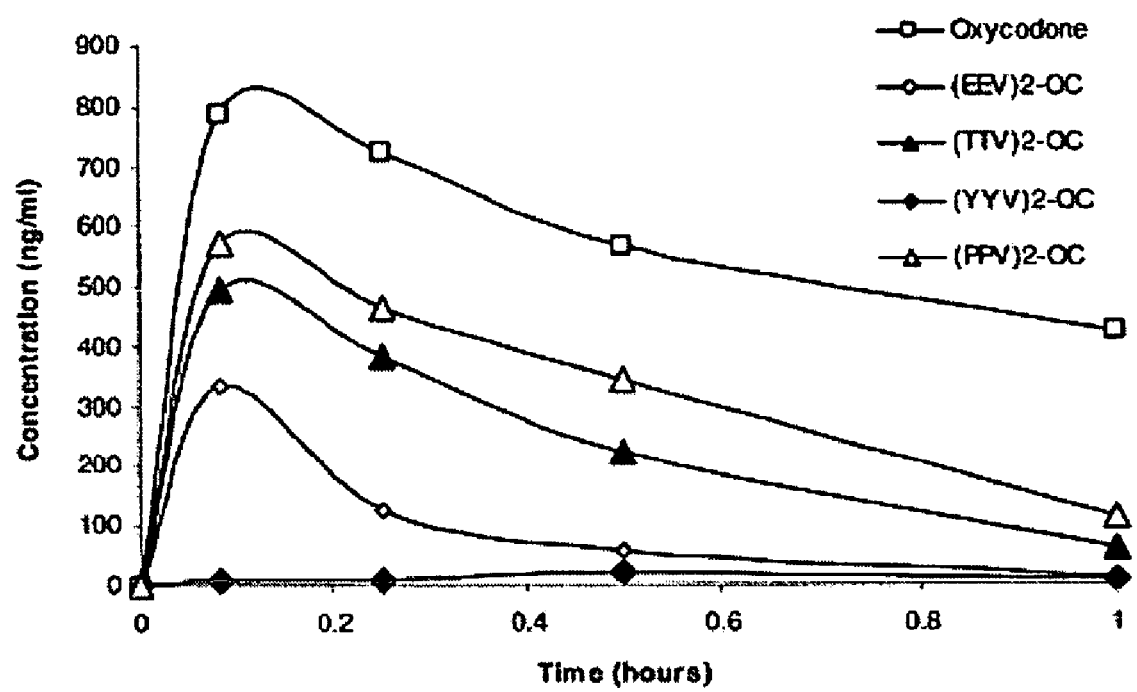

FIG. 177. Intranasal bioavailability of abuse-resistant oxycodone disubstituted tripeptide conjugates, measured as free oxycodone.

Figure 178:
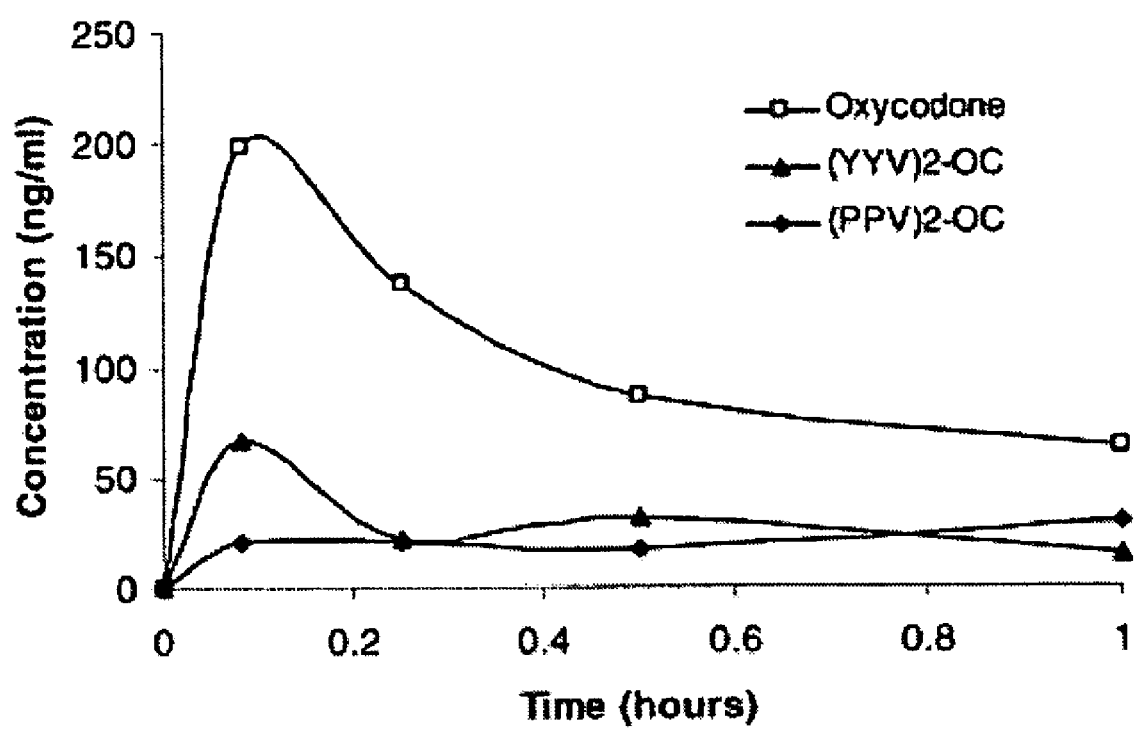

FIG. 178. Intravenous bioavailability of abuse-resistant oxycodone disubstituted tripeptide conjugates, measured as free oxycodone.

Figure 179:
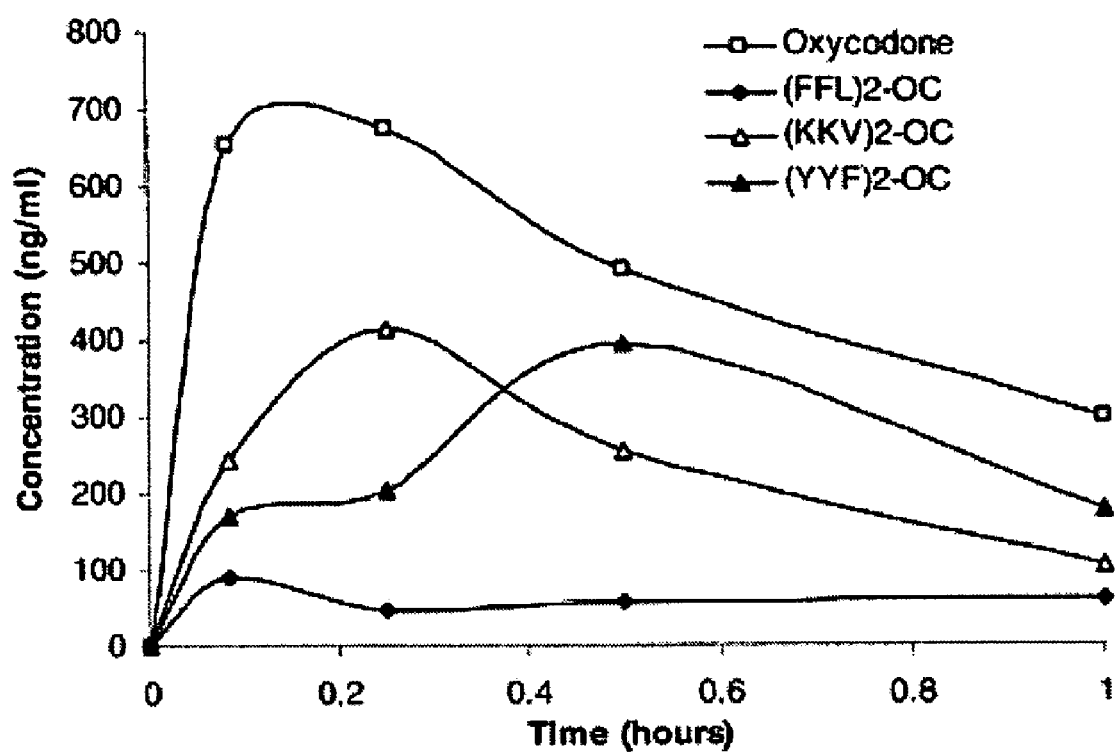

FIG. 179. Intranasal bioavailability of abuse-resistant oxycodone disubstituted tripeptide conjugates, measured as free oxycodone.

Figure 180:
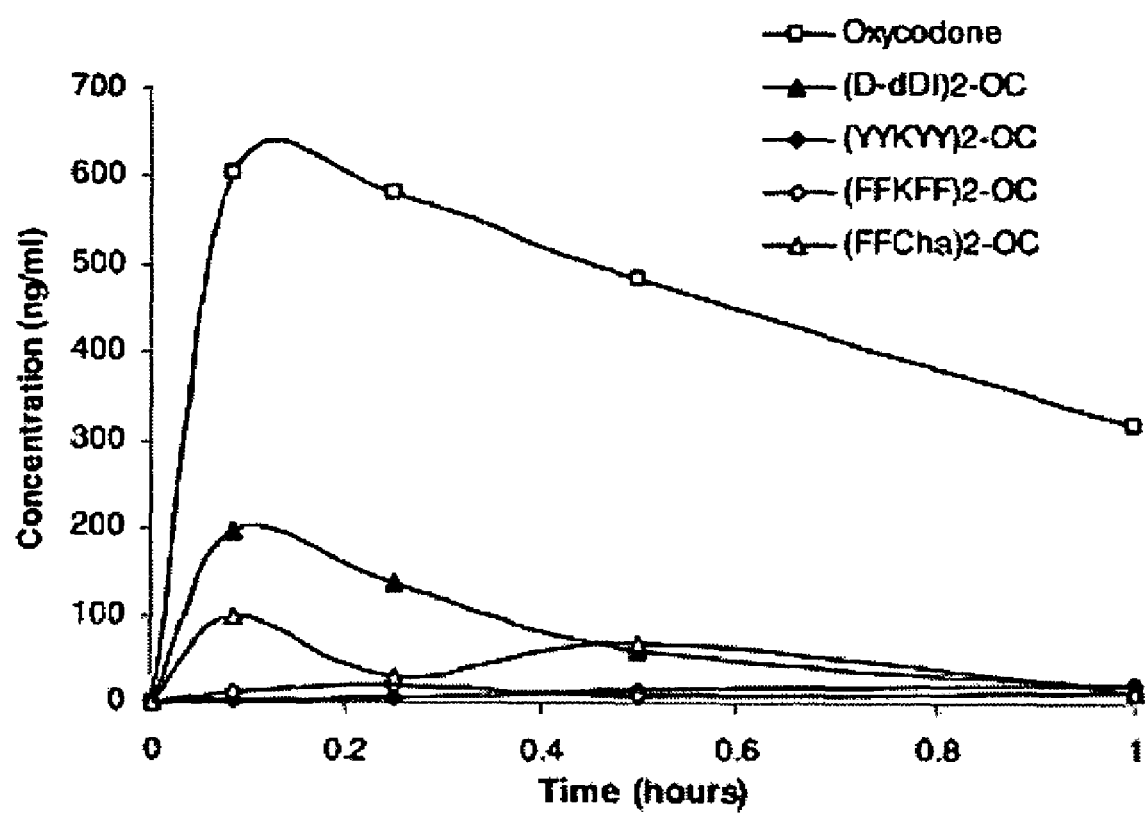

FIG. 180. Intranasal bioavailability of abuse-resistant oxycodone disubstituted tripeptide conjugates, measured as free oxycodone.

Figure 181:
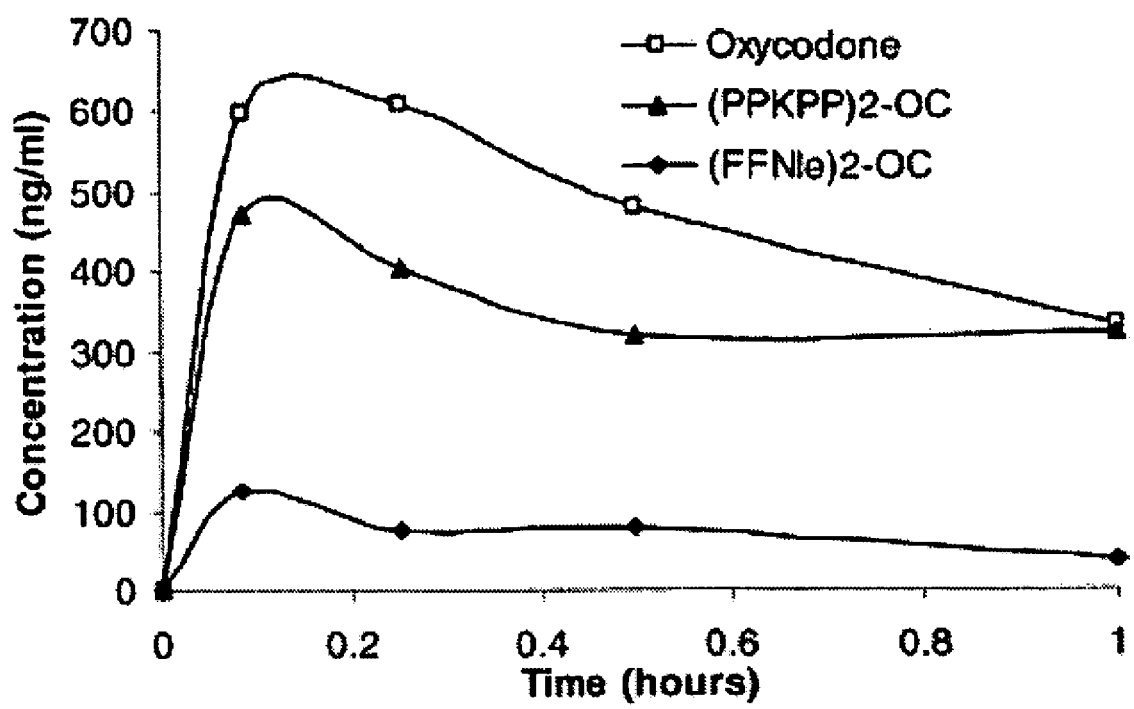

FIG. 181. Intranasal bioavailability of abuse-resistant oxycodone disubstituted tripeptide conjugates, measured as free oxycodone.

Figure 182:
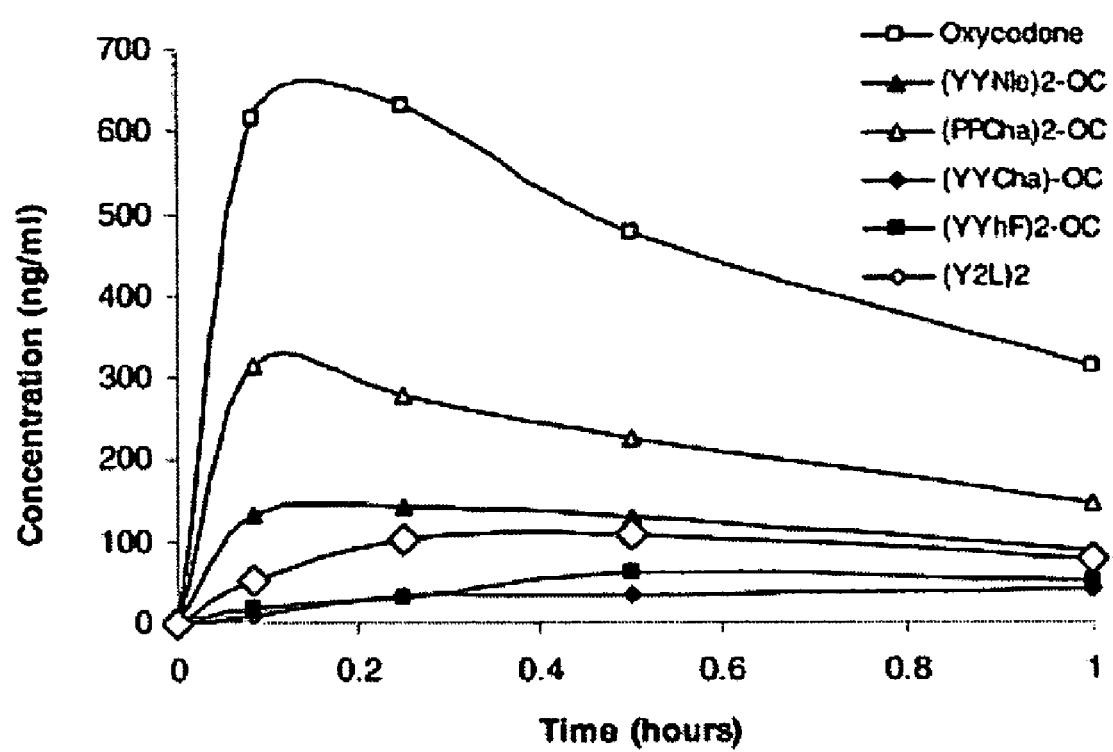

FIG. 182. Intranasal bioavailability of abuse-resistant oxycodone disubstituted tripeptide conjugates, measured as free oxycodone.

Figure 183:
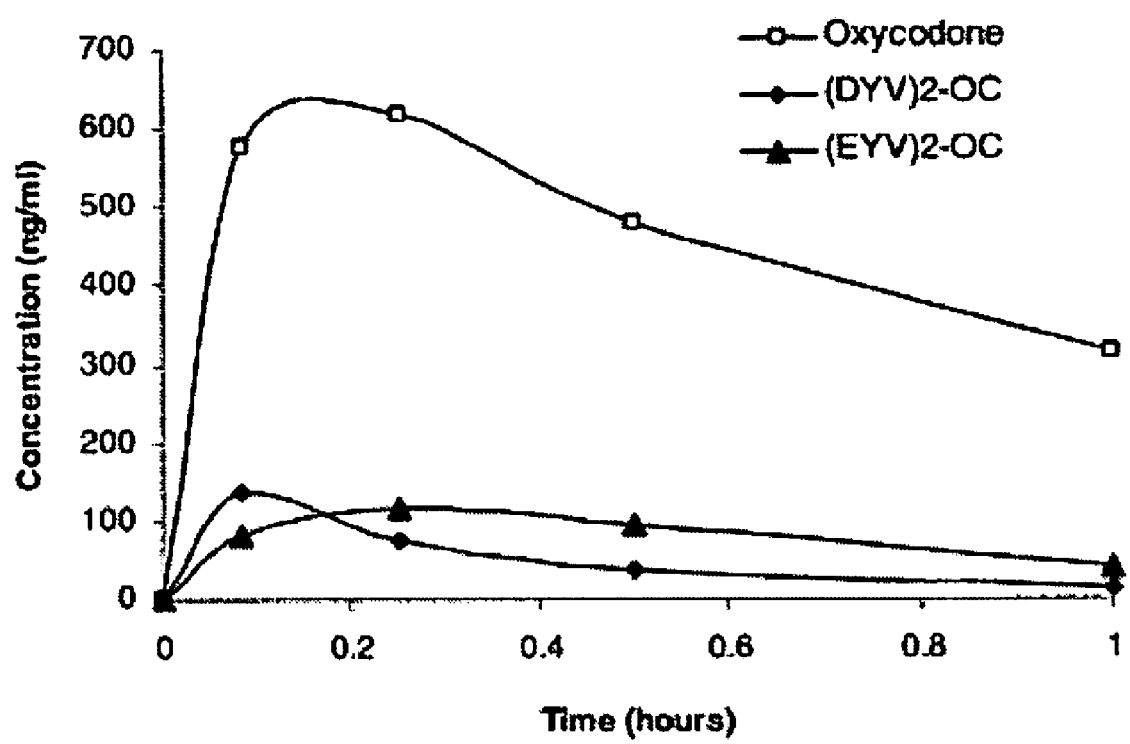

FIG. 183. Intranasal bioavailability of abuse-resistant oxycodone disubstituted tripeptide conjugates, measured as free oxycodone.

Figure 184:
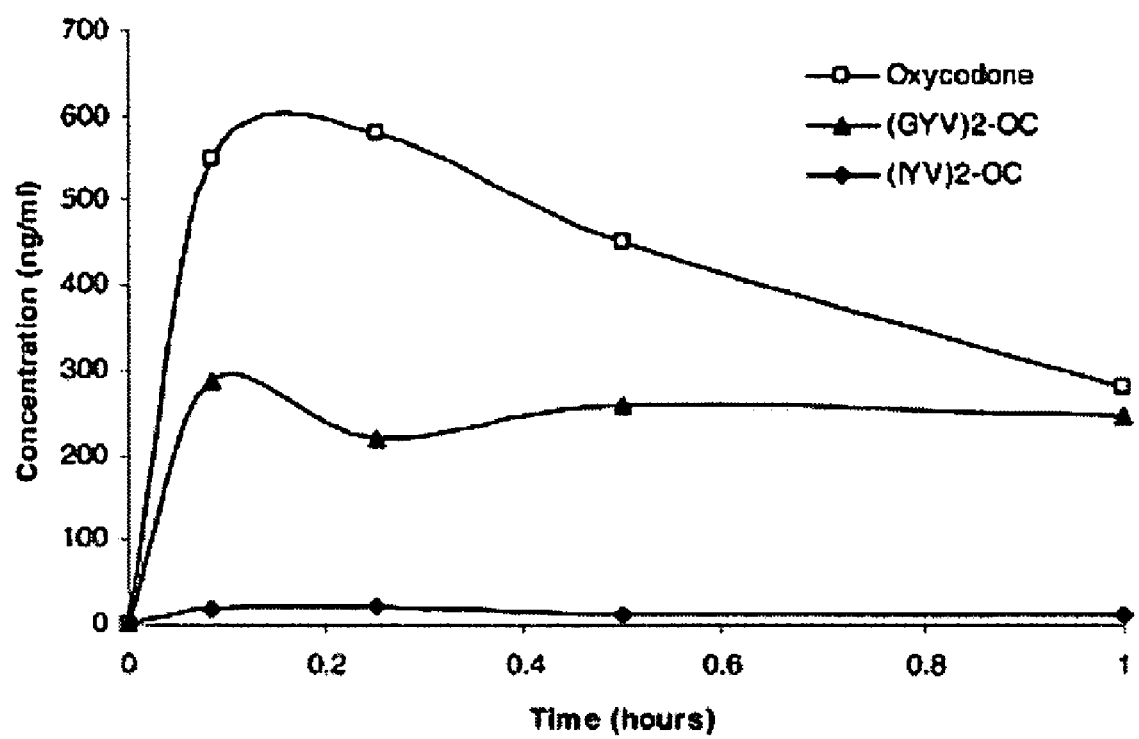

FIG. 184. Intranasal bioavailability of abuse-resistant oxycodone disubstituted tripeptide conjugates, measured as free oxycodone.

Figure 185:
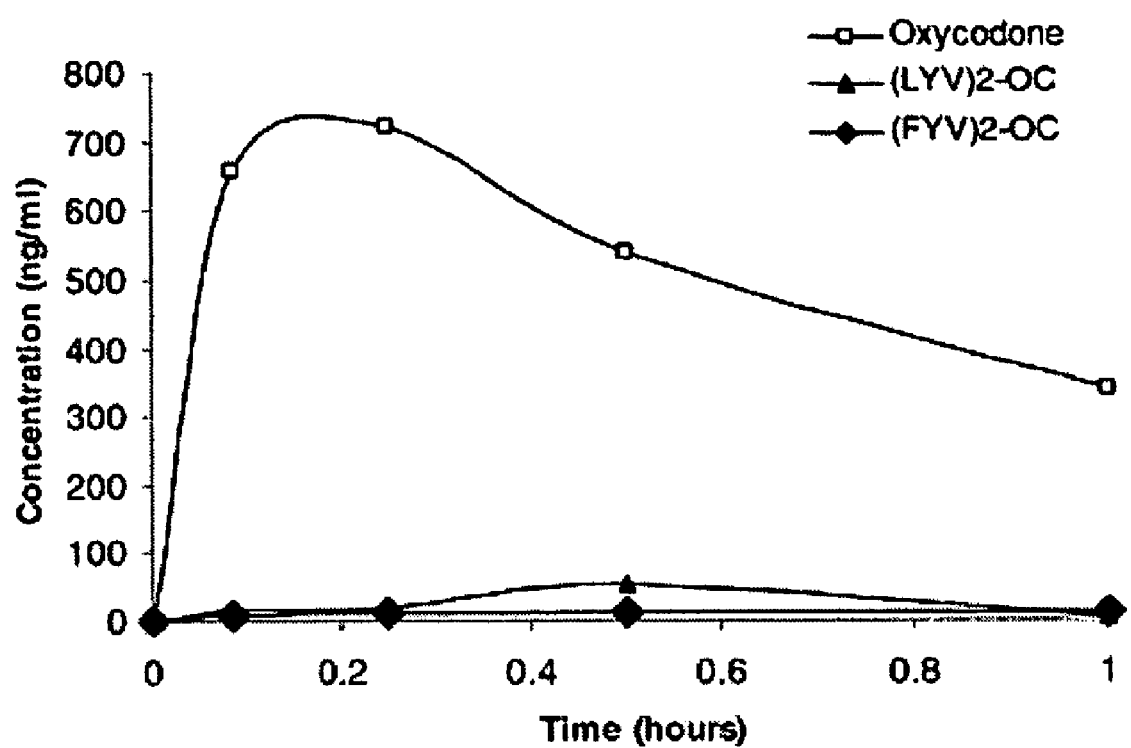

FIG. 185. Intranasal bioavailability of abuse-resistant oxycodone disubstituted tripeptide conjugates, measured as free oxycodone.

Figure 186:
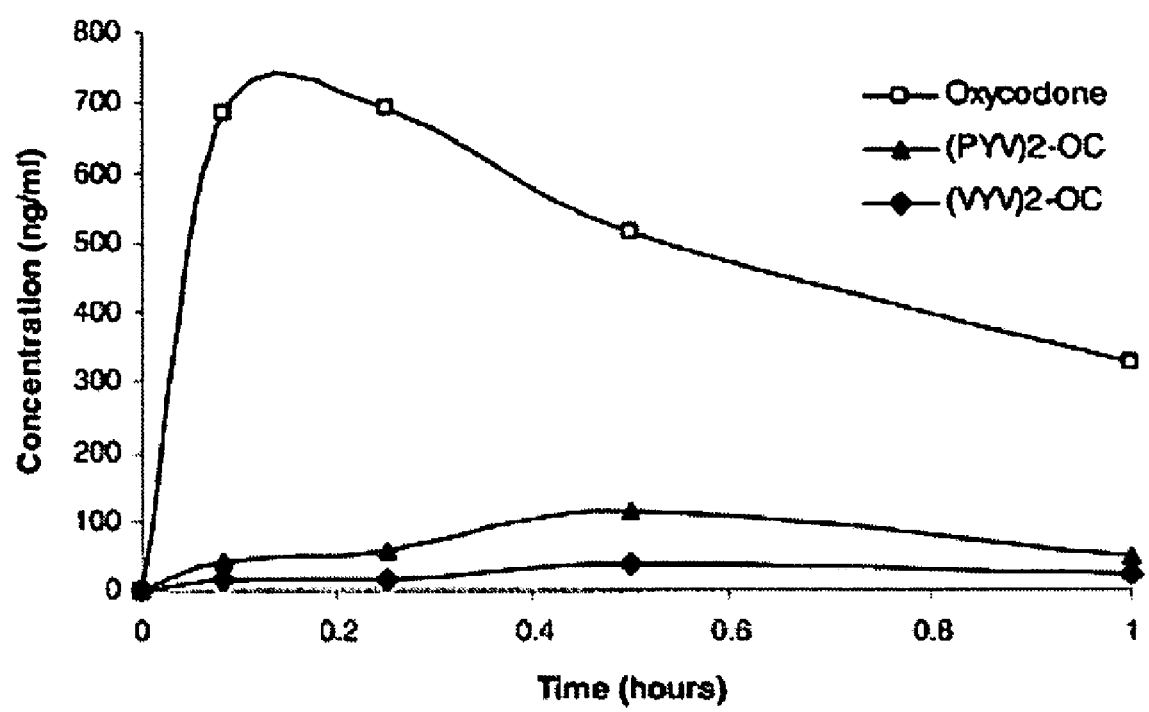

FIG. 186. Intranasal bioavailability of abuse-resistant oxycodone disubstituted tripeptide conjugates, measured as free oxycodone.

Figure 187:
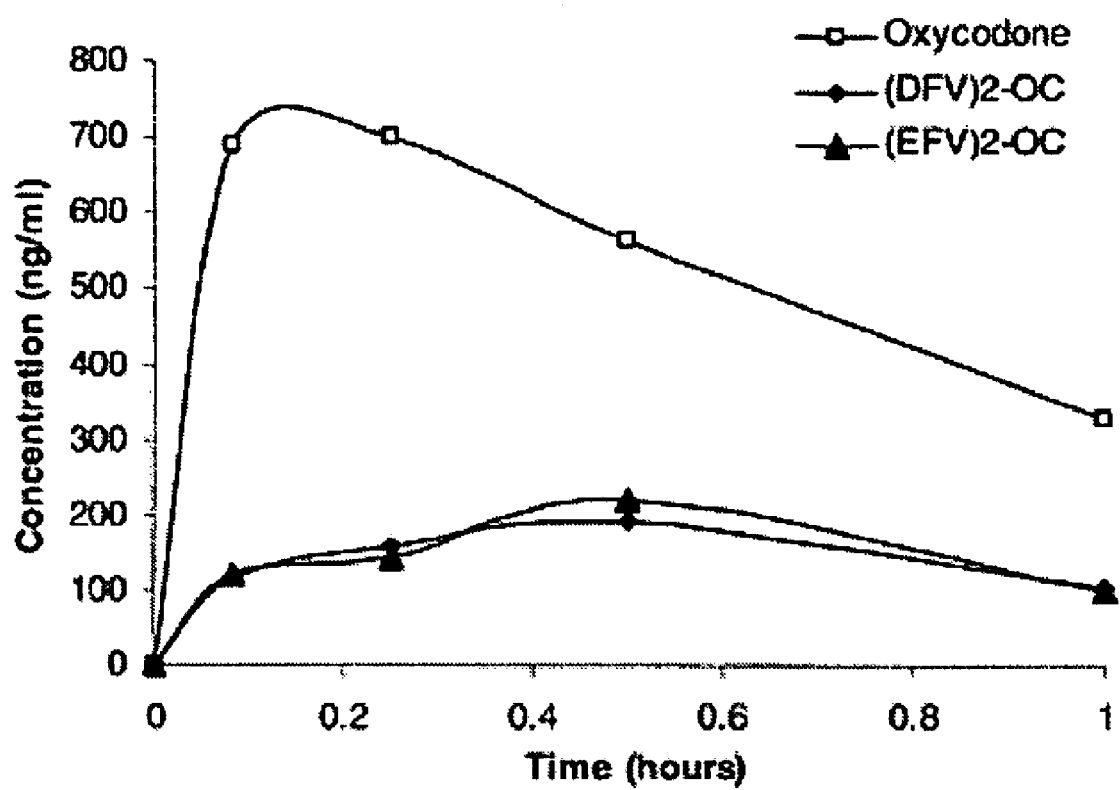

FIG. 187. Intranasal bioavailability of abuse-resistant oxycodone disubstituted tripeptide conjugates, measured as free oxycodone.

Figure 188:
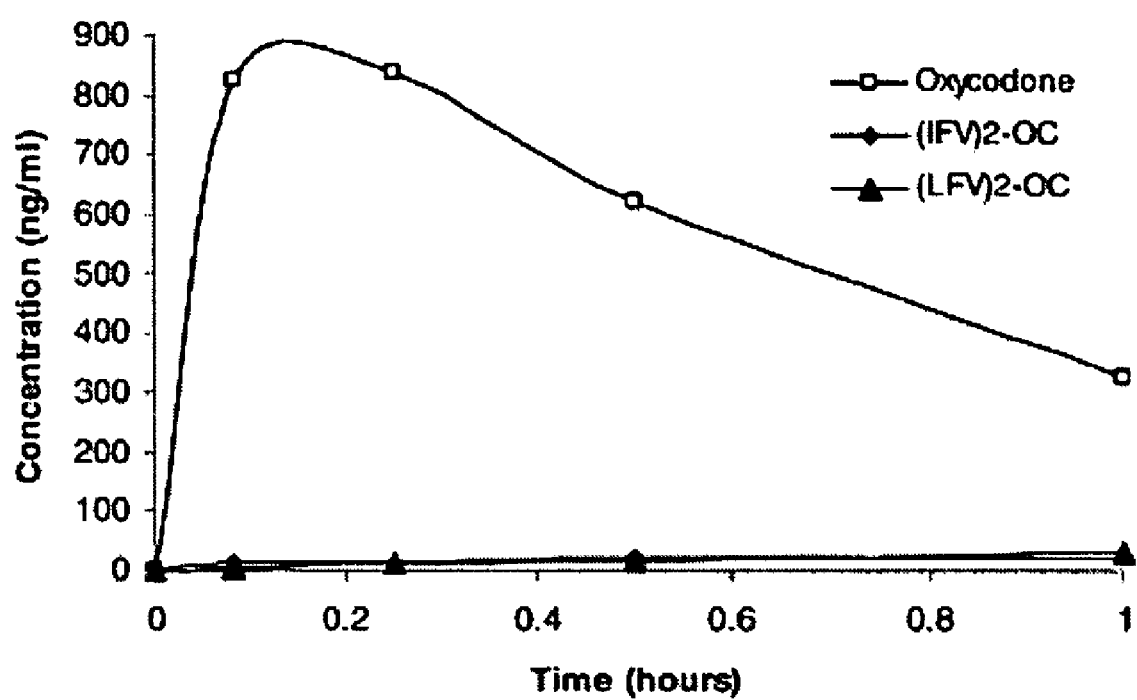

FIG. 188. Intranasal bioavailability of abuse-resistant oxycodone disubstituted tripeptide conjugates, measured as free oxycodone.

Figure 189:
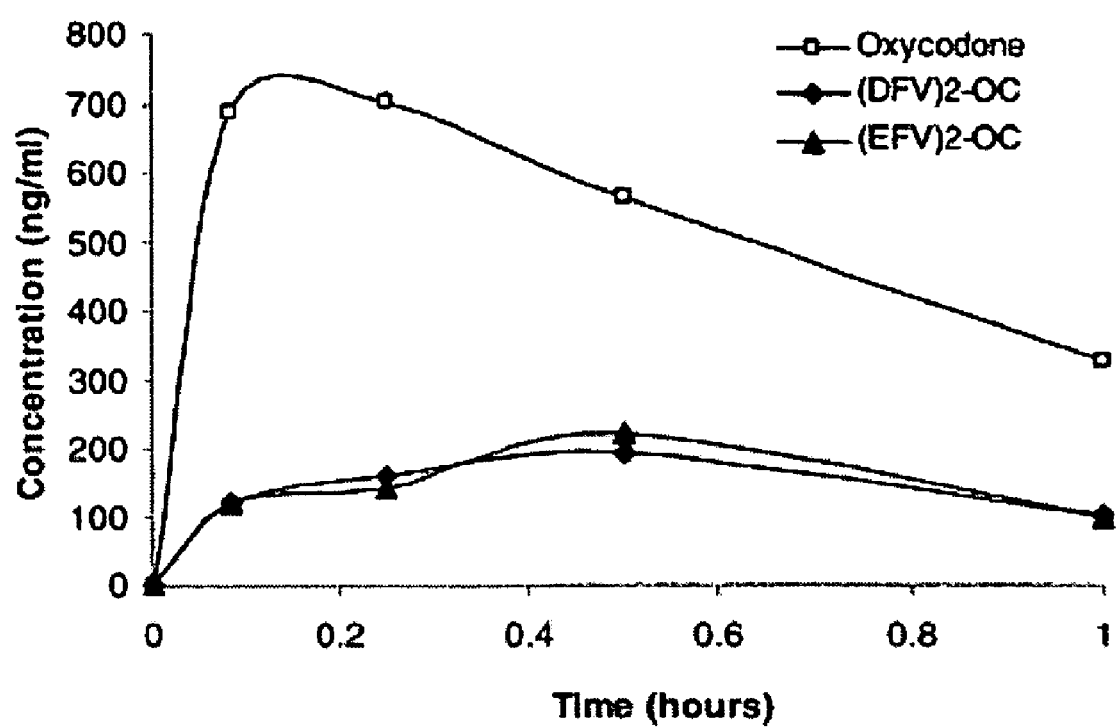

FIG. 189. Intranasal bioavailability of abuse-resistant oxycodone disubstituted tripeptide conjugates, measured as free oxycodone.

Figure 190:
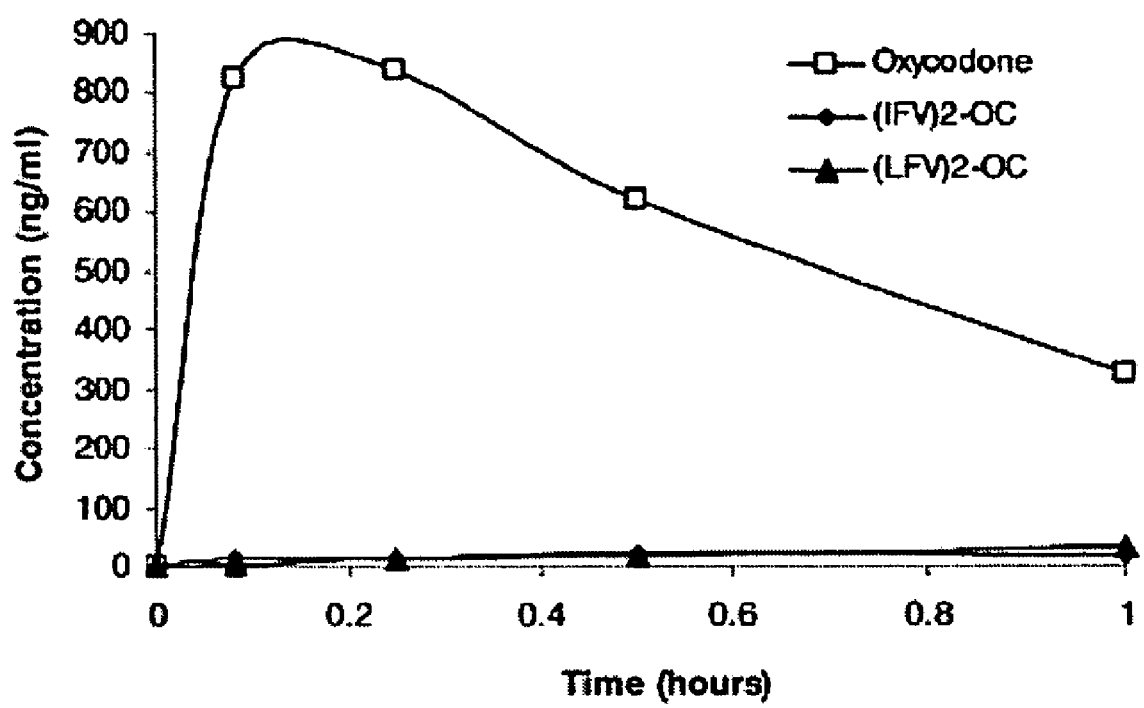

FIG. 190. Intranasal bioavailability of abuse-resistant oxycodone disubstituted tripeptide conjugates, measured as free oxycodone.

Figure 191:
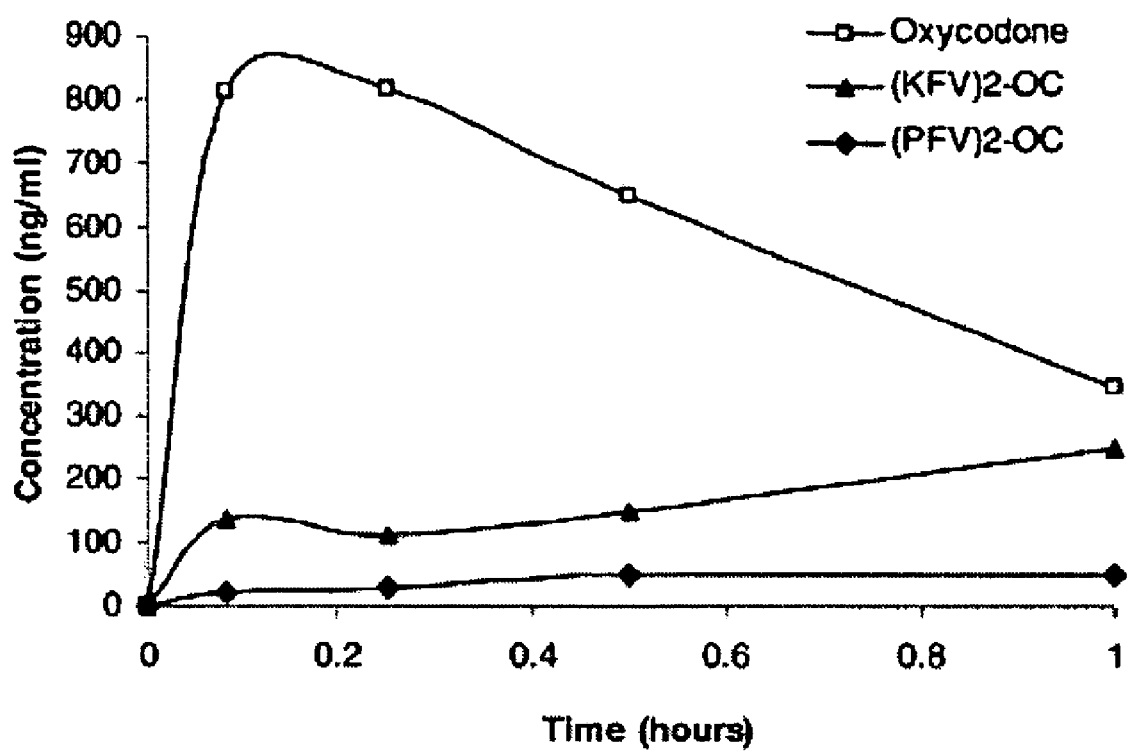

FIG. 191. Intranasal bioavailability of abuse-resistant oxycodone disubstituted tripeptide conjugates, measured as free oxycodone.

Figure 192:
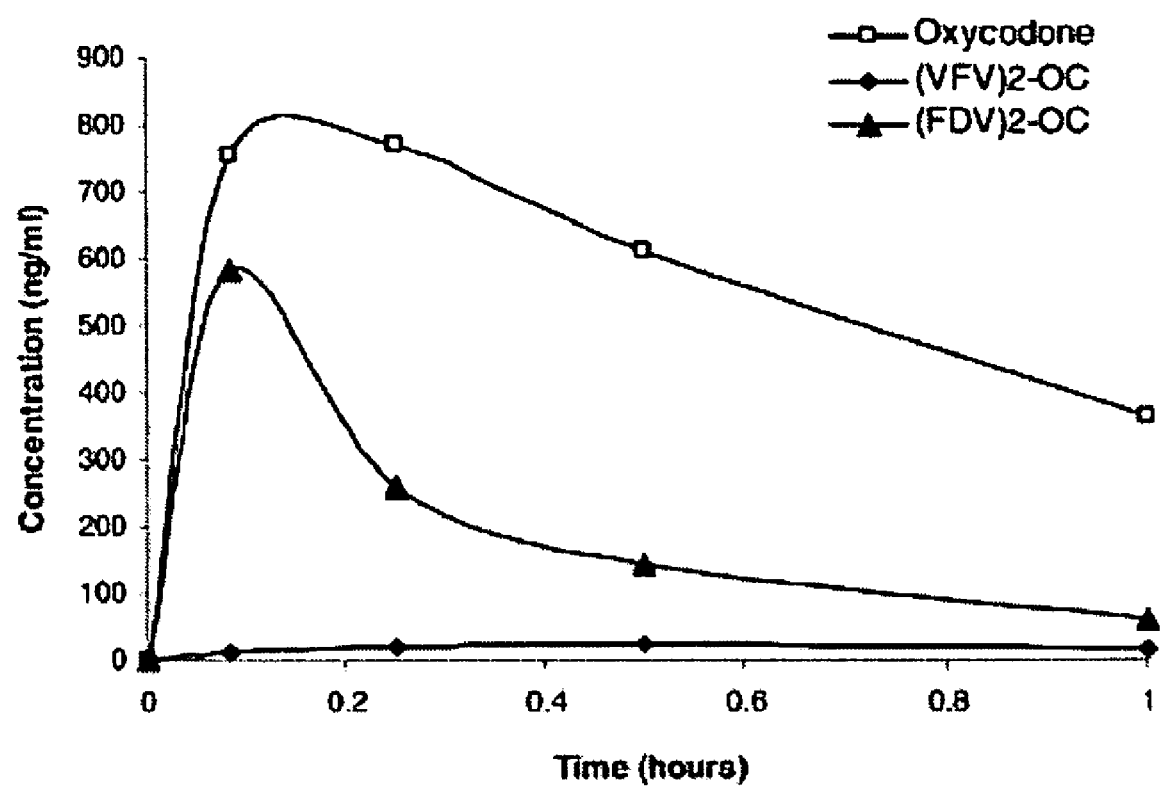

FIG. 192. Intranasal bioavailability of abuse-resistant oxycodone disubstituted tripeptide conjugates, measured as free oxycodone.

Figure 193:
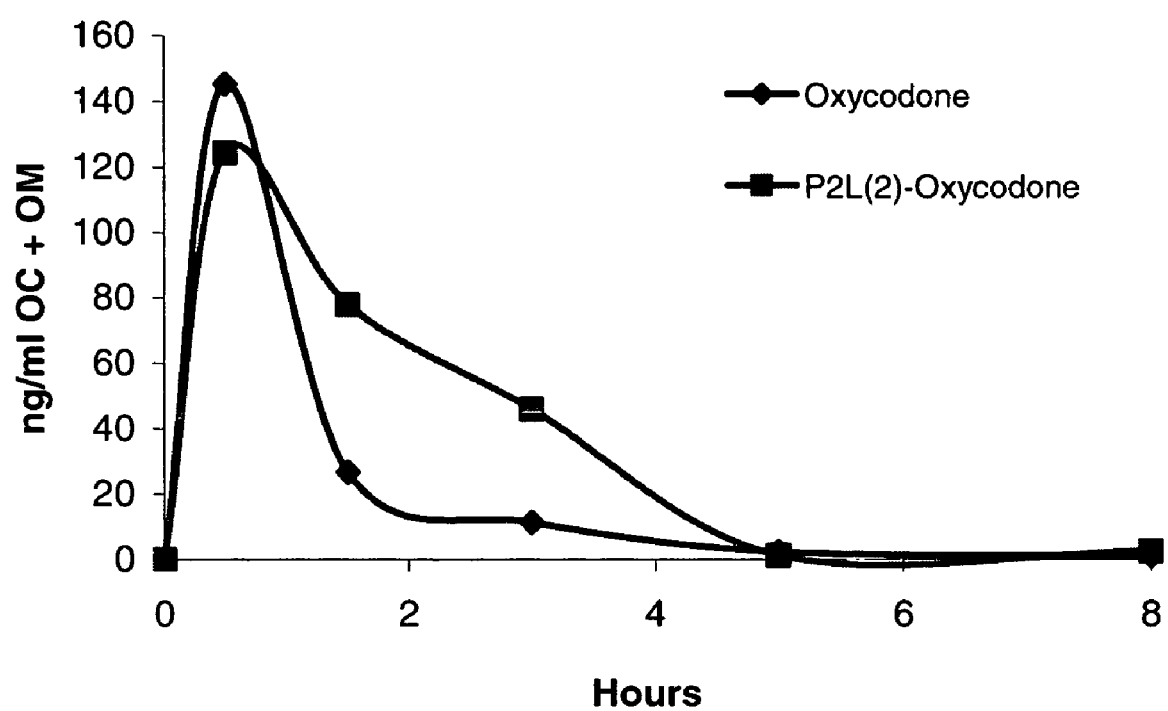

FIG. 193. Oral bioavailability in rats of oxycodone vs. $[PPL]_2$-Oxycodone at a dose (2.5 mg/kg) approximating a therapeutic human dose equivalent measured as free oxycodone.

Figure 194:
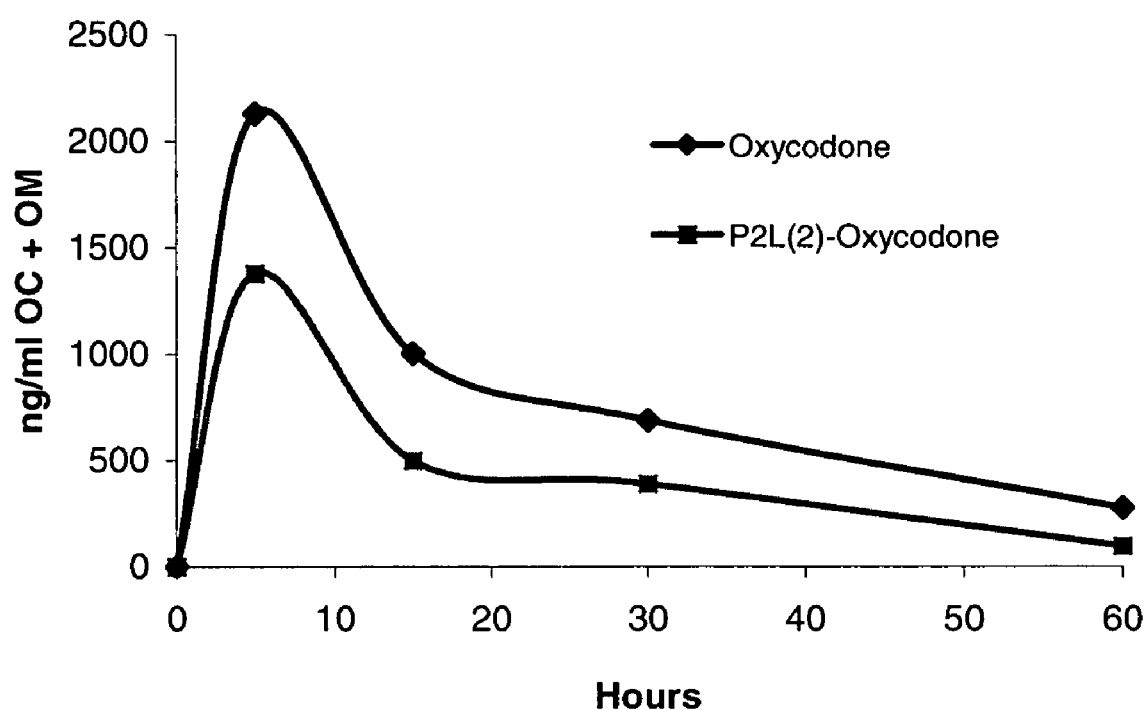

FIG. 194. Decrease in bioavailability of $[PPL]_2$-Oxycodone as compared to oxycodone by the intranasal route of administration-dose 2.5 mg/kg measured as free oxycodone.

Figure 195:
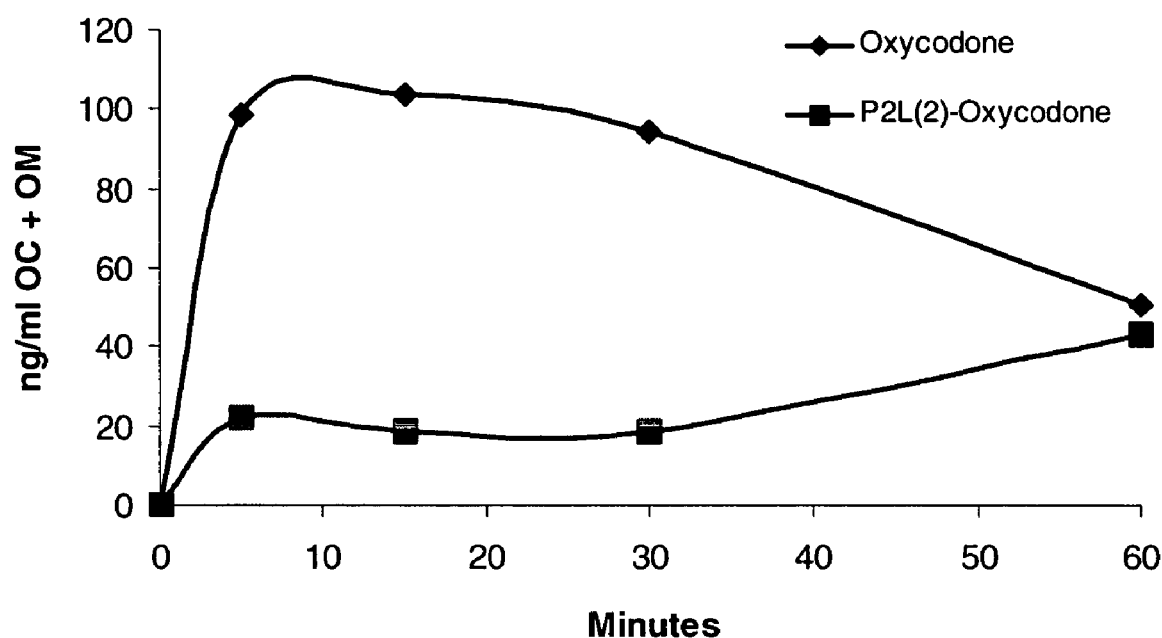

FIG. 195. Decrease in bioavailability of $[PPL]_2$-Oxycodone as compared to oxycodone by the intravenous route of administration-dose 0.5 mg/kg measured as free oxycodone.

DETAILED DESCRIPTION OF THE INVENTION

The present invention relates to changing the pharmacokinetic and pharmacological properties of active agents through covalent modification. Covalent attachment of a chemical moiety to an active agent can change the rate and extent of absorption, metabolism, distribution, and elimination of the active agent. When administered at a normal therapeutic dose the bioavailablility (area under the time-versus-concentration curve; AUC) of the active agent is similar to that of the parent active agent compound. As the oral dose is increased, however, the bioavailability of the covalently modified active agent relative to the parent active agent begins to decline. At suprapharmacological doses the bioavailability of the active agent conjugate is substantially decreased as compared to the parent active agent. The relative decrease in bioavailability at higher doses abates the euphoria obtained when doses of the active agent conjugate are taken above those of the intended prescription. This in turn diminishes the abuse potential, whether unintended or intentionally sought.

Persons that abuse prescription drugs commonly seek to increase their euphoria by snorting or injecting the drugs. These routes of administration increase the rate and extent of drug absorption and provide a faster, nearly instantaneous, effect. This increases the amount of drug that reaches the central nervous system where it has its effect. In a particular embodiment of the invention the bioavailability of the covalently modified active agent is substantially decreased by the intranasal and intravenous routes as compared to the parent active agent. Thus the illicit practice of snorting and shooting the drug loses its advantage.

In accordance with the present invention and as used herein, the following terms are defined with the following meanings, unless explicitly stated otherwise. For additional methods of attaching active agents to carriers, see application number U.S. Ser. No. 10/156,527, and/or PCT/US03/05524, and/or PCT/US03/05525 and/or PCT/US04/17204 each of which is hereby incorporated by reference in its entirety.

The invention utilizes covalent modification of an active agent to decrease its potential for causing overdose or being abused. The active agent is covalently modified in a manner that decreases its pharmacological activity, as compared to the unmodified active agent, at doses above those considered therapeutic, e.g., at doses inconsistent with the manufacturer's instructions. When given at lower doses, such as those intended for therapy, the covalently modified active agent retains pharmacological activity similar to that of the unmodified active agent. The covalent modification of the active agent may comprise the attachment of any chemical moiety through conventional chemistry.

Compounds, compositions and methods of the invention provide reduced potential for overdose, reduced potential for abuse or addiction and/or improve the active agent's characteristics with regard to high toxicities or suboptimal release profiles. Without wishing to be limited to the below theory, we believe that in some instances (e.g., with amphetamines) overdose protection results from a natural gating mechanism at the site of hydrolysis that limits the release of the active agent from the prodrug at greater than therapeutically prescribed amounts. Therefore, abuse resistance is provided by limiting the "rush" or "high" available from the active agent released by the prodrug and limiting the effectiveness of alternative routes of administration.

"Amphetamine" shall mean any of the sympathomimetic phenethylamine derivatives which have central nervous system stimulant activity, such as but not limited to, amphetamine, methamphetamine, p-methoxyamphetamine, methylenedioxyamphetamine, 2,5-dimethoxy-4-methylamphetamine, 2,4,5-trimethoxyamphetamine and 3,4-methylenedioxymethamphetamine.

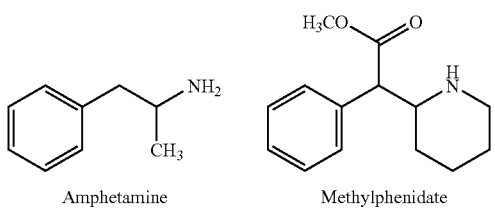

Amphetamine    Methylphenidate

Other embodiments of amphetamine are described according to the following abbreviations.
L-lysine-d-amphetamine=Lys-Amp, Lys-Amph, Lysine-Amphetamine, KAMP, K-amphetamine, or: =2,6-diaminohexanoic acid-(1-methyl-2-phenylethyl)-amide
Phe-Amp=Phenylalanine-Amphetamine, FAMP,
  =2-amino-3-phenylpropanoic acid-(1-methyl-2-phenylethyl)-amide,
Ser-Amp=Serine-Amphetamine, SAMP
  =2-amino-3-hydroxylpropanoic acid-(1-methyl-2-phenylethyl)-amide, $Gly_3$-Amp
  =GGG-Amphetamine, GGGAMP
    =2-Amino-N-({[(1-methyl-2-phenyl-ethylcarbomyl)-methyl]-carbomyl}-methyl)-acetamide Throughout this application the use of "opioid" is meant to include any drug that activates the opioid receptors found in the brain, spinal cord and gut. There are three broad classes of opioids: naturally occurring opium alkaloids, such as morphine (the prototypical opioid) and codeine; semi-synthetics such as heroine, oxycodone and hydrocodone that are produced by modifying natural opium alkaloids and have similar chemical structures; and pure synthetics such as fentanyl and methadone that are not produced from opium and may have very different chemical structures than the opium alkaloids. Other opioids include hydroxymorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

Throughout this application the use of "oxyocodone" is meant to include a narcotic alkaloid (chemical formula $C_{18}H_{21}NO_4$) and its derivatives such as the hydrochloride salt of oxycodone. Oxycodone is related to codeine and is used as an analgesic and/or a sedative. Oxycodone is a powerful and potentially addictive opioid analgesic synthesized from thebaine. It is similar to codeine, but is more potent and has a higher dependence potential. It is effective orally and is often marketed in combination with aspirin (Percodan®) or acetaminophen (Percocet®) for the relief of pain. It is also sold in a sustained-release form under the trade name Oxycontin®. All of these deriviatives or combinations of oxycodone are encompassed by the present invention.

Throughout this application the use of "hydrocodone" is meant to include a semisynthetic narcotic analgesic and antitussive prepared from codeine with multiple actions qualitatively similar to those of codeine. It is commonly used for the relief of moderate to moderately severe pain. Trade names include Anexsia®, Hycodan®, Hycomine®, Lorcet®, Lortab®, Norco®, Tussionex®, Tylox®, and Vicodin®. Derivatives of hydrocodone, such as hydrocodone bitartrate and hydrocodone polistirex, are encompassed by the present invention.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein.

Throughout this application the use of "chemical moiety" is meant to include at least amino acids, peptides, glycopeptides, carbohydrates, lipids, nucleosides, or vitamins.

"Carbohydrates" includes sugars, starches, cellulose, and related compounds. e.g., $(CH_2O)_n$, wherein n is an integer larger than 2 or $C_n(H_2O)_{n-1}$, with n larger than 5. More specific examples include for instance, fructose, glucose, lactose, maltose, sucrose, glyceraldehyde, dihydroxyacetone, erythrose, ribose, ribulose, xylulose, galactose, mannose, sedoheptulose, neuraminic acid, dextrin, and glycogen.

A "glycoprotein" is a compound containing carbohydrate (or glycan) covalently linked to protein. The carbohydrate may be in the form of a monosaccharide, disaccharide(s). oligosaccharide(s), polysaccharide(s), or their derivatives (e.g. sulfo- or phospho-substituted).

A "glycopeptide" is a compound consisting of carbohydrate linked to an oligopeptide composed of L- and/or D-amino acids. A glyco-amino-acid is a saccharide attached to a single amino acid by any kind of covalent bond. A glycosyl-amino-acid is a compound consisting of saccharide linked through a glycosyl linkage (O—, N— or S—) to an amino acid.

A "composition" as used herein, refers broadly to any composition containing a described molecule conjugates. The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g., sodium dodecyl sulfate (SDS), and other components.

A "controlled substance" is a substance subject to federal regulation of its manufacture, sale, or distribution because of the potential for, or proved evidence of, abuse; because of its potential for psychic or physiological dependence; because it constitutes a public health risk; because of the scientific evidence of its pharmacologic effect; or because of its role as a precursor of other controlled substances.

Important note regarding stereochemistry: This patent is meant to cover all compounds discussed regardless of absolute configurations. Thus, natural, L-amino acids are discussed but the use of D-amino acids are also included.

The following abbreviations may be in this application:
BOC=t-butyloxycarbonyl
CMC=carboxymethylcellulose
DIPEA=di-isopropyl ethyl amine
mp=melting point
NMR=nuclear magnetic resonance
  OSu=hydroxysuccinimido ester
  Nia=Niacin
  Bio=Biotin The attached chemical moiety may be any chemical substance that decreases the pharmacological activity until the active agent is released. Preferably the chemical moiety is a single amino acid, dipeptide or tripeptide, tetrapeptide, pentapeptide, or hexapeptide. The active agent binds to specific sites to produce various effects (Hoebel, et al., 1989). The attachment of certain chemical moieties can therefore diminish or prevent binding to these biological target sites. Preferably, absorption of the composition into the brain is prevented or substantially diminished and/or delayed when delivered by routes other than oral administration.

The attached chemical moiety may further comprise naturally occurring or synthetic substances. This would include but is not limited to the attachment of an active agent to one or more amino acids, peptides, lipids, carbohydrates, glycopeptides, nucleic acids or vitamins. These chemical moieties could be expected to affect delayed release in the gastrointestinal tract and prevent rapid onset of the desired activity, particularly when delivered by parenteral routes. (Hoebel, B. G., L. Hernandez, et al. (1989). "Microdialysis studies of brain norepinephrine, serotonin, and dopamine release during ingestive behavior. Theoretical and clinical implications." *Ann N Y Acad Sci* 575: 171-91).

For each of the embodiments recited herein, the amino acid or peptide may comprise of one or more of the naturally occurring (L-) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more of the naturally occurring (D) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment the amino acid or peptide is comprised of one or more unnatural, non-standard or synthetic amino acids such as, aminohexanoic acid, biphenylalanine, cyclohexylalanine, cyclohexylglycine, diethylglycine, dipropylglycine, 2,3-diaminoproprionic acid, homophenylalanine, homoserine, homotyrosine, naphthylalanine, norleucine, ornithine, pheylalanine(4-fluoro), phenylalanine(2,3,4,5,6 pentafluoro), phenylalanine(4-nitro), phenylglycine, pipecolic acid, sarcosine, tetrahydroisoquinoline-3-carboxylic acid, and tert-leucine. In another embodiment the amino acid or peptide comprises of one or more amino acid alcohols. In another embodiment the amino acid or peptide comprises of one or more N-methyl amino acids.

In another embodiment, the specific carriers are utilized as a base short chain amino acid sequence and additional amino acids are added to the terminus or side chain. In another embodiment, the above amino acid sequence may have one or more of the amino acids substituted with one of the 20 naturally occurring amino acids. It is preferred that the substitution be with an amino acid which is similar in structure or charge compared to the amino acid in the sequence. For instance, isoleucine (Ile)[I] is structurally very similar to leucine (Leu)[L], whereas, tyrosine (Tyr)[Y] is similar to phenylalanine (Phe)[F], whereas serine (Ser)[S] is similar to threonine (Thr)[T], whereas cysteine (Cys)[C] is similar to methionine (Met)[M], whereas alanine (Ala)[A] is similar to valine (Val)[V], whereas lysine (Lys)[K] is similar to arginine (Arg)[R], whereas asparagine (Asn)[N] is similar to glutamine (Gln)[Q], whereas aspartic acid (Asp)[D] is similar to glutamic acid (Glu)[E], whereas histidine (His)[H] is similar to proline (Pro)[P], and glycine (Gly)[G] is similar to tryptophan (Trp)[W]. In the alternative the preferred amino acid substitutions may be selected according to hydrophilic properties (i.e. polarity) or other common characteristics associated with the 20 essential amino acids. While preferred embodiments utilize the 20 natural amino acids for their GRAS characteristics, it is recognized that minor substitutions along the amino acid chain which do not effect the essential characteristics of the amino are also contemplated.

In one embodiment the carrier range is between one to 12 chemical moieties with one to 8 moieties being preferred. In another embodiment the number of chemical moieties attached is selected from 1, 2, 3, 4, 5, 6, or 7, etc. In another embodiment of the invention the molecular weight of the carrier portion of the conjugate is below about 2,500, more preferably below about 1,000 and most preferably below about 500.

The compositions and methods of the invention may be applied to various therapeutically valuable active agents (e.g., drugs) and include, for example, stimulants such as amphetamines, anticonvulsants, muscle relaxants, antidepressants, anxiolytics, benzodiazepines, sedatives, hypnotics, narcotics, steroids, respiratory agents, including antihistamines, antipsychotics including risperidone, and nonsteroidal anti-inflammatory agents.

Exemplary narcotics include opioids, hydrocodone, oxycodone, morphine, codeine, hydroxymorphone, oxymorphone, methadone, fentanyl, levorphanol, dihydrocodeine, meperidine, diphenoxylate, sufentanil, alfentanil, propoxyphene, pentazocine, nalbuphine, butorphanol, buprenorphine, meptazinol, dezocine or pharmaceutically acceptable salts thereof.

Exemplary benzodiazepines include alprazolam, chlordiazepoxide, clonazepam, clorazepate, diazepam, estazolam, flurazepam, halazepam, lorazepam, midazolam, oxazepam, quazepam, temazepam, or triazolam.

Exemplary nonsteroidal anti-inflammatory agents include ibuprofen, naproxen or indomethacin, aspirin or a salicylic acid derivative, or acetaminophen.

Exemplary anti-depressants include citalopram, fluoxetine, norfluoxetine, fluvoxamine, paroxetine, sertraline, amitriptyline, desipramine, doxepin, imipramine, nortryiptyline, bupropion, mirtazapine, nefazodone, trazodone, or venlafaxine.

Exemplary anti-psychotics include clozapine, haloperidol, olanzapine, quetiapine, or risperidone.

Exemplary amphetamines include amphetamine, methamphetamine, p-methoxyamphetamine, methylenedioxyamphetamine, 2,5-dimethoxy-4-methylamphetamine, 2,4,5-trimethoxyamphetamine and 3,4-methylenedioxymethamphetamine.

The compositions and methods of the invention provide active agents which when bound to the chemical moiety provide safer and/or more effective dosages for the above recited active agent classes through improved bioavailability curves and/or safer $C_{max}$ and/or reduce area under the curve for bioavailability, particularly for abused substances taken in doses above therapeutic levels. As a result, the compositions and methods of the invention may provide improved methods of treatment for attention deficit hyperactivity, attention deficit hyperactivity disorder (ADHD), attention deficit disorder (ADD), cognitive decline associated with acquired immunodeficiency syndrome (AIDS) or AIDS-related complex, depression, anxiety and anxiety related disorders, psychosis, nicotine addiction, narcotic addiction, alcoholism, narcolepsy, and/or analgesia.

In one embodiment the chemical moiety is comprised of an amino acid or a polypeptide. Preferred amino acid and peptide chemical moieties include, for example, Lys, Ser, Ala, Phe, Ile, Pro-Pro-Leu, Pro-Pro-Ile, Val-Val, Lys-Lys, Gly-Gly-Ile, Phe-Phe-Ile, Phe-Phe-Leu, Thr-Thr-Val, Tyr-Tyr-Val, Tyr-Tyr-Phe, Glu-Glu-Val, Asp-Asp-Val, Lys-Lys-Val, Glu-Glu-Phe-Phe-Ile[SEQ ID NO: 6], Glu-Glu-Phe-Phe-Phe[SEQ ID NO: 7], Tyr-Tyr-Ile, Asp-Asp-Ile, Tyr-Tyr-Phe-Phe-Ile[SEQ ID NO: 8], Tyr-Tyr-Lys-Tyr-Tyr[SEQ ID NO: 9], Phe-Phe-Lys-Phe-Phe[SEQ ID NO: 10], (Lys-Lys-Gly-Gly)$_2$[SEQ ID NO: 11] and [(l)-Lys-(d)-Lys-Leu]$_2$. In some embodiments, the active agent is disubstituted with one or more of the preceding chemical moieties.

Another embodiment of the invention is a composition for preventing overdose comprising an active agent which has been covalently bound to a chemical moiety.

Another embodiment of the invention is a composition for safely delivering an active agent comprising providing a therapeutically effective amount of said active agent which has been covalently bound to a chemical moiety wherein said chemical moiety reduces the rate of absorption of the active agent as compared to delivering the unbound active agent.

Another embodiment of the invention is a composition for reducing drug toxicity comprising providing a patient with an active agent which has been covalently bound to a chemical moiety wherein said chemical moiety increases the rate of clearance of an active agent when given at doses exceeding those within the therapeutic range of said active agent.

Another embodiment of the invention is a composition for reducing drug toxicity comprising providing a patient with an active agent which has been covalently bound to a chemical moiety wherein said chemical moiety provides a serum release curve which does not increase above said active agent toxicity level when given at doses exceeding those within the therapeutic range of said active agent.

Another embodiment of the invention is a composition for reducing bioavailability of active agent comprising active agent covalently bound to a chemical moiety wherein said bound active agent maintains a steady-state serum release curve which provides a therapeutically effective bioavailability but prevents spiking or increase blood serum concentrations compared to unbound active agent when given at doses exceeding those within the therapeutic range of said active agent.

Another embodiment of the invention is a composition for preventing a $C_{max}$ spike for active agent while still providing a therapeutically effective bioavailability curve comprising an active agent which has been covalently bound to a chemical moiety.

Another embodiment of the invention is a composition for preventing a toxic release profile in a patient comprising active agent covalently bound to a chemical moiety wherein said bound active agent maintains a steady-state serum release curve which provides a therapeutically effective bioavailability but prevents spiking or increase blood serum concentrations compared to unbound active agent.

Another embodiment of the invention is a compound of Formula I:

$$A\text{-}X_n\text{-}Z_m$$

wherein A is active agent as defined herein; X is a chemical moiety as defined herein and n is between 1 and 50 and increments thereof; and Z is a further chemical moiety different from X which acts as an adjuvant and m is between 1 and 50 and increments thereof. In another embodiment n is between 1 and 10 and m is 0. It should be recognized that the compounds of this formula may be used alone or in combination with any of the recited embodiments of the invention.

Embodiments of the invention provide compositions which allow the active agent to be therapeutically effective when delivered at the proper dosage but reduces the rate of absorption or extent of bioavailability of the active agent when given at doses exceeding those within the therapeutic range of the active agent. Embodiments of the invention also provide compositions wherein the covalently bound chemical moiety increases the rate of clearance of active agent when given at doses exceeding those within the therapeutic range of the active agent.

In another embodiment the compositions have substantially lower toxicity compared to unbound active agent. In another embodiment the compositions reduce or eliminate the possibility of overdose by oral administration. In another embodiment the compositions reduce or eliminate the possibility of overdose by intranasal administration. In another embodiment the compositions reduce or eliminate the possibility of overdose by injection.

In another embodiment, the conjugates of the invention may further comprise a polymer blend which comprises at least one hydrophilic polymer and at least one water-insoluble polymer. The polymer may be used according to industry standard to further enhance the sustained release properties of the active agent conjugate without reducing the abuse resistance. For instance, a composition might include: about 75% to about 95% active agent conjugate by weight, from about 0.5% to about 10% of a hydrophilic polymer (e.g. hydroxypropyl methylcellulose), from about 0.5% to about 2.5% of a water-insoluble polymer (e.g. acrylic resin), from about 0.4% to about 1.5% of additives (e.g. magnesium stearate), and from about 0.01% to about 1% colorant by weight. Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and would dissolve slowly in aqueous acidic media thereby allowing the active agent conjugate to diffuse from the gel in the stomach. When the gel reaches the intestines it would dissolve in controlled quantities in the higher pH medium to allow sustained release. Preferred hydrophilic polymers are the hydroxypropyl methylcelluloses such as those manufactured by The Dow Chemical Company and known as Methocel ethers, such as Methocel E10M.

Other formulations may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red No. 40, FD&C Yellow No. 6, D&C Yellow No. 10, or FD&C Blue No. 1 and other various certified color additives (See 21 CFR, Part 74). In one preferred embodiment, a sustained release formulation further comprises magnesium stearate and Emerald Green Lake.

An active agent conjugate, which is further formulated with excipients may be manufactured according to any appropriate method known to those of skill in the art of pharmaceutical manufacture. For instance, the active agent conjugate and a hydrophilic polymer may be mixed in a mixer with an aliquot of water to form a wet granulation. The granulation may be dried to obtain hydrophilic polymer encapsulated granules of active agent-conjugate. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

However, it should be noted that the active agent conjugate controls the release of active agent into the digestive tract over an extended period of time resulting in an improved profile when compared to immediate release combinations and reduces and/or prevents abuse without the addition of the above additives. In a preferred embodiment no further sustained release additives are required to achieve a blunted or reduced pharmacokinetic curve (e.g. reduced euphoric effect) while achieving therapeutically effective amounts of active agent release.

The compounds of the invention can be administered by a variety of dosage forms. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, health bars, confections, animal feeds, cereals, yogurts, cereal coatings, foods, nutritive foods, functional foods and combinations thereof.

However, the most effective means for delivering the abuse-resistant compounds of the invention is orally, to permit maximum release of the active agent to provide therapeutic effectiveness and/or sustained release while maintaining abuse resistance. When delivered by the oral route the active agent is released into circulation, preferably over an extended period of time as compared to active agent alone.

Formulations of the invention suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of this invention can include other suitable agents such as flavoring agents, preservatives and antioxidants. Such antioxidants would be food acceptable and could include vitamin E, carotene, BHT or other antioxidants known to those of skill in the art.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient and the administration route. Tablets and other forms of presentation provided in discrete units conveniently contain a daily dose, or an appropriate fraction thereof, of one of the present compounds. For example, units may contain from 5 mg to 500 mg, but more usually from 10 mg to 250 mg, of one of the present compounds.

It is also possible for the dosage form to combine any forms of release known to persons of ordinary skill in the art. These include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the invention may be provided in a blister pack or other such pharmaceutical package. Further, the compositions of the present inventive subject matter may further include or be accompanied by indicia allowing individuals to identify the compositions as products for a prescribed treatment. The indicia may further additionally include an indication of the above specified time periods for administering the compositions. For example the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques are well known in the art.

In another embodiment of the invention, the solubility and dissolution rate of the composition is substantially changed under physiological conditions encountered in the intestine, at mucosal surfaces, or in the bloodstream. In another embodiment the solubility and dissolution rate substantially decrease the bioavailability of the said pharmaceutical, particularly at doses above those intended for therapy. In another embodiment the decrease in bioavailability occurs upon oral administration. In another embodiment the decrease in bioavailability occurs upon intranasal administration. In another embodiment the decrease in bioavailability occurs upon intravenous administration.

Another particular embodiment of the invention provides that when the covalently modified active agent is provided for oral dosing in the form (e.g., a tablet or capsule) it is resistant to manipulation. Crushing of the tablet or disruption of the capsule does not substantially increase the rate and amount of active agent absorbed when compositions of the invention are ingested.

For each of the described embodiments one or more of the following characteristics may be realized. The toxicity of the compound is substantially lower than that of the unbound active agent. The covalently bound chemical moiety reduces or eliminates the possibility of overdose by oral administration. The covalently bound chemical moiety reduces or eliminates the possibility of overdose by intranasal administration. The covalently bound chemical moiety reduces or eliminates the possibility of overdose by injection.

The invention further provides methods for altering active agent in a manner that decreases their potential for abuse. Methods of the invention provide various ways to regulate pharmaceutical dosage through covalent attachment of active agent to different chemical moieties. One embodiment provides a method of preventing overdose comprising administering to an individual an active agent which has been covalently bound to a chemical moiety.

Another embodiment provides a method of safely delivering an active agent comprising providing a therapeutically effective amount of an active agent which has been covalently bound to a chemical moiety wherein the chemical moiety reduces the rate of absorption of active agent as compared to delivering the unbound active agent.

Another embodiment provides a method of reducing drug toxicity comprising providing a patient with an active agent which has been covalently bound to a chemical moiety wherein the chemical moiety increases the rate of clearance of a pharmacologically active active agent when given at doses exceeding those within the therapeutic range of active agent.

Another embodiment provides a method of reducing drug toxicity comprising providing a patient with an active agent which has been covalently bound to a chemical moiety wherein the chemical moiety provides a serum release curve which does not increase above the active agent's toxicity level when given at doses exceeding those within the therapeutic range for the unbound active agent.

Figure 1:
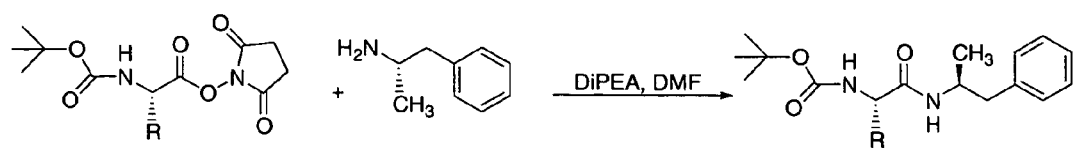
FIG. 1. Synthesis of amino acid amphetamine conjugates.
Figure 1:
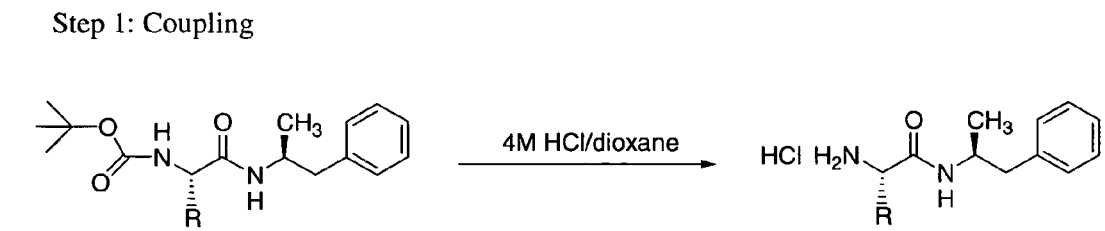
Figure 2:
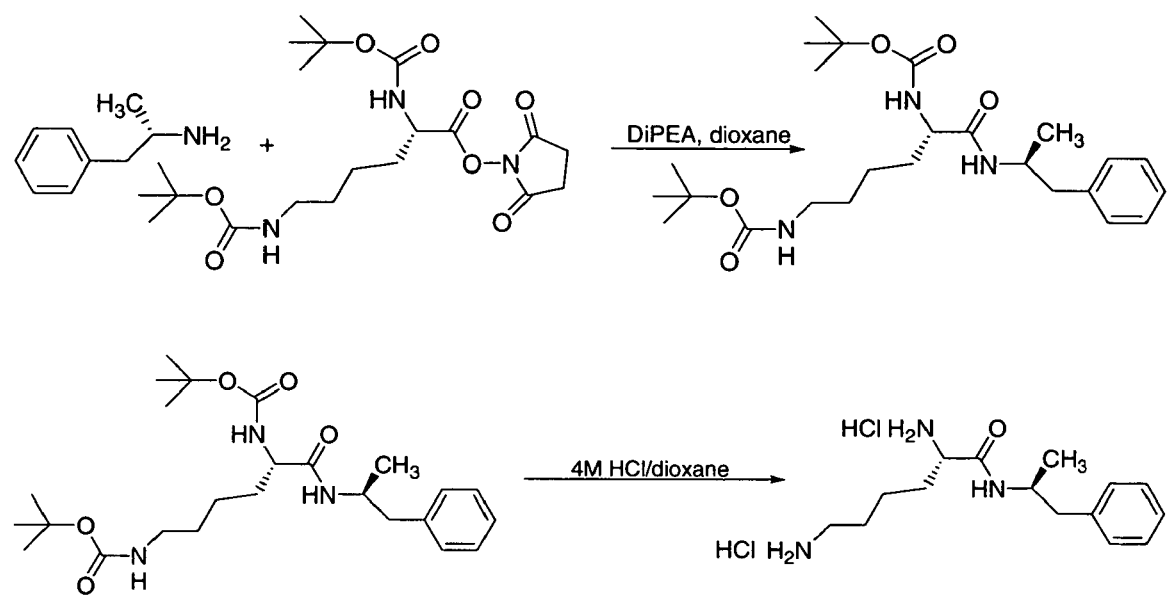
FIG. 2. Synthesis of lysine amphetamine conjugate.
Figure 3:
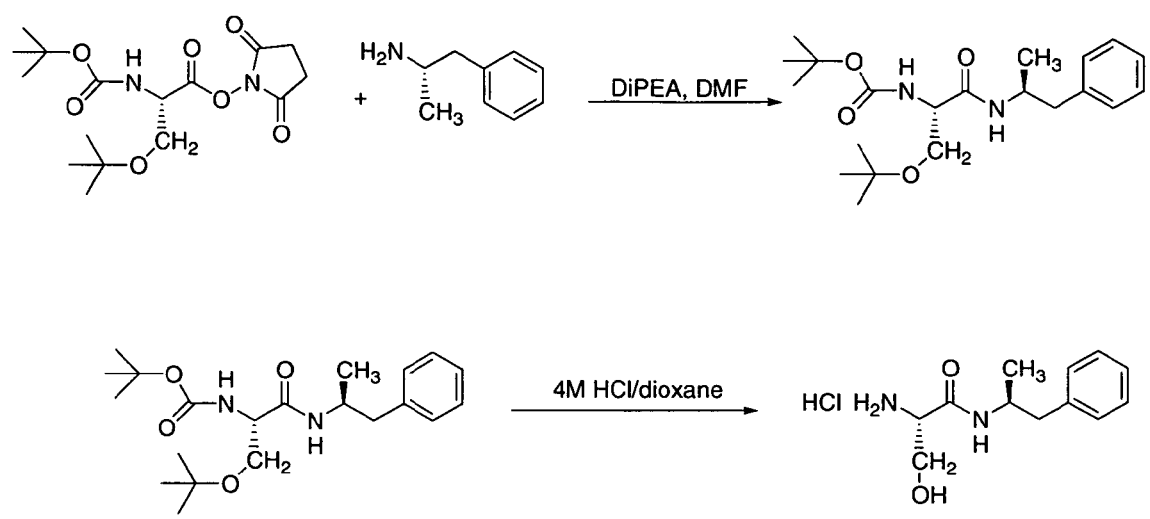
FIG. 3. Synthesis of serine amphetamine conjugate.
Figure 4:
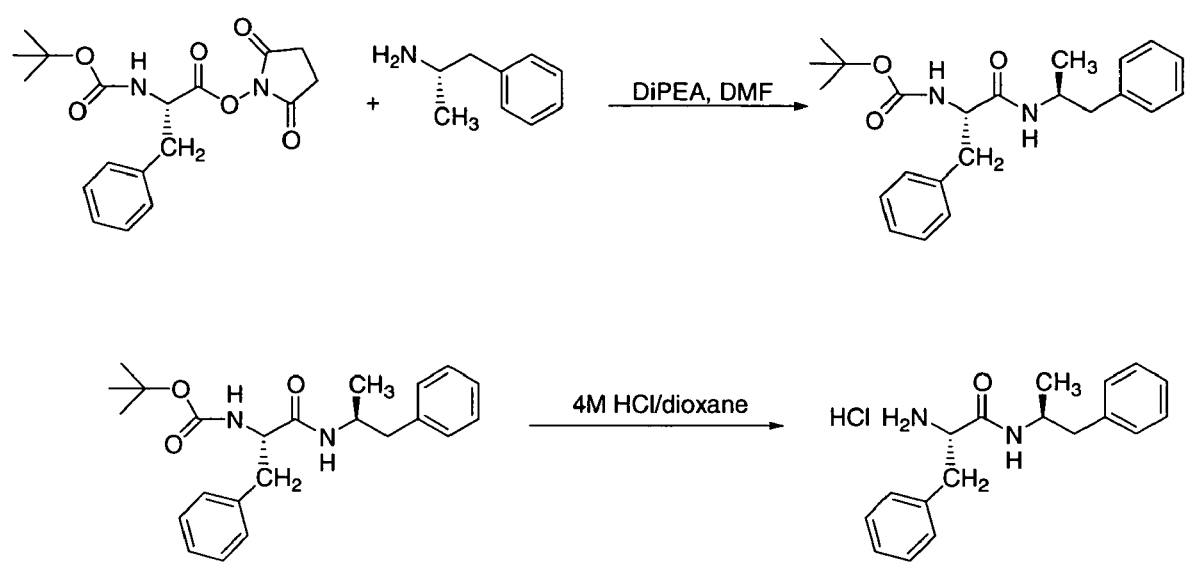
FIG. 4. Synthesis of phenylalanine amphetamine conjugate.
Figure 5:
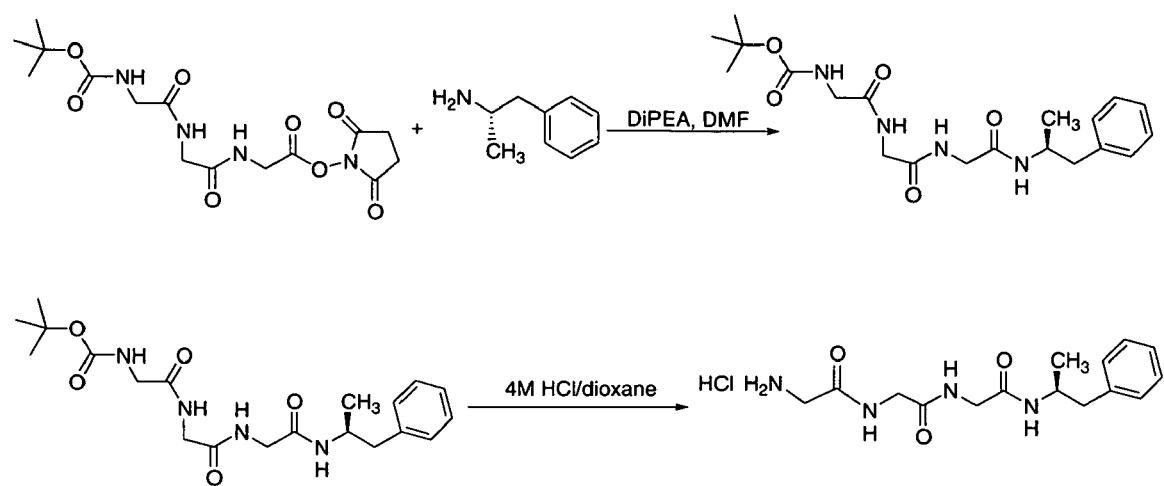
FIG. 5. Synthesis of triglycine amphetamine conjugate.

Another embodiment provides a method of reducing bioavailability of an active agent comprising providing active agent covalently bound to a chemical moiety wherein the bound active agent maintains a steady-state serum release curve which provides a therapeutically effective bioavailability but prevents spiking or increase blood serum concentrations compared to unbound active agent when given at doses exceeding those within the therapeutic range for the unbound active agent. Another embodiment provides a method of preventing a $C_{max}$ spike for active agent while still providing a therapeutically effective bioavailability curve comprising providing an active agent which has been covalently bound to a chemical moiety. In another embodiment, methods of the invention provide bioavailability curves similar to those found in FIGS. 1-195.

Another embodiment provides a method for preventing a toxic release profile in a patient comprising administering to a patient an active agent covalently bound to a chemical moiety wherein said bound active agent maintains a steady-state serum release curve which provides a therapeutically effective bioavailability but prevents spiking or increase blood serum concentrations compared to unbound active agent.

Another embodiment of the invention is a method for reducing or preventing abuse of a pharmaceutical composition, comprising providing, administering, or prescribing said composition to a human in need thereof, wherein said composition comprises a chemical moiety covalently attached to an active agent such that the pharmacological activity of active agent is substantially decreased when the composition is used in a manner inconsistent with the manufacturer's instructions. Another embodiment of the invention is a method for reducing or preventing abuse of a pharmaceutical composition, comprising consuming said composition, wherein said composition comprises a chemical moiety covalently attached to an active agent such that the pharmacological activity of the active agent is substantially decreased when the composition is used in a manner inconsistent with the manufacturer's instructions.

Another embodiment of the invention is a method of preventing overdose of a pharmaceutical composition, comprising providing, administering, or prescribing said pharmaceutical composition to a human in need thereof, wherein said composition comprises a chemical moiety covalently attached to an active agent in a manner that substantially decreases the potential of overdose from active agent. Another embodiment of the invention is a method of preventing overdose of a pharmaceutical composition, comprising consuming said pharmaceutical composition, wherein said composition comprises a chemical moiety covalently attached to active agent in a manner that substantially decreases the potential of overdose from the active agent.

Another embodiment of the invention is a method for reducing or preventing the euphoric effect of a pharmaceutical composition, comprising providing, administering, or prescribing said composition to a human in need thereof, wherein said composition comprises a chemical moiety covalently attached to an active agent such that the pharmacological activity of active agent is substantially decreased when the composition is used in a manner inconsistent with the manufacturer's instructions. Another embodiment of the invention is a method for reducing or preventing the euphoric effect of a pharmaceutical composition, comprising consuming said composition, wherein said composition comprises a chemical moiety covalently attached to an active agent such that the pharmacological activity of active agent is substantially decreased when the composition is used in a manner inconsistent with the manufacturer's instructions.

Another embodiment of the invention is any of the preceding methods wherein said pharmaceutical composition is adapted for oral administration, and wherein said active agent is resistant to release from said chemical moiety when the composition is administered parenterally, such as intranasally or intravenously. Preferably, said active agent may be released from said chemical moiety in the presence of acid and/or enzymes present in the stomach, intestinal tract, or blood serum. Optionally, said composition may be in the form of a tablet, capsule, oral solution, or oral suspension.

Another embodiment of the invention is any of the preceding methods wherein said chemical moiety is an amino acid, oligopeptide, polypeptide, carbohydrate, glycopeptide, nucleic acid, or vitamin. Preferably, said chemical moiety is an amino acid, oligopeptide, or polypeptide. Where the chemical moiety is a polypeptide, preferably said polypeptide comprises fewer than 70 amino acids, fewer than 50 amino acids, fewer than 10 amino acids, or fewer than 6 amino acids.

Another embodiment of the invention is any of the preceding methods wherein said covalent attachment comprises an ester or carbonate bond. Another embodiment of the invention is any of the preceding methods wherein said active agent covalently attaches to a chemical moiety through a ketone and/or hydroxyl in a pharmaceutically acceptable oral dosage form.

Another embodiment of the invention is any of the preceding methods wherein said composition yields a therapeutic effect without substantial euphoria. Preferably, said active agent provides a therapeutically bioequivalent AUC when compared to active agent alone but does provide a $C_{max}$ which results in euphoria.

Another embodiment of the invention is a method for reducing or preventing abuse of a pharmaceutical composition, comprising orally administering said composition to a human in need thereof, wherein said composition comprises an amino acid or peptide covalently attached to active agent such that the pharmacological activity of active agent is substantially decreased when the composition is used in a manner inconsistent with the manufacturer's instructions.

Another embodiment is a method of preventing overdose of a pharmaceutical composition, comprising orally administering said pharmaceutical composition to a human in need thereof, wherein said composition comprises an amino acid or peptide covalently attached to active agent in a manner that substantially decreases the potential of active agent to result in overdose.

Another embodiment is a method for reducing or preventing the euphoric effect of a pharmaceutical composition, comprising orally administering said composition to a human in need thereof, wherein said composition comprises an amino acid or peptide covalently attached to active agent such that the pharmacological activity of active agent is substantially decreased when the composition is used in a manner inconsistent with the manufacturer's instructions.

For each of the recited methods of the invention the following properties may be achieved through bonding active agent to the chemical moiety. In one embodiment, the toxicity of the compound may be substantially lower than that of the active agent when delivered in its unbound state or as a salt thereof. In another embodiment, the possibility of overdose by oral administration is reduced or eliminated. In another embodiment, the possibility of overdose by intranasal administration is reduced or eliminated. In another embodiment, the possibility of overdose by injection administration is reduced or eliminated.

Another embodiment of the invention provides methods of treating various diseases or conditions comprising administering compounds or compositions of the invention which further comprise commonly prescribed active agents for the respective illness or diseases wherein the amphetamine is covalently attached to a chemical moiety. For instance, one embodiment of the invention comprises a method of treating attention deficit hyperactivity comprising administering to a patient amphetamine covalently bound to a chemical moiety. Another embodiment provides a method of treating attention deficit hyperactivity disorder (ADHD) comprising administering to a patient compounds or compositions of the invention, such as amphetamine covalently bound to a chemical moiety. Another embodiment provides a method of treating attention deficit disorder (ADD) comprising administering to a patient compounds or compositions of the invention, amphetamine covalently bound to a chemical moiety.

Another embodiment of the invention provides a method of treating cognitive decline associated with acquired immunodeficiency syndrome (AIDS) or AIDS-related complex comprising administering to a patient compounds or compositions of the invention.

Another embodiment of the invention provides a method of treating depression comprising administering to a patient compounds or compositions of the invention. Another embodiment of the invention provides a method of treating anxiety and anxiety related disorders comprising administering to a patient compounds or compositions of the invention. Another embodiment of the invention provides a method of treating psychosis comprising administering to a patient compounds or compositions of the invention.

Another embodiment of the invention provides a method of treating nicotine addiction comprising administering to a patient compounds or compositions of the invention. Another embodiment of the invention provides a method of treating narcotic addiction comprising administering to a patient compounds or compositions of the invention. Another embodiment of the invention provides a method of treating alcoholism comprising administering to a patient compounds or compositions of the invention.

Another embodiment of the invention provides a method of treating narcolepsy comprising administering to a patient compounds or compositions of the invention. Another embodiment of the invention provides a method of providing analgesia comprising administering to a patient compounds or compositions of the invention.

In order to facilitate a more complete understanding of the invention, Examples are provided below. However, the scope of the invention is not limited to specific embodiments disclosed in these Examples, which are for purposes of illustration only.

EXAMPLES

The invention is illustrated by pharmacokinetic studies with amphetamine, hydrocodone, and oxycodone that have been covalently modified by attachment to various moieties such as an individual amino acid, specific short chained amino acid sequences such as di-, tri-, and pentapeptides, or carbohydrates such as ribose, etc. Studies include pharmacokinetic evaluations of the various drug conjugates administered by the oral, intranasal, and intravenous routes. Collectively the compounds demonstrate that active agents may be modified by covalent attachment to various moieties and retain their therapeutic value at normal doses while preventing potential overdose by oral administration and prevention of abuse through intranasal and intravenous administration.

Carrier Bound Amphetamine

Examples 1 through 32 demonstrate the use and effectiveness of an chemical moiety conjugated to an active agent for reducing the potential for overdose while maintaining its therapeutic value wherein the amino acid lysine (K) is conjugated to the active agent amphetamine (K-amphetamine). However, the example is illustrative of the attachment of amphetamine to any variety of chemical moieties.

Further, examples of amphetamine attachment include for instance and may be synthesized through similar procedures described in examples 1-32 and throughout the specification.

A. Synthesis of Amphetamine Compositions

Example 1

General Synthesis of Amino Acid-amphetamine Conjugates

Amino acid conjugates were synthesized by the general method described in FIGS. 1-5.

Example 2

Synthesis of L-lysine-d-amphetamine

L-lysine-d-amphetamine was synthesized (see FIG. 2) by the following method:
 a. Coupling

| Reagents | MW | Weight | mmoles | Molar Equivalents |
|---|---|---|---|---|
| d-amphetamine freebase | 135.2 | 4.75 g | 35.13 | 1 |
| Boc-Lys(Boc)-OSu | 443.5 | 15.58 g | 35.13 | 1 |
| Di-iPr-Et-Amine | 129 | 906 mg | 7.03 | 0.2, d = 0.74, 1.22 mL |
| 1,4-Dioxane | — | 100 mL | — | — |

To a solution of Boc-Lys(Boc)-OSu (15.58 g, 35.13 mmol) in dioxane (100 mL) under an inert atmosphere was added d-amphetamine freebase (4.75 g, 35.13 mmol) and DiPEA (0.9 g, 1.22 mL, 7.03 mmol). The resulting mixture was allowed to stir at room temperature overnight. Solvent and excess base were then removed using reduced pressure evaporation. The crude product was dissolved in ethyl acetate and loaded on to a flash column (7 cm wide, filled to 24 cm with silica) and eluted with ethyl acetate. The product was isolated; the solvent reduced by rotary evaporation and the purified protected amide was dried by high-vac to obtain a white solid. $^1$H NMR (DMSO-$d_6$) δ 1.02-1.11 (m, 2H, Lys γ-CH$_2$), δ 1.04 (d, 3H, Amp α-CH$_3$), δ 1.22-1.43 (m, 4H, Lys-β and δ-CH$_2$), δ 1.37 (18H, Boc, 6× CH$_3$), δ 2.60-2.72 (2H, Amp CH$_2$), δ 3.75-3.83 (m, 1H, α-H) δ 3.9-4.1 (m, 1H, Amp α-H), δ 6.54-6.61 (d, 1H, amide NH), δ 6.7-6.77 (m, 1H, amide NH), δ 7.12-7.29 (m, 5H, ArH), δ 7.65-7.71 (m, 1, amide NH); mp=86-88° C.
 b. Deprotection

| Reagents | MW | Weight | mmoles | Molar Equivalents |
|---|---|---|---|---|
| 4 M HCl in dioxane | 4 mmol/mL | 50 mL | 200 | 6.25 |
| Boc-Lys(Boc)-Amp | 463.6 | 14.84 g | 32 | 1 |
| 1,4-Dioxane | — | 50 mL | — | — |

The protected amide was dissolved in 50 mL of anhydrous dioxane and stirred while 50 mL (200 mmol) of 4M HCl/dioxane was added and stirred at room temperature overnight. The solvents were then reduced by rotary evaporation to afford a viscous oil. Addition of 100 mL MeOH followed by rotary evaporation resulted in a golden colored solid material that was further dried by storage at room temperature under high vacuum. $^1$H NMR (DMSO-$d_6$) δ 0.86-1.16 (m, 2H, Lys γ-CH$_2$), δ 1.1 (d, 3H, Amp α-CH$_3$), δ 1.40-1.56 (m, 4H, Lys-β and δ-CH$_2$), δ 2.54-2.78 (m, 2H, Amp CH$_2$, 2H, Lys ε-CH$_2$), 3.63-3.74 (m, 1H, Lys α-H), δ 4.00-4.08 (m, 1H, Amp α-H), δ 7.12-7.31 (m, 5H, Amp ArH), δ 8.13-8.33 (d, 3H, Lys amine) δ 8.70-8.78 (d, 1H, amide NH); mp=120-122° C.

Example 3

Synthesis of Ser-Amp

Ser-Amp was synthesized by a similar method (see FIG. 3) except the amino acid starting material was Boc-Ser(O-tBu)-OSu and the deprotection was done using a solution of trifluoroacetic acid instead of HCl.

Example 4

Synthesis of Phe-Amp

Phe-Amp was synthesized by a similar method (see FIG. 4) except the amino acid starting material was Boc-Phe-OSu.

Example 5

Synthesis of Gly$_3$-Amp

Gly$_3$-Amp was synthesized by a similar method (see FIG. 5) except the amino acid starting material was Boc-GGG-OSu.

B. Pharmacokinetics of L-lysine-d-amphetamine

ELISA Analysis

Example 6

Pharmacokinetics of L-lysine-d-amphetamine Compared to d-amphetamine Sulfate

Male Sprague-Dawley rats were provided water ad libitum, fasted overnight and dosed by oral gavage L-lysine-d-amphetamine or d-amphetamine sulfate. In all studies doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. L-lysine-d-amphetamine was also determined to be essentially unreactive in the ELISA (<1%).

Figure 6:
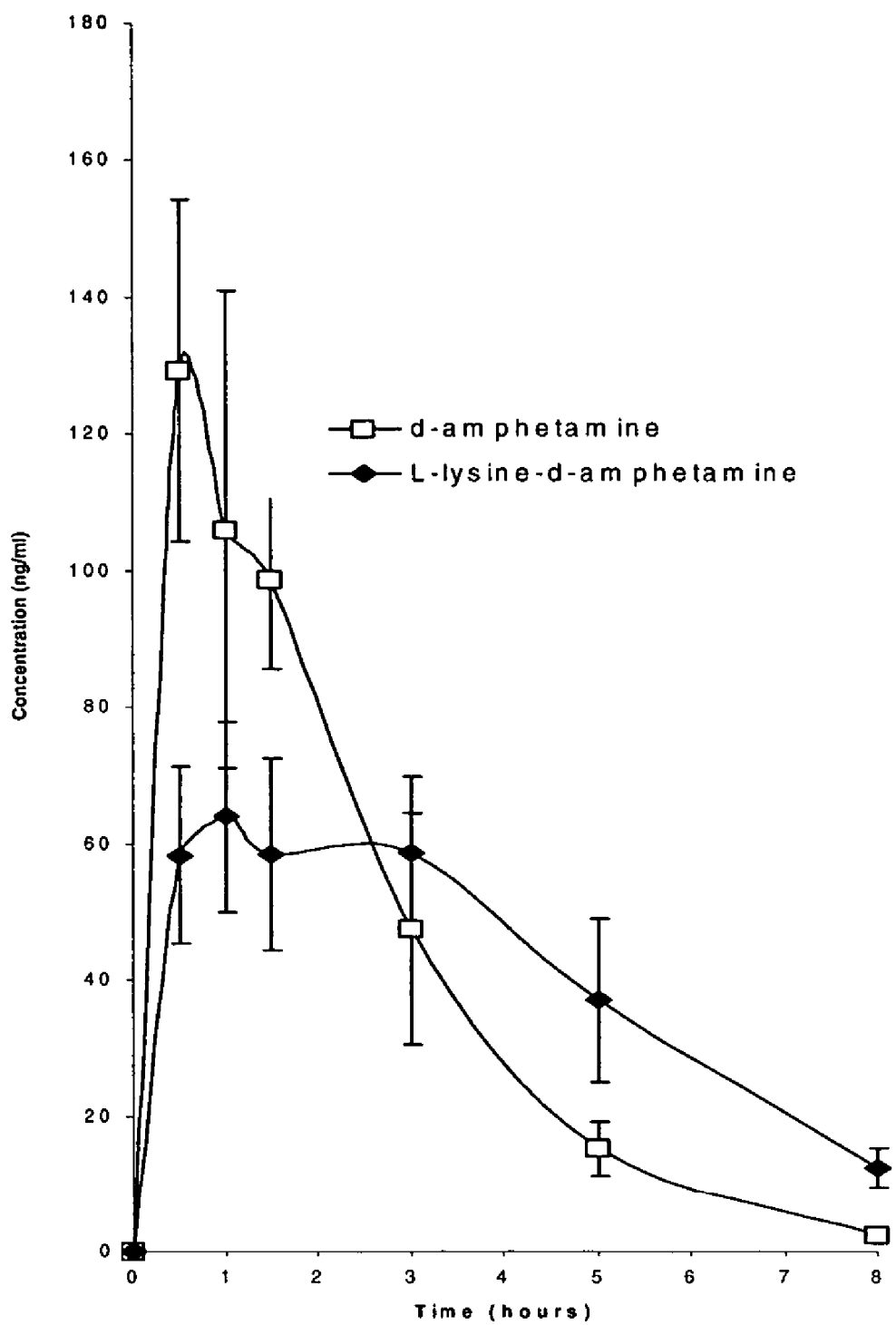
FIG. 6. Plasma concentrations of d-amphetamine from individual animals orally administered d-amphetamine or L-lysine-d-amphetamine.

Mean (n=4) plasma concentration curves of d-amphetamine or L-lysine-d-amphetamine are shown in FIG. 6. Extended release was observed in all four L-lysine-d-amphetamine dosed animals and $C_{max}$ was substantially decreased as compared to animals dosed with d-amphetamine sulfate. Plasma d-amphetamine concentrations of individual animals for d-amphetamine or L-lysine-d-amphetamine are shown in Table 1. The mean plasma d-amphetamine concentrations are shown in Table 2. The time to peak concentration for L-lysine-d-amphetamine was similar to that of d-amphetamine. Pharmacokinetic parameters for oral administration of d-amphetamine or L-lysine-d-amphetamine are summarized in Table 3.

TABLE 1

Plasma Concentrations of d-amphetamine from Individual Animals Orally Administered d-amphetamine or L-lysine-d-amphetamine (3 mg/kg d-amphetamine base).

| Time (hours) | d-amphetamine (ng/ml) | | | | L-lysine-d-amphetamine (ng/ml) | | | |
| --- | --- | --- | --- | --- | --- | --- | --- | --- |
| | Rat #1 | Rat #2 | Rat #3 | Rat #4 | Rat #1 | Rat #2 | Rat #3 | Rat #4 |
| 0.5 | 144 | 157 | 101 | 115 | 52 | 62 | 74 | 44 |
| 1 | 152 | 78 | 115 | 78 | 48 | 72 | 79 | 57 |
| 1.5 | 85 | 97 | 117 | 95 | 42 | 62 | 76 | 53 |
| 3 | 34 | 45 | 72 | 38 | 61 | 60 | 71 | 43 |
| 5 | 20 | 14 | 12 | 15 | 49 | 33 | 44 | 22 |
| 8 | 3 | 3 | 2 | 2 | 15 | 14 | 12 | 8 |

TABLE 2

Mean Plasma Concentrations of d-amphetamine Following Oral Administration of d-amphetamine or L-lysine-d-amphetamine.

| | Plasma d-amphetamine Concentrations (ng/ml) | | | | | |
| --- | --- | --- | --- | --- | --- | --- |
| | d-amphetamine | | | L-lysine-d-amphetamine | | |
| Hours | Mean | +/−SD | CV | Mean | +/−SD | CV |
| 0.5 | 129 | 25 | 20 | 58 | 13 | 22 |
| 1 | 106 | 35 | 33 | 64 | 14 | 22 |
| 1.5 | 99 | 13 | 14 | 58 | 14 | 25 |
| 3 | 47 | 17 | 36 | 59 | 11 | 19 |
| 5 | 15 | 4 | 24 | 37 | 12 | 32 |
| 8 | 2 | 1 | 35 | 12 | 3 | 24 |

TABLE 3

Pharmacokinetic Parameters of d-amphetamine Following Oral Administration of d-amphetamine or L-lysine-d-amphetamine.

| Drug | AUC (0-8 h) ng/ml h | Percent Amphetamine | Cmax (ng/ml) | Percent Amphetamine | Mean Peak (ng/ml) | Percent Amphetamine |
| --- | --- | --- | --- | --- | --- | --- |
| Amphetamine | 341 +/− 35 | 100 | 111 +/− 27 | 100 | 129 | 100 |
| Lys-Amp | 333 +/− 66 | 98 | 61 +/− 13 | 55 | 64 | 50 |

Example 6 illustrates that when lysine is conjugated to the active agent amphetamine the peak levels of amphetamine are decreased while bioavailability is maintained approximately equal to amphetamine. The bioavailability of amphetamine released from L-lysine-d-amphetamine is similar to that of amphetamine sulfate at the equvalent dose, thus L-lysine-d-amphetamine maintains its therapeutic value. The gradual release of amphetamine from L-lysine-d-amphetamine and decrease in peak levels reduce the possibility of overdose.

Example 7

Figure 7:
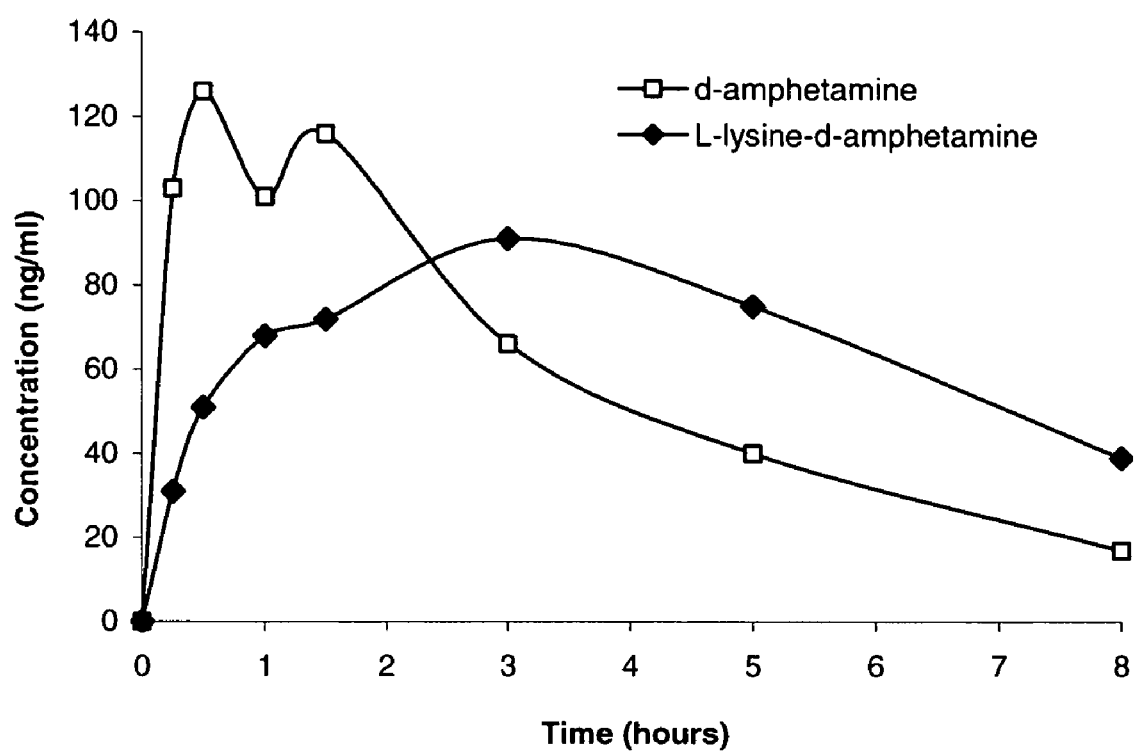
FIG. 7. Plasma concentrations of d-amphetamine following oral administration of d-amphetamine sulfate or L-lysine-d-amphetamine (1.5 mg/kg d-amphetamine base) to rats (ELISA analysis).
Figure 8:
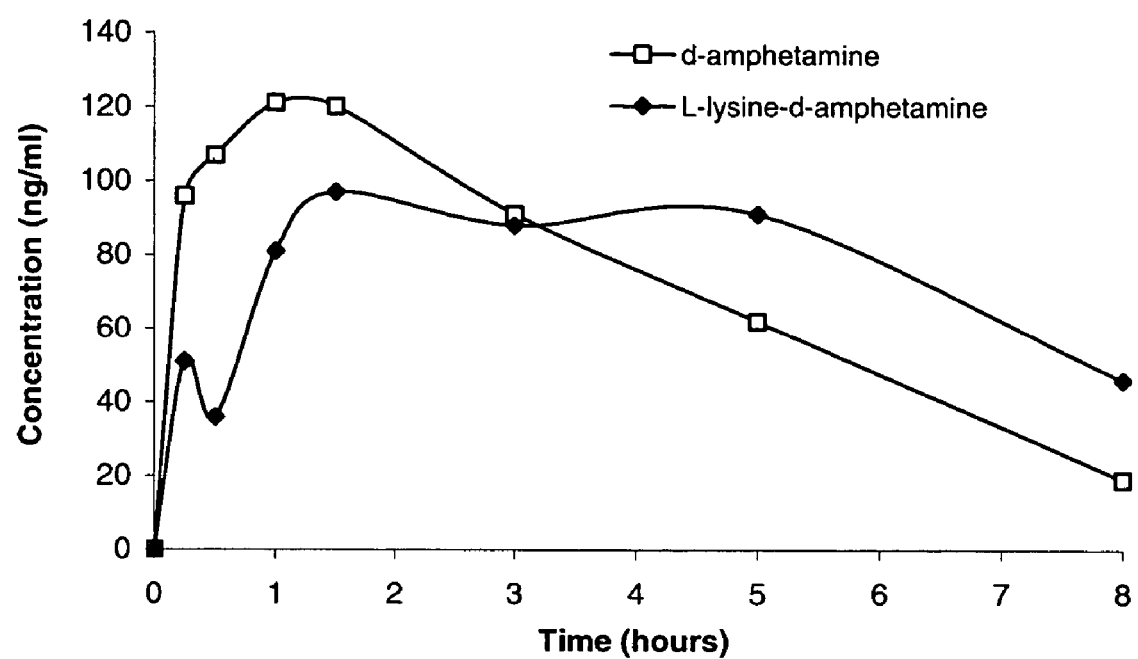
FIG. 8. Plasma concentrations of d-amphetamine following oral administration of d-amphetamine sulfate or L-lysine-d-amphetamine (3 mg/kg d-amphetamine base) to rats (ELISA analysis).
Figure 9:
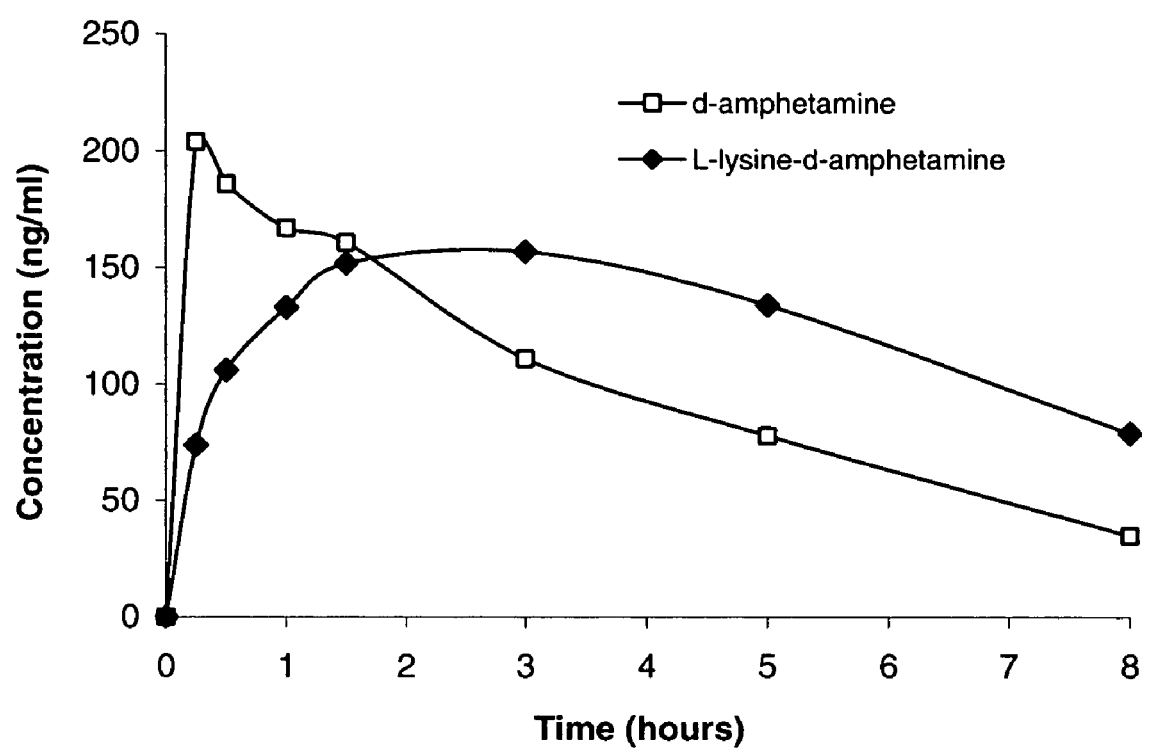
FIG. 9. Plasma concentrations of d-amphetamine following oral administration of d-amphetamine sulfate or L-lysine-d-amphetamine (6 mg/kg d-amphetamine base) to rats (ELISA analysis).

Oral Bioavailability of L-lysine-d-amphetamine at Various Doses Approximating a Range of Therapeutic Human Doses Mean (n=4) plasma concentration curves of d-amphetamine vs. L-lysine-d-amphetamine are shown for rats orally administered 1.5, 3, and 6 mg/kg in FIGS. 7, 8 and 9, respectively. Extended release was observed at all three doses for L-lysine-d-amphentamine dosed animals. The mean plasma concentrations for 1.5, 3, and 6 mg/kg are shown in Tables 4, 5 and 6, respectively. Pharmacokinetic parameters for oral administration of d-amphetamine vs. L-lysine-d-amphetamine at the various doses are summarized in Table 7.

TABLE 4

Mean Plasma Concentrations of d-amphetamine vs. L-lysine-d-amphetamine Following Oral Admistration (1.5 mg/kg)

| | Plasma Amphetamine Concentrations (ng/ml) | | | | | |
| --- | --- | --- | --- | --- | --- | --- |
| | d-amphetamine | | | L-lysine-d-amphetamine | | |
| Hours | Mean | +/−SD | CV | Mean | +/−SD | CV |
| 0 | 0 | 0 | 0 | 0 | 0 | 0 |
| 0.25 | 103 | 22 | 21 | 31 | 11 | 37 |
| 0.5 | 126 | 20 | 16 | 51 | 23 | 45 |
| 1 | 101 | 27 | 27 | 68 | 23 | 34 |
| 1.5 | 116 | 28 | 24 | 72 | 10 | 14 |
| 3 | 66 | 13 | 20 | 91 | 5 | 5 |
| 5 | 40 | 7 | 18 | 75 | 16 | 22 |
| 8 | 17 | 2 | 15 | 39 | 13 | 34 |

TABLE 5

Mean Plasma Concentrations of d-amphetamine vs. L-lysine-d-amphetamine Following Oral Admistration (3 mg/kg)

| | Plasma Amphetamine Concentrations (ng/ml) | | | | | |
| --- | --- | --- | --- | --- | --- | --- |
| | d-amphetamine | | | L-lysine-d-amphetamine | | |
| Hours | Mean | +/−SD | CV | Mean | +/−SD | CV |
| 0 | 0 | | | 0 | | |
| 0.25 | 96 | 41 | 43 | 51 | 49 | 97 |
| 0.5 | 107 | 49 | 46 | 36 | 35 | 96 |
| 1 | 121 | 17 | 14 | 81 | 44 | 54 |
| 1.5 | 120 | 33 | 27 | 97 | 32 | 33 |
| 3 | 91 | 30 | 33 | 88 | 13 | 15 |
| 5 | 62 | 22 | 36 | 91 | 21 | 23 |
| 8 | 19 | 6 | 33 | 46 | 16 | 34 |

TABLE 6

Mean Plasma Concentrations of d-amphetamine vs.
L-lysine-d-amphetamine Following Oral Administration (6 mg/kg).

Plasma Amphetamine Concentrations (ng/ml)

| | d-amphetamine | | | L-lysine-d-amphetamine | | |
|---|---|---|---|---|---|---|
| Hours | Mean | +/−SD | CV | Mean | +/−SD | CV |
| 0 | 0 | | | 0 | | |
| 0.25 | 204 | 14 | 7 | 74 | 38 | 51 |
| 0.5 | 186 | 9 | 5 | 106 | 39 | 37 |
| 1 | 167 | 12 | 7 | 133 | 33 | 24 |
| 1.5 | 161 | 24 | 15 | 152 | 22 | 15 |
| 3 | 111 | 29 | 26 | 157 | 15 | 10 |
| 5 | 78 | 9 | 11 | 134 | 18 | 13 |
| 8 | 35 | 5 | 15 | 79 | 12 | 15 |

TABLE 7

Pharmacokinetic Parameters of d-amphetamine Following Oral Administration of d-amphetamine or L-lysine-d-amphetamine.

| | 1.5 mg/kg | | 3 mg/kg | | 6 mg/kg | |
|---|---|---|---|---|---|---|
| Parameter | d-amphetamine | L-lysine-d-amphetamine | d-amphetamine | L-lysine-d-amphetamine | d-amphetamine | L-lysine-d-amphetamine |
| AUC (ng/ml h) | 481 | 538 | 587 | 614 | 807 | 1005 |
| Percent | 100 | 112 | 100 | 105 | 100 | 125 |
| Cmax (ng/ml) | 133 | 93 | 587 | 614 | 807 | 1005 |
| Percent | 100 | 70 | 100 | 105 | 100 | 125 |
| Tmax (hours) | 0.938 | 3.5 | 1 | 1.56 | 0.563 | 2.625 |
| Percent | 100 | 373 | 100 | 156 | 100 | 466 |

Example 8

Oral Bioavailability of L-lysine-d-amphetamine at Various Doses Approximating a Range of Therapeutic Human Doses Compared to a Suprapharmacological Dose Male Sprague-Dawley rats were provided water ad libitum, fasted overnight and dosed by oral gavage with 1.5, 3, 6, 12, and 60 mg/kg of amphetamine sulfate or L-lysine-d-amphetamine containing the equivalent amounts of d-amphetamine. Concentrations of d-amphetamine were measured by ELISA.

Figure 10:
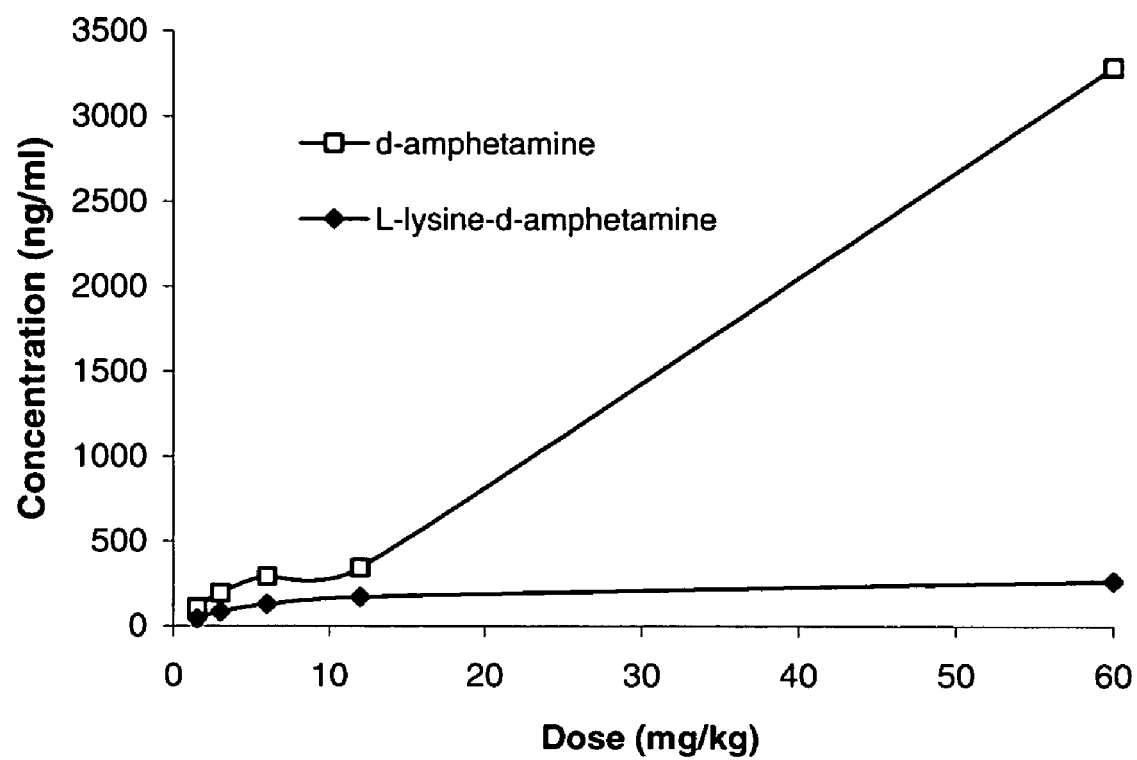
FIG. 10. Plasma concentrations of d-amphetamine at 30-minutes post-dose for escalating doses of L-lysine-d-amphetamine or d-amphetamine sulfate (ELISA analysis).

It has been demonstrated that when lysine is conjugated to the active agent d-amphetamine the levels of d-amphetamine at 30 minutes post-administration are decreased by approximately 50% over a dose range of 1.5 to 12 mg/kg. However, when a suprapharmcological dose (60 mg/kg) is given the levels of d-amphetamine from L-lysine-d-amphetamine only reached 8% of those seen for d-amphetamine sulfate (Tables 8 and 9, FIG. 10). The substantial decrease in oral bioavailability at a high dose greatly reduces the abuse potential of L-lysine-d-amphetamine.

TABLE 8

Levels of d-amphetamine vs. Dosage at 0.5 h Post Dosing with d-amphetamine Sulfate.

| | Dose mg/kg | | | | |
|---|---|---|---|---|---|
| | 1.5 | 3 | 6 | 12 | 60 |
| ng/ml 0.5 h | 109 +/− 59 | 196 +/− 72 | 294 +/− 202 | 344 +/− 126 | 3239 +/− 73 |
| Percent | 100 | 100 | 100 | 100 | 100 |

TABLE 9

Levels of d-amphetamine vs. Dosage at 0.5 h Post Dosing with L-lysine-d-amphetamine.

| | Dose mg/kg | | | | |
|---|---|---|---|---|---|
| | 1.5 | 3 | 6 | 12 | 60 |
| ng/ml 0.5 h | 45 +/− 10 | 86 +/− 26 | 129 +/− 46 | 172 +/− 113 | 266 +/− 18 |
| Percent | 41 | 44 | 44 | 50 | 8 |

Figure 11:
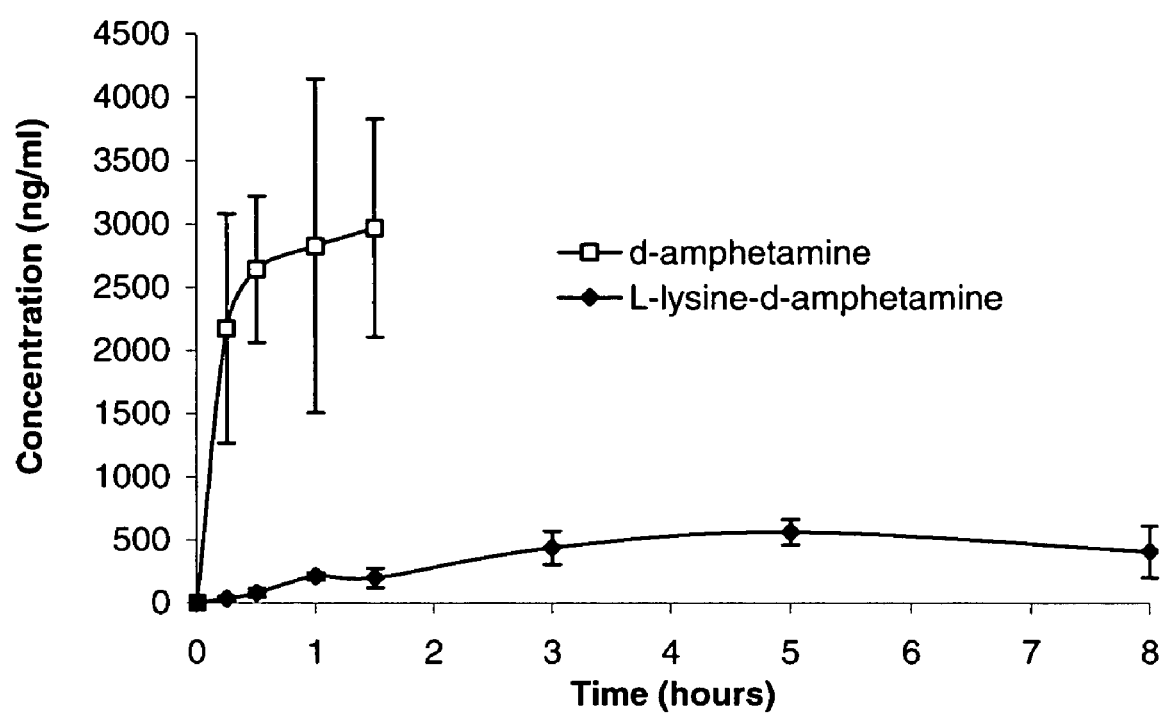
FIG. 11. Plasma concentrations of d-amphetamine following oral administration of L-lysine-d-amphetamine or d-amphetamine sulfate (60 mg/kg d-amphetamine base) to rats (ELISA analysis).

Example 9
Decreased Oral Bioavailability of L-lysine-d-amphetamine at a High Dose An additional oral PK study illustrated in FIG. 11 shows the d-amphetamine blood levels of a 60 mg/kg dose over an 8 h time course. In the case of d-amphetamine blood levels quickly reached a very high level and 8 of 12 animals either died or were sacrificed due to acute symptoms of toxicity.

Blood levels (Tables 10-11) of animals administered L-lysine-d-amphetamine, on the other hand, did not peak until 5 hours and reached only a fraction of the levels of the animals receiving amphetamine (note: valid data past 3 h for d-amphetamine could not be determined due to death and sacrifice of animals).

TABLE 10

Mean Plasma Concentrations of d-amphetamine vs. L-lysine-d-amphetamine Following Oral Administration of a High Dose (60 mg/kg).

| | Plasma Amphetamine Concentrations (ng/ml) | | | | | |
|---|---|---|---|---|---|---|
| | d-amphetamine | | | L-lysine-d-amphetamine | | |
| Hours | Mean | +/−SD | CV | Mean | +/−SD | CV |
| 0 | NA | NA | NA | NA | NA | NA |
| 0.25 | 2174 | 907 | 42 | 35 | 17 | 48 |
| 0.5 | 2643 | 578 | 22 | 81 | 33 | 41 |
| 1 | 2828 | 1319 | 47 | 212 | 30 | 14 |
| 1.5 | 2973 | 863 | 29 | 200 | 79 | 40 |
| 3 | 2944 | 95 | 3 | 440 | 133 | 30 |
| 5 | NA | NA | NA | 565 | 100 | 18 |
| 8 | NA | NA | NA | 410 | 206 | 50 |

TABLE 11

Pharmacokinetic Parameters of d-amphetamine vs. L-lysine-d-amphetamine

| Drug | AUC ng/ml h | Percent d-amphetamine | Cmax (ng/ml) | Percent d-amphetamine | Mean Peak (ng/ml) | Percent d-amphetamine |
|---|---|---|---|---|---|---|
| d-mphetamine | 8,130 | 100 | 3623 | 100 | 2973 | 100 |
| L-lysine-d-amphetamine | 3,143 | 39 | 582 | 16 | 565 | 19 |

Example 10

Figure 14:
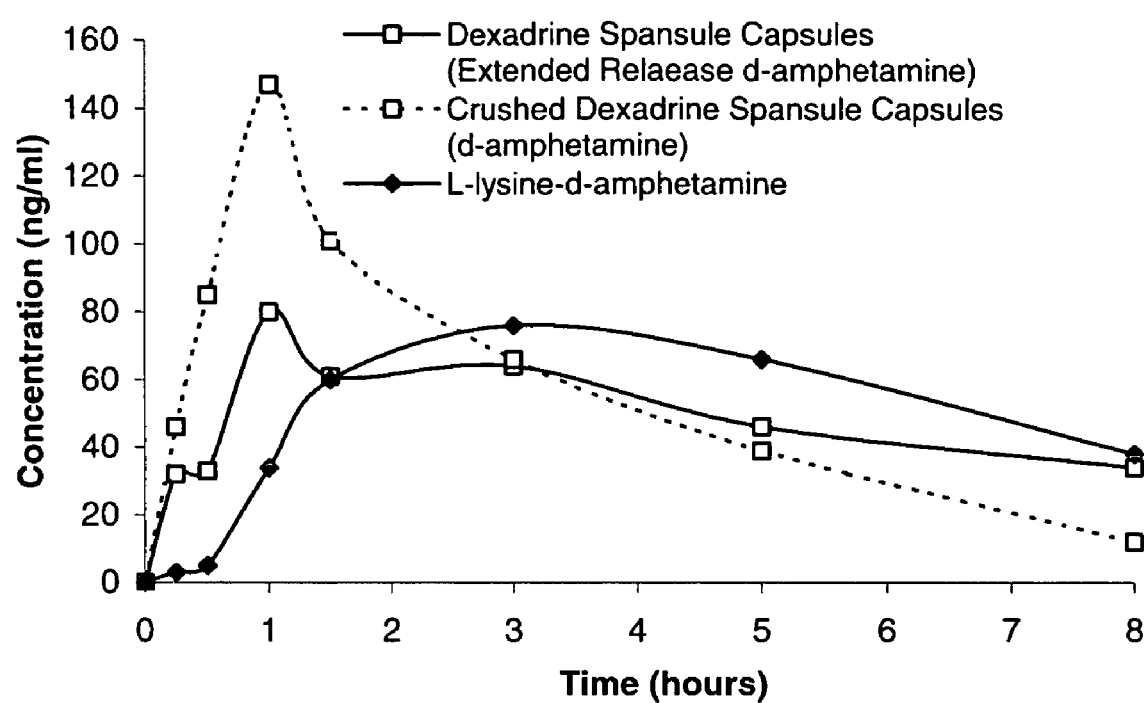
FIG. 14. Plasma concentrations of d-amphetamine levels following oral administration of Dexadrine Spansule capsules, crushed Dexadrine Spansule capsules, or L-lysine-d-amphetamine (3 mg/kg d-amphetamine base) to rats (ELISA analysis).
Figure 15A:
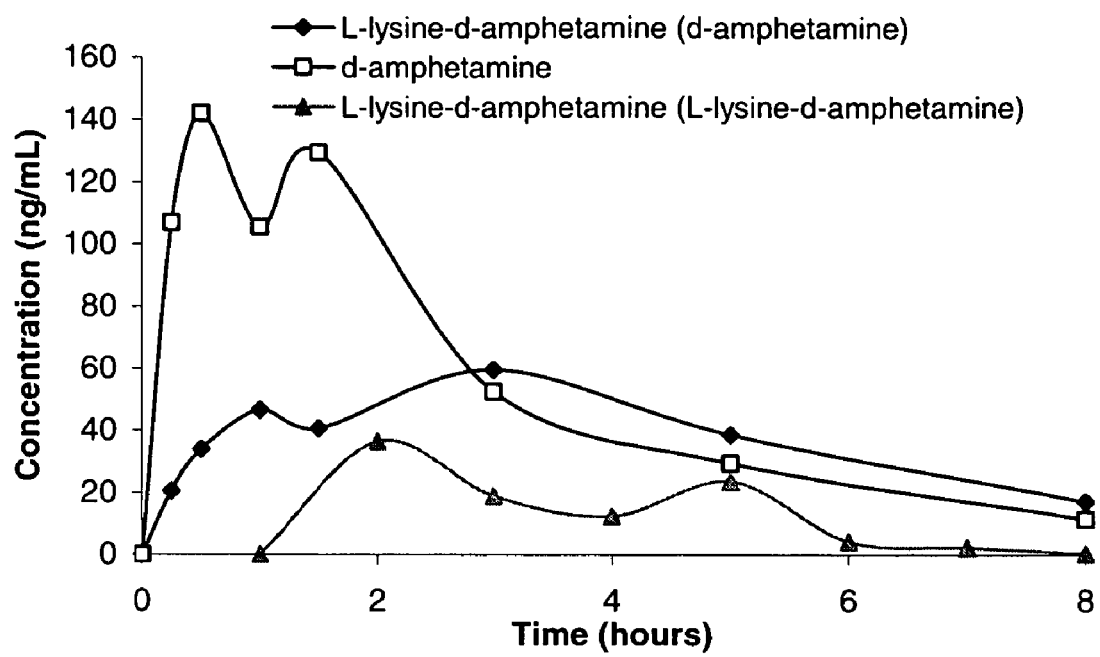
FIGS. 15A-B. Plasma concentrations of d-amphetamine in ng/mL (FIG. 15A), and in uM (FIG. 15B), following oral administration of L-lysine-d-amphetamine or d-amphetamine sulfate (1.5 mg/kg d-amphetamine base) to rats (LC/MS/MS analysis).
Figure 15B:
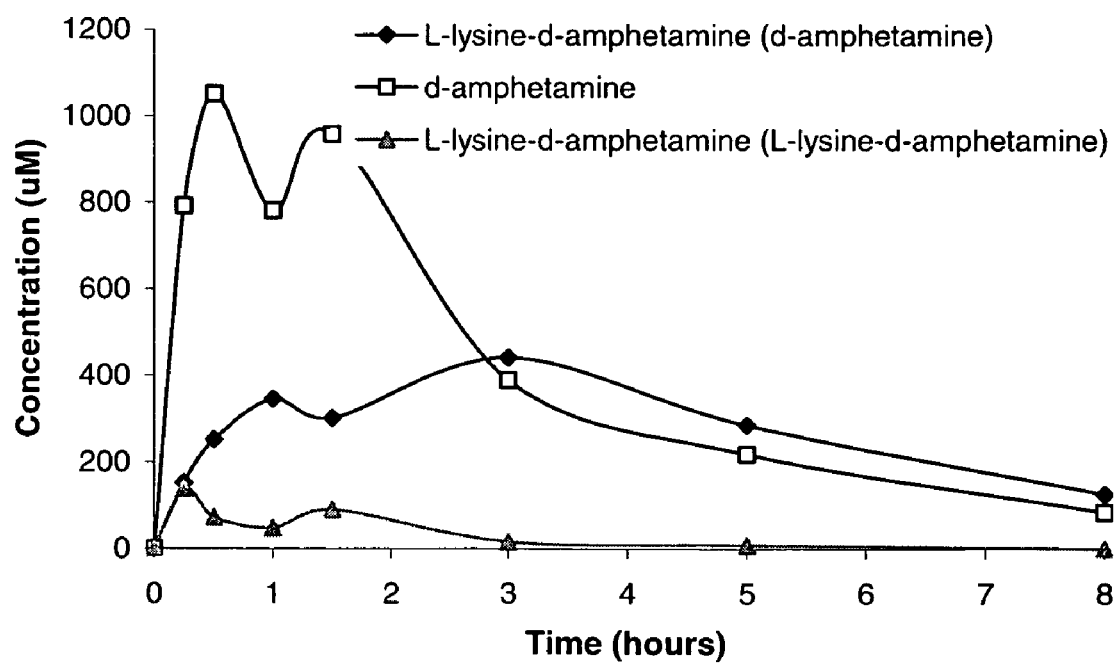
Figure 16A:
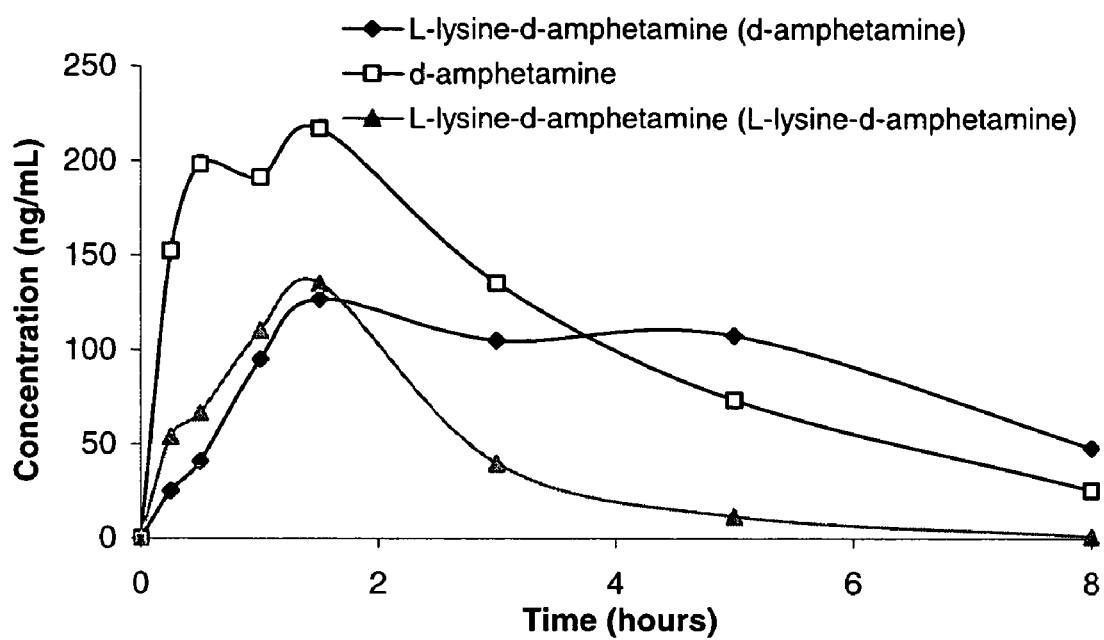
FIGS. 16A-B. Plasma concentrations of d-amphetamine in ng/mL (FIG. 16A), and in uM (FIG. 16B), following oral administration of L-lysine-d-amphetamine or d-amphetamine sulfate (3 mg/kg d-amphetamine base) to rats (LC/MS/MS analysis).
Figure 16B:
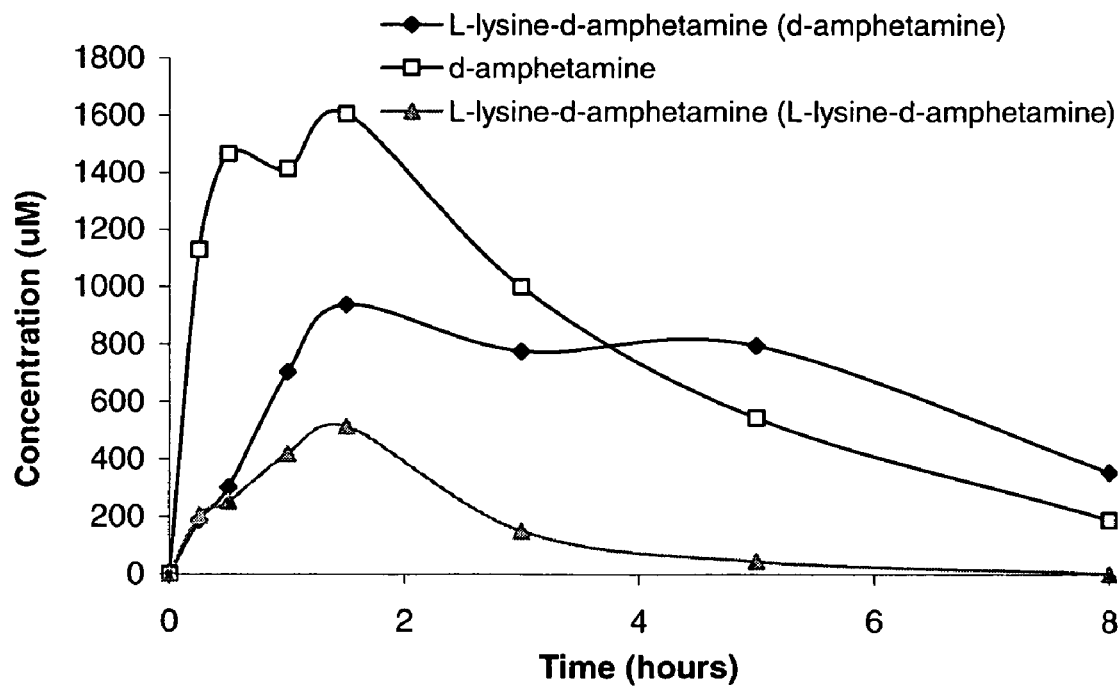
Figure 17A:
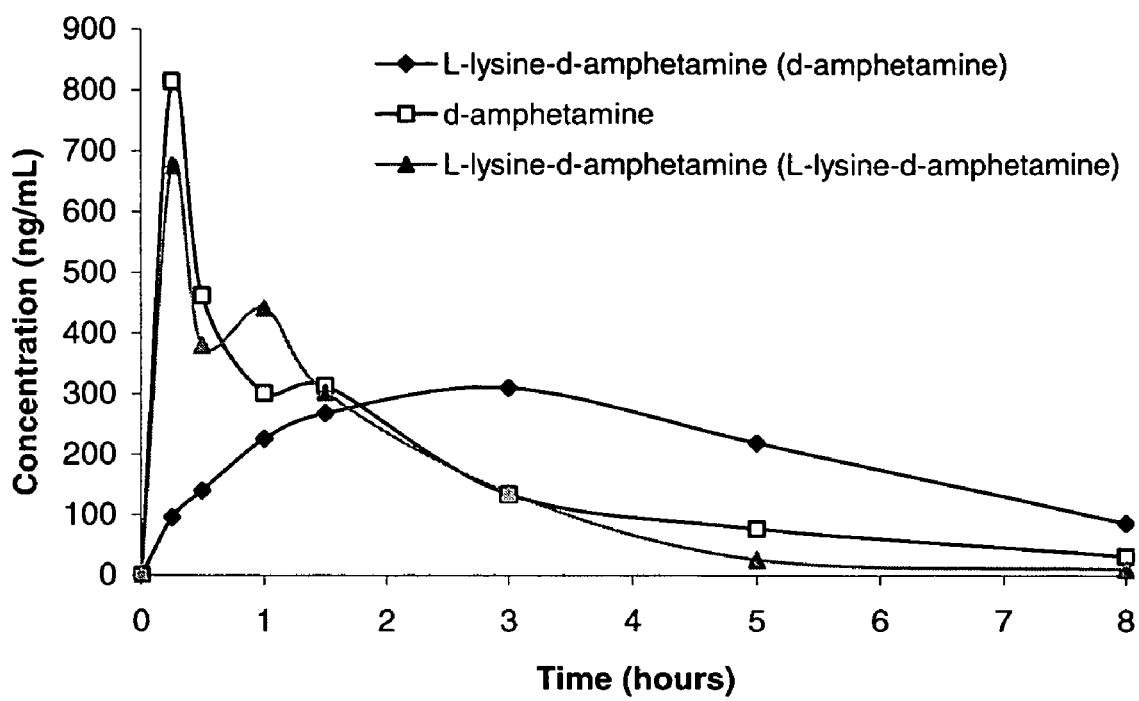
FIGS. 17A-B. Plasma concentrations of d-amphetamine in ng/mL (FIG. 17A), and in uM (FIG. 17B), following oral administration of L-lysine-d-amphetamine or d-amphetamine sulfate (6 mg/kg d-amphetamine base) to rats (LC/MS/MS analysis).
Figure 17B:
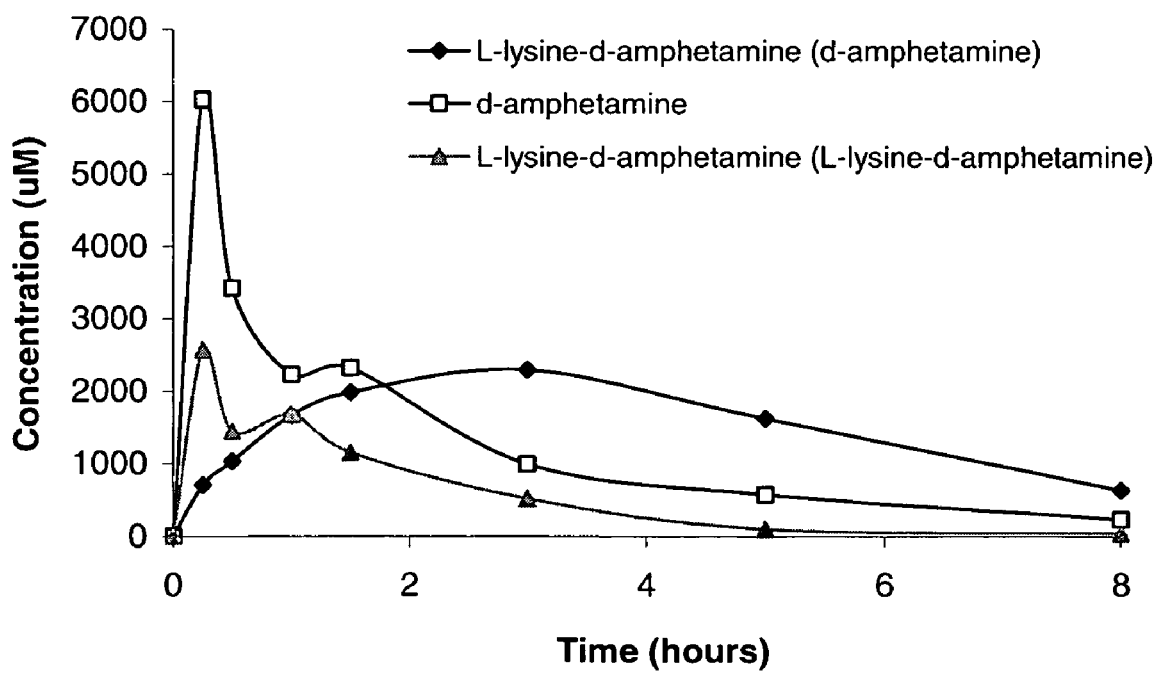
Figure 18A:
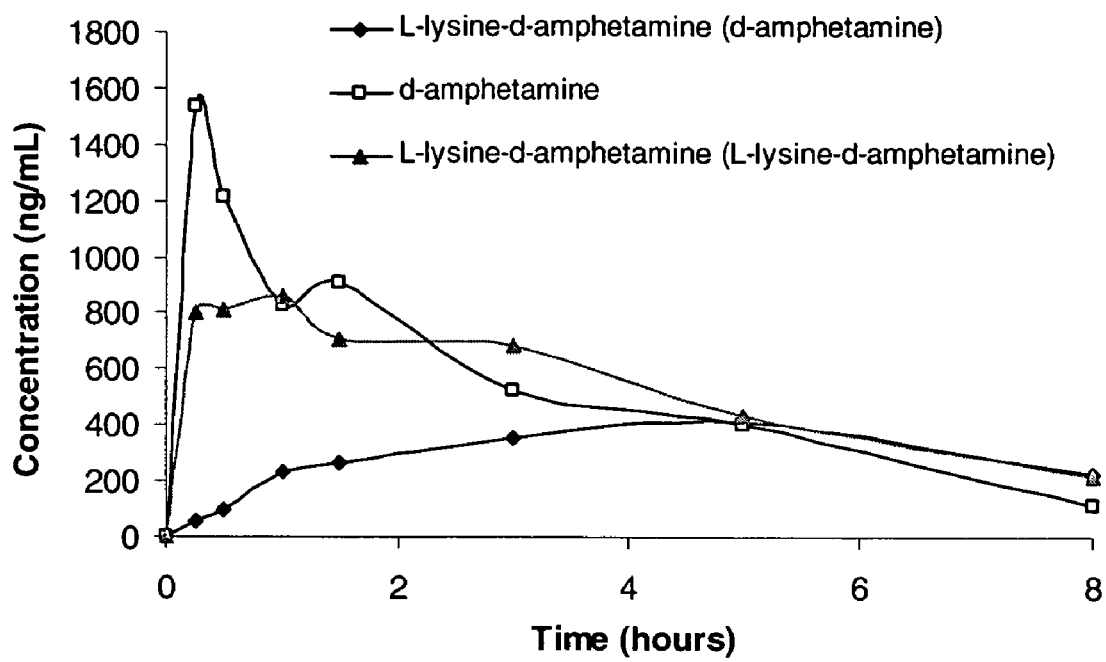
FIGS. 18A-B. Plasma concentrations of d-amphetamine in ng/mL (FIG. 18A), and in uM (FIG. 18B), following oral administration of L-lysine-d-amphetamine or d-amphetamine sulfate (12 mg/kg d-amphetamine base) to rats (LC/MS/MS analysis).
Figure 18B:
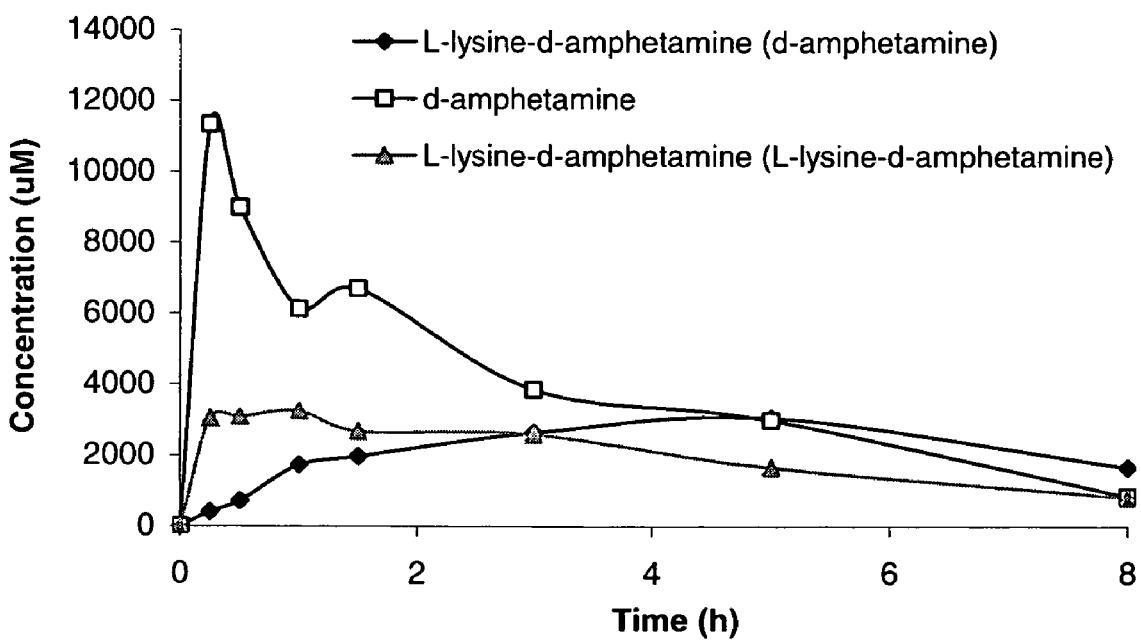
Figure 19A:
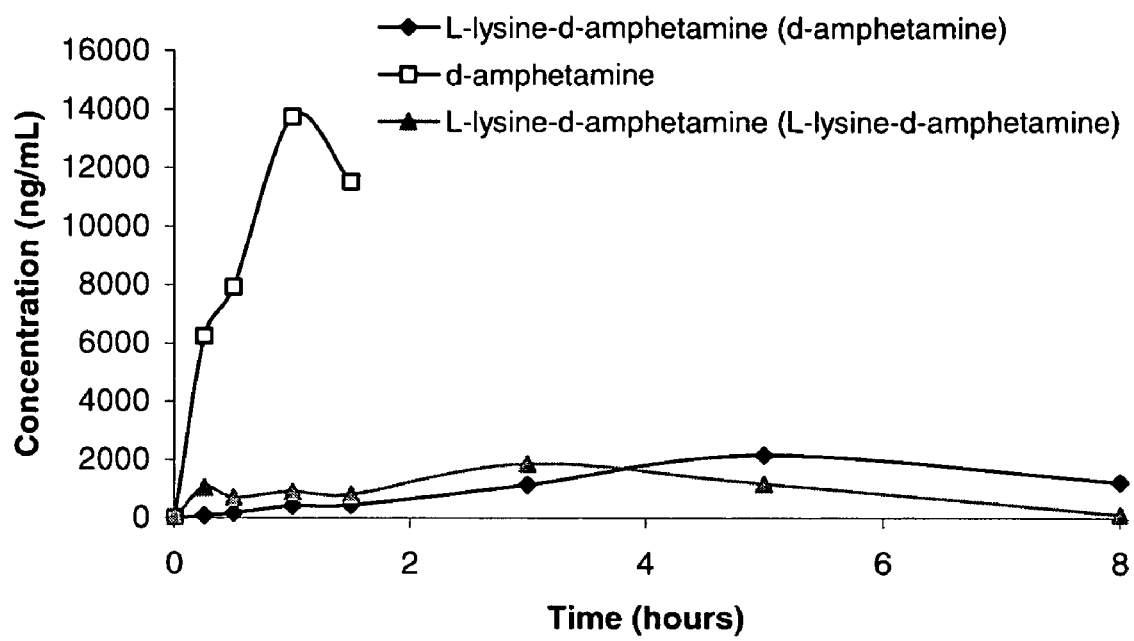
FIGS. 19A-B. Plasma concentrations of d-amphetamine in ng/m-L (FIG. 19A), and in uM (FIG. 19B), following oral administration of or d-amphetamine sulfate (60 mg/kg d-amphetamine base) to rats (LC/MS/MS analysis).
Figure 19B:
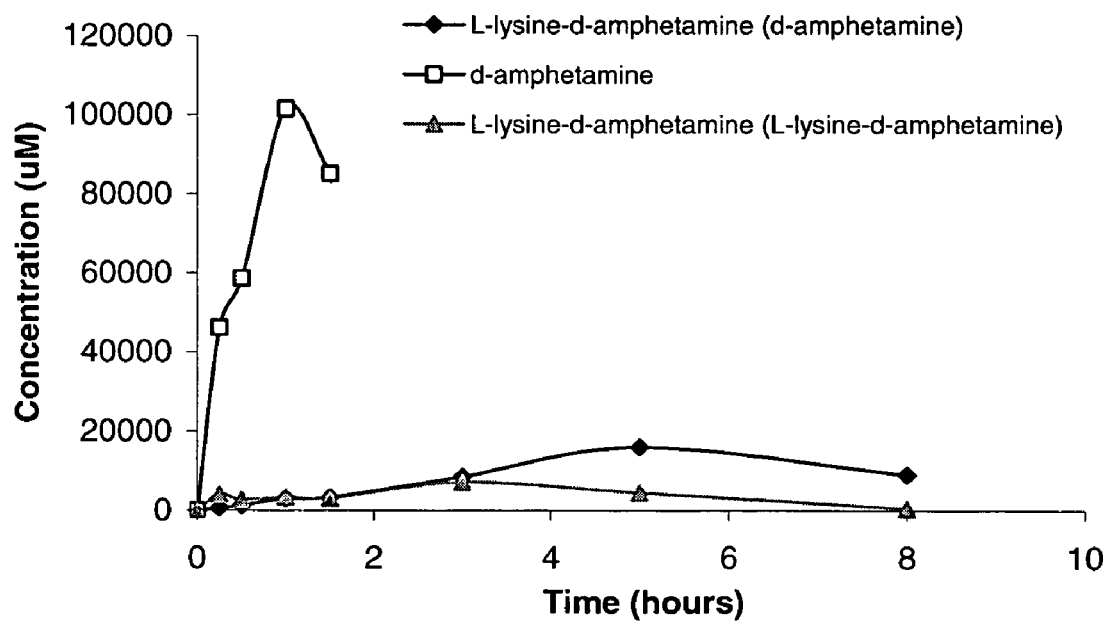

Oral Bioavailability of d-amphetamine Following Administration of an Extended Release Formulation (Intact or Crushed) or L-lysine-d-amphetamine Doses of an extended release formulation of d-amphetamine sulfate (Dexadrine Spansule capsules) were orally administered to rats as intact capsules or as crushed capsules and compared to a dose of L-lysine-d-amphetamine containing an equivalent amount of d-amphetamine base (FIG. 14). The crushed capsules showed an increase in $C_{max}$ and $AUC_{inf}$ of 84 and 13 percent, respectively, as compared to intact capsules (Tables 12-13). In contrast, $C_{max}$ and $AUC_{inf}$ of d-amphetamine following administration of L-lysine-d-amphetamine were similar to that of the intact capsule illustrating that extended release is inherent to the compound itself and can not be circumvented by simple manipulation.

TABLE 12

Time-course Concentrations of d-amphetamine Following Oral Administration of Extended Release Dexadrine Spansule Capsules or Crushed Extended Release Dexadrine Spansule Capsules or L-lysine-d-amphetamine at Doses Containing 3 mg/kg d-Amphetamine Base.

| | Plasma Concentration (ng/ml) | | |
|---|---|---|---|
| Hours | Intact Spansule Capsule | Crushed Spansule Capsule | L-lysine-d-amphetamine |
| 0 | 0 | 0 | 0 |
| 0.25 | 32 | 46 | 3 |
| 0.5 | 33 | 85 | 5 |
| 1 | 80 | 147 | 34 |
| 1.5 | 61 | 101 | 60 |
| 3 | 64 | 66 | 76 |
| 5 | 46 | 39 | 66 |
| 8 | 34 | 12 | 38 |

TABLE 13

Time-course Concentrations of d-amphetamine Following Oral Administration of Extended Release Dexadrine Spansule Capsules or Crushed Extended Release Dexadrine Spansule Capsules or L-lysine-d-amphetamine at Doses Containing 3 mg/kg d-Amphetamine Base.

| Parameter | Intact Spansule Capsule | Crushed Spansule Capsule | L-lysine-d-amphetamine |
|---|---|---|---|
| $AUC_{0-8\ h}$ (ng · h/ml) | 399 | 449 | 434 |
| Percent | 100 | 113 | 109 |
| $C_{max}$ (ng/ml) | 80 | 147 | 76 |
| Percent | 100 | 184 | 95 |
| $T_{max}$ (hours) | 1 | 1 | 3 |
| Percent | 100 | 100 | 300 |

Example 10 illustrates the advantage of the invention over conventional controlled release formulations of d-amphetamine.

Example 11

Figure 12:
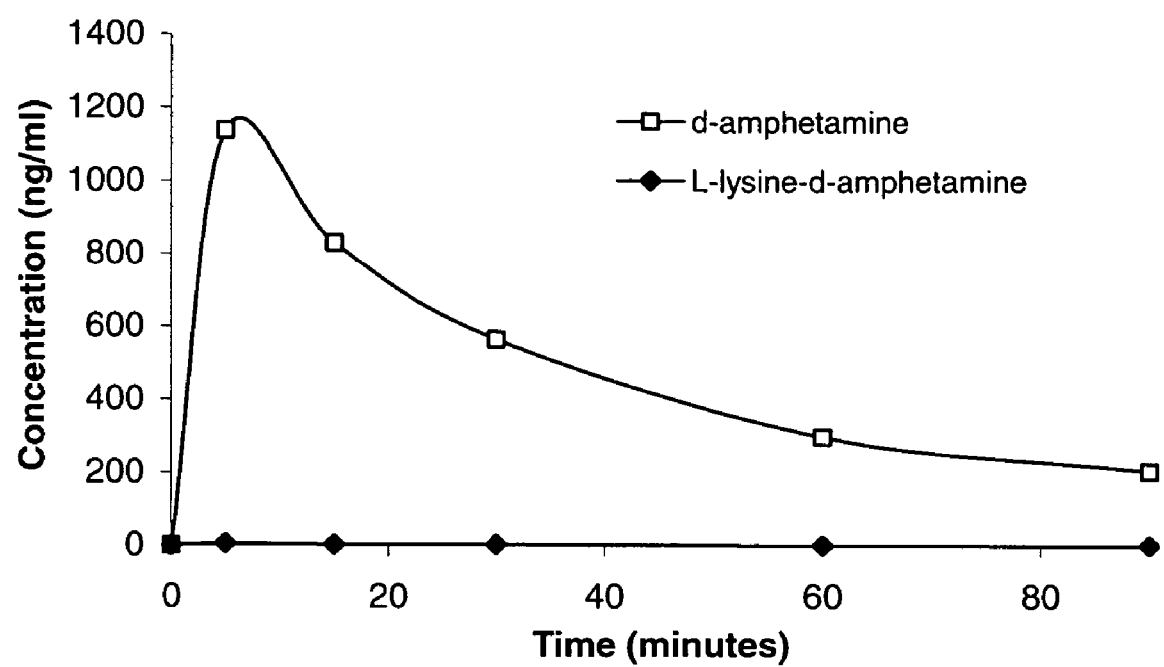
FIG. 12. Plasma concentrations of d-amphetamine following intranasal administration of L-lysine-d-amphetamine or d-amphetamine sulfate (3 mg/kg d-amphetamine base) to rats (ELISA analysis).

Decreased Intranasal Bioavailability of L-lysine-d-amphetamine vs. Amphetamine Male Sprague-Dawley rats were dosed by intranasal administration with 3 mg/kg of amphetamine sulfate or L-lysine-d-amphetamine hydrochloride containing the equivalent amounts of d-amphetamine. L-lysine-d-amphetamine did not release any significant amount of d-amphetamine into circulation by IN administration. Mean (n=4) plasma amphetamine concentration curves of amphetamine vs. L-lysine-d-amphetamine are shown in FIG. 12. Pharmacokinetic parameters for IN administration of L-lysine-d-amphetamine are summarized in Table 14.

TABLE 14

Pharmacokinetic Parameters of Amphetamine vs. L-lysine-d-amphetamine by IN Administration.

| Drug | AUC (0-1.5 h) ng/ml h | Percent d-amphetamine | Cmax (ng/ml) | Percent d-amphetamine |
|---|---|---|---|---|
| Amphetamine | 727 | 100 | 1,377 | 100 |
| L-lysine-d-amphetamine | 4 | 0.5 | 7 | 0.5 |

Example 11 illustrates that when lysine is conjugated to the active agent d-amphetamine the bioavailability by the intranasal route is substantially decreased thereby diminishing the ability to abuse the drug by this route.

Example 12

Intravenous Bioavailability of Amphetamine vs. L-lysine-d-amphetamine

Figure 13:
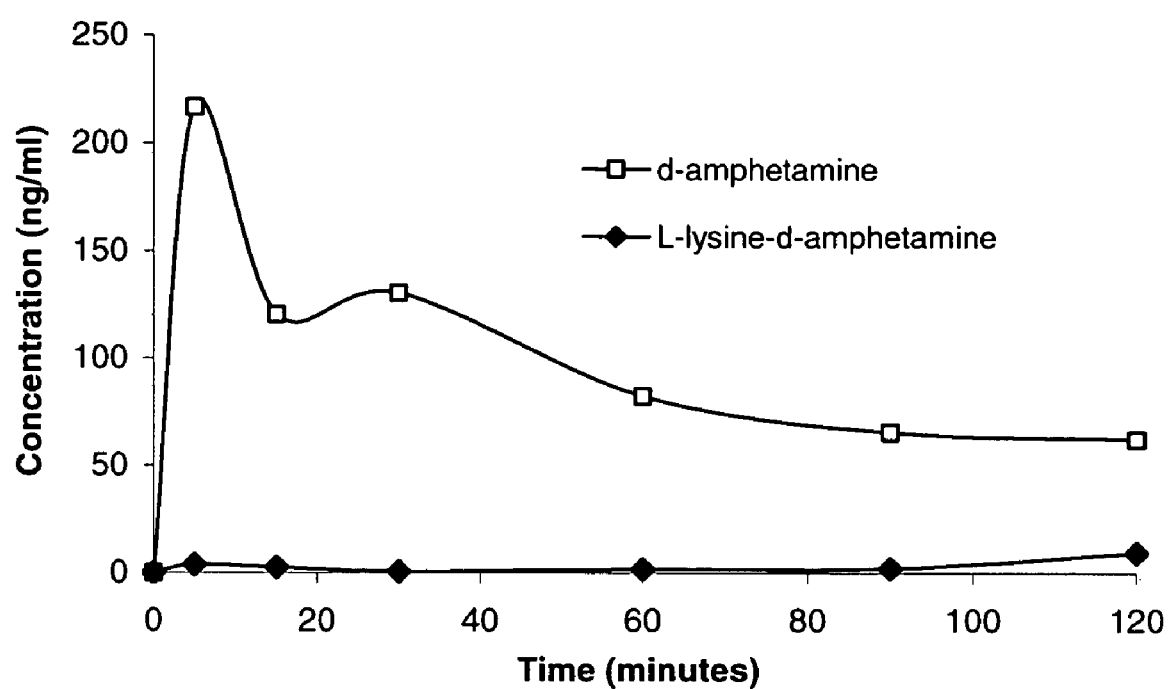
FIG. 13. Plasma concentrations of d-amphetamine following bolus intravenous administration of L-lysine-d-amphetamine or d-amphetamine sulfate (1.5 mg/kg d-amphetamine base) to rats (ELISA analysis).

Male Sprague-Dawley rats were dosed by intravenous tail vein injection with 1.5 mg/kg of d-amphetamine or L-lysine-d-amphetamine containing the equivalent amount of amphetamine. As observed with IN dosing, the conjugate did not release a significant amount of d-amphetamine. Mean (n=4) plasma concentration curves of amphetamine vs. L-lysine-d-amphetamine are shown in FIG. 13. Pharmacokinetic parameters for IV administration of L-lysine-d-amphetamine are summarized in Table 15.

TABLE 15

Pharmacokinetic Parameters of d-amphetamine vs. L-lysine-d-amphetamine by IV Administration.

| Drug | AUC (0-1.5 h) ng/ml h | % Amphetamine | Cmax (ng/ml) | % Amphetamine |
|---|---|---|---|---|
| Amphetamine | 190 | 100 | 169 | 100 |
| K-amphetamine | 6 | 3 | 5 | 3 |

Example 12 illustrates that when lysine is conjugated to the active agent amphetamine the bioavailability of amphetamine by the intravenous route is substantially decreased, thereby diminishing the ability to abuse the drug by this route.

LC/MS/MS Analysis

Example 13

Oral Bioavaialability of L-lysine-d-amphetamine Compared to d-amphetamine at Escalating Doses As shown in FIGS. 15-19, the fraction of intact L-lysine-d-amphetamine absorbed following oral administration in rats increased non-linearly in proportion to escalating doses from 1.5 to 12 mg/kg (d-amphetamine base). The fraction absorbed at 1.5 mg/kg was only 2.6 percent whereas it increased to 24.6 percent by 12 mg/kg. The fraction absorbed fell to 9.3 percent at the high dose of 60 mg/kg. $T_{max}$ ranged from 0.25 to 3 hours and peak concentrations occurred earlier than for d-amphetamine in L-lysine-d-amphetamine dosed rats. L-lysine-d-amphetamine was cleared more rapidly than d-amphetamine with nearly undetectable concentrations by 8 hours at the lowest dose.

$T_{max}$ for d-amphetamine from L-lysine-d-amphetamine ranged from 1.5 to 5 hours as compared to 0.5 to 1.5 following administration of d-amphetamine sulfate. The difference in time to reach maximum concentration was greater at higher doses. $C_{max}$ of d-amphetamine following oral delivery of L-lysine-d-amphetamine was reduced by approximately half as compared to $C_{max}$ following d-amphetamine sulfate administration at doses of 1.5 to 6 mg/kg, approximating human equivalent doses (HEDs) in the therapeutic range (HED d-amphetamine sulfate; 19.9 to 39.9 mg). HEDs are defined as the equivalent dose for a 60 kg person in accordance to the body surface area of the animal model. The adjustment factor for rats is 6.2. The HED for a rat dose of 1.5 mg/kg of d-amphetamine, for example, is equivalent to 1.5/6.2×60=14.52 d-amphetamine base; which is equivalent to 14.52/0.7284=19.9 mg d-amphetamine sulfate, when adjusted for the salt content.

At doses above HEDs in the targeted therapeutic range (12 and 60 mg/kg; HED d-amphetamine sulfate 79.8 and 399 mg), $C_{max}$ was reduced by 73 and 84 percent, respectively, as compared to d-amphetamine sulfate. AUCs of d-amphetamine following oral administration of L-lysine-d-amphetamine were similar to those of d-amphetamine sulfate at lower doses. As observed with $C_{max}$, however, the AUCs for d-amphetamine from L-lysine-d-amphetamine were substantially decreased compared to those of d-amphetamine sulfate at higher doses with the $AUC_{inf}$ reduced by 76% at the highest dose (60 mg/kg; HED 399 mg d-amphetamine sulfate.

In summary, oral bioavailability of d-amphetamine from L-lysine-d-amphetamine decreased to some degree at higher doses in rats. However, pharmacokinetics with respect to dose were nearly linear for L-lysine-d-amphetamine at doses from 1.5 to 60 mg/kg (HED d-amphetamine sulfate; 19.9 to 797.2 mg) with the fraction absorbed ranging from 52 to 81 percent (extrapolated form 1.5 mg/kg dose). Pharmacokinetics of d-amphetamine sulfate was also nearly linear at lower doses of 1.5 to 6 mg/kg (HED; 19.9 to 79.7) with the fraction absorbed ranging form 62 to 84. In contrast to L-lysine-d-amphetamine, however, parameters were disproportionately increased at higher doses for d-amphetamine sulfate with the fraction absorbed calculated as 101 and 223 percent (extrapolated form 1.5 mg/kg dose), respectively, for the suprapharmacological doses of 12 and 60 mg/kg (HED d-amphetamine sulfate; 159.4 and 797.2 mg).

Figure 20:
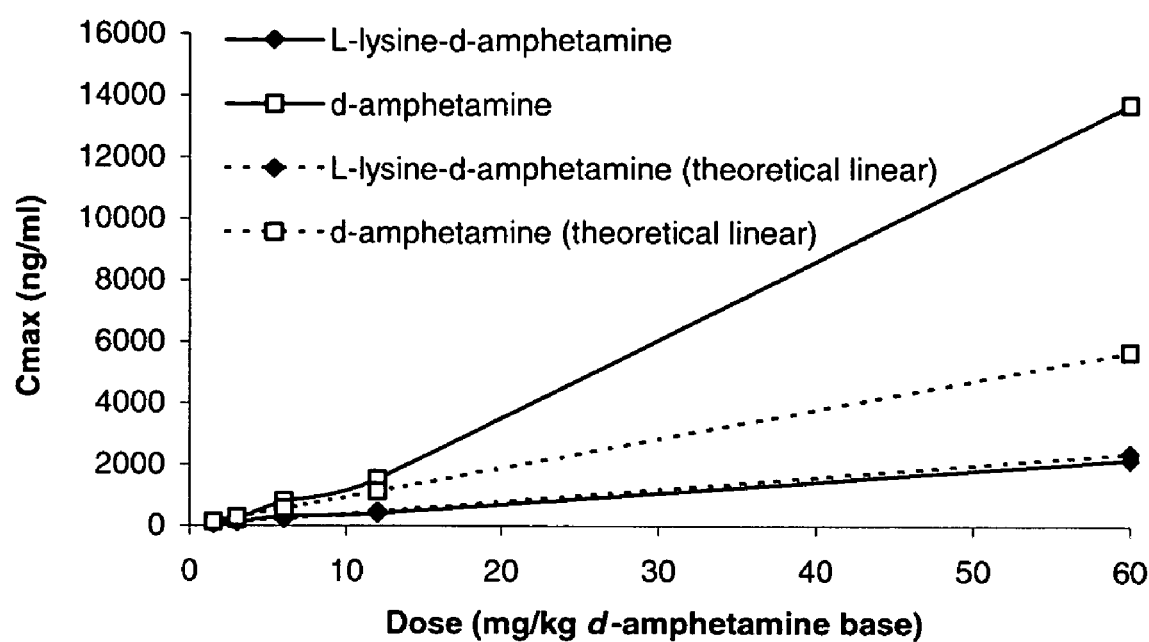
FIG. 20. Comparative bioavailability ($C_{max}$) of L-lysine-d-amphetamine and d-amphetamine in proportion to escalating human equivalent doses in rats (mg/kg d-amphetamine base).
Figure 21:
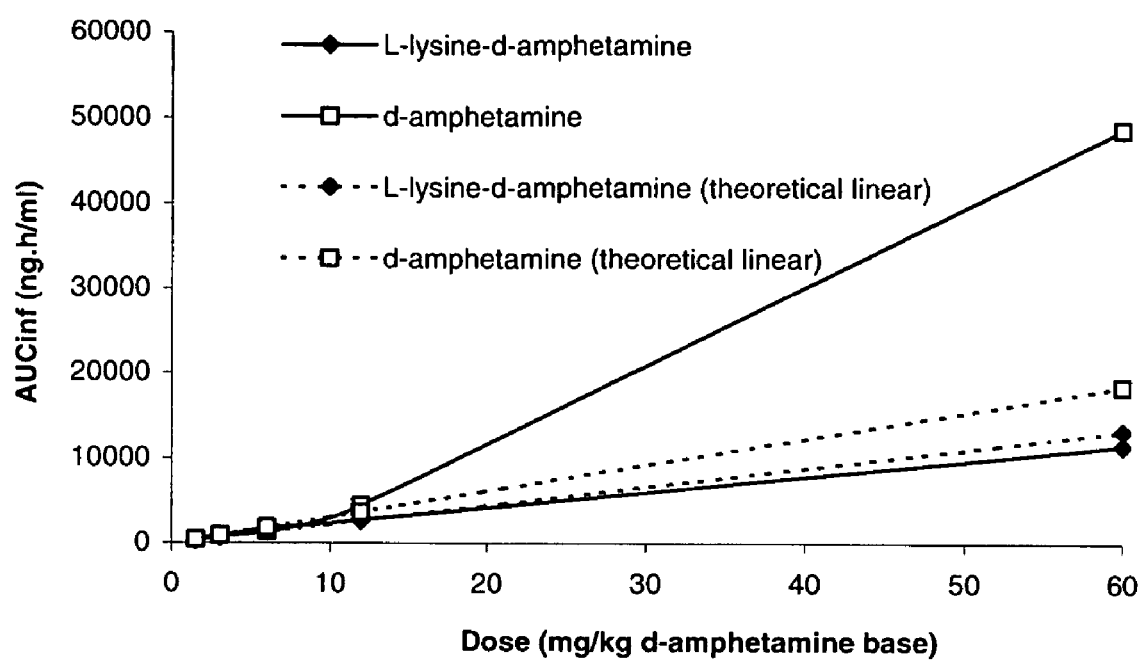
FIG. 21. Comparative bioavailability ($AUC_{inf}$) of L-lysine-d-amphetamine and d-amphetamine in proportion to escalating doses in rats (mg/kg d-amphetamine base).
Figure 22:
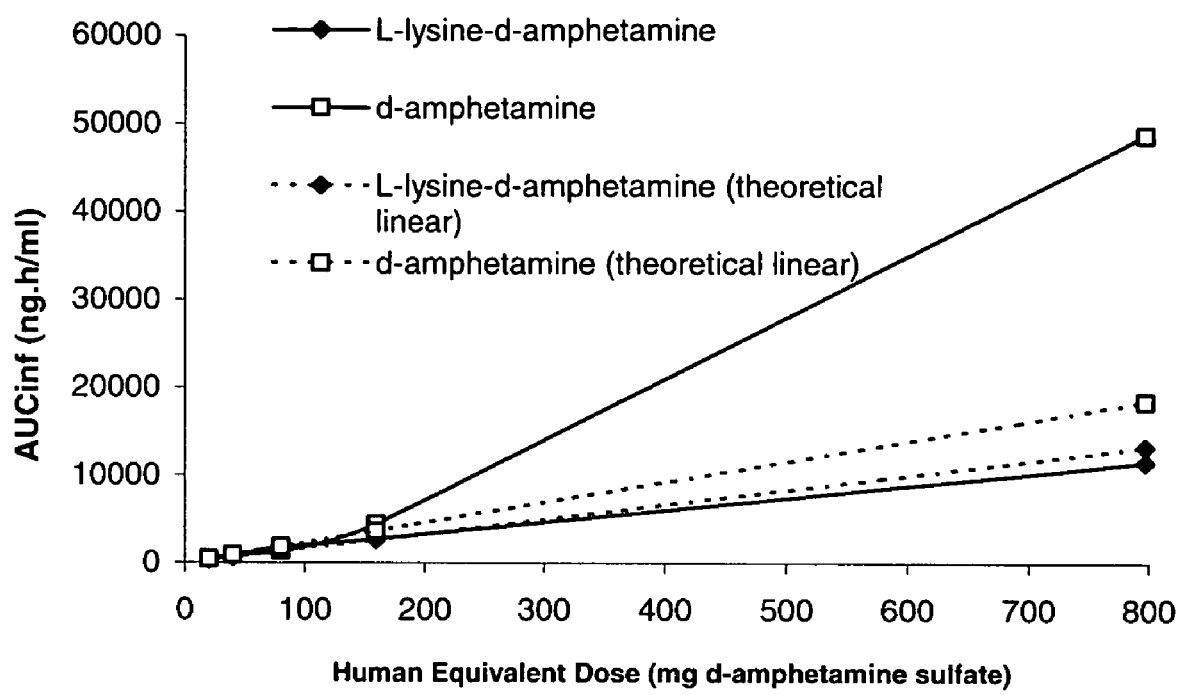
FIG. 22. Comparative Bioavailability ($AUC_{inf}$) of L-lysine-d-amphetamine and d-amphetamine in proportion to escalating human equivalent doses in rats (mg/kg d-amphetamine base).

The results suggest that the capacity for clearance of d-amphetamine when delivered as the sulfate salt becomes saturated at the higher doses whereas the gradual hydrolysis of L-lysine-d-amphetamine precludes saturation of d-amphetamine elimination at higher doses. The difference in proportionality of dose to bioavailability (Cmax and AUC) for d-amphetamine and L-lysine-d-amphetamine is illustrated in FIGS. 20-22. The pharmacokinetic properties of L-lysine-d-amphetamine as compared to d-amphetamine at the higher doses decrease the ability to escalate doses. This improves the safety and reduces the abuse liability of L-lysine-d-amphetamine as a method of delivering d-amphetamine for the treatment of ADHD or other indicated conditions.

Example 14

Intranasal Bioavailability of
L-lysine-d-amphetamine Compared to
d-amphetamine

Figure 23:
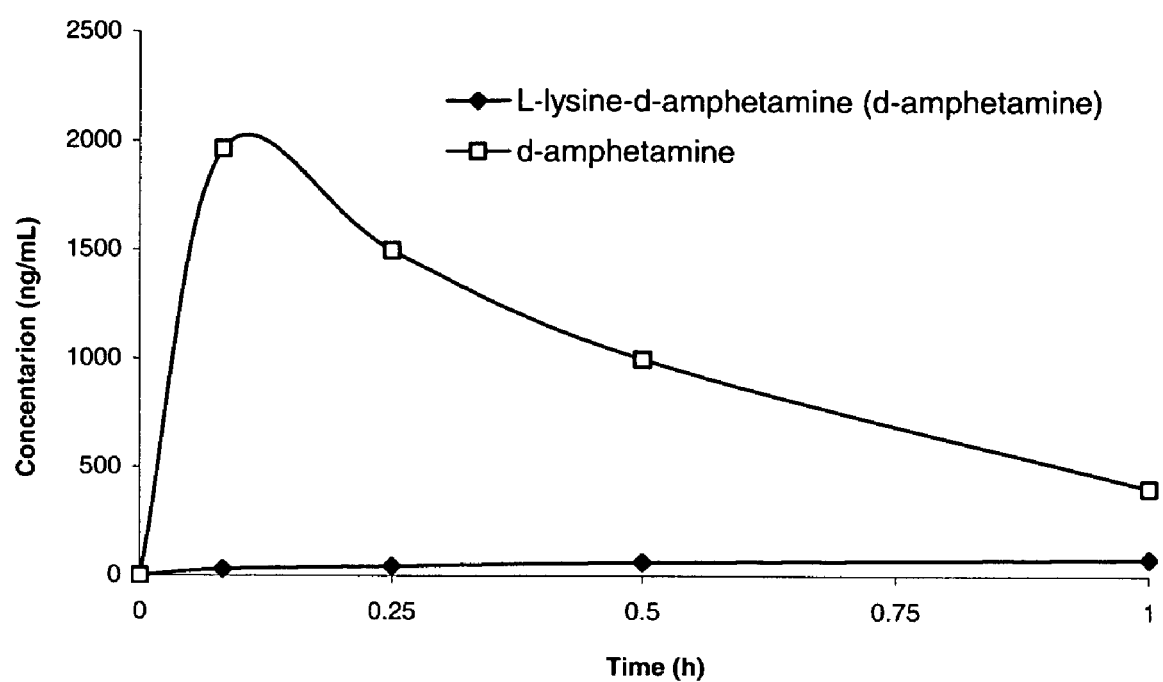
FIG. 23. Plasma concentrations of d-amphetamine following intranasal administration of L-lysine-d-amphetamine or d-amphetamine sulfate (3 mg/kg d-amphetamine base) to rats (LC/MS/MS analysis).
Figure 24A:
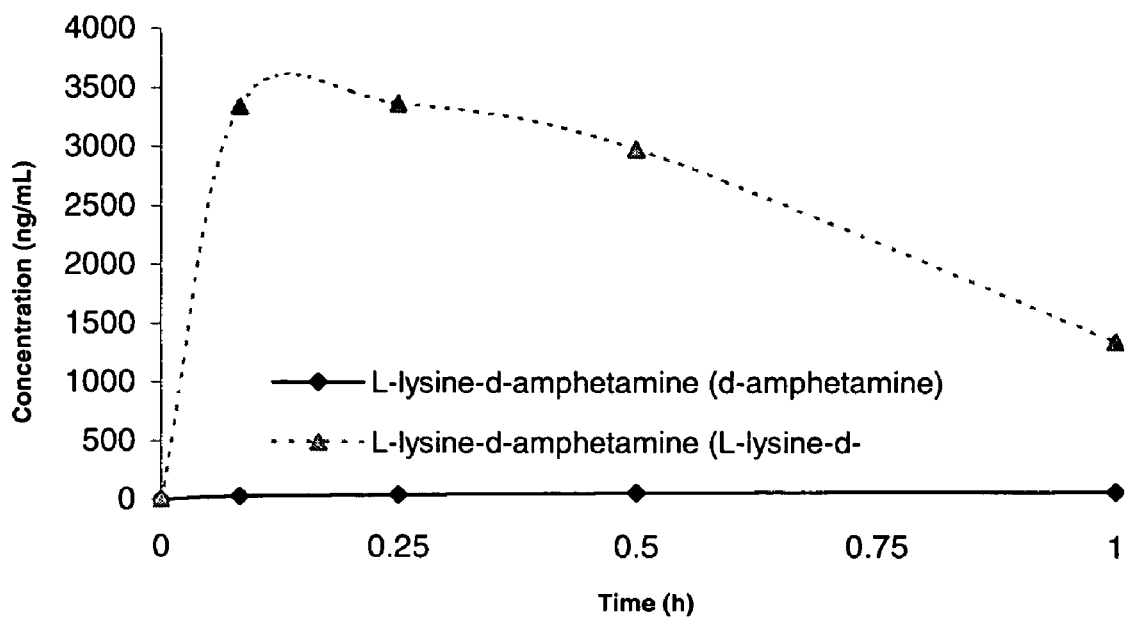
FIG. 24. Plasma concentrations of d-amphetamine and L-lysine-d-amphetamine in ng/mL (FIG. 24A), and in μM (FIG. 24B), following intranasal administration of L-lysined-amphetamine or d-amphetamine sulfate (3 mg/kg d-amphetamine base) to rats (LC/MS/MS analysis.
Figure 24B:
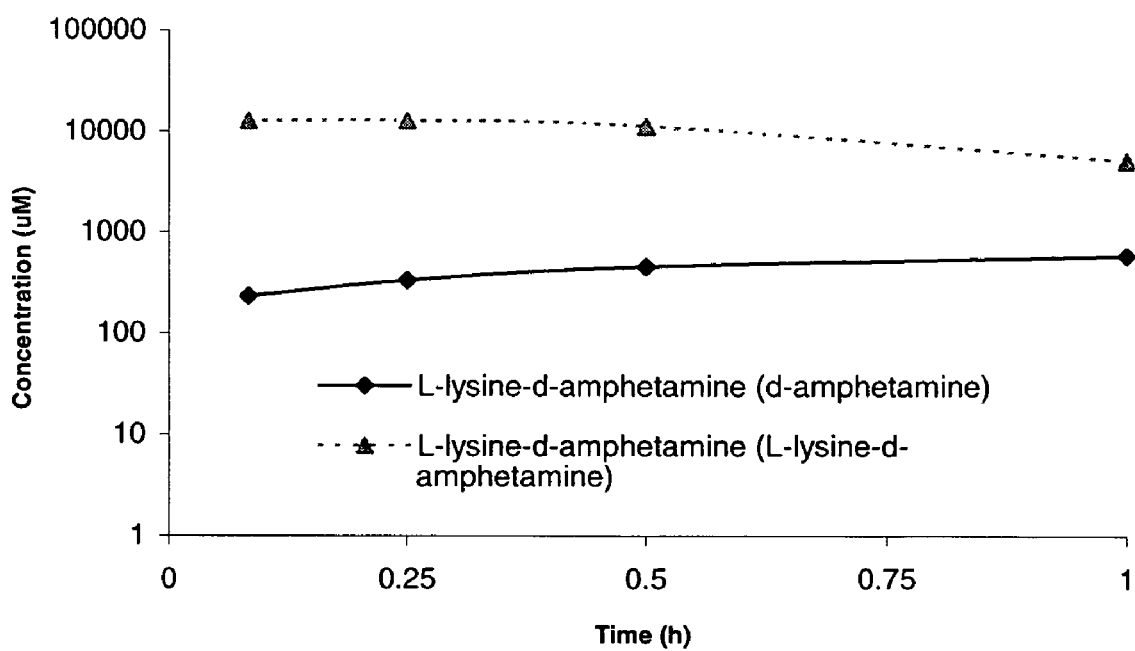

As shown in FIGS. 23-24, bioavailability of d-amphetamine following bolus intranasal administration of L-lysine-d-amphetamine was approximately 5 percent of that of the equivalent d-amphetamine sulfate dose with $AUC_{inf}$ values of 56 and 1032, respectively. $C_{max}$ of d-amphetamine following L-lysine-d-amphetamine administration by the intranasal route was also about 5 percent of that of the equivalent amount of d-amphetamine sulfate with values of 78.6 ng/mL and 1962.9 ng/mL, respectively. As with intravenous administration, $T_{max}$ of d-amphetamine concentration was delayed substantially for L-lysine-d-amphetamine (60 minutes) as compared to $T_{max}$ of d-amphetamine sulfate (5 minutes), again reflecting the gradual hydrolysis of L-lysine-d-amphetamine. A high concentration of intact L-lysine-d-amphetamine was detected following intranasal dosing suggesting that the large decrease in bioavailability of d-amphetamine was due to minimal hydrolysis of L-lysine-d-amphetamine when delivered by this route. It appears that only minimal amounts of d-amphetamine can be delivered by intranasal administration of L-lysine-d-amphetamine.

Example 15

Figure 25:
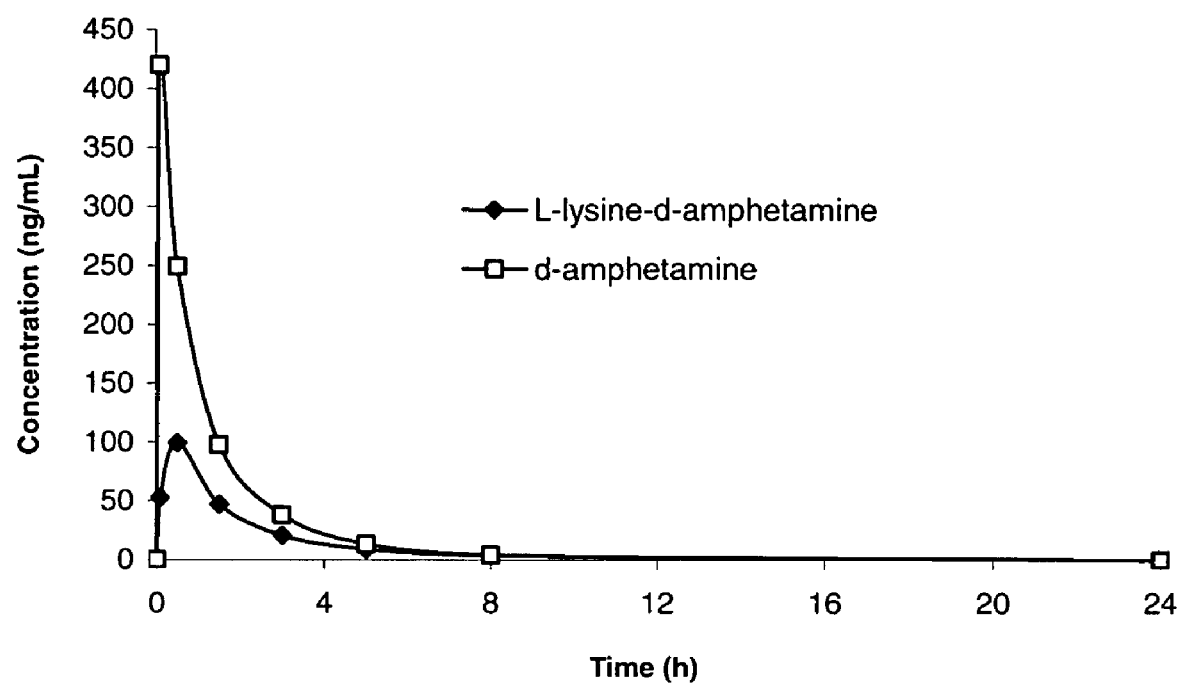
FIG. 25. Plasma concentrations of d-amphetamine following bolus intravenous administration of L-lysine-d-amphetamine or d-amphetamine sulfate (1.5 mg/kg d-amphetamine base) to rats (LC/MS/MS analysis).
Figure 26A:
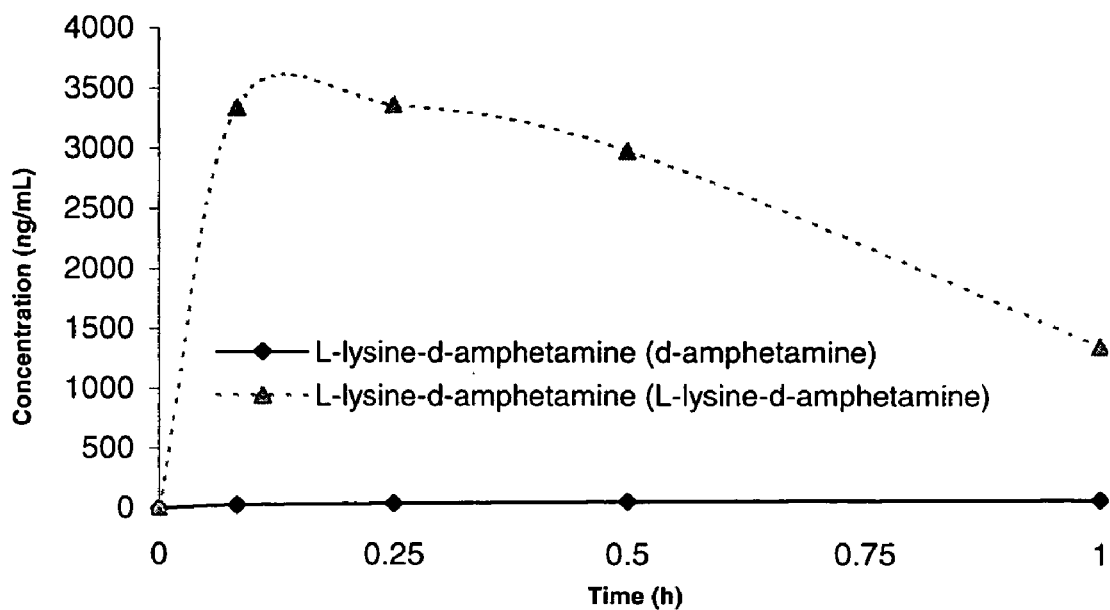
FIGS. 26A-B. Plasma concentrations of d-amphetamine in ng/mL (FIG. 26A), and in µM (FIG. 26B), following intranasal administration of L-lysine-d-amphetamine or d-amphetamine sulfate (3 mg/kg d-amphetamine base) to rats (LC/MS/MS analysis).
Figure 26B:
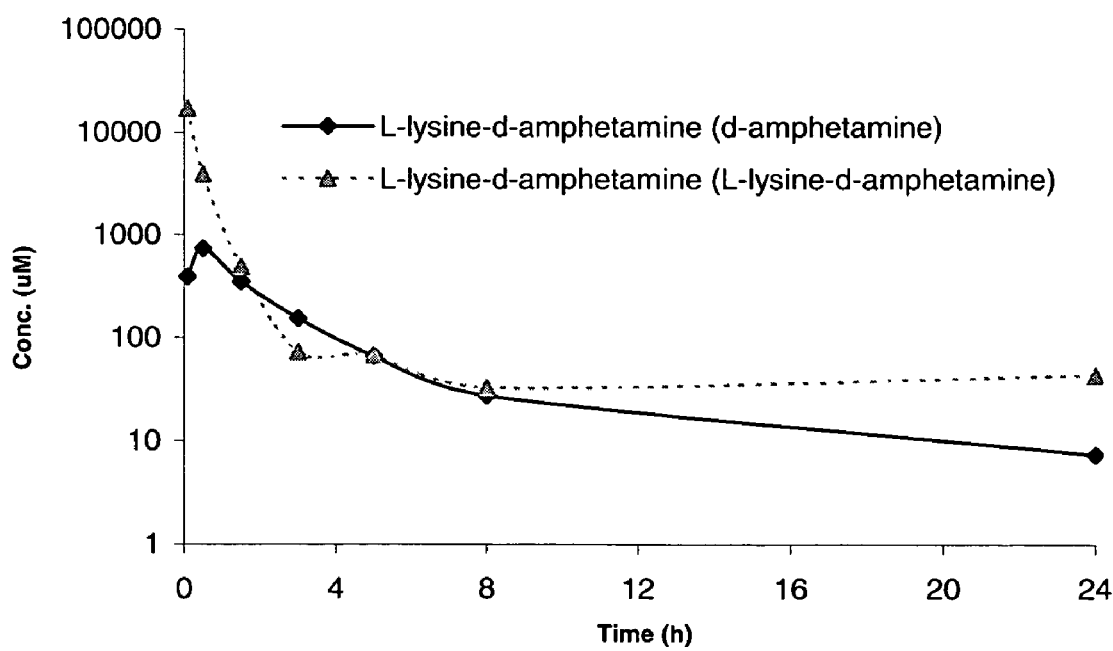

Intravenous Bioavaialability of
L-lysine-d-amphetamine Compared to
d-amphetamine As shown in FIGS. 25-26, bioavailability of d-amphetamine following bolus intravenous administration of L-lysine-d-amphetamine was approximately one-half that of the equivalent d-amphetamine sulfate dose with $AUC_{inf}$ values of 237.8 and 420.2, respectively. $C_{max}$ of d-amphetamine following L-lysine-d-amphetamine administration was only about one-fourth that of the equivalent amount of d-amphetamine with values of 99.5 and 420.2, respectively. $T_{max}$ of d-amphetamine concentration was delayed substantially for L-lysine-d-amphetamine (30 minutes) as compared to $T_{max}$ of d-amphetamine sulfate (5 minutes), reflecting the gradual hydrolysis of L-lysine-d-amphetamine. In conclusion, the bioavailability of d-amphetamine by the intravenous route is substantially decreased and delayed when given as L-lysine-d-amphetamine. Moreover, bioavailability is less than that obtained by oral administration of the equivalent dose of L-lysine-d-amphetamine.

Summary of LC/MS/MS Bioavailability Data in Rats

The following tables summarize the bioavailability data collected in the experiments discussed in examples 13-15. Tables 15-17 summarize the pharmacokinetic parameters of d-amphetamine following oral, intransal, or bolus intravenous administration of d-amphetamine or L-lysine-d-amphetamine.

TABLE 15

Pharmacokinetic Parameters of d-amphetamine Following Oral Administration of L-lysine-d-amphetamine or d-amphetamine at Escalating Doses.

| Route | Drug | Dose (mg/kg) | Cmax (ng/mL) | Tmax (h) | AUC(0-8) (ng · mL/h) | AUC(inf) (ng · mL/h) | F (%) | AUC/Dose (ng · h · kg/mL/mg) | Cmax/Dose ng · kg/mL/mg |
|---|---|---|---|---|---|---|---|---|---|
| Oral | L-lysine-d-amphetamine | 1.5 | 59.6 | 3 | 308 | 331 | 61 | 220.7 | 39.7 |
| Oral | d-amphetamine | 1.5 | 142.2 | 0.5 | 446 | 461 | 84 | 307.3 | 94.8 |
| Oral | L-lysine-d-amphetamine | 3 | 126.9 | 1.5 | 721 | 784 | 72 | 261.3 | 42.3 |
| Oral | d-amphetamine | 3 | 217.2 | 1.5 | 885 | 921 | 84 | 307.0 | 72.4 |
| Oral | L-lysine-d-amphetamine | 6 | 310.8 | 3 | 1,680 | 1,797 | 82 | 299.5 | 51.8 |
| Oral | d-amphetamine | 6 | 815.3 | 0.25 | 1,319 | 1,362 | 62 | 227.0 | 135.9 |
| Oral | L-lysine-d-amphetamine | 12 | 412.6 | 5 | 2,426 | 2,701 | 62 | 225.1 | 34.4 |
| Oral | d-amphetamine | 12 | 1,533.1 | 0.25 | 4,252 | 4,428 | 101 | 369.0 | 127.8 |
| Oral | L-lysine-d-amphetamine | 60 | 2,164.3 | 5 | 9995.1 | 11,478 | 52 | 191.3 | 36.1 |
| Oral | d-amphetamine | 60 | 13,735 | 1 | 32,323 | 48,707 | 223 | 811.8 | 228.9 |

TABLE 16

Pharmacokinetic Parameters of d-amphetamine Following Bolus Intravenous Administration of L-lysine-d-amphetamine.

| Route | Drug | Dose (mg/kg) | Cmax (ng/mL) | Tmax (h) | AUC(0-24) (ng · mL/h) | AUC(inf) (ng · mL/h) |
|---|---|---|---|---|---|---|
| IV | L-lysine-d-amphetamine | 1.5 | 99.5 | 0.5 | 237.8 | 237.9 |
| IV | d-amphetamine | 1.5 | 420.2 | 0.083 | 546.7 | 546.9 |

TABLE 17

Pharmacokinetic Parameters of d-amphetamine Following Intranasal Administration of L-lysine-d-amphetamine.

| Route | Drug | Dose (mg/kg) | Cmax (ng/mL) | Tmax (h) | AUC(0-1) (ng · mL/h) | AUC(inf) (ng · mL/h) |
|---|---|---|---|---|---|---|
| IN | L-lysine-d-amphetamine | 10.16 | 78.6 | 1 | 56 | 91 |
| IN | d-amphetamine | 4.12 | 1962.9 | 0.083 | 1032 | 7291 |

Tables 18-20 summarize the pharmacokinetic parameters of L-lysine-d-amphetamine following oral, bolus intravenous, or intransal administration of L-lysine-d-amphetamine.

TABLE 18

Pharmacokinetic Parameters of L-lysine-d-amphetamine Following Oral Administration of L-lysine-d-amphetamine at Escalating Doses.

| Dose | Drug | Dose (mg/kg) | Cmax (ng/ml) | Tmax (ng/ml) | AUC(0-8) (ng · ml/h) | AUC(inf) (ng · ml/h) | F (%) |
|---|---|---|---|---|---|---|---|
| Oral | L-lysine-d-amphetamine | 1.5 | 36.5 | 0.25 | 59.4 | 60 | 2.6 |
| Oral | L-lysine-d-amphetamine | 3 | 135.4 | 1.5 | 329.7 | 332.1 | 7.2 |
| Oral | L-lysine-d-amphetamine | 6 | 676.8 | 0.25 | 1156.8 | 1170.8 | 12.8 |
| Oral | L-lysine-d-amphetamine | 12 | 855.9 | 1 | 4238.6 | 4510.4 | 24.6 |
| Oral | L-lysine-d-amphetamine | 60 | 1870.3 | 3 | 8234.3 | 8499.9 | 9.3 |

TABLE 19

Pharmacokinetic Parameters of L-lysine-d-amphetamine Following Bolus Intravenous Administration of L-lysine-d-amphetamine.

| Route | Drug | Dose (mg/kg) | Cmax (ng/mL) | Tmax (h) | AUC(0-24) (ng · mL/h) | AUC(inf) (ng · mL/h) |
|---|---|---|---|---|---|---|
| IV | L-lysine-d-amphetamine | 1.5 | 4513.1 | 0.083 | 2,282 | 2,293 |

TABLE 20

Pharmacokinetic Parameters of L-lysine-d-amphetamine Following Intranasal Administration of L-lysine-d-amphetamine.

| Route | Drug | Dose (mg/kg) | Cmax (ng/mL) | Tmax (h) | AUC(0-1) (ng · mL/h) | AUC(inf) (ng · mL/h) |
|---|---|---|---|---|---|---|
| IN | L-lysine-d-amphetamine | 3 | 3345.1 | 0.25 | 2,580 | 9,139 |

Tables 21 and 22 summarize the percent bioavailability of d-amphetamine following oral, intranasal, or intravenous administration of L-lysine-d-amphetamine as compared to d-amphetamine sulfate.

TABLE 21

Percent Bioavailability (AUC$_{inf}$) of d-amphetamine Following Administration of L-lysine-d-amphetamine by Various Routes as Compared to Bioavailability Following Administration of d-amphetamine Sulfate.

| | Dose (mg/kg) d-amphetamine base | | | | |
|---|---|---|---|---|---|
| | 1.5 | 3 | 6 | 12 | 60 |
| HED | 19.9 | 39.9 | 79.7 | 159.4 | 797.2 |
| Oral | 72 | 85 | 132 | 61 | 24 |
| IV | 43 | NA | NA | NA | NA |
| IN | NA | 1 | NA | NA | NA |

TABLE 22

Percent Bioavailability (C$_{max}$) of d-amphetamine Following Administration of L-lysine-d-amphetamine by Various Routes as Compared to Bioavailability Following Administration of d-amphetamine Sulfate.

| | Dose (mg/kg) d-amphetamine base | | | | |
|---|---|---|---|---|---|
| | 1.5 | 3 | 6 | 12 | 60 |
| HED | 19.9 | 39.9 | 79.7 | 159.4 | 797.2 |
| Oral | 42 | 58 | 38 | 27 | 16 |
| IV | 24 | NA | NA | NA | NA |
| IN | NA | 4 | NA | NA | NA |

Tables 23-28 summarize the time-course concentrations of d-amphetamine and L-lysine-d-amphetamine following oral, intranasal or intravenous administration of either d-amphetamine or L-lysine-d-amphetamine.

TABLE 23

Time-course Concentrations of d-amphetamine Following Bolus Intravenous Administration of L-lysine-d-amphetamine or d-amphetamine Sulfate at Doses Containing 1.5 mg/kg d-amphetamine Base.

| | Concentration (ng/ml) | |
|---|---|---|
| Time (hours) | L-lysine-d-amphetamine | d-amphetamine sulfate |
| 0 | 0 | 0 |
| 0.083 | 52.8 | 420.2 |
| 0.5 | 99.5 | 249.5 |
| 1.5 | 47.1 | 97.9 |
| 3 | 21.0 | 38.3 |
| 5 | 9.0 | 13.2 |
| 8 | 3.7 | 4.3 |
| 24 | 0.1 | 0.2 |

TABLE 24

Time-course Concentrations of L-lysine-d-amphetamine Following Bolus Intravenous Administration of L-lysine-d-amphetamine at a Dose Containing 1.5 mg/kg d-amphetamine Base.

| Time (hours) | Concentration (ng/ml) L-lysine-d-amphetamine |
|---|---|
| 0 | 0 |
| 0.083 | 4513.1 |
| 0.5 | 1038.7 |
| 1.5 | 131.4 |
| 3 | 19.3 |
| 5 | 17.9 |
| 8 | 8.7 |
| 24 | 11.5 |

TABLE 25

Time-course Concentrations of d-amphetamine Following Oral Administration of L-lysine-d-amphetamine at Various Doses (mg/kg d-amphetamine base).

| Time | Concentration (ng/ml) | | | | |
|---|---|---|---|---|---|
| (hours) | 1.5 mg/kg | 3 mg/kg | 6 mg/kg | 12 mg/kg | 60 mg/kg |
| 0 | 0 | 0 | 0 | 0 | 0 |
| 0.25 | 20.5 | 25.3 | 96 | 54.3 | 90.9 |
| 0.5 | 34 | 40.9 | 140.2 | 96 | 175.1 |
| 1 | 46.7 | 95.1 | 225.9 | 233.3 | 418.8 |
| 1.5 | 40.7 | 126.9 | 268.4 | 266 | 440.7 |
| 3 | 59.6 | 105 | 310.8 | 356.8 | 1145.5 |
| 5 | 38.6 | 107.6 | 219.5 | 412.6 | 2164.3 |
| 8 | 17.1 | 48 | 86 | 225.1 | 1227.5 |

TABLE 26

Time-course Concentrations of d-amphetamine Following Oral Administration of d-amphetamine Sulfate at Various Doses (mg/kg d-amphetamine Base).

| Time | Concentration (ng/ml) | | | | |
|---|---|---|---|---|---|
| (hours) | 1.5 mg/kg | 3 mg/kg | 6 mg/kg | 12 mg/kg | 60 mg/kg |
| 0 | 0 | 0 | 0 | 0 | 0 |
| 0.25 | 107.1 | 152.6 | 815.3 | 1533.1 | 6243.6 |
| 0.5 | 142.2 | 198.4 | 462.7 | 1216 | 7931.6 |
| 1 | 105.7 | 191.3 | 301.3 | 828.8 | 13735.2 |
| 1.5 | 129.5 | 217.2 | 314 | 904.8 | 11514.9 |
| 3 | 52.6 | 135.3 | 134.6 | 519.9 | NA |
| 5 | 29.5 | 73.5 | 77.4 | 404.3 | NA |
| 8 | 11.5 | 25.7 | 31.8 | 115.4 | NA |

TABLE 27

Time-course Concentrations of d-amphetamine Following Intranasal Administration of L-lysine-d-amphetamine or d-amphetamine Sulfate at Doses Containing 3 mg/kg d-amphetamine Base.

| | Concentration (ng/ml) | |
|---|---|---|
| Time (hours) | L-lysine-d-amphetamine | d-amphetamine sulfate |
| 0 | 0 | 0 |
| 0.083 | 31.2 | 1962.9 |
| 0.25 | 45.3 | 1497.3 |
| 0.5 | 61.3 | 996.2 |

TABLE 27-continued

Time-course Concentrations of d-amphetamine Following Intranasal Administration of L-lysine-d-amphetamine or d-amphetamine Sulfate at Doses Containing 3 mg/kg d-amphetamine Base.

| | Concentration (ng/ml) | |
|---|---|---|
| Time (hours) | L-lysine-d-amphetamine | d-amphetamine sulfate |
| 1 | 78.6 | 404.6 |
| AUC | 56 | 1032.3 |

TABLE 28

Time-course Concentrations of L-lysine-d-amphetamine Following Intranasal Administration of L-lysine-d-amphetamine at a Dose Containing 3 mg/kg d-amphetamine Base.

| Time (h) | Conc. (ng/ml) L-lysine-d-amphetamine |
|---|---|
| 0 | 0 |
| 0.083 | 3345.1 |
| 0.25 | 3369.7 |
| 0.5 | 2985.8 |
| 1 | 1359.3 |

Example 19

LC/MS/MS Analysis of Bioavailability in Dogs

Example Experimental Design:

This was a non-randomized, two-treatment crossover study. All animals were maintained on their normal diet and were fasted overnight prior to each dose administration. L-lysine-d-amphetamine dose was based on the body weight measured on the morning of each dosing day. The actual dose delivered was based on syringe weight before and after dosing. Serial blood samples were obtained from each animal by direct venipuncture of a jugular vein using vacutainer tubes containing sodium heparin as the anticoagulant. Derived plasma samples were stored frozen until shipment to the Quest Pharmaceutical Services, Inc. (Newark, Del.). Pharmacokinetic analysis of the plasma assay results was conducted by Calvert. Animals were treated as follows:

| # of Dog/Sex | Route of Administration | Treatment | Dose Concn (mg/mL) | Dose Vol (mL/kg) | Dose Level (mg/kg) |
|---|---|---|---|---|---|
| 3M | PO | 1 | 0.2 | 10 | 2 |
| 3M | IV | 2 | 1 | 2 | 2 |

The mg units in the dose concentration and dose level refer to the free base form of test article.

Administration of the Test Article:

Oral: The test article was administered to each animal via a single oral gavage. On Day 1, animals received the oral dose by gavage using an esophageal tube attached to a syringe. Dosing tubes were flushed with approximately 20 mL tap water to ensure the required dosing solution was delivered.

Intravenous: On Day 8, animals received L-lysine-d-amphetamine as a single 30-minute intravenous infusion into a cephalic vein.

Sample Collection:

Dosing Formulations: Post-dosing, remaining dosing formulation was saved and stored frozen.

Blood: Serial blood samples (2 mL) were collected using venipuncture tubes containing sodium heparin. Blood samples were taken at 0, 0.25, 0.5, 1, 2, 4, 8, 12, 24, 48, and 72 hours post-oral dosing. Blood samples were collected at 0, 0.167, 0.33, 0.49 (prior to stop of infusion), 0.583, 0.667, 0.75, 1, 2, 3, 4, 8, 12, and 23 hours post-intravenous infusion start. Collected blood samples were chilled immediately.

Plasma: Plasma samples were obtained by centrifugation of blood samples. Duplicate plasma samples (about 0.2 mL each) were transferred into prelabeled plastic vials and stored frozen at approximately −70° C.

Sample Assay:

Plasma samples were analyzed for L-lysine-d-amphetamine and d-amphetamine using a validated LC-MS/MS method with an LLOQ of 1 ng/mL for both analytes.

Microsoft Excel (Version 6, Microsoft Corp., Redmond, Wash.) was used for calculation of mean plasma concentration and graphing of the plasma concentration-time data. Pharmacokinetic analysis (non-compartmental) was performed using the WinNonlin® software program (Version 4.1, Pharsight, Inc. Mountain View, Calif.). The maximum concentration, $C_{max}$, and the time to $C_{max}$, $T_{max}$, were observed values. The area under the plasma concentration-time curve (AUC) was determined using linear-log trapezoidal rules. The apparent terminal rate constant ($\lambda z$) was derived using linear least-squares regression with visual inspection of the data to determine the appropriate number of points (minimum of 3 data points) for calculating $\lambda z$. The AUC(0-inf) was calculated as the sum of AUC(0-t) and Cpred/$\lambda z$, where Cpred was the predicted concentration at the time of the last quantifiable concentration. The plasma clearance (CL/F) was determined as the ratio of Dose/AUC (0-inf). The mean residence time (MRT) was calculated as the ratio of AUMC(0-inf)/AUC (0-inf), where AUMC(0-inf) was the area under the first moment curve from the time zero to infinity. The volume of distribution at steady state ($V_{ss}$) was estimated as CL*MRT. Half-life was calculated as ln2/$\lambda z$. The oral bioavailability (F) was calculated as the ratio of AUC(0-inf) following oral dosing to AUC(0-inf) following intravenous dosing. Descriptive statistics (mean and standard deviation) of the pharmacokinetic parameters were calculated using Microsoft Excel.

Figure 27:
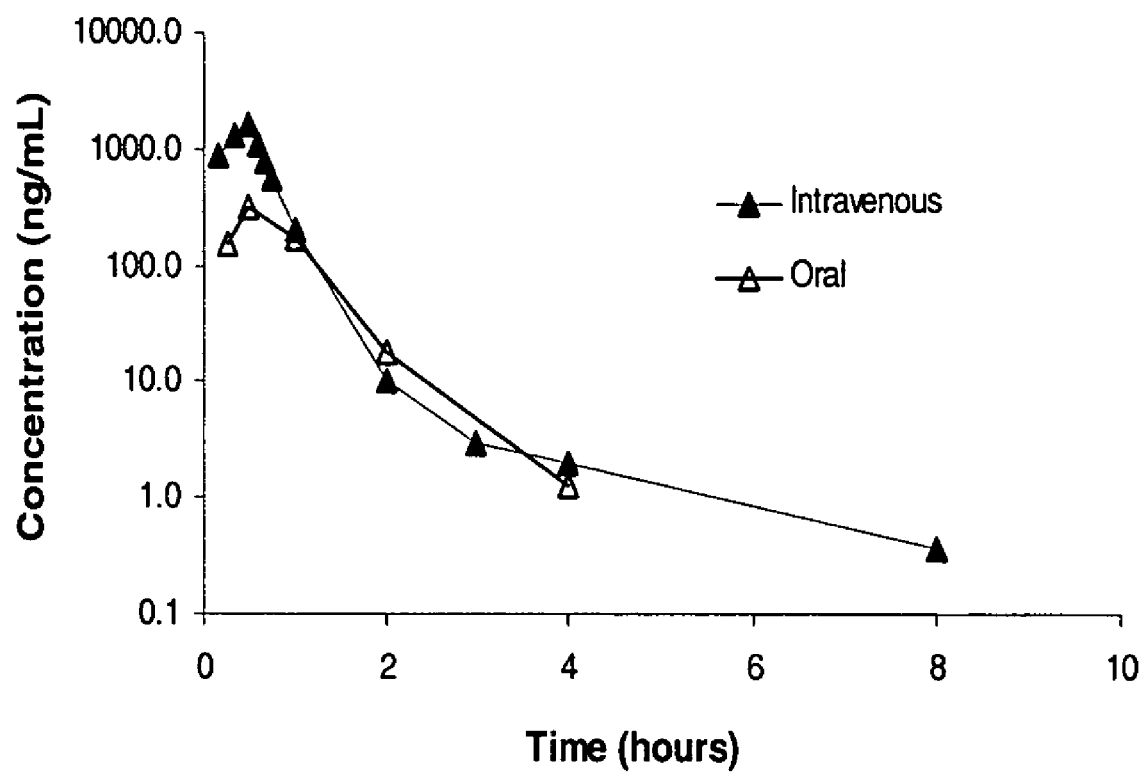
FIG. 27. Mean plasma concentration time profile of L-lysine-d-amphetamine following 30-min intravenous infusion (2 mg/kg) or oral administration of L-lysine-d-amphetamine (2 mg/kg) in conscious male beagle dogs (n=3).

The objectives of this study were to characterize the pharmacokinetics of L-lysine-d-amphetamine and d-amphetamine following administration of L-lysine-d-amphetamine in male beagle dogs. As shown in FIG. 27, in a cross-over design, L-lysine-d-amphetamine was administered to 3 male beagle dogs orally (2 mg/kg) and intravenously (2 mg/kg, 30-minute infusion). Blood samples were collected up to 24 and 72 hour after the intravenous and oral does, respectively. Plasma samples were analyzed using a LC-MS/MS assay which provided an LLOQ of 1 ng/mL for both analytes.

Figure 28:
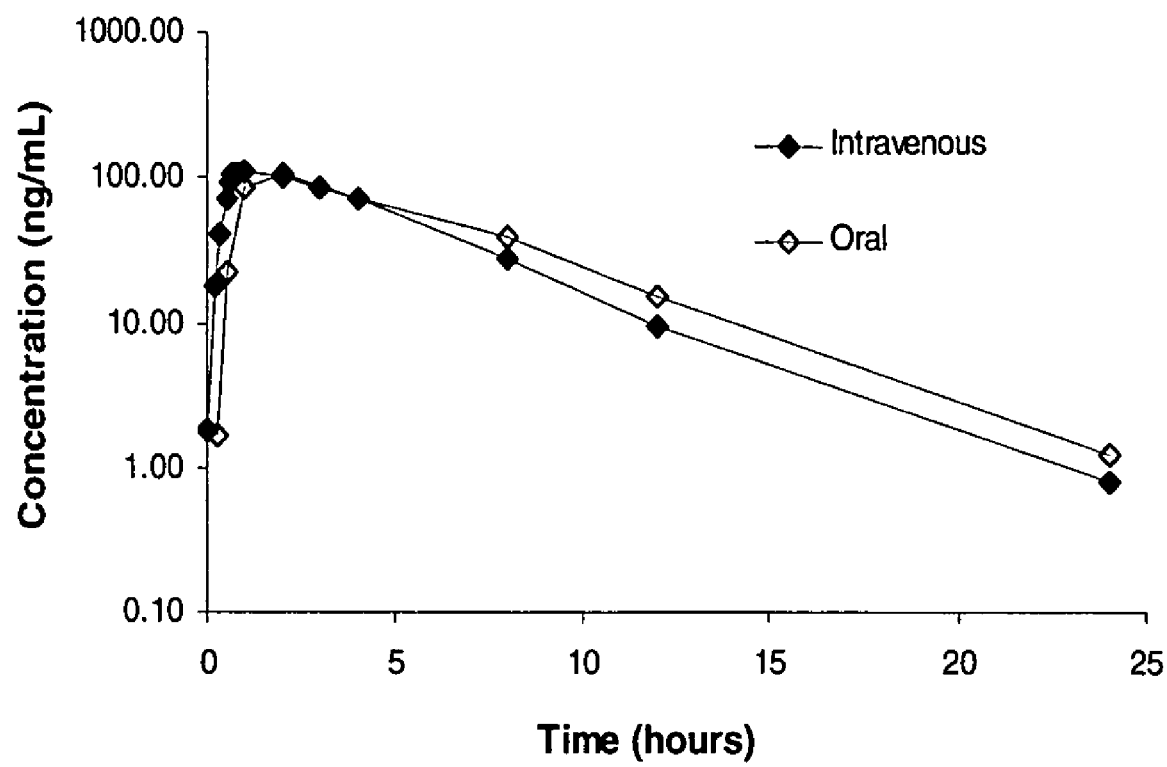
FIG. 28. Plasma concentration time profile of d-amphetamine following 30-min intravenous infusion or oral administration of L-lysine-d-amphetamine (2 mg/kg) in conscious male beagle dogs (n=3).
Figure 29A:
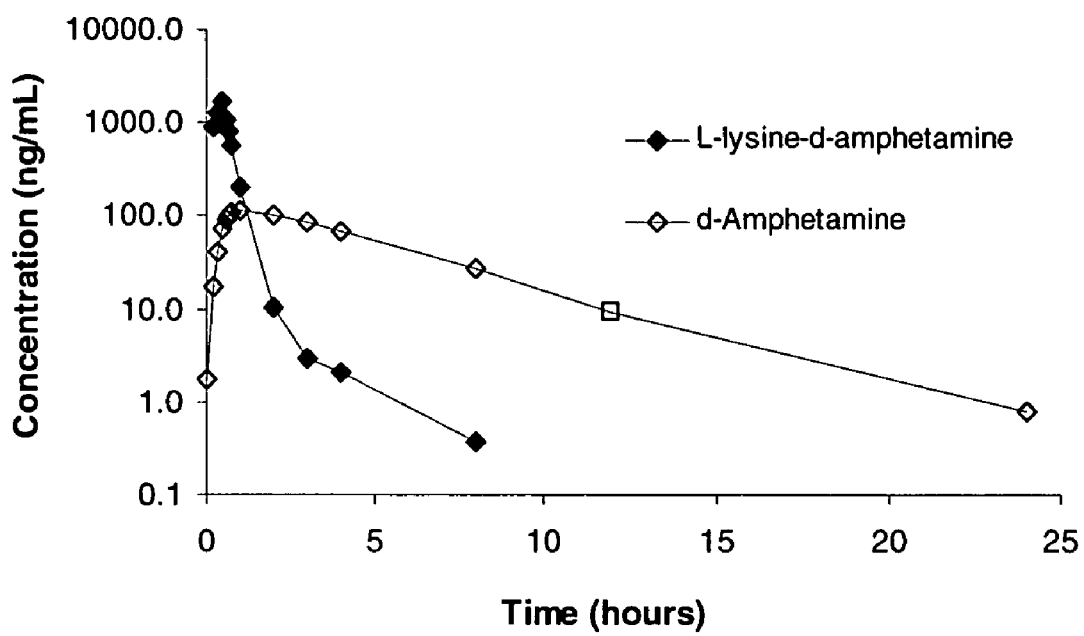
FIGS. 29A-B. Mean plasma concentration time profile of L-lysine-d-amphetamine and d-amphetamine levels in ng/ml (FIG. 29A), and in uM (FIG. 29B), following 30-min intravenous infusion (2 mg/kg) in conscious male beagle dogs (n=3).
Figure 29B:
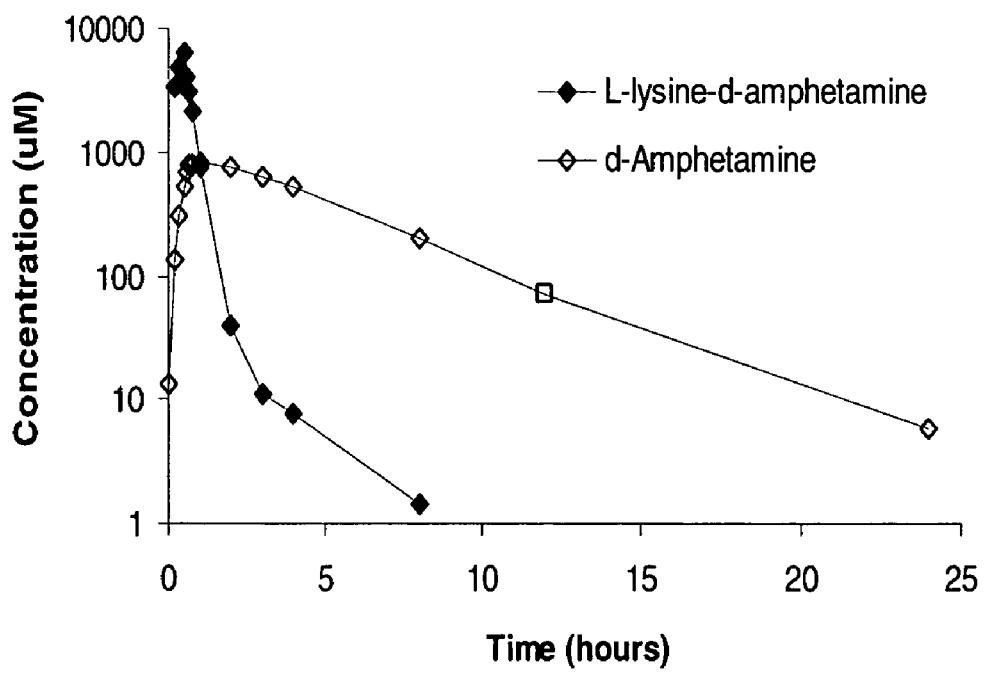
Figure 30A:
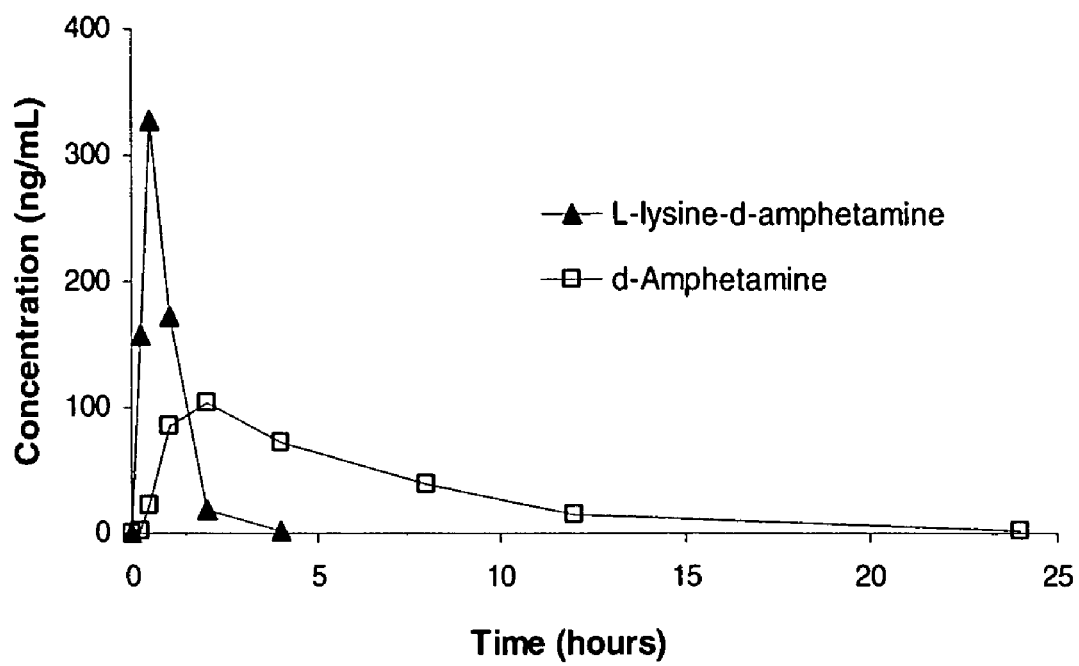
FIGS. 30A-B. Mean plasma concentration time profile of L-lysine-d-amphetamine and d-amphetamine levels in ng/ml (FIG. 30A), and in nM (FIG. 30B), following oral administration of L-lysine-d-amphetamine (2 mg/kg) in conscious male beagle dogs (n=3).
Figure 30B:
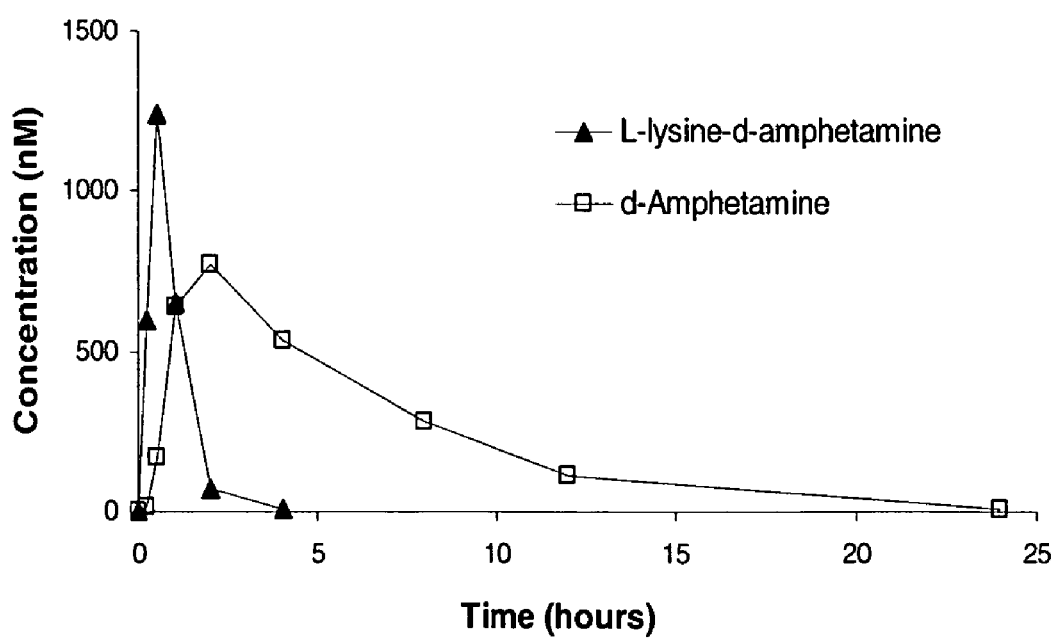
Figure 31A:
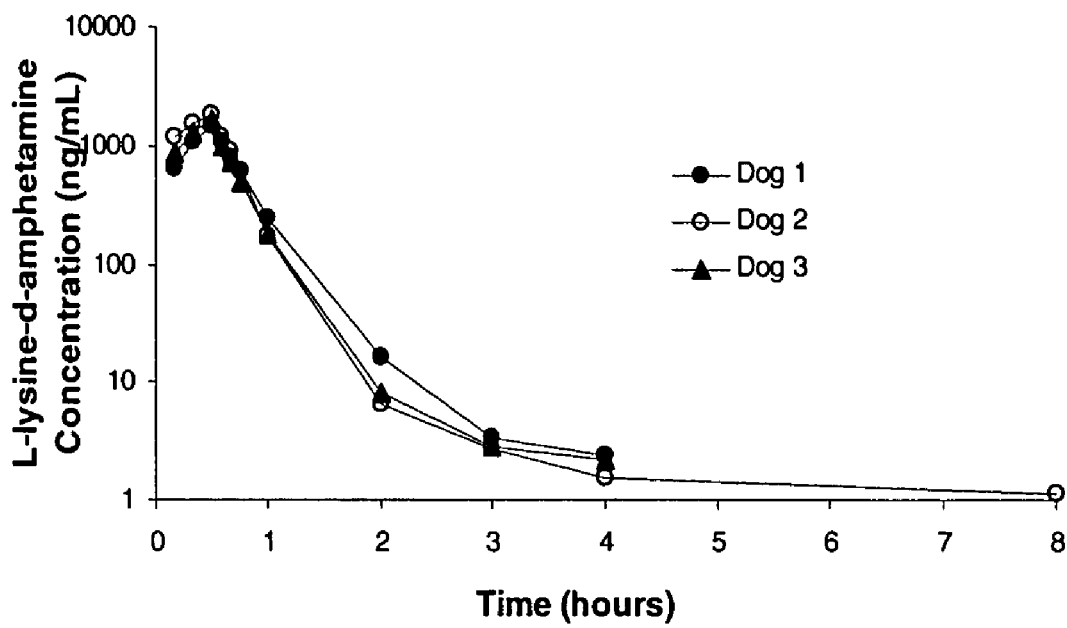
FIGS. 31A-B. Individual plasma concentration time profile of L-lysine-d-amphetamine following intravenous administration (FIG. 31A) or oral administration (FIG. 31B) of L-lysine-d-amphetamine in conscious male beagle dogs. The oral formulation used comprises solution and 0.2 mg/mL in water.
Figure 31B:
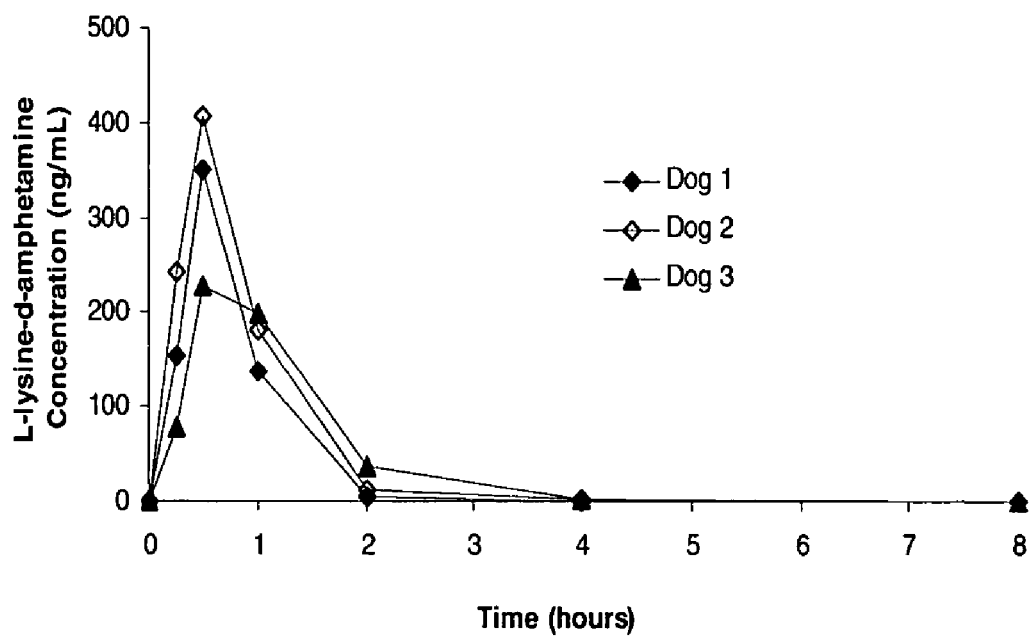
Figure 32A:
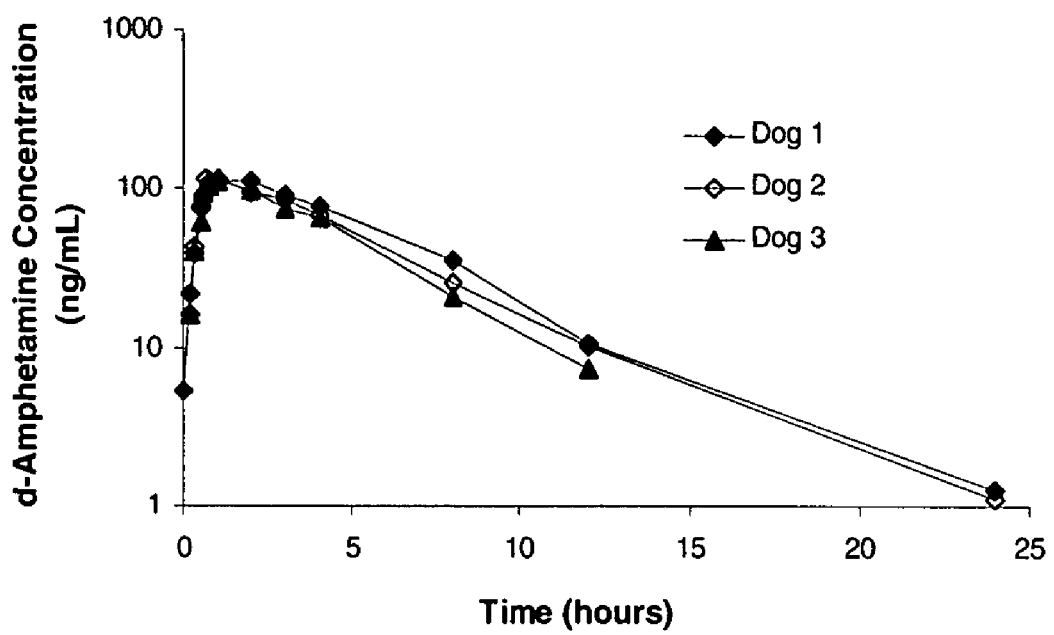
FIGS. 32A-B. Individual plasma concentration time profile of d-amphetamine following intravenous administration (FIG. 32A) or oral administration (FIG. 32B) of L-lysine-d-amphetamine in conscious male beagle dogs.
Figure 32B:
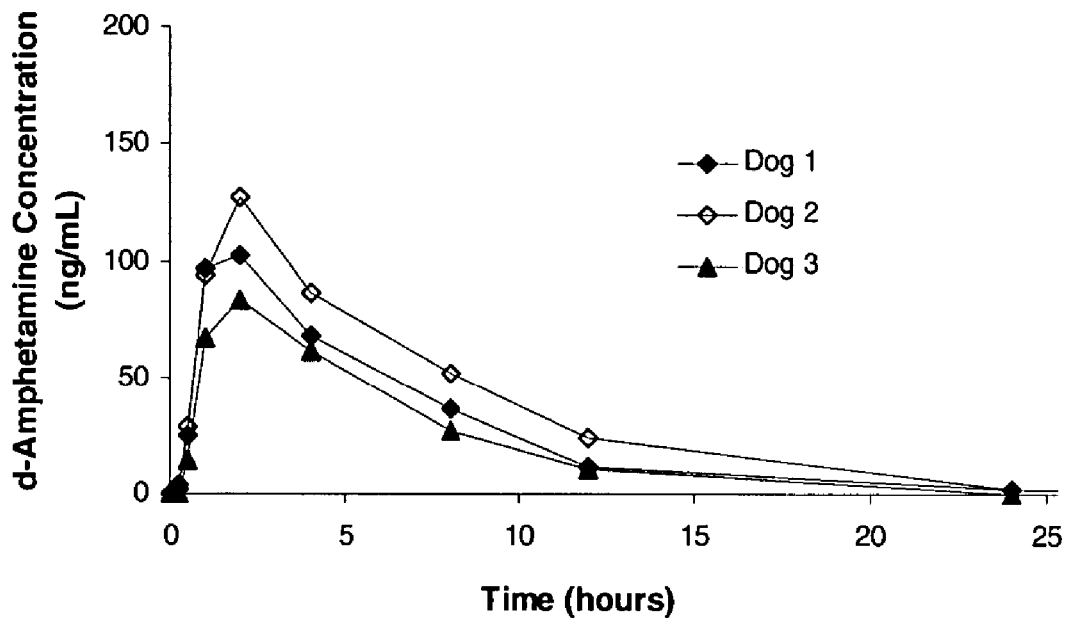
Figure 33:
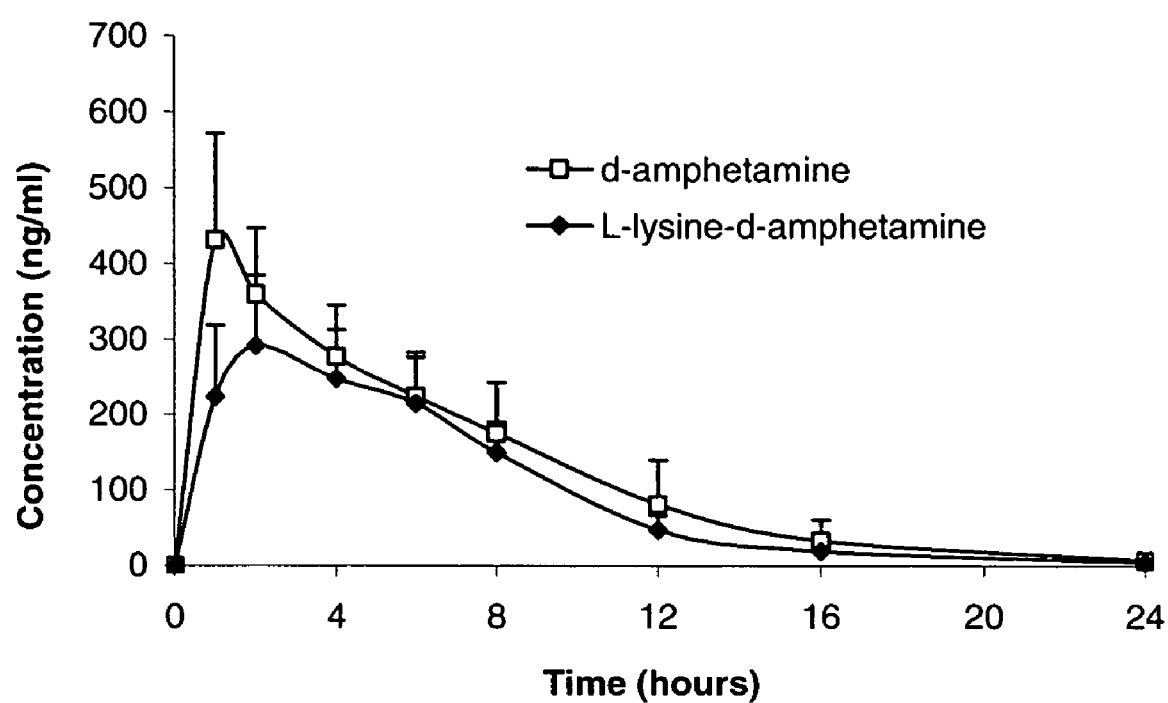
FIG. 33. Plasma concentrations of d-amphetamine following oral administration of L-lysine-d-amphetamine or d-amphetamine sulfate (1.8 mg/kg d-amphetamine base) to male dogs.
Figure 34:
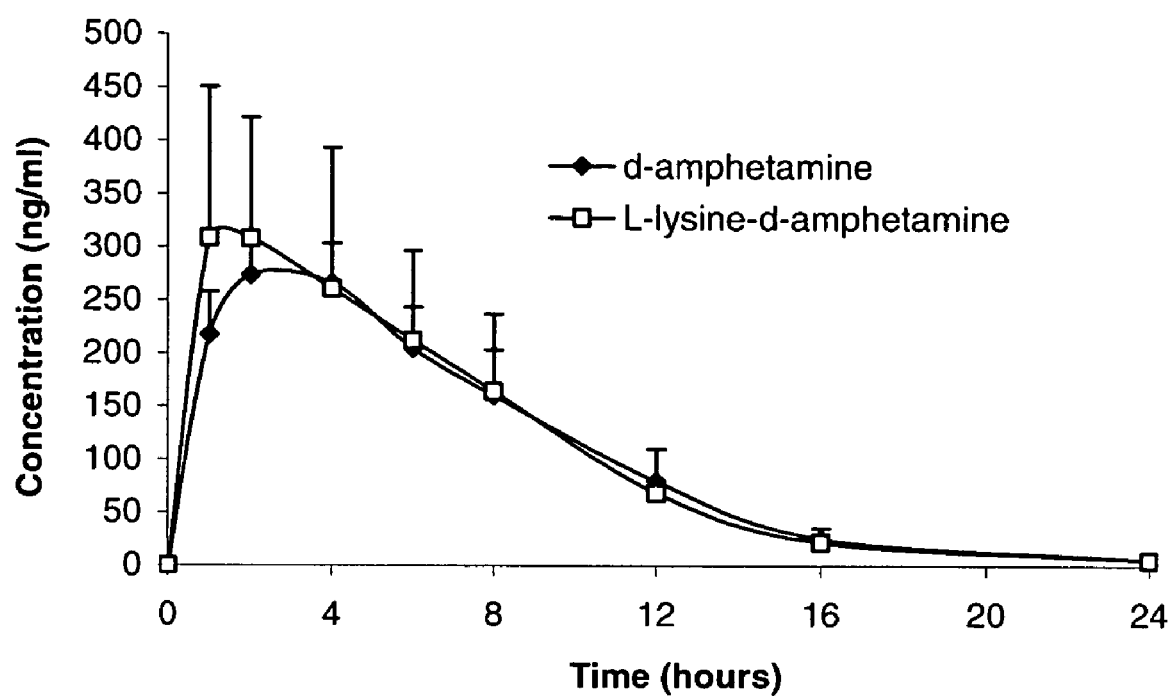
FIG. 34. Plasma concentrations of d-amphetamine following oral administration of L-lysine-d-amphetamine or d-amphetamine sulfate (1.8 mg/kg d-amphetamine base) to female dogs.

The mean L-lysine-d-amphetamine and d-amphetamine plasma concentration-time profiles following an intravenous or oral dose of L-lysine-d-amphetamine are presented in FIGS. 29 and 30, respectively. Comparative profiles of L-lysine-d-amphetamine to d-amphetamine following both routes are depicted in FIGS. 27-28. Individual plots are depicted in FIGS. 31-32. The pharmacokinetic parameters are summarized in Tables 29-37.

Following a 30-minute intravenous infusion of L-lysine-d-amphetamine, the plasma concentration reached a peak at the end of the infusion. Post-infusion L-lysine-d-amphetamine concentration declined very rapidly in a biexponential manner, and fell below the quantifiable limit (1 ng/mL) by approximately 8 hours post-dose. Results of non-compartmental pharmacokinetic analysis indicate that L-lysine-d-amphetamine is a high clearance compound with a moderate volume of distribution (Vss) approximating total body water (0.7 L/kg). The mean clearance value was 2087 mL/h·kg (34.8 mL/min·kg) and was similar to the hepatic blood flow in the dog (40 mL/min·kg). Consequently, L-lysine-d-amphetamine is a moderate to high hepatic extraction compound with significant first pass effects (including the conversion to d-amphetamine) following oral administration.

L-lysine-d-amphetamine was rapidly absorbed after oral administration with $T_{max}$ at 0.5 hours in all three dogs. Mean absolute oral bioavailablity was 33%. Since significant first pass effects are expected for L-lysine-d-amphetamine, a 33% bioavailability suggests that L-lysine-d-amphetamine is very well absorbed in the dog. The apparent terminal half-life was 0.39 hours, indicating rapid elimination, as observed following intravneous administration.

Plasma concentration-time profiles of d-amphetamine following intravenous or oral administration of L-lysine-d-amphetamine were very similar, with $C_{max}$, $T_{max}$ and AUC values for both routes essentially the same. At a 2 mg/kg oral dose of L-lysine-d-amphetamine, the mean $C_{max}$ of d-amphetamine was 104.3 ng/mL. The half-life of d-amphetamine was 3.1 to 3.5 hours, much longer when compared to L-lysine-d-amphetamine.

In this study, L-lysine-d-amphetamine was infused over a 30 minute time period. Due to rapid clearance of L-lysine-d-amphetamine it is likely that bioavailability of d-amphetamine from L-lysine-d-amphetamine would decrease if a similar dose were given by intravenous bolus injection. Even when given as an infusion the bioavailability of d-amphetamine from L-lysine-d-amphetamine did not exceed that of a similar dose given orally and the time to peak concentration was substantially delayed. This data further supports that L-lysine-d-amphetamine affords a decrease in the abuse liability of d-amphetamine by intravenous injection.

TABLE 29

Pharmacokinetic Parameters of L-lysine-d-amphetamine in Male Beagle Dogs Following Oral or Intravenous Administration of L-lysine-d-amphetamine (1 mg/kg d-amphetamine base).

| Route | Dose (mg/kg) | $C_{max}$ (ng/mL) | $T_{max}$[a] (h) | AUC(inf) (ng · h/mL) | $t_{1/2}$ (h) | MRT (h) | CL/F (mL/h · kg) | $V_{ss}$ (mL/kg) | F (%) |
|---|---|---|---|---|---|---|---|---|---|
| IV | 1 | 1650 | 0.49 | 964 | 0.88 | 0.33 | 2087 | 689 | NA |
|  | (0.00) | (178) | (0.49-0.49) | (97.1) | (0.2) | (0.03) | (199) | (105.9) |  |
| Oral | 1 | 328.2 | 0.5 | 319 | 0.39 | 0.81 | 6351 | NA | 33 |
|  | (0.00) | (91.9) | (0.5-0.5) | (46.3) | (0.1) | (0.19) | (898.3) |  | (1.9) |

[a]median (range)

TABLE 30

Pharmacokinetic Parameters of d-amphetamine in Male Beagle Dogs Following Oral or Intravenous Administration of L-lysine-d-amphetamine (1 mg/kg d-amphetamine base).

| Route | Dose (mg/kg) | $C_{max}$ (ng/mL) | $T_{max}$[a] (h) | AUC(inf) (ng · h/mL) | $t_{1/2}$ (h) |
|---|---|---|---|---|---|
| IV | 2 | 113.2 | 1.0 | 672.5 | 3.14 |
|  | (0.00) | (3.2) | (0.67-2.0) | (85.7) | (0.4) |
| Oral | 2 | 104.3 | 2.0 | 728.0 | 3.48 |
|  | (0.00) | (21.8) | (2-2) | (204.9) | (0.4) |

[a]median (range)

TABLE 31

Pharmacokinetics of L-lysine-d-amphetamine in Male Beagle Dogs Following Intravenous Administration of L-lysine-d-amphetamine (1 mg/kg d-amphetamine base). Dose Route: 30-min iv Infusion Dose: 2 mg/kg/h (free form)

| Dog ID | $C_{max}$ (ng/mL) | $T_{max}$[a] (h) | AUC(0-t) (ng · h/mL) | AUC(inf) (ng · h/mL) | $t_{1/2}$ (h) | CL (mL/h/kg) | Vss (mL/kg) | MRT (h) |
|---|---|---|---|---|---|---|---|---|
| 1 | 1470.3 | 0.49 | 898.2 | 900.2 | 0.72 | 2222 | 807.4 | 0.36 |
| 2 | 1826.4 | 0.49 | 1072.3 | 1076.1 | ND[b] | 1859 | 603.4 | 0.32 |

TABLE 31-continued

Pharmacokinetics of L-lysine-d-amphetamine in Male Beagle Dogs Following
Intravenous Administration of L-lysine-d-amphetamine (1 mg/kg d-amphetamine base).
Dose Route: 30-min iv Infusion Dose: 2 mg/kg/h (free form)

| Dog ID | $C_{max}$ (ng/mL) | $T_{max}^a$ (h) | AUC(0-t) (ng · h/mL) | AUC(inf) (ng · h/mL) | $t_{1/2}$ (h) | CL (mL/h/kg) | Vss (mL/kg) | MRT (h) |
|---|---|---|---|---|---|---|---|---|
| 3 | 1654.2 | 0.49 | 914.1 | 916.9 | 1.05 | 2181 | 656.0 | 0.30 |
| Mean | 1650 | 0.49 | 961.5 | 964.4 | 0.88 | 2087 | 689.0 | 0.33 |
| SD | 178 | 0.49-0.49 | 96.0 | 97.1 | 0.2 | 199 | 105.9 | 0.03 |

[a] median (range);
[b] not determined

Abbreviations of pharmacokinetic parameters are as follows:

$C_{max}$, maximum observed plasma concentration;

AUC(0-t), total area under the plasma concentration versus time curve from 0 to the last data point;

AUC(0-inf), total area under the plasma concentration versus time curve;

$t_{1/2}$, apparent terminal half-life;

CL, clearance following iv administration;

MRT, mean residence time;

Vss, volume of distribution at steady state.

TABLE 32

Pharmacokinetic Parameters of L-lysine-d-amphetamine in Male
Beagle Dogs Following Oral Administration of L-lysine-d-
amphetamine (1 mg/kg d-amphetamine base).
Dose Route: Oral Dose: 2 mg/kg (free form)

| Dog ID | $C_{max}$ (ng/mL) | $T_{max}^a$ (h) | AUC(0-t) (ng · h/mL) | AUC(inf) (ng · h/mL) | $t_{1/2}$ (h) | CL/F (mL/h/kg) | MRT (h) | F (%) |
|---|---|---|---|---|---|---|---|---|
| 1 | 350.2 | 0.5 | 275.3 | 277.1 | 0.24 | 7218 | 0.68 | 30.8 |
| 2 | 407.2 | 0.5 | 367.8 | 368.7 | 0.48 | 5424 | 0.74 | 34.3 |
| 3 | 227.4 | 0.5 | 310.8 | 312.0 | 0.45 | 6410 | 1.03 | 34.0 |
| Mean | 328.2 | 0.5 | 318.0 | 319.3 | 0.39 | 6351 | 0.81 | 33.0 |
| SD | 91.9 | 0.0 | 46.7 | 46.3 | 0.1 | 898.3 | 0.19 | 1.9 |

[a] median (range)

Abbreviations of pharmacokinetic parameters are as follows:

$C_{max}$, maximum observed plasma concentration;

$T_{max}$, time when $C_{max}$ observed;

AUC(0-t), total area under the plasma concentration versus time curve from 0 to the last data point;

AUC(0-inf), total area under the plasma concentration versus time curve;

$t_{1/2}$, apparent terminal half-life;

CL/F, oral clearance;

MRT, mean residence time;

F, bioavailability.

TABLE 33

Pharmacokinetics of L-lysine-d-amphetamine in Male Beagle Dogs Following Intravenous Administration of L-lysine-d-amphetamine (1 mg/kg d-amphetamine base). Dose Route: 30-min iv Infusion Dose: 2 mg/kg of L-lysine-d-amphetamine (free form)

| Dog ID | $C_{max}$ (ng/mL) | $T_{max}^a$ (h) | AUC(0-t) (ng·h/mL) | AUC(inf) (ng·h/mL) | $t_{1/2}$ (h) |
|---|---|---|---|---|---|
| 1 | 111.2 | 2.0 | 751.9 | 757.6 | 3.35 |
| 2 | 116.8 | 0.67 | 668.5 | 673.7 | 3.43 |
| 3 | 111.4 | 1.0 | 557.8 | 586.1 | 2.65 |
| Mean | 113.2 | 1.00 | 659.4 | 672.5 | 3.14 |
| SD | 3.2 | 0.67-2.0 | 97 | 85.7 | 0.4 |

[a]median (range)
Abbreviations of pharmacokinetic parameters are as follows:
$C_{max}$, maximum observed plasma concentration;
$T_{max}$, time when $C_{max}$ observed;
AUC(0-t), total area under the plasma concentration versus time curve from 0 to the last data point;
AUC(0-inf), total area under the plasma concentration versus time curve;
$t_{1/2}$, apparent terminal half-life;
CL/F, oral clearance;
MRT, mean residence time;
F, bioavailability.

TABLE 34

Pharmacokinetics of L-lysine-d-amphetamine in Male Beagle Dogs Following Oral Administration of L-lysine-d-amphetamine (1 mg/kg d-amphetamine base). Dose Route: Oral Dose: 2 mg/kg of L-lysine-d-amphetamine (free form)

| Dog ID | $C_{max}$ (ng/mL) | $T_{max}^a$ (h) | AUC(0-t) (ng·h/mL) | AUC(inf) (ng·h/mL) | $t_{1/2}$ (h) |
|---|---|---|---|---|---|
| 1 | 102.1 | 2.0 | 686.34 | 696.89 | 3.93 |
| 2 | 127.2 | 2.0 | 937.57 | 946.62 | 3.44 |
| 3 | 83.7 | 2.0 | 494.61 | 540.38 | 3.06 |
| Mean | 104.3 | 2.0 | 706.2 | 728.0 | 3.48 |
| SD | 21.8 | 2.0-2.0 | 222.1 | 204.9 | 0.4 |

[a]median (range)
Abbreviations of pharmacokinetic parameters are as follows:
$C_{max}$, maximum observed plasma concentration;
$T_{max}$, time when $C_{max}$ observed;
AUC(0-t), total area under the plasma concentration versus time curve from 0 to the last data point;
AUC(0-inf), total area under the plasma concentration versus time curve;
$t_{1/2}$, apparent terminal half-life;
CL/F, oral clearance;
MRT, mean residence time;
F, bioavailability.

TABLE 35

Pharmacokinetics of d-amphetamine in Male Beagle Dogs Following Oral Administration of L-lysine-d-amphetamine or d-amphetamine sulfate (1.8 mg/kg d-amphetamine base).

| | Mean Plasma Concentration | | Standard Deviation (SD) | | Coefficient of Variation (CV) | |
|---|---|---|---|---|---|---|
| Time (hours) | d-amphetamine | L-lysine-d-amphetamine | d-amphetamine | L-lysine-d-amphetamine | d-amphetamine | L-lysine-d-amphetamine |
| 0 | 0 | 0 | 0 | 0 | 0 | 0 |
| 1 | 431.4 | 223.7 | 140.7 | 95.9 | 32.6 | 42.9 |
| 2 | 360 | 291.8 | 87.6 | 93.6 | 24.3 | 32.1 |
| 4 | 277.7 | 247.5 | 68.1 | 66 | 24.5 | 26.7 |
| 6 | 224.1 | 214.7 | 59.3 | 62.1 | 26.5 | 28.9 |
| 8 | 175.4 | 150 | 66.7 | 40.1 | 38.0 | 26.7 |
| 12 | 81.4 | 47.6 | 58.7 | 19 | 72.1 | 39.9 |
| 16 | 33 | 19.6 | 28.1 | 9 | 85.2 | 45.9 |
| 24 | 7.2 | 4.5 | 4.5 | 1.7 | 62.5 | 37.8 |

TABLE 36

Pharmacokinetics of d-amphetamine in Female Beagle Dogs Following Oral Administration of L-lysine-d-amphetamine or d-amphetamine sulfate (1.8 mg/kg d-amphetamine base).

| | Mean Plasma Concentration | | Standard Deviation (SD) | | Coefficient of Variation (CV) | |
|---|---|---|---|---|---|---|
| Time (hours) | d-amphetamine | L-lysine-d-amphetamine | d-amphetamine | L-lysine-d-amphetamine | d-amphetamine | L-lysine-d-amphetamine |
| 0 | 0 | 0 | 0 | 0 | 0 | 0 |
| 1 | 217.8 | 308.8 | 141.7 | 40.7 | 65.1 | 13.2 |

TABLE 36-continued

Pharmacokinetics of d-amphetamine in Female Beagle Dogs Following Oral Administration of L-lysine-d-amphetamine or d-amphetamine sulfate (1.8 mg/kg d-amphetamine base).

| Time (hours) | Mean Plasma Concentration | | Standard Deviation (SD) | | Coefficient of Variation (CV) | |
|---|---|---|---|---|---|---|
| | d-amphetamine | L-lysine-d-amphetamine | d-amphetamine | L-lysine-d-amphetamine | d-amphetamine | L-lysine-d-amphetamine |
| 2 | 273.5 | 308 | 113.7 | 29.6 | 41.6 | 9.6 |
| 4 | 266 | 260.9 | 132.7 | 37.3 | 49.9 | 14.3 |
| 6 | 204.7 | 212.1 | 84.5 | 38.7 | 41.3 | 18.2 |
| 8 | 160.1 | 164.3 | 72.7 | 43.5 | 45.4 | 26.5 |
| 12 | 79.4 | 68.7 | 41.3 | 31 | 52.0 | 45.1 |
| 16 | 25.5 | 22.3 | 13.4 | 4.7 | 52.5 | 21.1 |
| 24 | 5.6 | 5.4 | 4.1 | 1.9 | 73.2 | 35.2 |

TABLE 37

Pharmacokinetic Parameters of d-amphetamine in Male and Female Beagle Dogs Following Oral Administration of L-lysine-d-amphetamine or d-amphetamine sulfate (1.8 mg/kg d-amphetamine base).

| Parameter | Males Compound | | Females Compound | |
|---|---|---|---|---|
| | d-amphetamine | L-lysine-d-amphetamine | d-amphetamine | L-lysine-d-amphetamine |
| AUCinf | 3088.9 | 2382.2 | 2664.5 | 2569.9 |
| Percent | 100 | 77 | 100 | 96 |
| Cmax | 431.4 | 291.8 | 308.8 | 273.5 |
| Percent | 100 | 67 | 100 | 89 |
| Tmax(hours) | 1 | 2 | 1 | 2 |
| Percent | 100 | 200 | 100 | 200 |

Example 20

Figure 35:
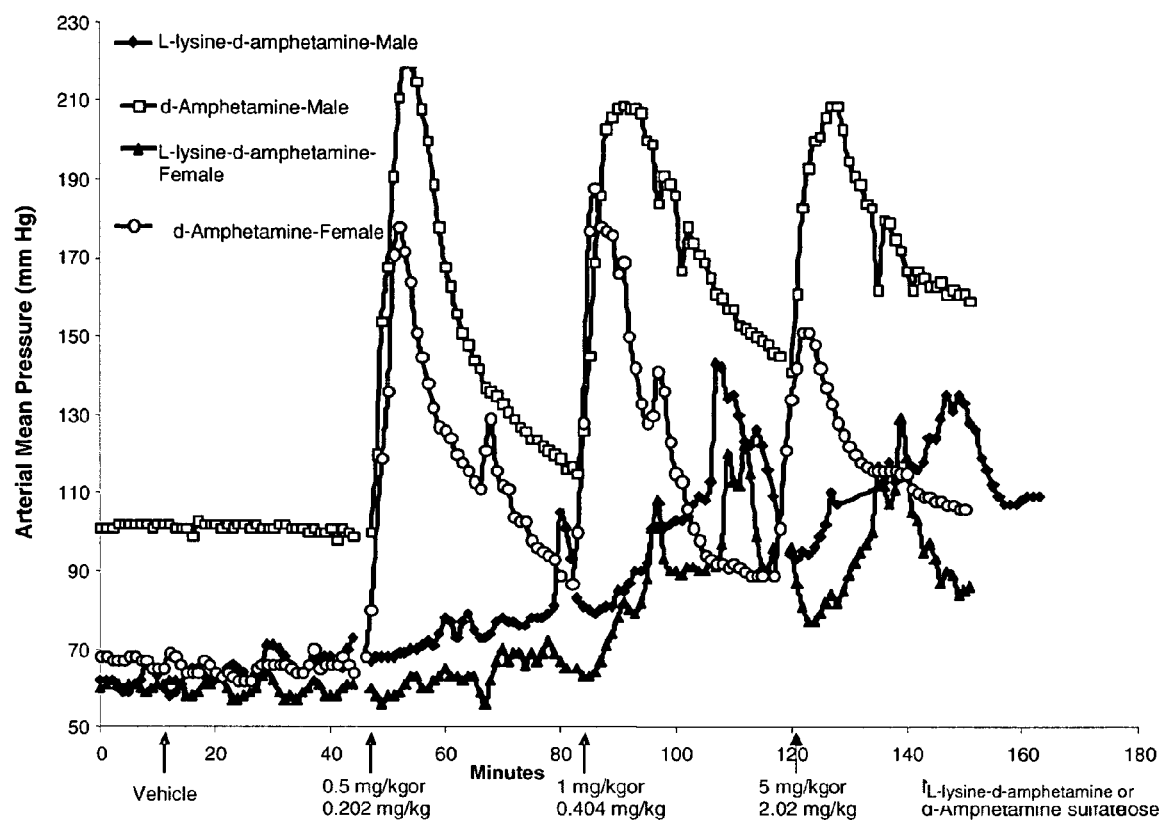
FIG. 35. Mean blood pressure following intravenous bolus injection of increasing amounts of L-lysine-d-amphetamine or d-amphetamine in male and female dogs.

Delayed Cardiovascular Effects of L-lysine-d-amphetamine as Compared to d-amphetamine Following Intravenous Infusion Systolic and diastolic blood pressure (BP) are increased by d-amphetamine even at therapeutic doses. Since L-lysine-d-amphetamine is expected to release d-amphetamine (albeit slowly) as a result of systemic metabolism, a preliminary study was done using equimolar doses of d-amphetamine or L-lysine-d-amphetamine to 4 dogs (2 male and 2 female). The results suggest that the amide prodrug is inactive and that slow release of some d-amphetamine, occurs beginning 20 minutes after the first dose. Relative to d-amphetamine, however, the effects are less robust. For example, the mean blood pressure is graphed in FIG. 35. Consistent with previously published data (Kohli and Goldberg, 1982), small doses of d-amphetamine were observed to have rapid effects on blood pressure. The lowest dose (0.202 mg/kg, equimolar to 0.5 mg/kg of L-lysine-d-amphetamine) produced an acute doubling of the mean BP followed by a slow recovery over 30 minutes.

Figure 36:
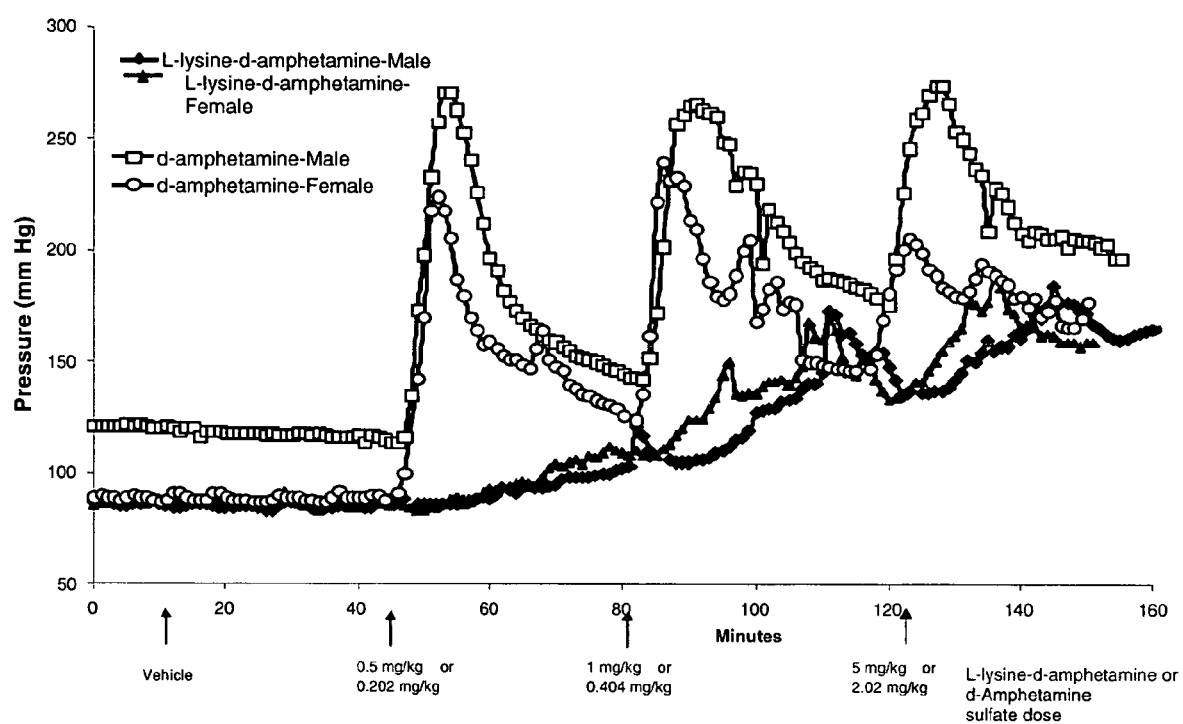
FIG. 36. Left ventricular blood pressure following intravenous bolus injection of increasing amounts of L-lysine-d-amphetamine or d-amphetamine in male and female dogs.

By contrast, L-lysine-d-amphetamine produced very little change in mean BP until approximately 30 minutes after injection. At that time, pressure increased by about 20-50%. Continuous release of d-amphetamine is probably responsible for the slow and steady increase in blood pressure over the remaining course of the experiment. Upon subsequent injections, d-amphetamine is seen to repeat its effect in a non-dose dependent fashion. That is, increasing dose 10-fold from the first injection produced a rise to the same maximum pressure. This may reflect the state of catecholamine levels in nerve terminals upon successive stimulation of d-amphetamine, bolus injections. Note that the rise in mean blood pressure seen after successive doses of L-lysine-d-amphetamine (FIG. 35) produces a more gradual and less intense effect. Similar results were observed for left ventricular pressure (FIG. 36). These results further substantiate the significant decrease in d-amphetamine bioavailability by the intravenous route when given as L-lysine-d-amphetamine. As a result the rapid onset of the pharmacological effect of d-amphetamine that is sought by persons injecting the drug is eliminated.

TABLE 38

Effects of L-lysine-d-amphetamine on Cardiovascular Parameters in the Anesthetized Dog - Mean Values (n = 2)

| TREATMENT | TIME | SAP | % Change | DAP | % Change | MAP | % Change | LVP | % Change |
|---|---|---|---|---|---|---|---|---|---|
| 0.9% Saline | 0 | 81 | 0 | 48 | 0 | 61 | 0 | 87 | 0 |
| 1 ml/kg | 30 | 87 | 7 | 54 | 11 | 67 | 10 | 87 | 0 |
| L-lysine-d-amphetamine | 0 | 84 | 0 | 51 | 0 | 64 | 0 | 86 | 0 |
| 0.5 mg/kg | 5 | 87 | 4 | 52 | 3 | 66 | 3 | 87 | 2 |
| | 15 | 93 | 11 | 51 | 1 | 67 | 5 | 95 | 11 |
| | 25 | 104 | 25 | 55 | 8 | 73 | 15 | 105 | 22 |
| | 30 | 107 | 28 | 58 | 14 | 77 | 21 | 108 | 26 |
| L-lysine-d-amphetamine | 0 | 105 | 0 | 55 | 0 | 74 | 0 | 108 | 0 |
| 1.0 mg/kg | 5 | 121 | 15 | 63 | 15 | 85 | 15 | 120 | 11 |
| | 15 | 142 | 35 | 73 | 33 | 100 | 35 | 140 | 29 |
| | 25 | 163 | 55 | 97 | 75 | 124 | 68 | 162 | 50 |
| | 30 | 134 | 28 | 73 | 32 | 98 | 32 | 144 | 33 |

TABLE 38-continued

Effects of L-lysine-d-amphetamine on Cardiovascular Parameters in the Anesthetized Dog - Mean Values (n = 2)

| TREATMENT | TIME | SAP | % Change | DAP | % Change | MAP | % Change | LVP | % Change |
|---|---|---|---|---|---|---|---|---|---|
| L-lysine-d-amphetamine | 0 | 132 | 0 | 71 | 0 | 95 | 0 | 144 | 0 |
| 5.0 mg/kg | 5 | 142 | 7 | 71 | 0 | 99 | 4 | 151 | 5 |
|  | 15 | 176 | 33 | 98 | 39 | 130 | 37 | 184 | 28 |
|  | 25 | 126 | −5 | 69 | −3 | 96 | 1 | 160 | 11 |
|  | 30 | 132 | 0 | 70 | −1 | 99 | 4 | 163 | 13 |

SAP - systolic arterial pressure (mmHg)
MAP - mean arterial pressure (mmHg)
DAP - diastolic arterial pressure (mmHg)
LVP - left ventricular pressure (mmHg)
% Change - percent change from respective Time 0.

TABLE 39

Effects of d-Amphetamine on Cardiovascular Parameters in the Anesthetized Dog - Mean Values (n = 2)

| TREATMENT | TIME | SAP | % Change | DAP | % Change | MAP | % Change | LVP | % Change |
|---|---|---|---|---|---|---|---|---|---|
| 0.9% Saline | 0 | 110 | 0 | 67 | 0 | 84 | 0 | 105 | 0 |
| 1 ml/kg | 30 | 108 | −2 | 65 | −3 | 82 | −2 | 101 | −3 |
| d-amphetamine | 0 | 111 | 0 | 67 | 0 | 84 | 0 | 104 | 0 |
| 0.202 mg/kg | 5 | 218 | 97 | 145 | 117 | 176 | 109 | 214 | 107 |
|  | 15 | 168 | 52 | 97 | 45 | 125 | 49 | 157 | 52 |
|  | 25 | 148 | 34 | 87 | 30 | 110 | 31 | 142 | 37 |
|  | 30 | 140 | 26 | 80 | 20 | 103 | 23 | 135 | 30 |
| d-amphetamine | 0 | 139 | 0 | 78 | 0 | 101 | 0 | 133 | 0 |
| 0.404 mg/kg | 5 | 240 | 73 | 147 | 88 | 187 | 85 | 238 | 79 |
|  | 15 | 193 | 39 | 112 | 44 | 145 | 43 | 191 | 43 |
|  | 25 | 166 | 19 | 92 | 17 | 122 | 20 | 168 | 26 |
|  | 30 | 160 | 16 | 87 | 11 | 117 | 16 | 163 | 22 |
| d-amphetamine | 0 | 158 | 0 | 87 | 0 | 115 | 0 | 162 | 0 |
| 2.02 mg/kg | 5 | 228 | 44 | 128 | 48 | 169 | 47 | 227 | 40 |
|  | 15 | 196 | 24 | 107 | 23 | 142 | 23 | 200 | 24 |
|  | 25 | 189 | 20 | 102 | 17 | 135 | 17 | 192 | 19 |
|  | 30 | 183 | 16 | 98 | 13 | 129 | 12 | 187 | 16 |

SAP - systolic arterial pressure (mmHg)
MAP - mean arterial pressure (mmHg)
DAP - diastolic arterial pressure (mmHg)
LVP - left ventricular pressure (mmHg)
% Change - percent change from respective Time 0.

Example 21

Figure 37:
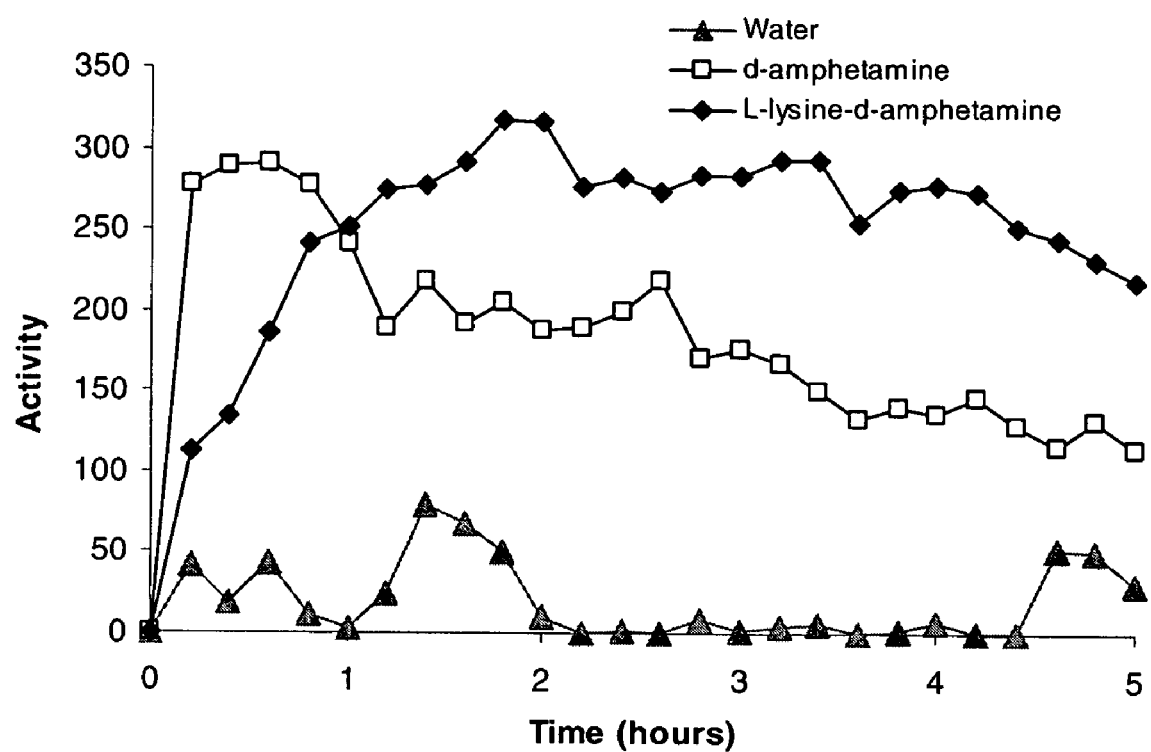
FIG. 37. Locomotor activity of rats following oral administration of L-lysine-d-amphetamine or d-amphetamine (5 hour time-course).
Figure 38:
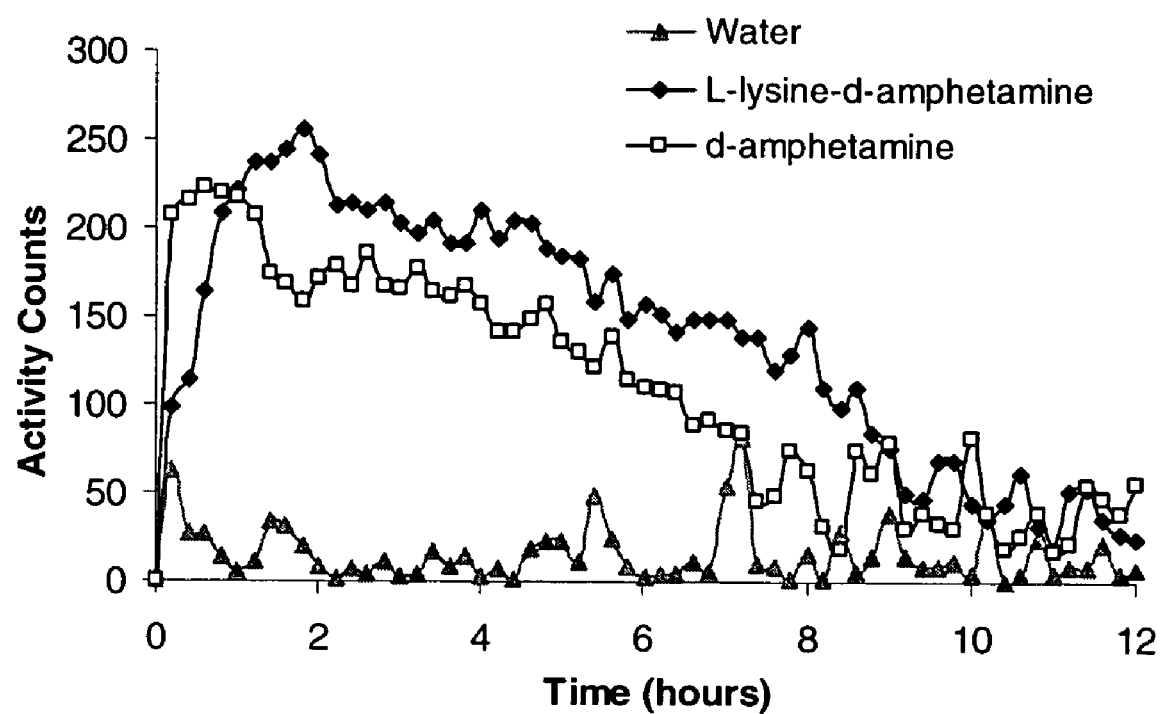
FIG. 38. Locomotor activity of rats following oral administration of L-lysine-d-amphetamine or d-amphetamine (12 hour time-course).

Pharmacodynamic (Locomotor) Response to Amphetamine vs. L-lysine-d-amphetamine by Oral Administration Male Sprague-Dawley rats were provided water ad libitum, fasted overnight and dosed by oral gavage with 6 mg/kg of amphetamine or L-lysine-d-amphetamine containing the equivalent amount of d-amphetamine. Horizontal locomotor activity (HLA) was recorded during the light cycle using photocell activity chambers (San Diego Instruments). Total counts were recorded every 12 minutes for the duration of the test. Rats were monitored in three separate experiments for 5, 8, and 12 hours, respectively. Time vs. HLA counts for d-amphetamine vs. L-lysine-d-amphetamine is shown in FIGS. 37-38. In each experiment the time until peak activity was delayed and the pharmacodynamic effect was evident for an extended period of time for L-lysine-d-amphetamine as compared to d-amphetamine. The total activity counts for HLA of Lys-Amp dosed rats were increased (11-41%) over those induced by d-amphetamine in all three experiments (Tables 40 and 41).

TABLE 40

Locomotor Activity of Rats Orally Administered d-amphetamine vs. L-lysine-d-amphetamine (5 Hours)

| Test Material | Total Activity Counts | Total Activity Counts Above Baseline | Peak of activity (Counts per 0.2 h) | Time of Peak (Counts per 0.2 h) | Time of Last Count Above 200 per 0.2 h |
|---|---|---|---|---|---|
| Vehicle | 4689 | 4174 | 80 | 1.4 | — |
| L-lysine-d- | 6417 | 5902 | 318 | 1.8 | 5 h |

TABLE 40-continued

Locomotor Activity of Rats Orally Administered d-amphetamine vs. L-lysine-d-amphetamine (5 Hours)

| Test Material | Total Activity Counts | Total Activity Counts Above Baseline | Peak of activity (Counts per 0.2 h) | Time of Peak (Counts per 0.2 h) | Time of Last Count Above 200 per 0.2 h |
|---|---|---|---|---|---|
| amphetamine d-amphetamine | 515 | 0 | 291 | 0.6 | 2.6 h |

TABLE 41

Locomotor Activity of Rats Orally Administered Amphetamine vs. L-lysine-d-amphetamine (12 Hours)

| Test Material | Total Activity Counts | Total Activity Counts Above Baseline | Peak of activity (Counts per 0.2 h) | Time of Peak (Counts per 0.2 h) | Time of Last Count Above 100 per 0.2 h |
|---|---|---|---|---|---|
| Vehicle | 936 | 0 | 81 | 7.2 | — |
| L-lysine-d-amphetamine | 8423 | 7487 | 256 | 1.8 | 8.6 h |
| d-amphetamine | 6622 | 5686 | 223 | 0.6 | 6.4 h |

Example 22

Figure 39:
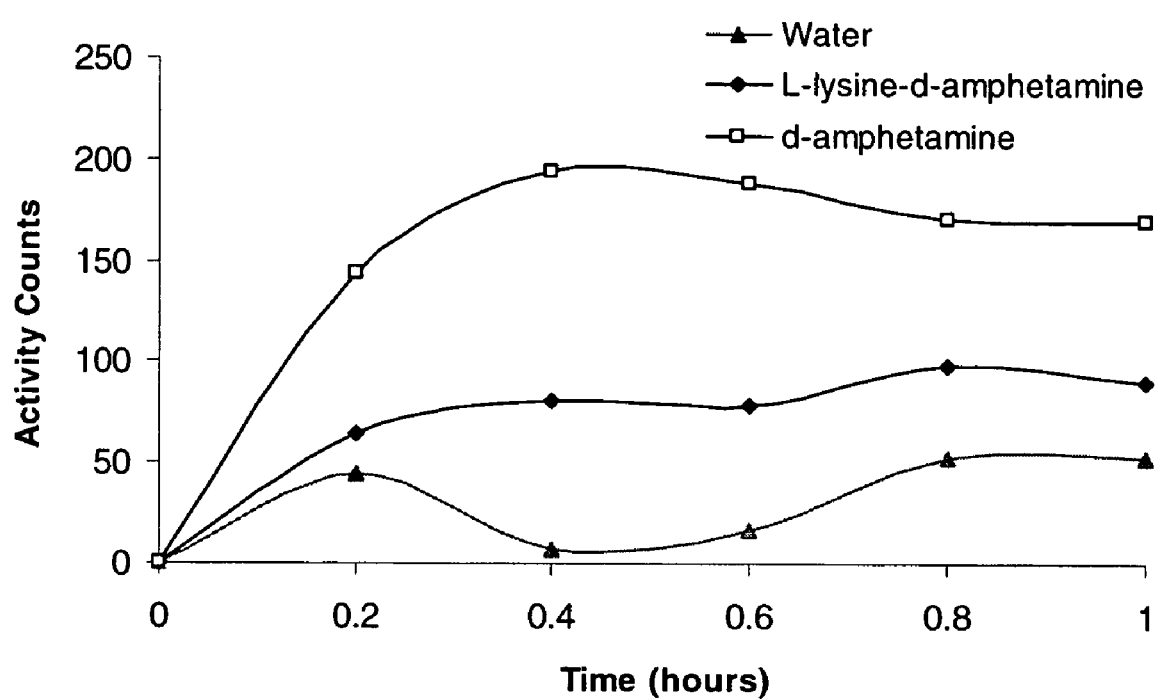
FIG. 39. Locomotor activity of rats following intranasal administration of L-lysine-d-amphetamine or d-amphetamine (1 hour time-course).
Figure 40:
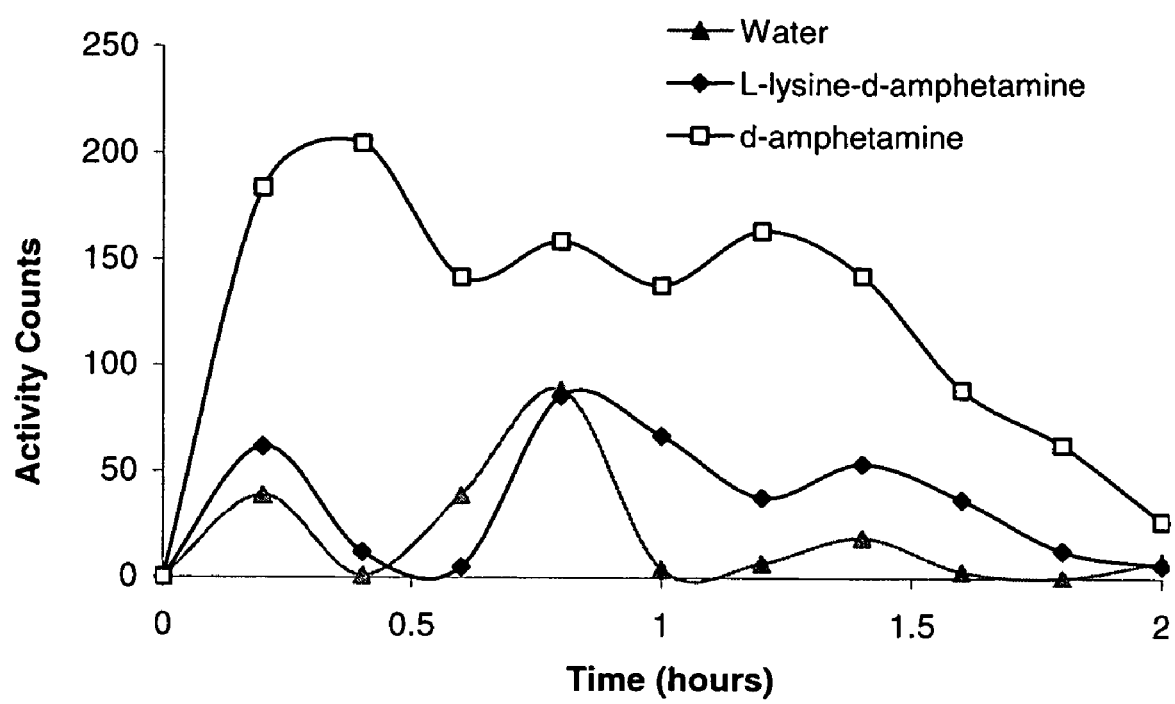
FIG. 40. Locomotor activity of rats following intranasal administration (with carboxymethylcellulose) of L-lysine-d-amphetamine or d-amphetamine (2 hour time-course).

Pharmacodynamic Response to Amphetamine vs. L-lysine-d-amphetamine by Intranasal Administration Male Sprague-Dawley rats were dosed by intranasal administration with 1.0 mg/kg of amphetamine or L-lysine-d-amphetamine containing the equivalent amount of d-amphetamine. In a second set of similarly dosed animals carboxymethyl cellulose (CMC) was added to the drug solutions at a concentration of 62.6 mg/ml (approximately 2-fold higher than the concentration of L-lysine-d-amphetamine and 5-fold higher than the d-amphetamine content). The CMC drug mixtures were suspended thoroughly before each dose was delivered. Locomotor activity was monitored using the procedure described in the section titled example 7. As shown in FIGS. 39-40, the activity vs. time (1 hour or 2 hours) is shown for amphetamine/CMC vs. L-lysine-d-amphetamine and compared to that of amphetamine vs. L-lysine-d-amphetamine CMC. As seen in FIG. 39, addition of CMC to L-lysine-d-amphetamine decreased the activity response of IN dosed rats to levels similar to the water/CMC control, whereas no effect was seen on amphetamine activity by the addition of CMC. The increase in activity over baseline of L-lysine-d-amphetamine with CMC was only 9% compared to 34% for Lys-Amp without CMC when compared to activity observed for d-amphetamine dosed animals (Table 42). CMC had no observable affect on d-amphetamine activity induced by IN administration.

TABLE 42

Locomotor Activity of Intranasal d-amphetamine vs. L-lysine-d-amphetamine with and without CMC

| Drug | n | Total Activity Counts (1 h) | Total Activity Counts Above Baseline | Percent d-amphetamine |
|---|---|---|---|---|
| d-mphetamine | 3 | 858 | 686 | 100 |
| d-amphetamine CMC | 3 | 829 | 657 | 100 |
| L-lysine-d-amphetamine | 4 | 408 | 237 | 35 |
| L-lysine-d-amphetamine CMC | 4 | 232 | 60 | 9 |
| Water | 1 | 172 | 0 | 0 |
| Water CMC | 1 | 172 | 0 | 0 |

Example 23

Figure 41:
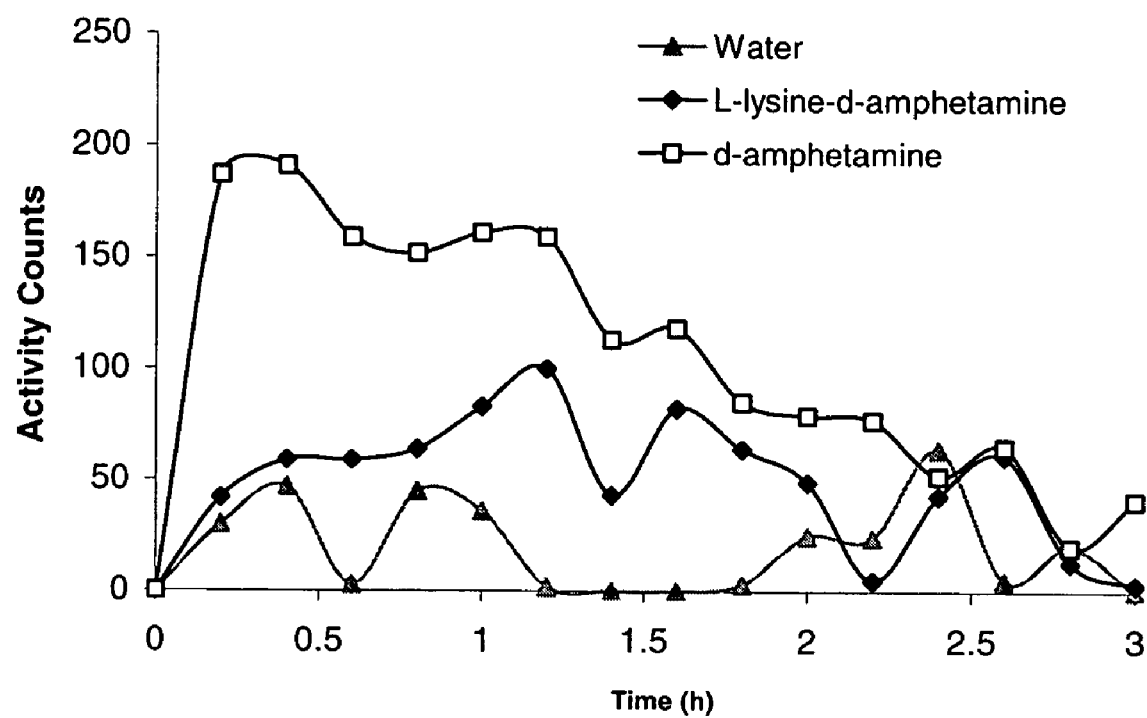
FIG. 41. Locomotor activity of rats following intravenous administration of L-lysine-d-amphetamine or d-amphetamine (3 hour time-course).
Figure 42:
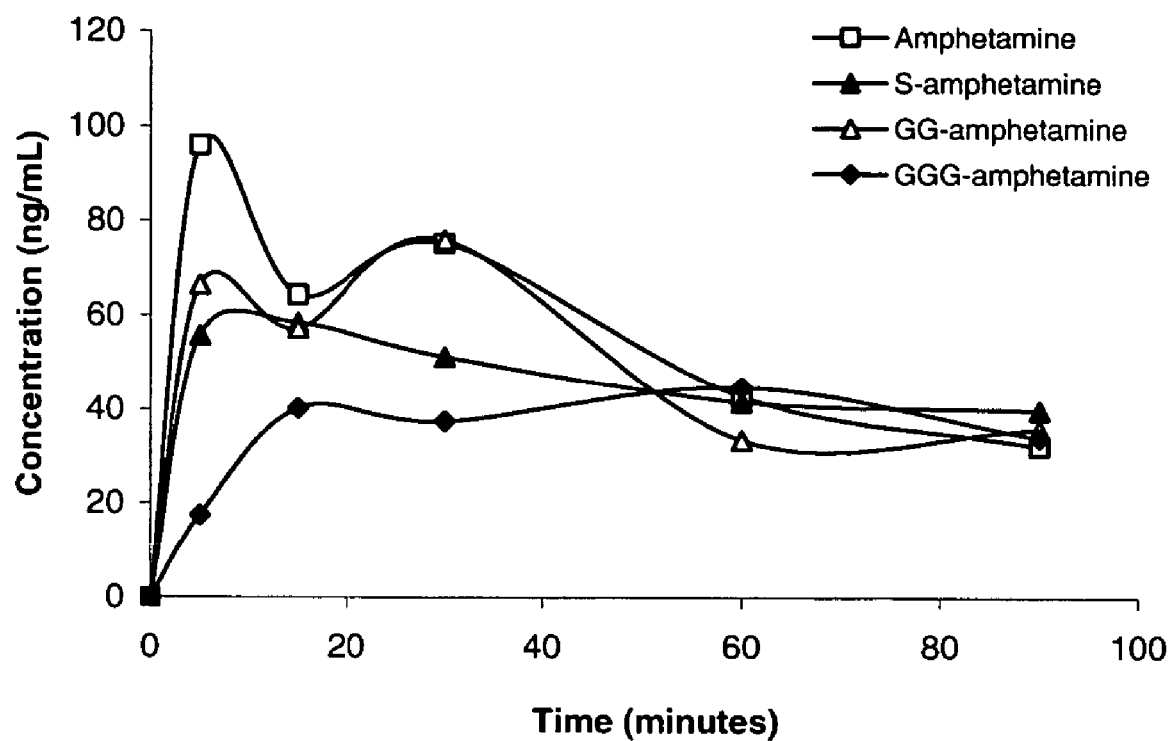
FIG. 42. Intranasal bioavailability of abuse-resistant amphetamine amino acid-, di-, and tri-peptide conjugates (ELISA analysis).
Figure 43:
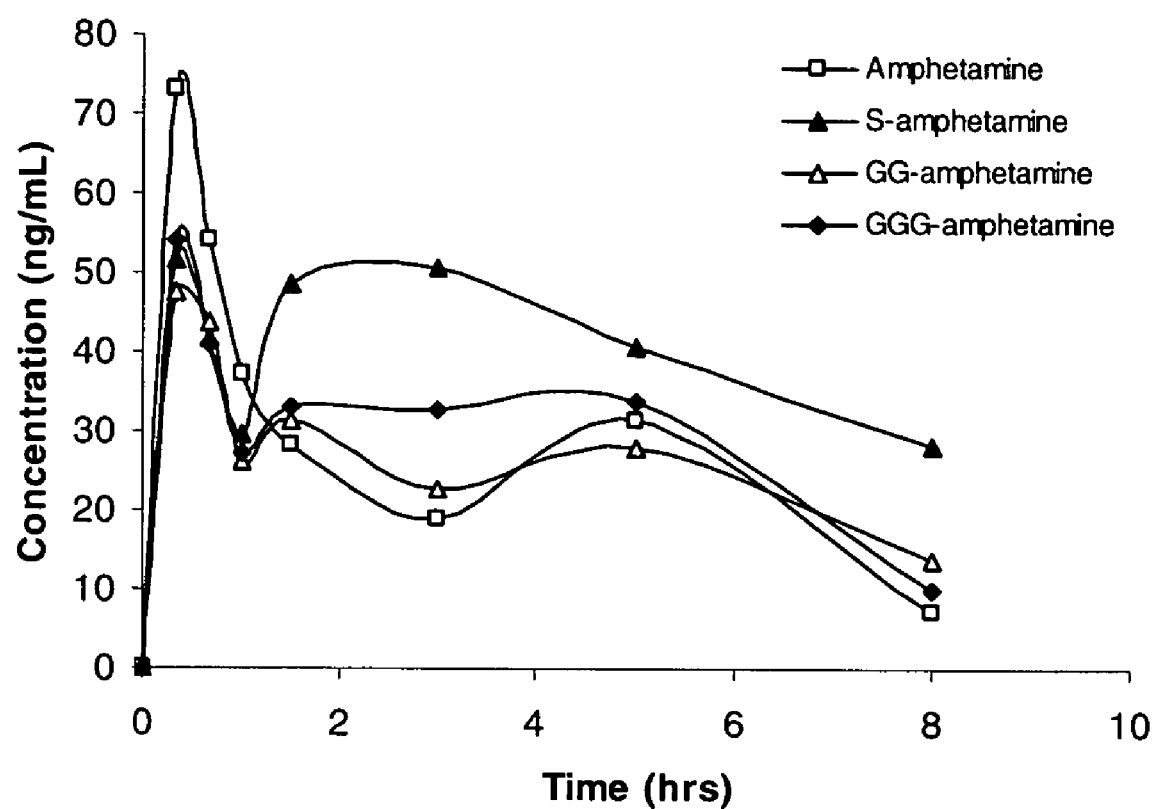
FIG. 43. Oral bioavailability of abuse-resistant amphetamine amino acid-, di-, and tri-peptide conjugates (ELISA analysis).
Figure 44:
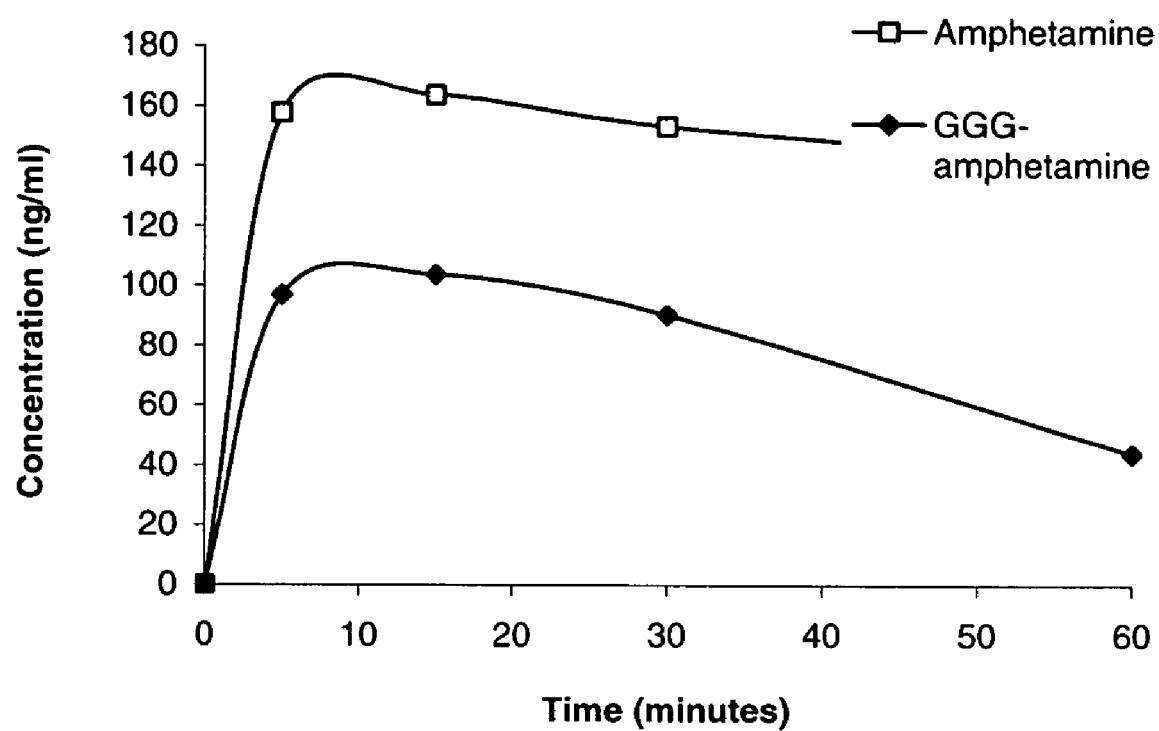
FIG. 44. Intravenous bioavailability of an abuse-resistant amphetamine tri-peptide conjugate (ELISA analysis).
Figure 45:
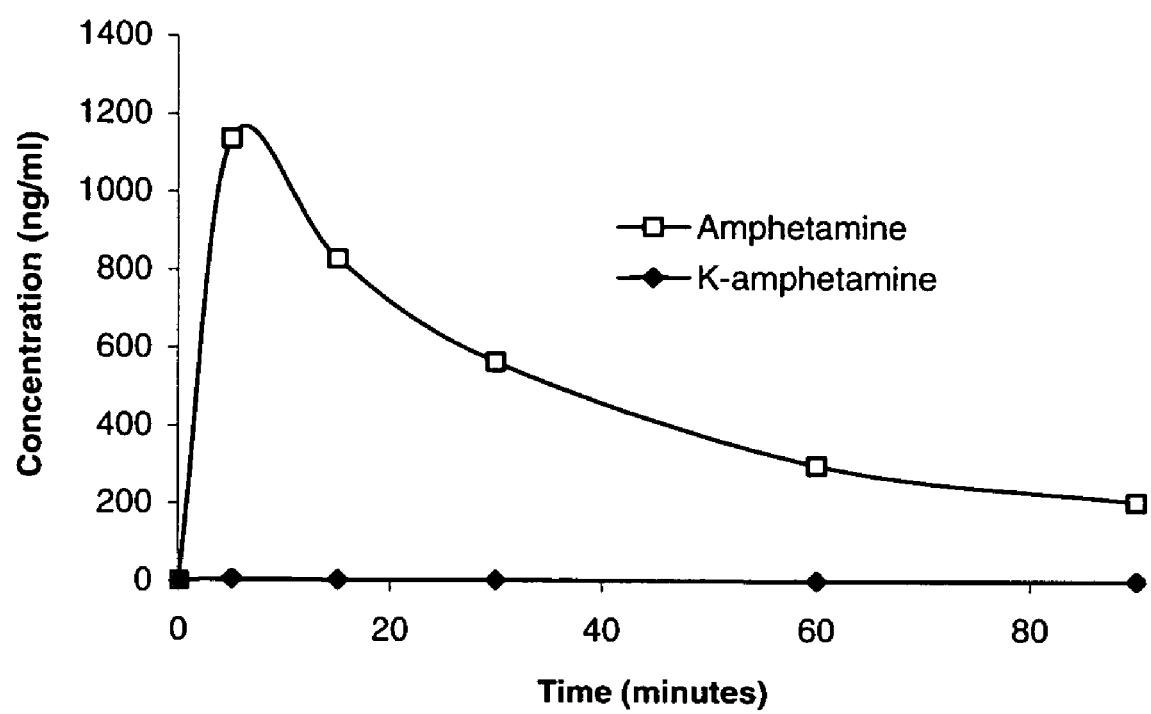
FIG. 45. Intranasal bioavailability of an abuse-resistant amphetamine amino acid conjugate (ELISA analysis).
Figure 46:
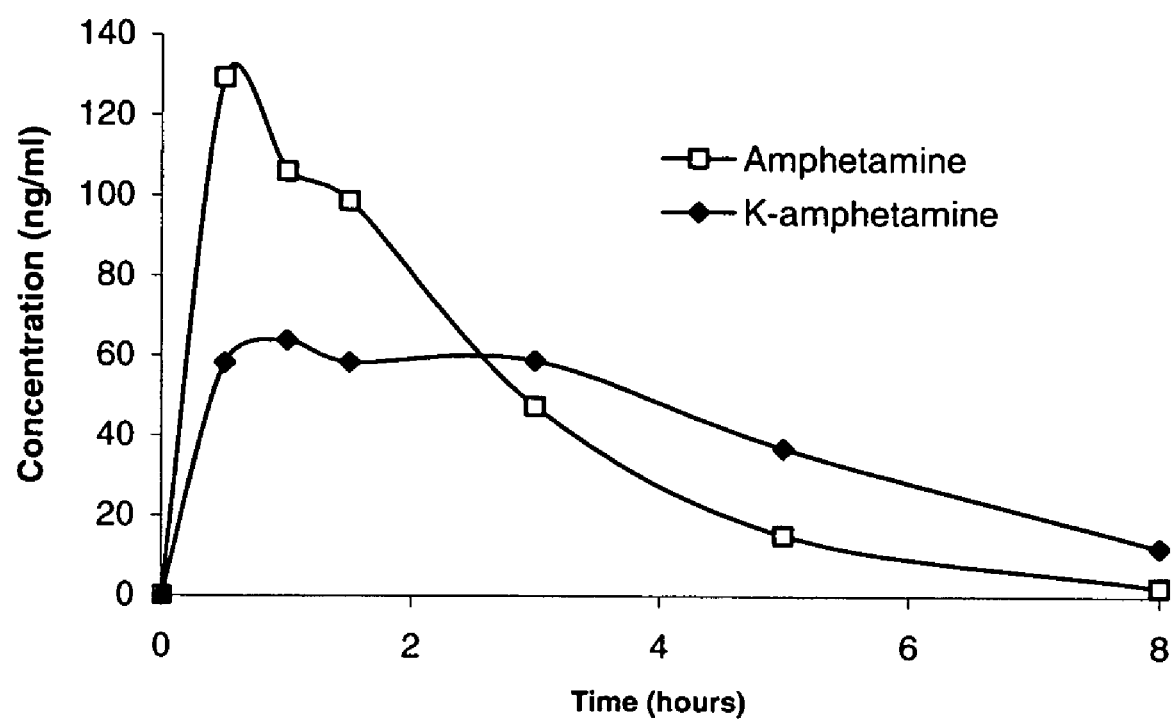
FIG. 46. Oral bioavailability of an abuse-resistant amphetamine amino acid conjugate (ELISA analysis).
Figure 47:
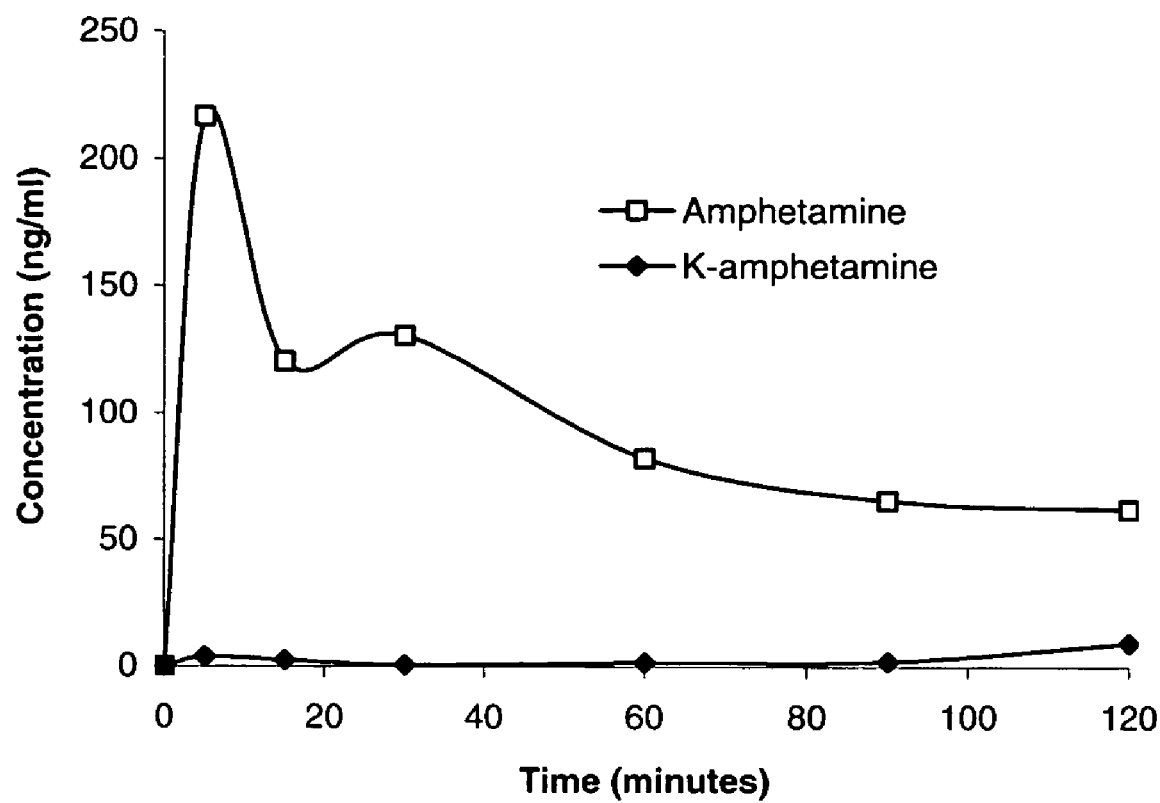
FIG. 47. Intravenous bioavailability of abuse-resistant amphetamine amino acid-, di-, and tri-peptide conjugates (ELISA analysis).
Figure 48:
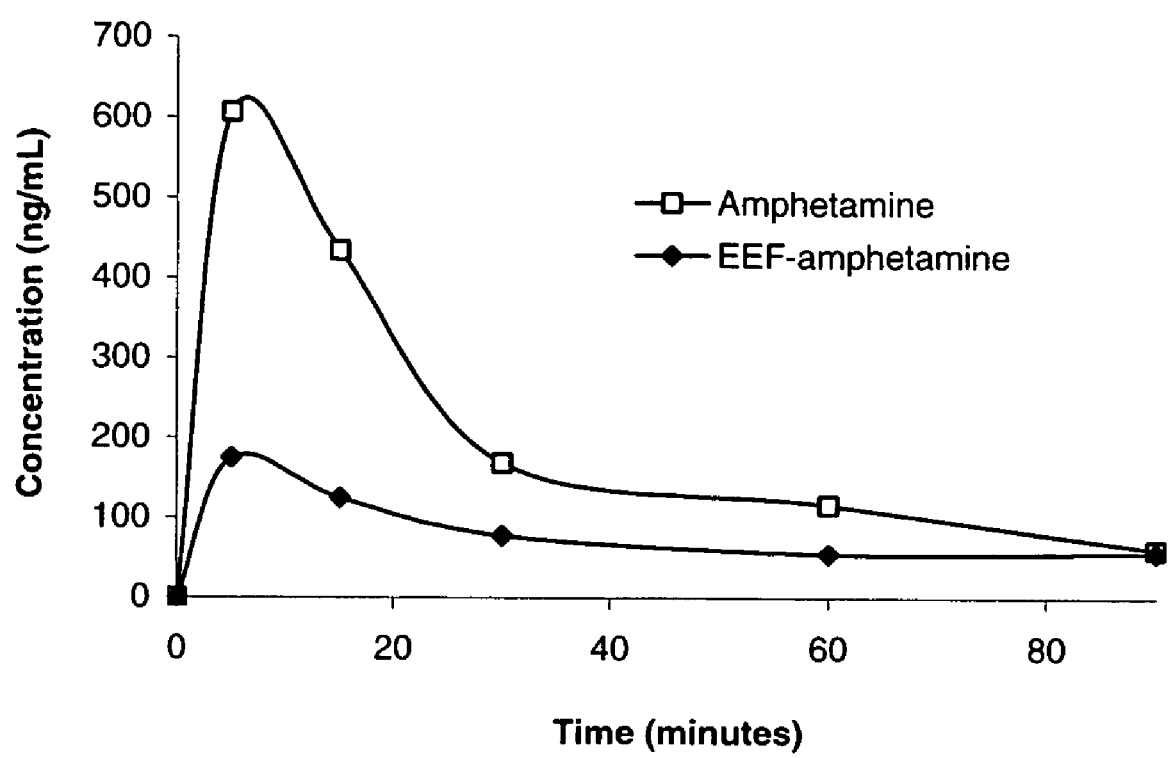
FIG. 48. Intranasal bioavailability of an abuse-resistant amphetamine amino tri-peptide conjugate (ELISA analysis).
Figure 49:
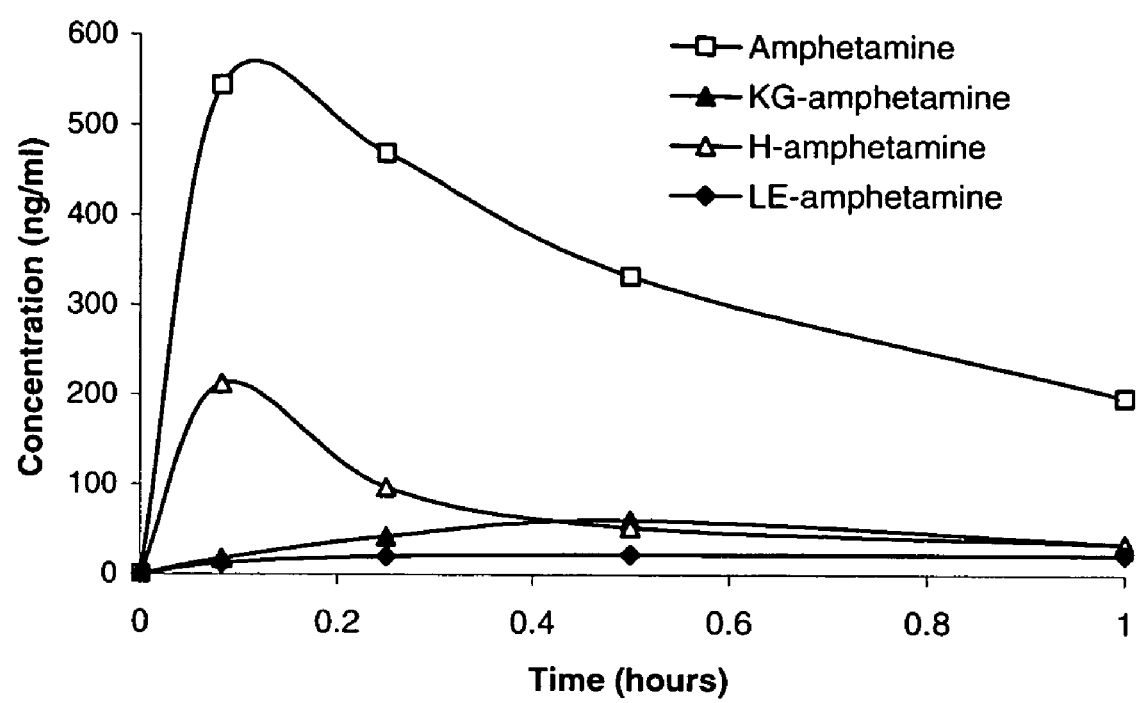
FIG. 49. Intranasal bioavailability of abuse-resistant amphetamine amino acid-, and di-peptide conjugates (ELISA analysis).
Figure 50:
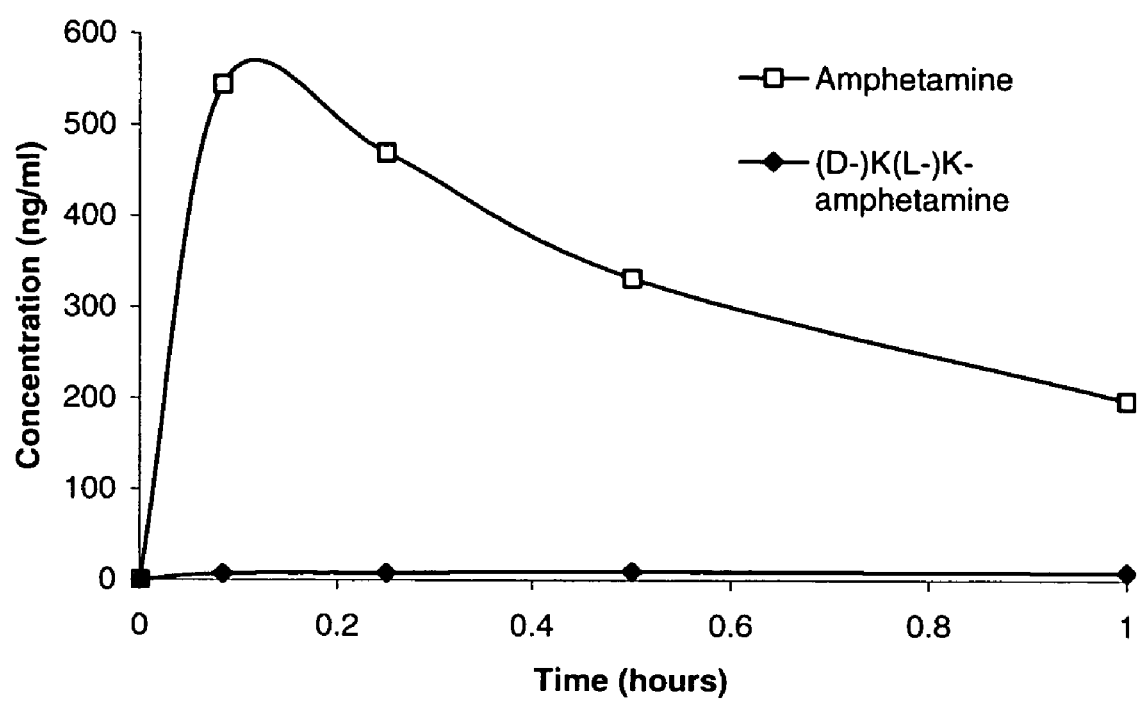
FIG. 50. Intranasal bioavailability of an abuse-resistant amphetamine di-peptide conjugate containing D- and L-amino acid isomers (ELISA analysis).

Pharmacodynamic Response to Amphetamine vs. L-lysine-d-amphetamine by Intravenous (IV) Administration Male Sprague-Dawley rats were dosed by intravenous administration with 1.0 mg/kg of d-amphetamine or L-lysine-d-amphetamine containing the equivalent amount of amphetamine. The activity vs. time (3 hours) is shown for d-amphetamine vs. L-lysine-d-amphetamine (FIG. 41). The activity induced by L-lysine-d-amphetamine was substantially decreased and time to peak activity was delayed. The activity expressed as total activity counts over a three hour period of time is shown in FIG. 41. The increase in activity over baseline of L-lysine-d-amphetamine was 34% for L-lysine-d-amphetamine when compared to activity observed for d-amphetamine dosed animals (Table 43).

TABLE 43

Total activity counts after d-amphetamine vs. L-lysine-d-amphetamine

| Drug | n | Total Activity Counts 3 h | Above Baseline | Percent d-amphetamine |
|---|---|---|---|---|
| d-amphetamine | 3 | 1659 | 1355 | 100 |
| L-lysine-d- | 4 | 767 | 463 | 34 |

TABLE 43-continued

Total activity counts after d-amphetamine vs. L-lysine-d-amphetamine

| Drug | n | Total Activity Counts 3 h | Above Baseline | Percent d-amphetamine |
|---|---|---|---|---|
| amphetamine Water | 1 | 304 | 0 | 0 |

Following Intravenous (IV) Administration.

Example 24

Decrease in Toxicity of Orally Administered L-lysine-d-amphetamine

Three male and three female Sprague Dawley rats per group were given a single oral administration of L-lysine-d-amphetamine at 0.1, 1.0, 10, 60, 100 or 1000 mg/kg (Table 44). Each animal was observed for signs of toxicity and death on Days 1-7 (with Day 1 being the day of the dose) and one rat/sex/group was necropsied upon death (scheduled or unscheduled).

TABLE 44

Dosing Chart Oral Administration of L-lysine-d-amphetamine Toxicity Testing.

| Groups | No. of Animals M | F | Test Article | Dosages (mg/kg) | Concentrations (mg/mL) |
|---|---|---|---|---|---|
| 1 | 3 | 3 | L-lysine-d-amphetamine | 0.1 | 0.01 |
| 2 | 3 | 3 | L-lysine-d-amphetamine | 1.0 | 0.1 |
| 3 | 3 | 3 | L-lysine-d-amphetamine | 10 | 1.0 |
| 4 | 3 | 3 | L-lysine-d-amphetamine | 60 | 6.0 |
| 5 | 3 | 3 | L-lysine-d-amphetamine | 100 | 10 |
| 6 | 3 | 3 | L-lysine-d-amphetamine | 1000 | 100 |

Key observations of this study include:
All animals in Groups 1-3 showed no observable signs throughout the conduct of the study.
All animals in Groups 4-6 exhibited increased motor activity within two hours post-dose and which lasted into Day 2.
One female rat dosed at 1000 mg/kg was found dead on Day 2. Necropsy revealed chromodacryorrhea, chromorhinorrhea, distended stomach (gas), enlarged adrenal glands, and edematous and distended intestines.
A total of 4 rats had skin lesions of varying degrees of severity on Day 3.
One male rat dosed at 1000 mg/kg was euthanatized on Day 3 due to open skin lesions on the ventral neck.
All remaining animals appeared normal from Day 4 through Day 7.

Animals were observed for signs of toxicity at 1, 2 and 4 h post-dose, and once daily for 7 days after dosing and cage-side observations were recorded. Animals found dead, or sacrificed moribund were necropsied and discarded. A total of one animal/sex/group was necropsied upon scheduled or unscheduled death.

Cage-side observations and gross necropsy findings are summarized in Table 5. The data are not sufficient to establish a lethal dose, however, the study indicates that the lethal oral dose of L-lysine-d-amphetamine is above 1000 mg/kg, because only one death occurred out of a group of six animals. Although a second animal in this dose group was euthanatized on Day 3, it was done for humane reasons and it was felt that this animal would have fully recovered. Observations suggested drug-induced stress in Groups 4-6 that is characteristic of amphetamine toxicity (NTP, 1990; NIOSH REGISTRY NUMBER: SI1750000; Goodman et. al., 1985). All animals showed no abnormal signs on Days 4-7 suggesting full recovery at each treatment level.

The lack of data to support an established lethal dose is believed to be due to a putative protective effect of conjugating amphetamine with lysine. Intact L-lysine-d-amphetamine has been shown to be inactive, but becomes active upon metabolism into the unconjugated form (d-amphetamine). Thus, at high doses, saturation of metabolism of L-lysine-d-amphetamine into the unconjugated form may explain the lack of observed toxicity, which was expected at doses greater than 100 mg/kg, which is consistent with d-amphetamine sulfate (NTP, 1990). The formation rate of d-amphetamine and the extent of the formation of amphetamine may both attribute to the reduced toxicity. Alternatively, oral absorption of L-lysine-d-amphetamine may also be saturated at such high concentrations, which may suggest low toxicity due to limited bioavailability of L-lysine-d-amphetamine.

Example 25

In Vitro Assessment of L-lysine-d-amphetamine Pharmacodynamic Activity

It was anticipated that the acylation of amphetamine, as in the amino acid conjugates discussed here, would significantly reduce the stimulant activity of the parent drug. For example, Marvola (1976) showed that N-acetylation of amphetamine completely abolished the locomotor activity increasing effects in mice. To confirm that the conjugate was not directly acting as a stimulant, we tested (Novascreen, Hanover, Md.) the specific binding of Lys-Amp ($10^{-9}$ to $10^{-5}$ M) to human recombinant dopamine and norepinephrine transport binding sites using standard radioligand binding assays. The results (see Table 45) indicate that the Lys-Amp did not bind to these sites. It seems unlikely that the conjugate retains stimulant activity in light of these results. (Marvola, M. (1976). "Effect of acetylated derivatives of some sympathomimetic amines on the acute toxicity, locomotor activity and barbiturate anesthesia time in mice." *Acta Pharmacol Toxicol* (*Copenh*) 38(5): 474-89).

TABLE 45

Results From Radioligand Binding Experiments with L-lysine-d-amphetamine

| Assay | Radioligand | Reference Compound | Ki (M) for Ref. Cpd. | Activity* |
|---|---|---|---|---|
| NE Transporter | [3H]-Nisoxetine | Desipramine | $4.1 \times 10^{-9}$ | No |
| DA Transporter | [3H]-WIN35428 | GBR-12909 | $7.7 \times 10^{-9}$ | No |

*No activity is defined as producing between −20% and 20% inhibition of radioligand binding (Novascreen).

Example 26

In Vitro Assessment "Kitchen Tests" to Release Amphetamine

It was anticipated that attempts would be made by illicit chemists to treat the compound with various easily accessible physical and chemical methods by which to release free amphetamine from the conjugate. An abuse-resistant preparation would have the additional feature of not releasing d-amphetamine when exposed to water, acid (vinegar), base (baking powder and baking soda), and heat. In several tests with L-lysine-d-amphetamine and GGG-Amp, no amphetamine was detected after the following treatments:

|  | Vinegar | Tap Water | Baking Powder | Baking Soda |
|---|---|---|---|---|
| L-lysine-d-amphetamine | 0% | 0% | 0% | 0% |
| Gly$_3$-Amp | 0% | 0% | 0% | 0% |

Samples were heated to boiling for 20-60 minutes in each test.

Example 27

Bioavailability of Various Amino Acid-Amphetamine Compounds Administered by Oral, Intranasal, and Intravenous Routes Oral Administration. Male Sprague-Dawley rats were provided water ad libitum, fasted overnight, and dosed by oral gavage with amphetamine or amino acid-amphetamine conjugates containing the equivalent amount of amphetamine.

Intranasal Administration. Male Sprague-Dawley rats were dosed by intranasal administration with 1.8 mg/kg of amphetamine or lysine-amphetamine containing the equivalent amount of amphetamine.

The relative in vivo performance of various amino acid-amphetamine compounds is shown in FIGS. 42-50 and summarized in Table 46. Intranasal bioavailability of amphetamine from Ser-Amp was decreased to some degree relative to free amphetamine. However, this compound was not bioequivalent with amphetamine by the oral route of administration. Phenylalanine was bioequivalent with amphetamine by the oral route of administration, however, little or no decrease in bioavailability by parenteral routes of administration was observed. Gly$_3$-Amp had nearly equal bioavailability (90%) by the oral route accompanied by a decrease in Cmax (74%). Additionally, Gly$_3$-Amp showed a decrease in bioavailability relative to amphetamine by intranasal and intravenous routes.

TABLE 46

Percent Bioavailability of Amino Acid Amphetamine Compounds Administered by Oral, Intranasal or Intravenous Routes

| Drug | Oral | | Intranasal | | Intravenous | |
|---|---|---|---|---|---|---|
|  | Percent AUC | Percent Cmax | Percent AUC | Percent Cmax | Percent AUC | Percent Cmax |
| Amphetamine | 100 | 100 | 100 | 100 | 100 | 100 |
| E-Amp | 73 | 95 | NA | NA | NA | NA |
| EE-Amp | 26 | 74 | NA | NA | NA | NA |
| L-Amp | 65 | 81 | NA | NA | NA | NA |
| S-Amp | 79/55 | 62/75 | 76 | 65 | NA | NA |
| GG-Amp | 79 | 88 | 88 | 85 | NA | NA |
| GGG-Amp | 111/68 | 74/73 | 32 | 38 | 45 | 46 |
| F-Amp | 95 | 91 | 97 | 95 | 87 | 89 |
| EEF-Amp | 42 | 73 | 39 | 29 | NA | NA |
| FF-Amp | 27 | 64 | NA | NA | NA | NA |
| Gulonate-Amp | 1 | 1 | 0.4 | 0.5 | 3 | 5 |
| K-Amp | 98 | 55 | 0.5 | 0.5 | 3 | 3 |
| KG-Amp | 69 | 71 | 13 | 12 | NA | NA |
| dK/K-Amp | 16 | 7 | 2 | 2 | NA | NA |
| LE-Amp | 40 | 28 | 6 | 6 | NA | NA |
| H-Amp | 16 | 21 | 22 | 42 | NA | NA |

C. Methods of In Vivo Testing of Abuse Resistant Amphetamine Conjugates

Example 28

Decreased Oral $C_{max}$ of d-Amphetamine Conjugates

Male Sprague-Dawley rats were provided water ad libitum, fasted overnight and dosed by oral gavage with amphetamine conjugate or d-amphetamine sulfate. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 29

Decreased Intranasal Bioavailability (AUC and $C_{max}$) of d-Amphetamine Conjugates Male Sprague-Dawley rats were provided water ad libitum and doses were administered by placing 0.02 ml of water containing amphetamine conjugate or d-amphetamine sulfate into the nasal flares. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 30

Decreased Intravenous Bioavailability (AUC and $C_{max}$) of d-Amphetamine Conjugates Male Sprague-Dawley rats were provided water ad libitum and doses were administered by intravenous tail vein injection of 0.1 ml of water containing amphetamine conjugate or d-amphetamine sulfate. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 31

Attachment of Amphetamine to Variety of Chemical Moieties

The above examples demonstrate the use of an amphetamine conjugated to a chemical moiety, such as an amino acid, which is useful in reducing the potential for overdose while maintaining its therapeutic value. The effectiveness of binding amphetamine to a chemical moiety was demonstrated through the attachment of amphetamine to lysine (K), however, the above examples are meant to be illustrative only. The attachment of amphetamine to any variety of chemical moieties (i.e. peptides, glycopeptides, carbohydrates, nucleosides, or vitamins) may be accomplished through similar procedures described throughout the Examples. For instance the below moieties may be attached to amphetamine using methods similar to those described in Example 2.

Amphetamine Synthetic Examples

Synthesis of Gly-Gly-Amp

Gly-Gly-Amp was synthesized by a similar method except the amino acid starting material was Boc-Gly-Gly-OSu.

Synthesis of Glu-Glu-Phe-Amp

Glu-Glu-Phe-Amp was synthesized by a similar method except the amino acid starting material was Boc-Glu(OtBu)-Glu(OtBu)-OSu and the starting drug conjugate was Phe-Amp (see Phe-Amp synthesis).

Synthesis of His-Amp

His-Amp was synthesized by a similar method except the amino acid starting material was Boc-His(Trt)-OSu.

Synthesis of Lys-Gly-Amp

Lys-Gly-Amp was synthesized by a similar method except the amino acid starting material was Boc-Lys(Boc)-OSu and the starting drug conjugate was Gly-Amp (see Gly-Amp synthesis).

Synthesis of Lys-Glu-Amp

Lys-Glu-Amp was synthesized by a similar method except the amino acid starting material was Boc-Lys(Boc)-OSu and the starting drug conjugate was Glu-Amp.

Synthesis of Glu-Amp

Glu-Amp was synthesized by a similar method except the amino acid starting material was Boc-Glu(OtBu)-OSu.

Synthesis of (d)-Lys-(l)-Lys-Amp (d)-Lys-(l)-Lys-Amp was synthesized by a similar method except the amino acid starting material was Boc-(d)-Lys(Boc)-(l)-Lys(Boc)-OSu.

Synthesis of Gulonic acid-Amp

Gul-Amp was synthesized by a similar method except the carbohydrate starting material was gulonic acid-OSu.

Example 32

Figure 51A:
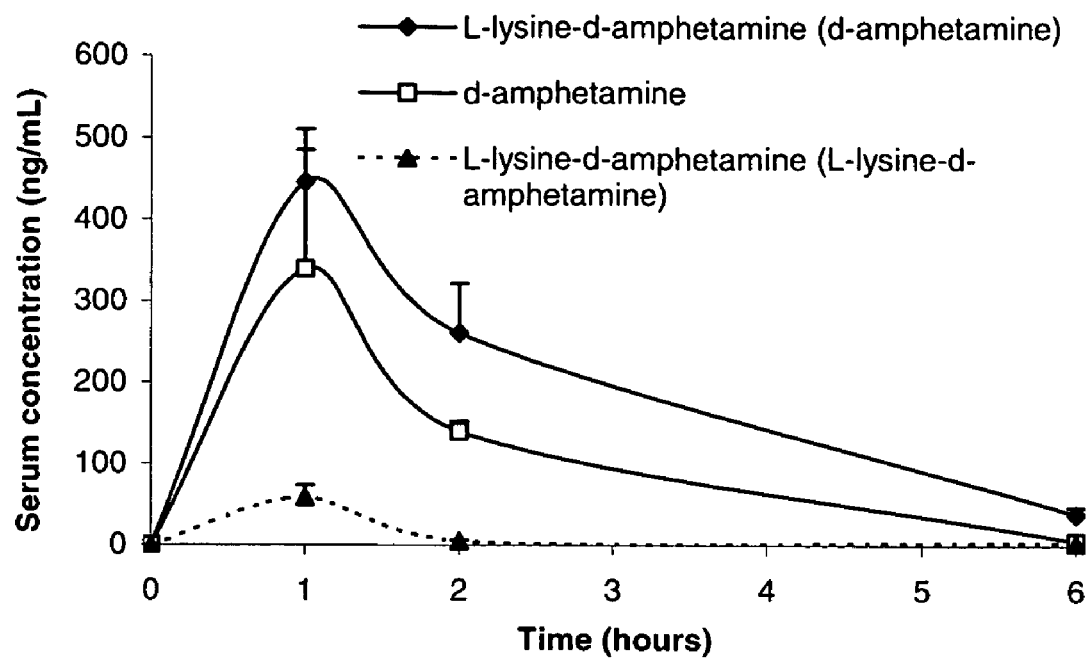
FIGS. 51A-B. Plasma concentrations of d-amphetamine and L-lysine-d-amphetamine in ng/mL for the serum levels (FIG. 51A), and in ng/g for brain tissue (FIG. 51B), following oral administration of L-lysine-d-amphetamine or d-amphetamine sulfate (5 mg/kg d-amphetamine base) to rats. Serum and brain tissue d-amphetamine and L-lysine-d-amphetamine concentrations were measured by LC/MS/MS (compound indicated in parenthesis).
Figure 51B:
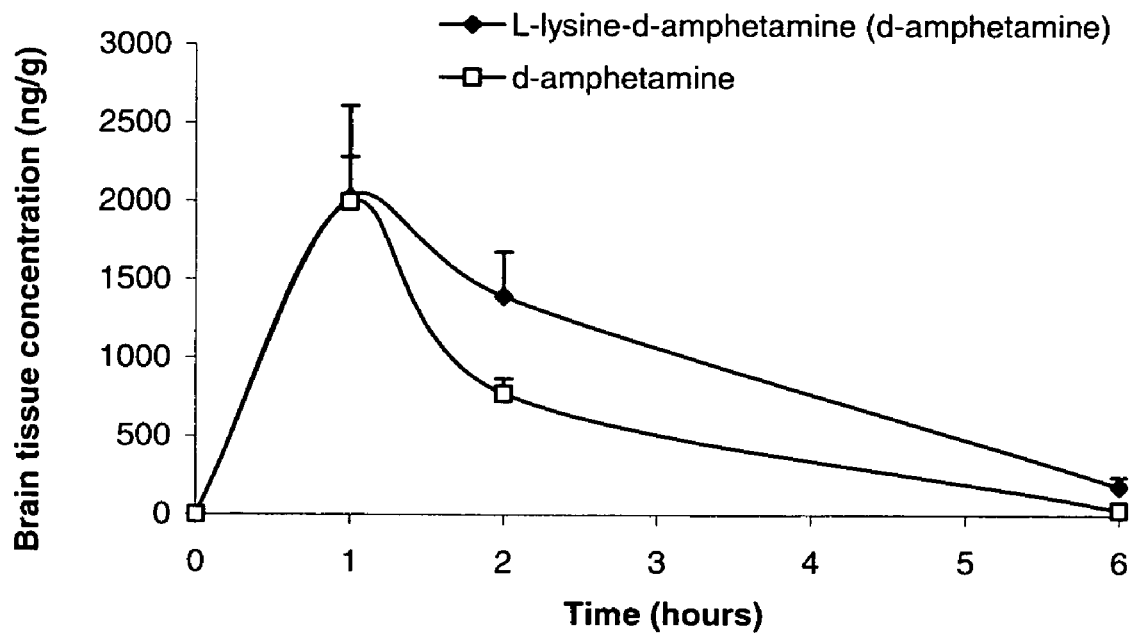

Lack of Detection of L-lysine-d-amphetamine in Brain Tissue Following Oral Administration Male Sprague-Dawley rats were provided water ad libitum, fasted overnight and dosed by oral gavage with L-lysine-d-amphetamine or d-amphetamine sulfate. All doses contained equivalent amounts of d-amphetamine base. As shown in FIGS. 51A-B, similar levels of d-amphetamine were detected in serum as well as in brain tissue following administration of d-amphetamine sulfate or L-lysine-d-amphetamine. The conjugate L-lysine-d-amphetamine, however, was present in appreciable amounts in serum but was not detected in brain tissue indicating that the conjugate does not cross the blood brain barrier to access the central nervous system site of action.

Carrier Bound Narcotics

Examples 33 through 83 Hydrocodone

Applicability of Abuse Resistance for the Narcotic Analgesics Demonstrated Through the Use of Hydrocodone.

Examples 33 through 83 illustrate the applicability of a number of peptide-active agent compositions in reducing the potential for overdose while maintaining their therapeutic value wherein the peptides are conjugated to the active agent hydrocodone (HC). Exemplary compounds which were substituted at the 6 position of hydrocodone are termed EEFFI-HC[SEQ ID NO: 6], EEFFF-HC[SEQ ID NO: 3], YYI-HC, DDI-HC, and YYFFI[SEQ ID NO: 8]-HC.

Oral, intranasal, and intravenous bioavailability studies of hydrocodone and hydrocodone conjugates were conducted in male Sprague-Dawley rats. Doses of hydrocodone bitartrate and hydrocodone conjugates containing equivalent amounts of hydrocodone were administered in deionized water. Oral administration was in 0.5 ml by gavage needle (with the exception of YYI-HC, which was delivered as a solid in gelatin capsules). Intranasal doses were administered by placing 20 microliters into the nasal flares of rats anesthetized with isoflurane. Intravenous administration was in 0.1 ml by tail vein injection. Plasma was collected by retroorbital sinus puncture under isoflurane anesthesia. Hydrocodone and hydromorphone (major active metabolite) concentrations were determined by LC/MS/MS.

The below examples are illustrative only and the below amino acid sequences attached to hydrocodone is not meant to be limiting. As such, synthesis and attachment of hydrocodone may be accomplished for instance view the following exemplary methods.

Hydrocodone Synthetic Examples Carbohydrates

Example 33

Galacto-Hydrocodone

Figure 52:
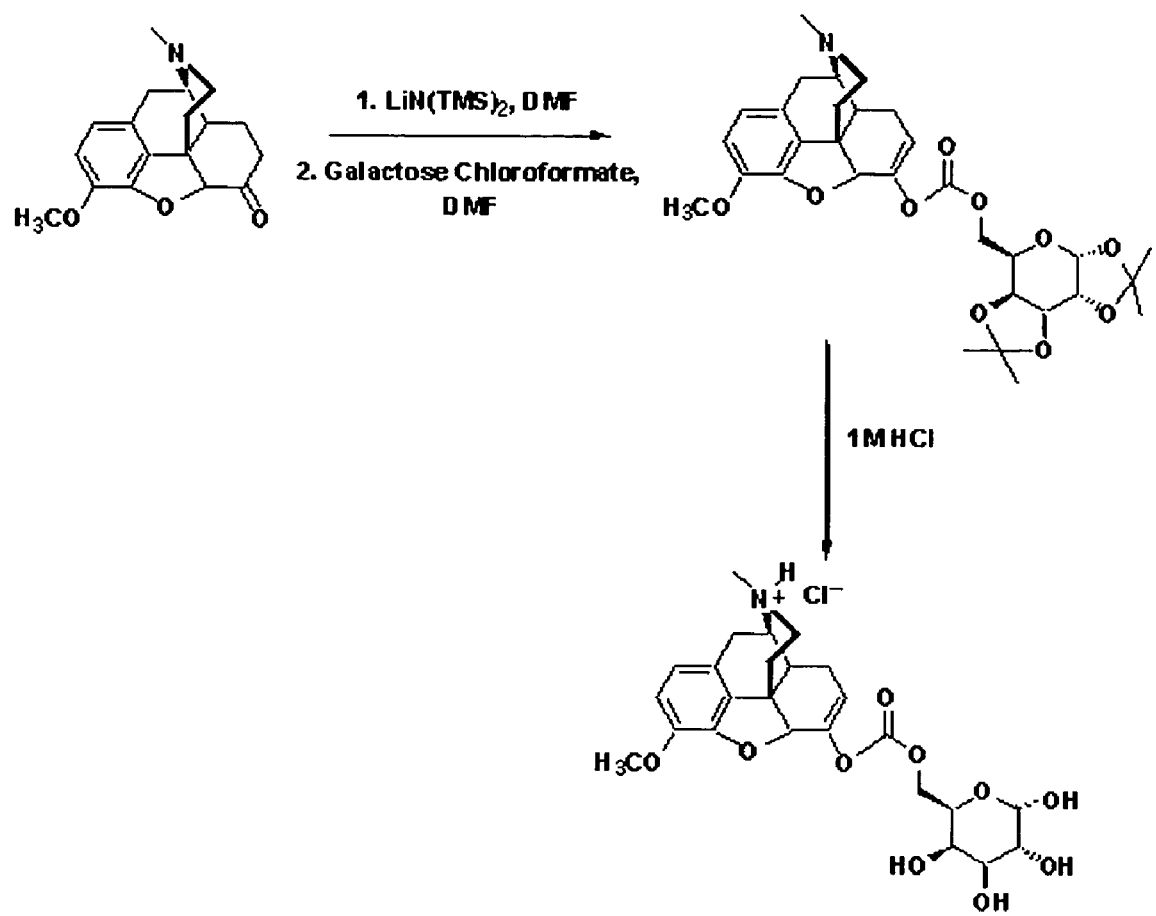
FIG. 52. illustrates preparation of Galacto-Hydrocodone.

FIG. 52 illustrates preparation of Galacto-Hydrocodone.

| Reagents | MW | Weight | mmoles | Molar Equivalents |
|---|---|---|---|---|
| 1. Hydrocodone | 299 | 0.223 g | 0.75 | 1.0 |
| 1. LiN(TMS)$_2$ in THF | 1M | 1.13 ml | 1.13 | 1.5 |
| 1. DMF | — | 5 ml | — | — |
| 2. Galactose Chloroformate | — | — | 1.49 | 2.0 |
| 2. DMF | — | 3 ml | — | — |
| 3. 1M HCl | 1M | 30 ml | — | — |
| 3. Acetone | — | 20 ml | — | — |

Galacto-Hydrocodone

To a solution of hydrocodone in DMF was added LiN(TMS)$_2$ in THF via syringe. The solution was stirred at ambient temperatures for 5 minutes then the chloroformate of galactose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 6M HCl. Solvent was removed. Final product was purified using preparative TLC (0-10% MeOH in CHCl$_3$).

Solid was collected as a white powder (0.180 g, 41% yield): $^1$H NMR (DMSO-d$_6$) δ 1.28 (2s, 6H), 1.37 (s, 3H), 1.44 (3, 3H), 1.49 (m, 2H), 1.88 (dt, 1H), 2.08 (m, 2H), 2.99 (s, 4H), 2.40 (m, 2H), 2.90 (d, 1H), 3.09 (s, 1H), 3.73 (s, 3H), 3.99 (dd, 1H), 4.14 (t, 1H), 4.26 (dt, 2H), 4.39 (d, 1H), 4.63 (d, 1H), 4.95 (s, 1H), 5.48 (d, 1H), 5.68 (d, 1H), 6.65 (d, 1H), 6.74 (d, 1H); MS Calculated mass=585.6 Found=586.4 (M+H).

To the protected galactose intermediate was added 30 ml of 1M HCl and 20ml acetone. The resulting solution was stirred at ambient temperatures for 3 hours. Solvent was removed and final product dried under vacuum. Solid was collected as a white solid: MS Calculated mass=505.5 Found=506.4 (M+H).

Figure 53:
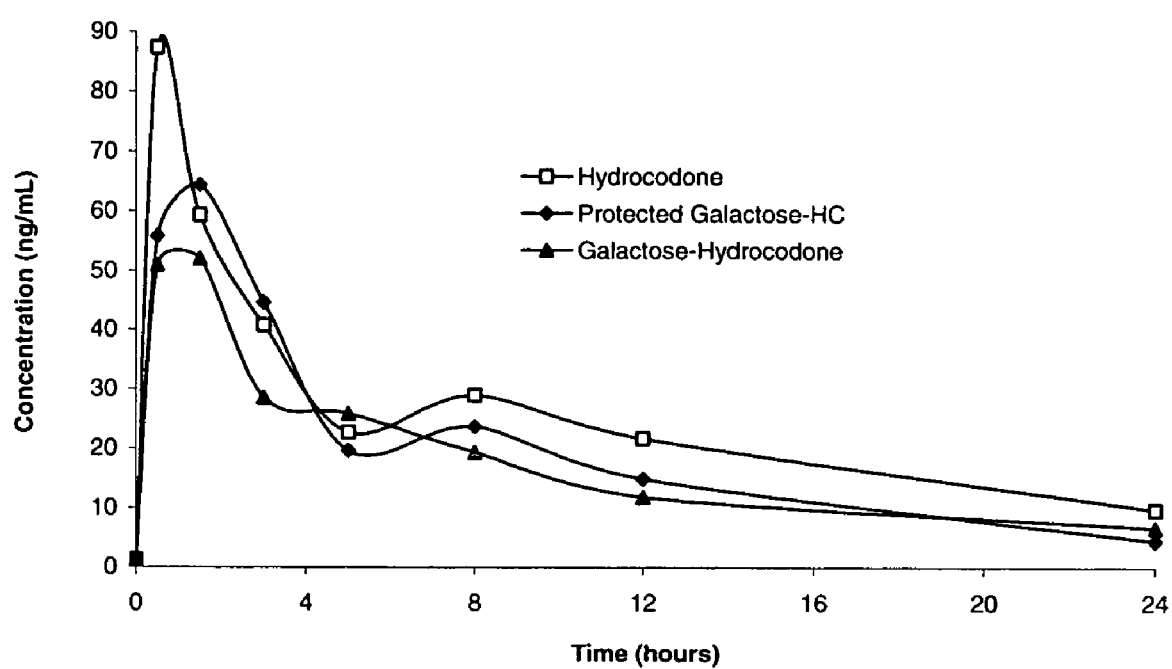
FIG. 53. Oral bioavailability of abuse-resistant hydrocodone carbohydrate conjugates, measured as free hydrocodone (with measured plasma levels by ELISA).

FIG. 53 depicts oral bioavailability of abuse-resistant hydrocodone carbohydrate conjugates, measured as free hydrocodone (with measured plasma levels by ELISA).

Example 34

Ribo-Hydrocodone

Figure 54:
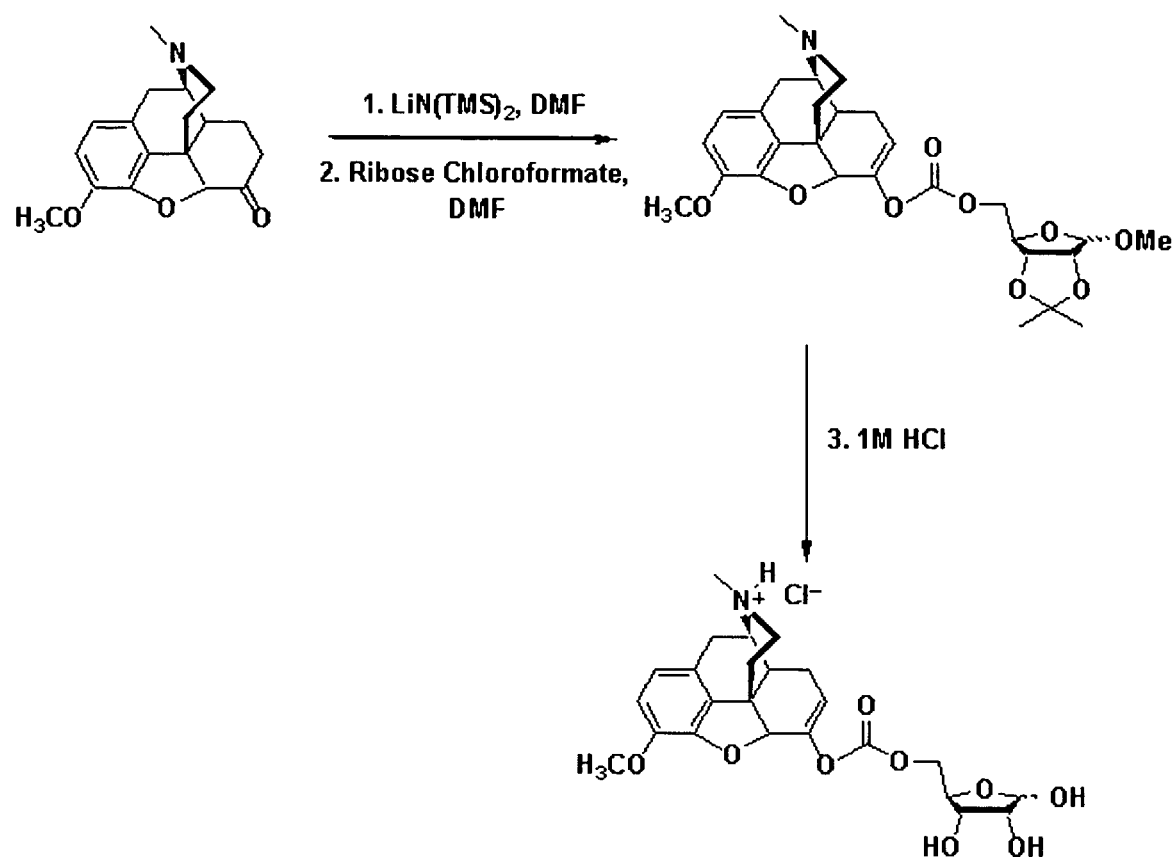
FIG. 54. illustrates preparation of Ribo-Hydrocodone.

FIG. 54 illustrates preparation of Ribo-Hydrocodone.

| Reagents | MW | Weight | mmoles | Molar Equivalents |
|---|---|---|---|---|
| 1. Hydrocodone | 299 | 0.733 g | 2.45 | 1.0 |
| 1. LiN(TMS)$_2$ in THF | 1M | 3.68 ml | 3.68 | 1.5 |
| 1. DMF | — | 8 ml | — | — |
| 2. Ribose Chloroformate | — | — | 4.90 | 2.0 |
| 2. DMF | — | 3 ml | — | — |
| 3. 1M HCl | 1M | 10 ml | — | — |

Ribo-Hydrocodone

To a solution of hydrocodone in DMF was added LiN(TMS)$_2$ in THF via syringe. The solution was stirred at ambient temperatures for 5 minutes then the chloroformate of ribose in DMF was added via syringe. The resulting solution was stirred at ambient temperatures for 2 hours. A TLC was taken (9:1 CHCl$_3$:MeOH; UV and 5% H$_2$SO$_4$ in MeOH; R$_{f(product)}$=~0.5). Reaction was neutralized to pH 7 with 1M HCl. Solvent was removed. Crude product was taken up in CHCl$_3$ (50 ml), washed with water (3×50 ml), dried over MgSO$_4$, filtered and solvent removed. Final product was purified using preparative HPLC (10 mM CH$_3$COONH$_4$/MeCN; 0-20 min: 80/20→0/100). Solid was collected as a clear, colorless glass (0.095 g, 7% yield): $^1$H NMR (DMSO-d$_6$) δ 1.26 (s, 3H), 1.39 (s, 3H), 1.50 (m, 2H), 1.89 (s, 4H), 2.08 (m, 2H), 2.29 (s, 4H), 2.40 (m, 2H), 2.88 (d, 1H), 3.08 (m, 1H), 3.25 (s, 3H), 3.73 (s, 3H), 4.12 (m, 2H), 4.28 (t, 1H), 4.58 (d, 1H), 4.72 (d, 1H), 4.97 (s, 1H), 4.98 (s, 1H), 5.70 (s, 1H), 6.66 (d, 1H), 6.75 (d, 1H). MS Calculated mass=529.2 Found=530.4 (M+H).

To the protected ribose intermediate was added 10 ml of 1M HCl. The resulting solution was stirred at ambient temperatures for 2 hours. Solvent was removed and final product dried under vacuum. Solid was collected as a waxy, slightly yellow solid (0.092 g, quant.): $^1$H NMR (DMSO-d$_6$) δ 1.51 (t, 1H), 1.83 (d, 1H), 2.41 (dt, 1H), 2.27 (t, 1H), 2.63 (dd, 1H), 2.80 (s, 3H), 2.96 (m, 2H), 3.20 (m, 1H), 3.75 (s, 3H), 3.82-4.34 (br m, 12H), 5.15 (s, 1H), 5.72 (s, 1H), 6.75 (d, 1H), 6.88 (d, 1H), 11.37 (br s, 1H).

Figure 55:
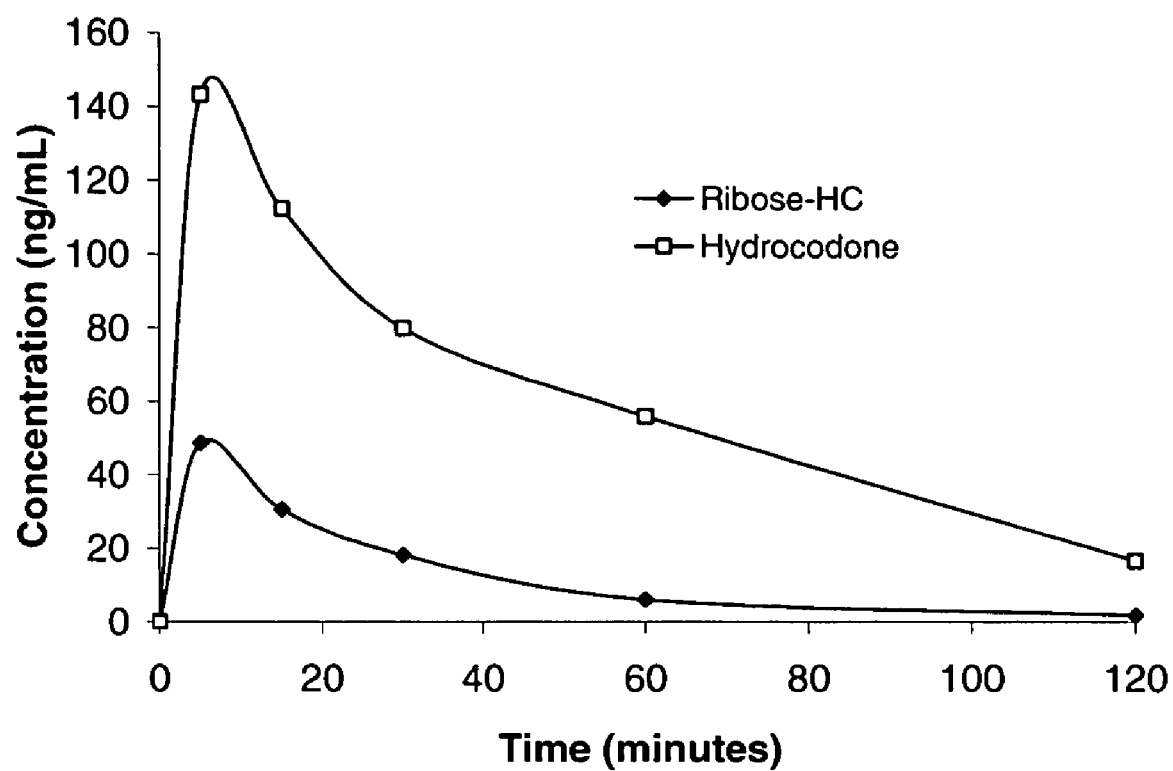
FIG. 55. Intranasal bioavailability of abuse-resistant hydrocodone carbohydrate conjugate, measured as free hydrocodone (with measured plasma levels by ELISA).

FIG. 55 illustrates intranasal bioavailability of abuse-resistant hydrocodone carbohydrate conjugate, measured as free hydrocodone (with measured plasma levels by ELISA).

Single Amino Acids

Example 35

Leu-Hydrocodone

Figure 56:
FIG. 56. illustrates preparation of Leu-Hydrocodone.

FIG. 56 illustrates preparation of Leu-Hydrocodone.

| Reagents | MW | Weight | mmoles | Molar Equivalents |
|---|---|---|---|---|
| 1. Hydrocodone | 299 | 1.00 g | 3.34 | 1.0 |
| 1. LiN(TMS)$_2$ in THF | 1M | 10.5 ml | 10.5 | 3.15 |
| 1. THF | — | 25 ml | — | — |
| 2. Boc-Leu-OSu | 328 | 3.28 g | 10.0 | 3.0 |

Leu-Hydrocodone

To a solution of hydrocodone in THF was added LiN(TMS)$_2$ in THF via syringe. The solution was stirred at ambient temperatures for 5 minutes then Boc-Leu-OSu was added. The resulting reaction mixture was stirred at ambient temperatures for 18 hours. Reaction was neutralized to pH 7 with 6M HCl. Solvent was removed. Crude material was taken up in CHCl$_3$ (100 ml), washed with sat. NaHCO$_3$ (3×100 ml), dried over MgSO$_4$, filtered, and solvent removed. Solid was collected as a yellow powder (1.98 g, 95% yield): $^1$H NMR (DMSO-d$_6$) δ 0.86 (dd, 6H), 1.31 (s, 9H), 1.46 (s, 2H), 1.55 (m, 2H), 1.69 (m, 1H), 1.87 (dt, 1H), 2.07 (dt, 2H), 2.29 (s, 3H), 2.43 (m, 2H), 2.93 (d, 1H), 3.11 (s, 1H), 3.72 (s, 3H), 3.88 (dt, 1H), 4.03 (dt, 1H), 4.87 (s, 1H), 5.51 (d, 1H), 6.65 (d, 1H), 6.73 (d, 1H), 6.90 (s, 1H).

To the Boc-Leu-Hydrocodone was added 25 ml of 4N HCl in dioxane. The resulting mixture was stirred at ambient temperatures for 18 hours. Solvent was removed and final product dried under vacuum. Solid was collected as a slightly yellow solid (1.96 g, 97% yield): $^1$H NMR (DMSO-d$_6$) δ 0.94 (d, 6H), 1.52 (m, 1H), 1.75-1.90 (m, 4H), 2.22 (dt, 1H), 2.34 (dt, 1H), 2.64 (q, 1H), 2.75 (s, 3H), 2.95-3.23 (m, 4H), 3.74 (s, 3H), 3.91 (d, 1H), 4.07 (s, 1H), 5.10 (s, 1H), 5.72 (d, 1H), 6.76 (d, 1H), 6.86 (d, 1H), 8.73 (br s, 3H).

Example 36

Glu-Hydrocodone

Synthesis of Glu-Hydrocodone

Glu-Hydrocodone was prepared by a similar method to Example 35 except the amino acid starting material was Boc-Glu(OtBu)-OSu.

Example 37

Ile-Hydrocodone

Synthesis of Ile-Hydrocodone

Ile-Hydrocodone was prepared by a similar method to Example 35 except the amino acid starting material was Boc-Ile-OSu.

Dipeptides

Figure 57:
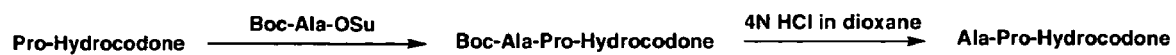
FIG. 57. illustrates preparation of Ala-Pro-Hydrocodone.

FIG. 57 illustrates preparation of Ala-Pro-Hydrocodone.

Example 38

Ala-Pro-Hydrocodone

| Reagents | MW | Weight | mmoles | Molar Equivalents |
|---|---|---|---|---|
| Pro-Hydrocodone | 468 | 0.25 g | 0.53 | 1.0 |
| Boc-Ala-OSu | 286 | 0.33 g | 1.2 | 2.26 |
| NMM | 101 | 0.50 ml | 5.38 | 10.2 |
| DMF | — | 10 ml | — | — |

Ala-Pro-Hydrocodone

To a solution of Pro-Hydrocodone in DMF was added NMM followed by Boc-Ala-OSu. The solution was stirred at ambient temperatures for 18 hours. Solvent was removed. Crude material was purified using preparative HPLC (Phenomenex Luna C18, 30×250 mm, 5 μM, 100 Å; Gradient: 100 water/O 0.1% TFA-MeCN→0/100; 30 ml/min.). Solid was collected as a slightly yellow powder (0.307 g, 85% yield): $^1$H NMR (DMSO-d$_6$) δ 1.16 (d, 3H), 1.35 (s, 9H), 1.51 (m, 2H), 1.86-2.10 (m, 6H), 2.50 (m, 1H), 2.54 (m, 1H), 2.69 (m, 1H), 2.88 (s, 3H), 3.02 (dd, 1H), 3.26 (d, 1H), 3.55 (m, 1H), 3.67 (m, 1H), 3.72 (s, 3H), 3.80 (s, 1H), 4.25 (m, 1H), 4.43 (d, 1H), 5.01 (s, 1H), 5.59 (d, 1H), 6.75 (d, 1H), 6.88 (d, 1H), 6.99 (t, 1H), 9.91 (br s, 1H).

To the Boc-Ala-Pro-Hydrocodone (0.100 g) was added 10 ml of 4N HCl in dioxane. The resulting mixture was stirred at ambient temperatures for 18 hours. Solvent was removed and final product dried under vacuum. Solid was collected as a slightly yellow solid (0.56 g, 71% yield): $^1$H NMR (DMSO-d$_6$) δ 1.38 (s, 3H), 1.48 (t, 1H), 1.80-2.29 (m, 8H), 2.65 (m, 1H), 2.80 (s, 3H), 2.96 (m, 3H), 3.23 (m, 2H), 3.76 (s, 3H), 3.92 (s, 1H), 4.22 (s, 1H), 4.53 (s, 1H), 5.00 (s, 1H), 5.84 (d, 1H), 6.77 (d, 1H), 6.86 (d, 1H), 8.25 (br s, 3H).

Example 39

Glu-Glu-Hydrocodone

Synthesis of Glu-Glu-Hydrocodone

Glu-Glu-Hydrocodone was prepared by a similar method to Example 38 except the amino acid starting material was Boc-Glu(OtBu)-OSu and the conjugate starting material was Glu-Hydrocodone.

Example 40

(pyro)Glu-Glu-Hydrocodone

Synthesis of (pyro)Glu-Glu-Hydrocodone

The compound (pyro)Glu-Glu-Hydrocodone was prepared by a similar method to Example 38 except the amino acid starting material was Boc-pyroglutamic acid-OSu and the conjugate starting material was Glu-Hydrocodone.

Tripeptides

Figure 58:
FIG. 58. illustrates the preparation of Gly-Gly-Leu-Hydrocodone.

FIG. 58 illustrates the preparation of Gly-Gly-Leu-Hydrocodone.

Example 41

Gly-Gly-Leu-Hydrocodone

| Reagents | MW | Weight | mmoles | Molar Equivalents |
|---|---|---|---|---|
| Leu-Hydrocodone | 484 | 2.21 g | 4.56 | 1.0 |
| Boc-Gly-Gly-OSu | 329 | 3.00 g | 9.12 | 2.0 |
| NMM | 101 | 5.0 ml | 45.6 | 10 |
| DMF | — | 100 ml | — | — |

Gly-Gly-Leu-Hydrocodone

To a solution of Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 90 water/10 0.1% TFA-MeCN→0/100; 30 ml/min.). Solid was collected as a slightly yellow powder (2.08 g, 73% yield): $^1$H NMR (DMSO-$d_6$) δ 0.88 (dd, 6H), 1.38 (s, 9H), 1.53-1.72 (m, 5H), 1.89 (d, 1H), 2.15 (m, 1H), 2.67 (m, 2H), 2.94 (s, 3H), 3.05 (m, 2H), 3.25 (m, 2H), 3.56 (d, 3H), 3.76 (d, 6H), 3.98 (s, 1H), 4.35 (q, 1H), 5.04 (s, 1H), 5.59 (d, 1H), 6.77 (d, 1H), 6.85 (d, 1H), 7.04 (t, 1H), 8.01 (t, 1H), 8.30 (d, 1H), 9.99 (br s, 1H).

To the Boc-Gly-Gly-Leu-Hydrocodone (2.08 g) was added 50 ml of 4N HCl in dioxane. The resulting mixture was stirred at ambient temperatures for 18 hours. Solvent was removed and final product dried under vacuum. Solid was collected as a slightly yellow solid (1.72 g, 86% yield): $^1$H NMR (DMSO-$d_6$) δ 0.89 (dd, 6H), 1.50-1.87 (m, 5H), 2.26 (m, 2H), 2.66 (m, 2H), 2.82-2.97 (m, 5H), 3.21 (m, 2H), 3.60 (m, 4H), 3.88 (m, 5H), 4.37 (m, 1H), 5.04 (s, 1H), 5.60 (s, 1H), 6.79 (d, 2H), 8.07 (br s, 3H), 8.54 (br s, 1H), 8.66 (br s, 1H), 11.29 (br s, 1H).

Example 42

Glu-Glu-Glu-Hydrocodone

Synthesis of Glu-Glu-Glu-Hydrocodone

Glu-Glu-Glu-Hydrocodone was prepared by a similar method to Example 41 except the amino acid starting material was Boc-Glu(OtBu)-Glu(OtBu)-OSu and the conjugate starting material was Glu-Hydrocodone.

Example 43

Pro-Pro-Leu-Hydrocodone

Synthesis of Pro-Pro-Leu-Hydrocodone

Pro-Pro-Leu-Hydrocodone was prepared by a similar method to Example 41 except the amino acid starting material was Boc-Pro-Pro-OSu.

Example 44

Leu-Leu-Leu-Hydrocodone

Synthesis of Leu-Leu-Leu-Hydrocodone

Leu-Leu-Leu-Hydrocodone was prepared by a similar method to Example 41 except the amino acid starting material was Boc-Leu-Leu-OSu.

Example 45

Pro-Pro-Ile-Hydrocodone

Synthesis of Pro-Pro-Ile-Hydrocodone

Pro-Pro-Ile-Hydrocodone was prepared by a similar method to Example 41 except the amino acid starting material was Boc-Pro-Pro-OSu and the conjugate starting material was Ile-Hydrocodone.

Example 46

Leu-Pro-Leu-Hydrocodone

Synthesis of Leu-Pro-Leu-Hydrocodone

Leu-Pro-Leu-Hydrocodone was prepared by similar methods except the amino acid starting material was Boc-Leu-Pro-OSu.

Example 47

Lys-Lys-Ile-Hydrocodone

Synthesis of Lys-Lys-Ile-Hydrocodone

Lys-Lys-Ile-Hydrocodone was prepared by similar methods except the amino acid starting material was Boc-Lys(Boc)-Lys(Boc)-OSu and the conjugate starting material was Ile-Hydrocodone.

Example 48

Glu-Glu-Ile-Hydrocodone

Synthesis of Glu-Glu-Ile-Hydrocodone

Glu-Glu-Ile-Hydrocodone was prepared by similar methods except the amino acid starting material was Boc-Glu(OtBu)-Glu(OtBu)-OSu and the conjugate starting material was Ile-Hydrocodone.

Example 49

Tyr-Tyr-Ile-Hydrocodone

Synthesis of Tyr-Tyr-Ile-Hydrocodone

Tyr-Tyr-Ile-Hydrocodone was prepared by similar methods except the amino acid starting material was Boc-Tyr(tBu)-Tyr(tBu)-OSu and the conjugate starting material was Ile-Hydrocodone.

Pentapeptides

Example 50

Gly-Gly-Gly-Gly-Leu[SEQ ID NO: 1]-Hydrocodone

Figure 59:
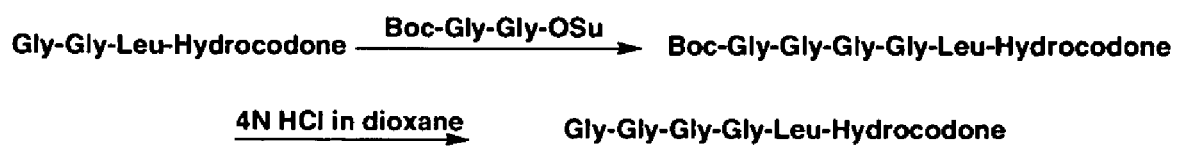
FIG. 59. illustrates preparation of Gly-Gly-Gly-Gly-Leu-[SEQ ID NO: 1]-Hydrocodone.
Figure 60:
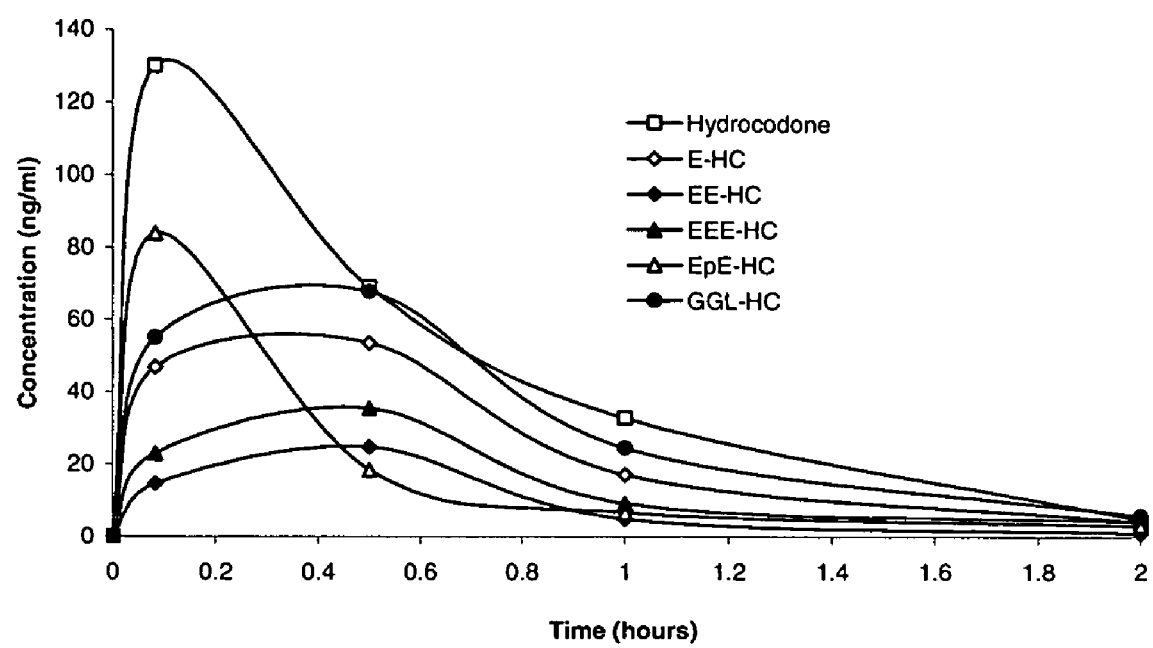
FIG. 60. Intranasal bioavailability of abuse-resistant hydrocodone amino acid, di- and tri-peptide conjugates, measured as free hydrocodone.
Figure 61:
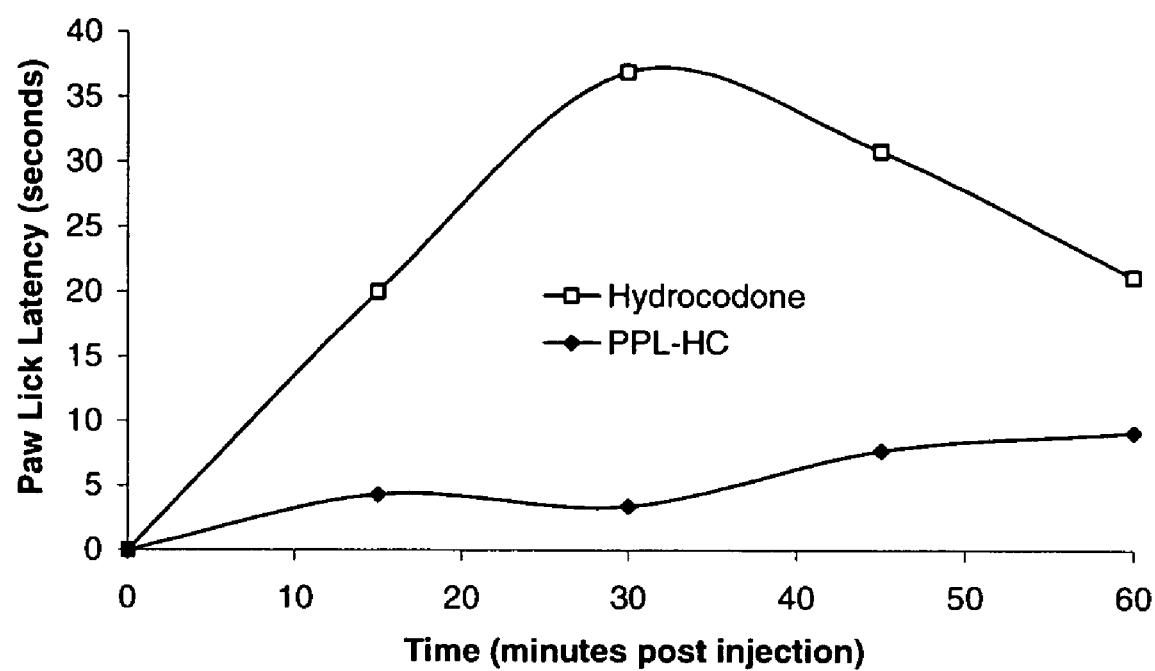
FIG. 61. Analgesic effect of abuse-resistant hydrocodone tri-peptide conjugate following intranasal administration, measured as free hydrocodone.
Figure 62:
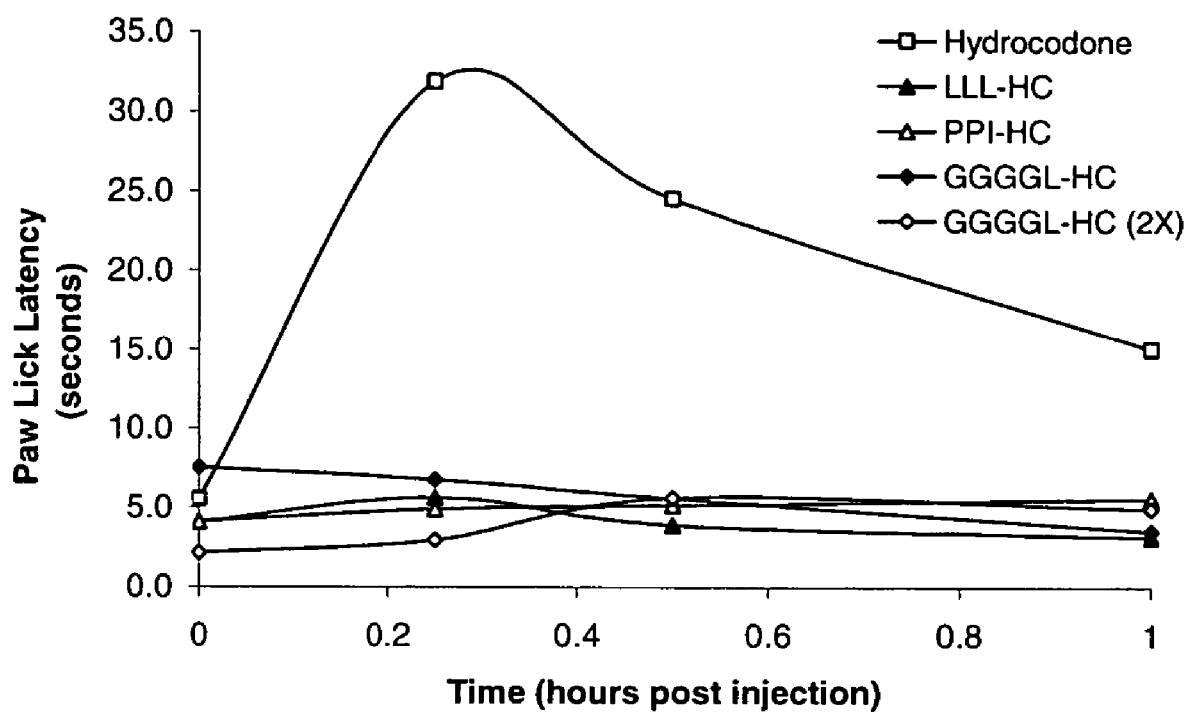
FIG. 62. Analgesic effect of abuse-resistant hydrocodone tri- and penta-peptide conjugates following subcutaneous administration, measured as free hydrocodone.
Figure 63:
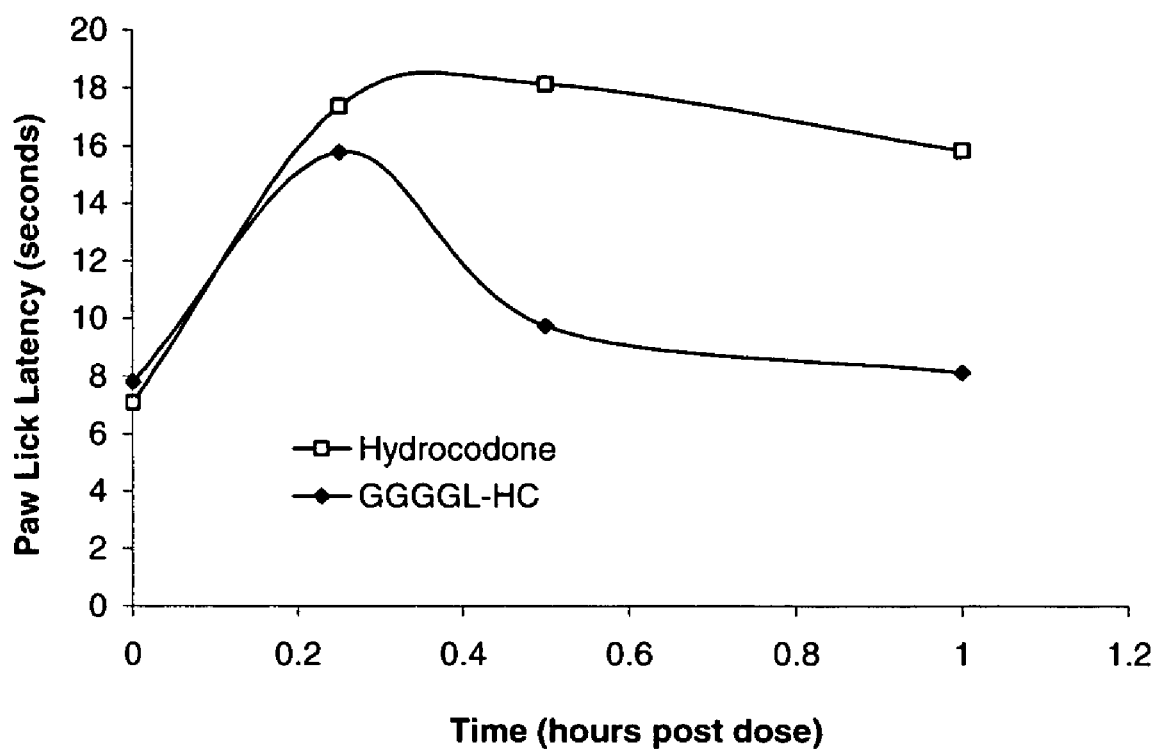
FIG. 63. Analgesic effect of abuse-resistant hydrocodone penta-peptide conjugate following intranasal administration, measured as free hydrocodone.
Figure 64:
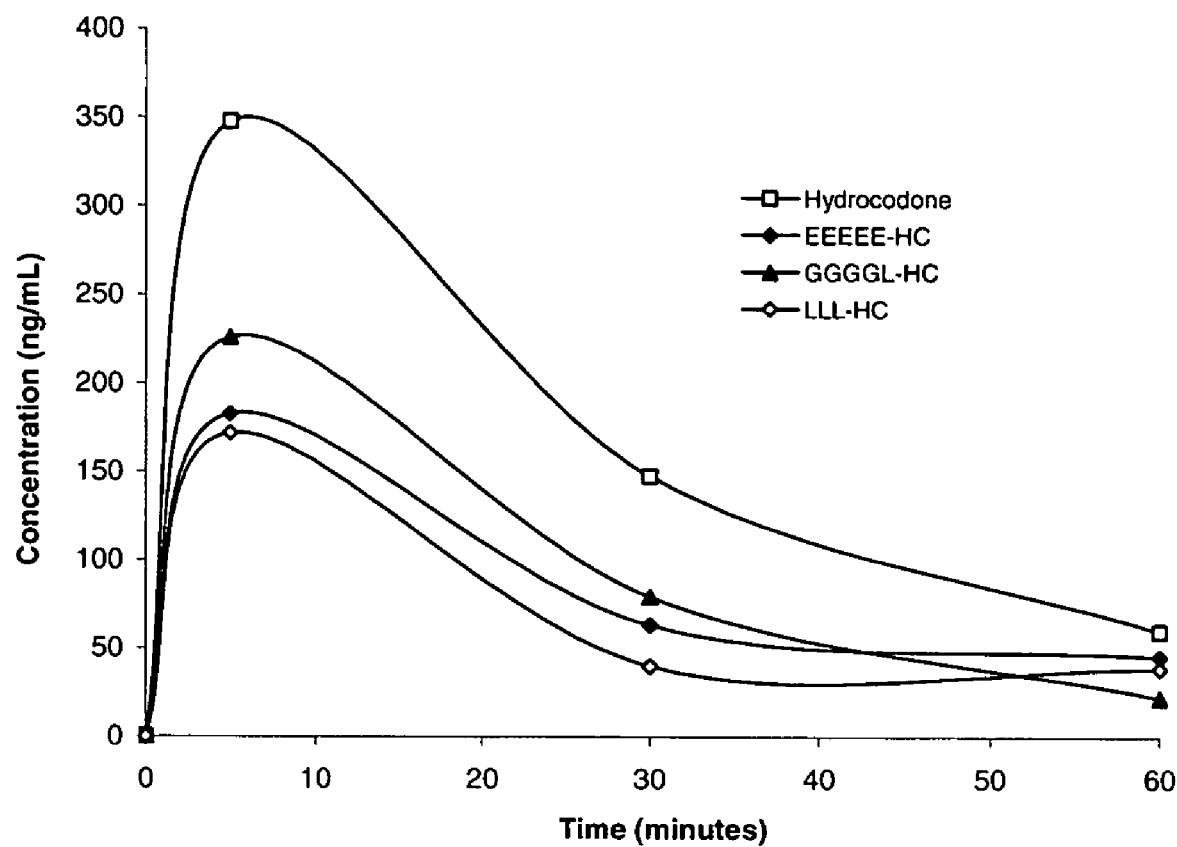
FIG. 64. Intranasal bioavailability of abuse-resistant hydrocodone tri- and penta-peptide conjugates, measured as free hydrocodone.
Figure 65:
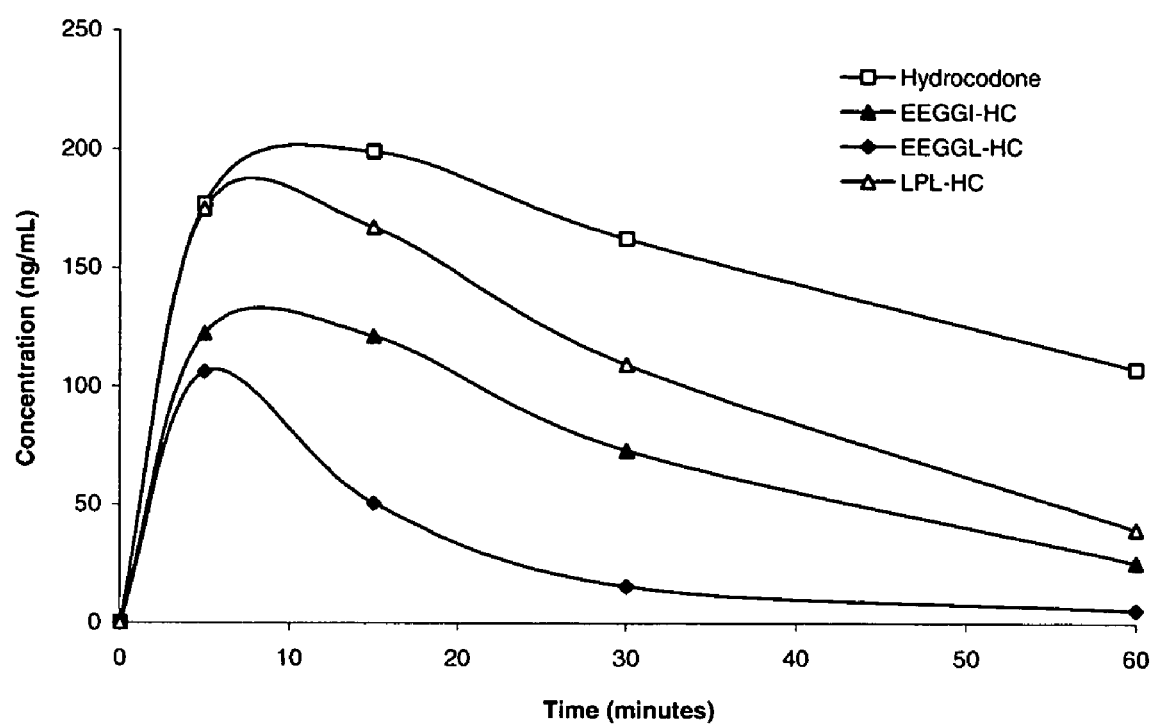
FIG. 65. Intranasal bioavailability of abuse-resistant hydrocodone tri- and penta-peptide conjugates, measured as free hydrocodone.
Figure 66:
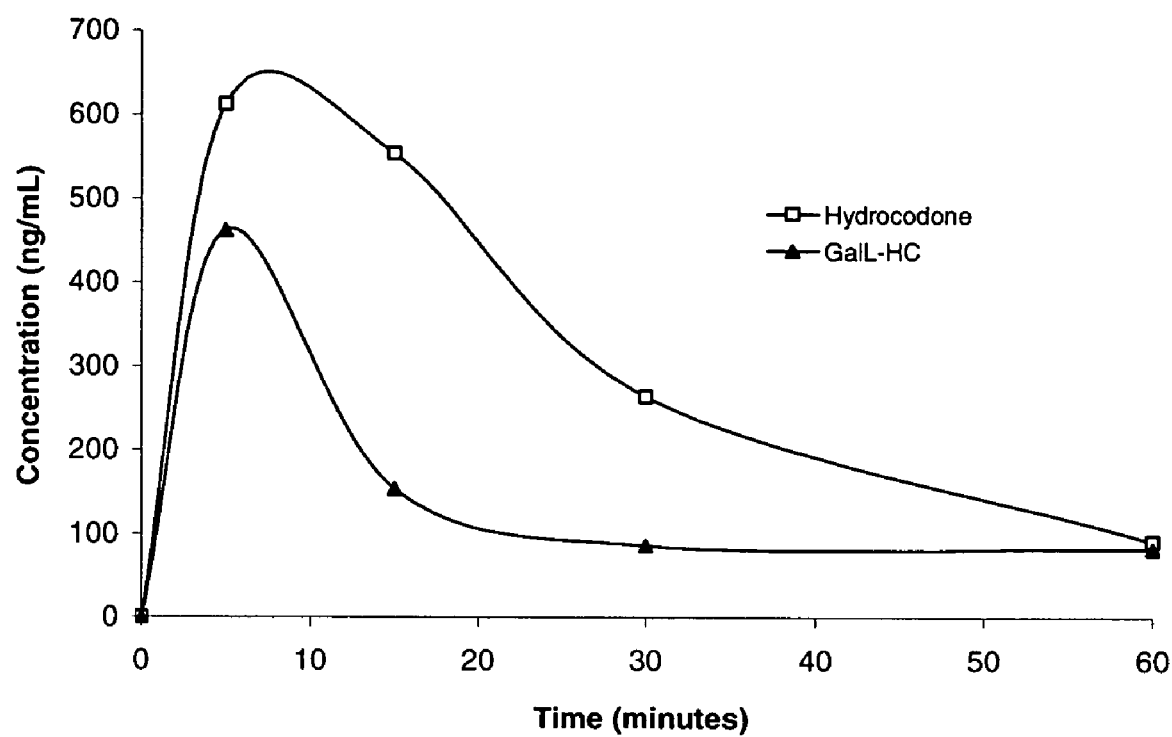
FIG. 66. Intranasal bioavailability of abuse-resistant hydrocodone an amino acid-carbohydrate peptide conjugate, measured as free hydrocodone.
Figure 67:
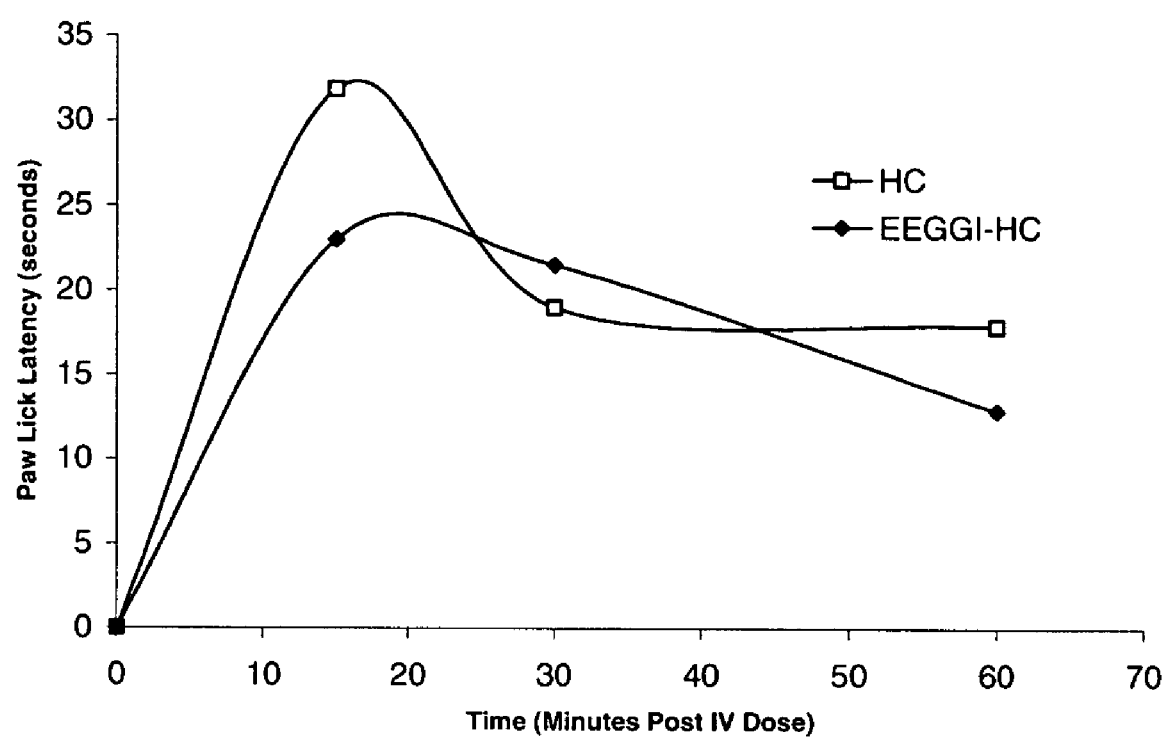
FIG. 67. Analgesic effect of abuse-resistant hydrocodone penta-peptide conjugate following intravenous administration, measured as free hydrocodone.
Figure 68:
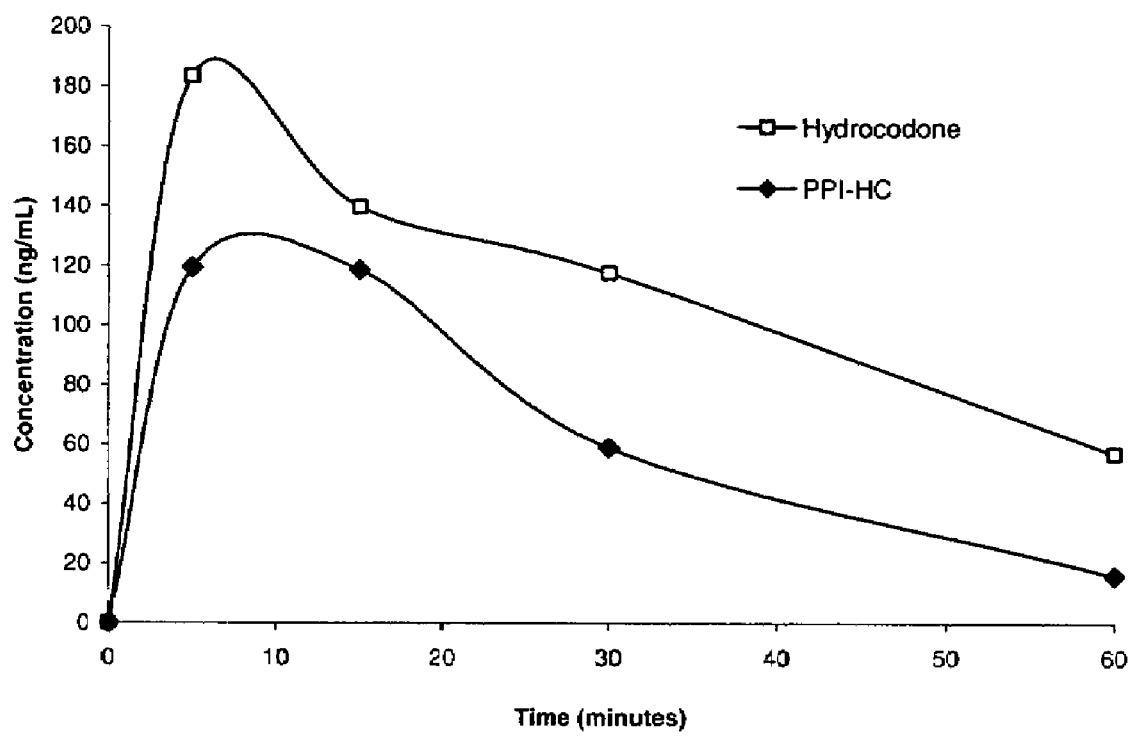
FIG. 68. Intranasal bioavailability of an abuse-resistant hydrocodone tri-peptide conjugate, measured as free hydrocodone.
Figure 69:
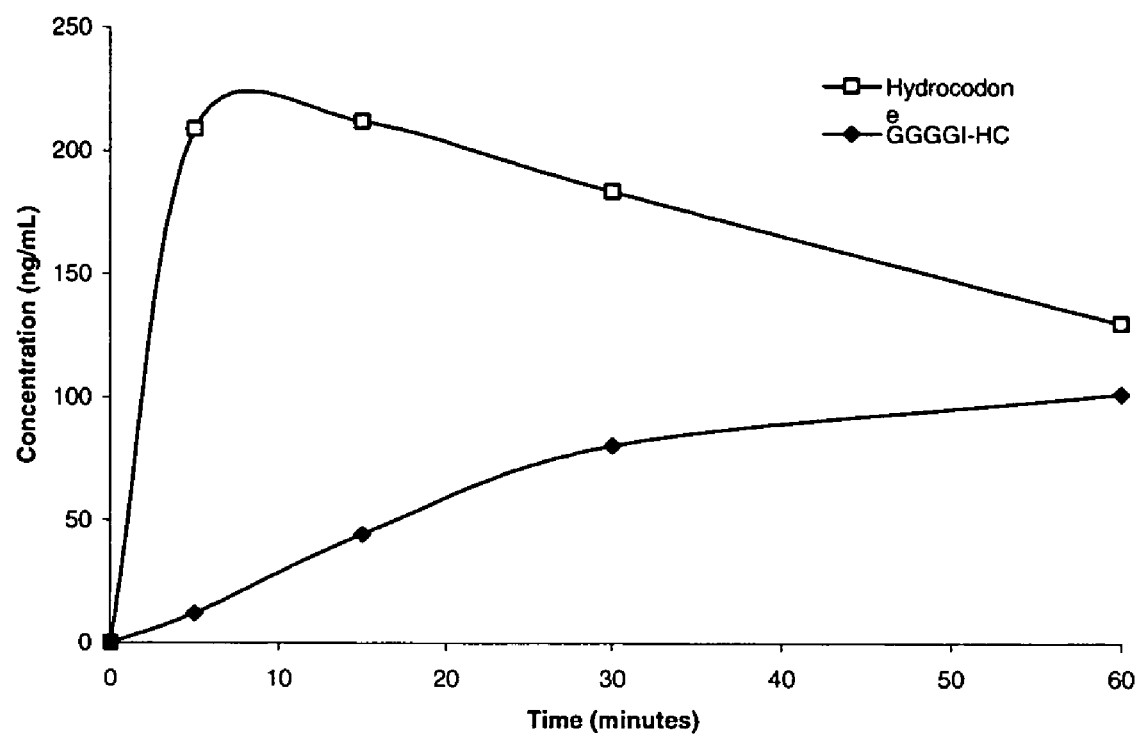
FIG. 69. Intranasal bioavailability of an abuse-resistant hydrocodone penta-peptide conjugate, measured as free hydrocodone.
Figure 70:
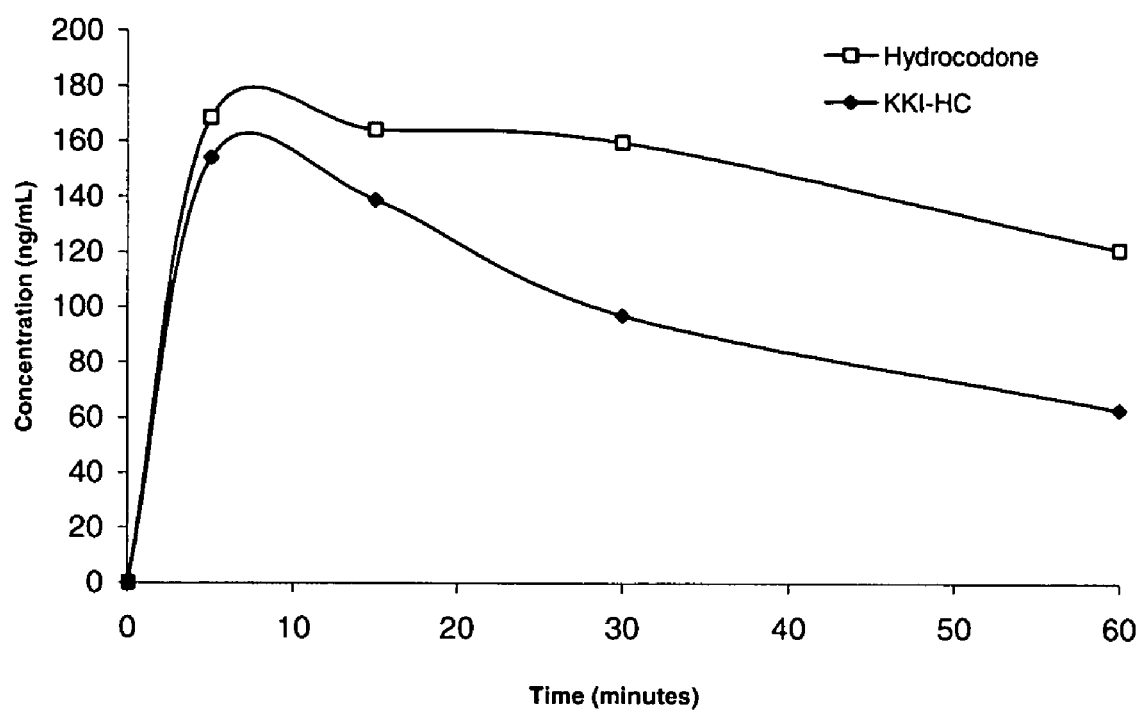
FIG. 70. Intranasal bioavailability of an abuse-resistant hydrocodone tri-peptide conjugate, measured as free hydrocodone.
Figure 71:
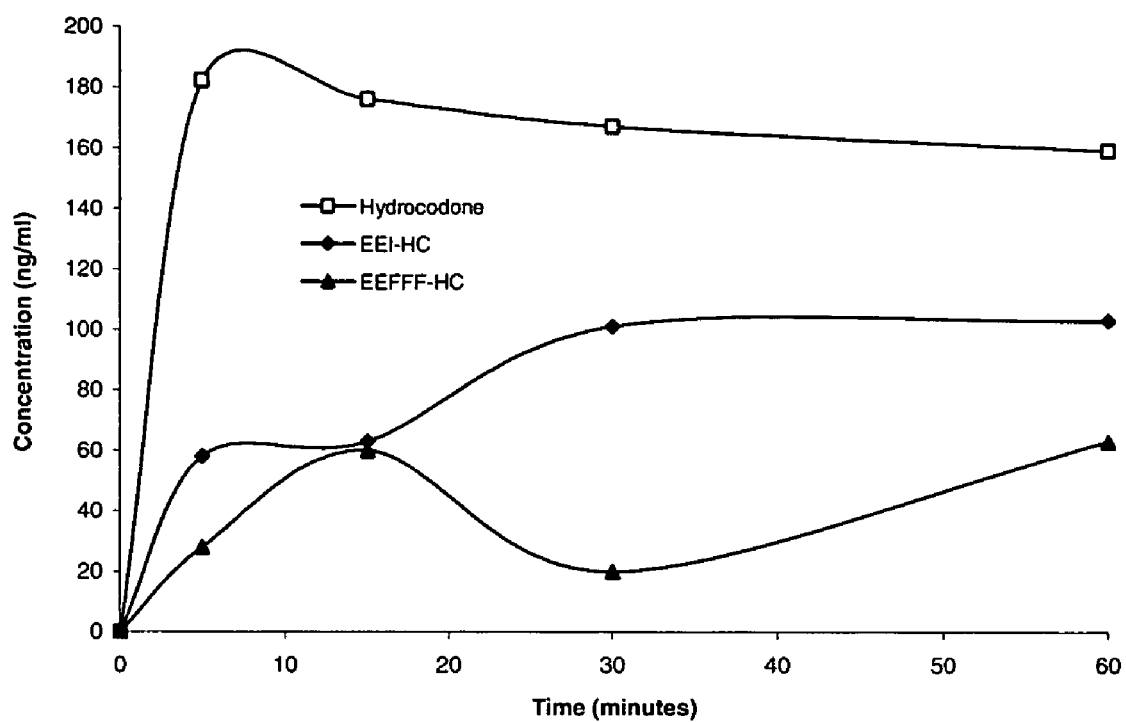
FIG. 71. Intranasal bioavailability of abuse-resistant hydrocodone tri- and penta-peptide conjugates, measured as free hydrocodone.
Figure 72:
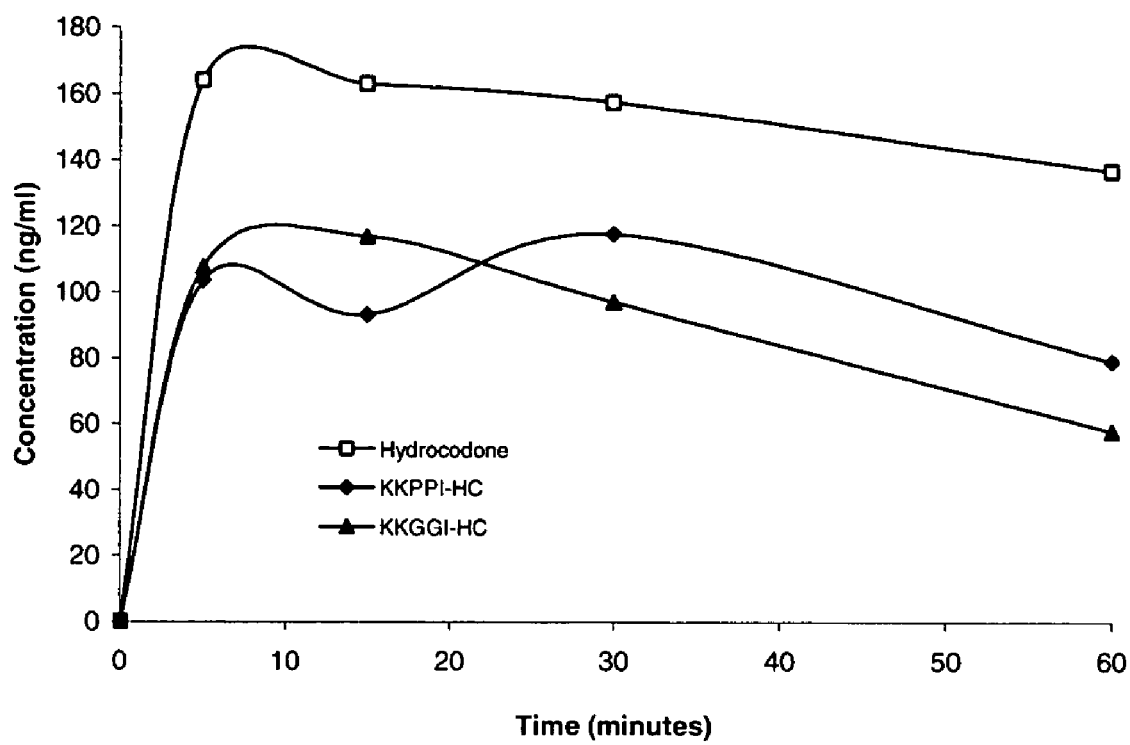
FIG. 72. Intranasal bioavailability of abuse-resistant hydrocodone penta-peptide conjugates, measured as free hydrocodone.
Figure 73:
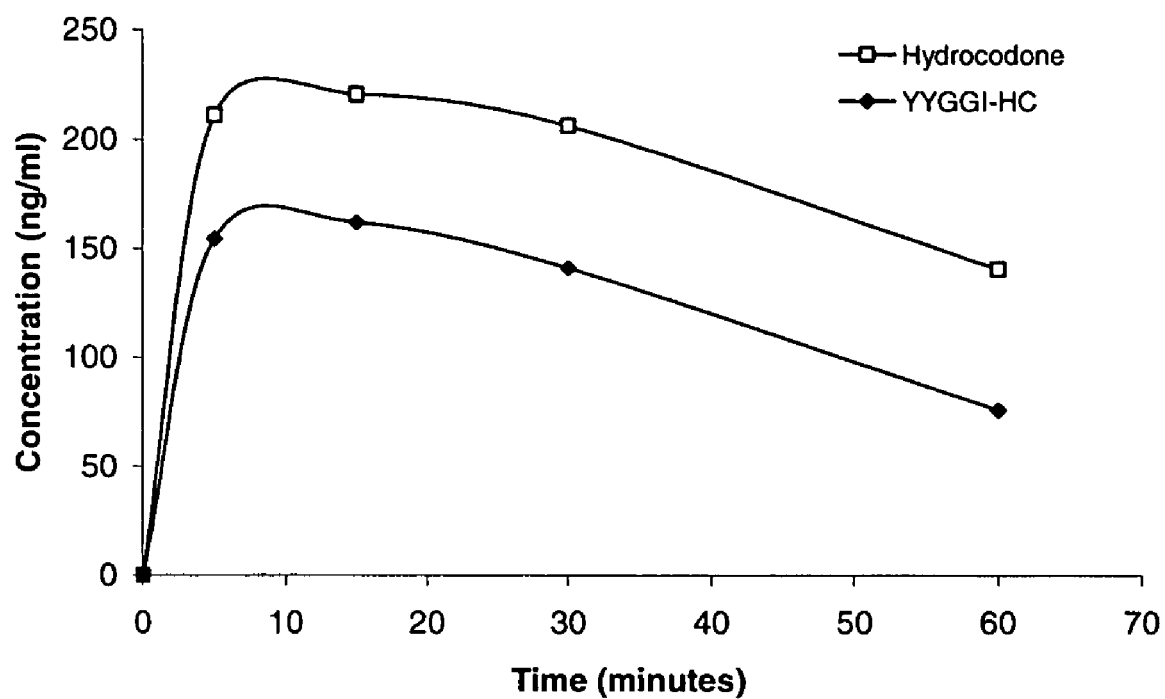
FIG. 73. Intranasal bioavailability of an abuse-resistant hydrocodone penta-peptide conjugate, measured as free hydrocodone.

FIG. 59 illustrates preparation of Gly-Gly-Gly-Gly-Leu [SEQ ID NO: 1]-Hydrocodone.

| Reagents | MW | Weight | mmoles | Molar Equivalents |
|---|---|---|---|---|
| Gly-Gly-Leu-Hydrocodone | 599 | 0.580 g | 0.970 | 1.0 |
| Boc-Gly-Gly-OSu | 329 | 0.638 g | 1.94 | 2.0 |

| Reagents | MW | Weight | mmoles | Molar Equivalents |
|---|---|---|---|---|
| NMM | 101 | 1.06 ml | 9.70 | 10 |
| DMF | — | 20 ml | — | — |

Gly-Gly-Gly-Gly-Leu[SEQ ID NO: 1]-Hydrocodone

To a solution of Gly-Gly-Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 85 water/15 0.1% TFA-MeCN→50/50; 30 ml/min.). Solid was collected as a slightly yellow powder (0.304 g, 37% yield).

To the Boc-Gly-Gly-Gly-Gly-Leu[SEQ ID NO: 1]-Hydrocodone (0.304 g) was added 25 ml of 4N HCl in dioxane. The resulting mixture was stirred at ambient temperatures for 18 hours. Solvent was removed and final product dried under vacuum. Solid was collected as a slightly yellow solid (0.247 g, 97% yield): $^1$H NMR (DMSO-d6) d 0.87 (m, 6H), 1.23 (s, 1H), 1.51-1.86 (m, 4H), 2.18 (m, 1H), 2.71 (m, 2H), 2.77 (s, 3H), 2.96 (m, 2H), 3.17 (m, 2H), 3.61 (s, 3H), 3.81-3.84 (m, 10H), 4.22 (m, 1H), 4.36 (m, 1H), 5.09 (m, 1H), 5.59 (d, 1H), 6.74 (dd, 2H), 8.16 (br s, 4H), 8.38 (br s, 1H), 8.74 (br s, 1H), 11.42 (br s, 1H).

Example 51

Glu-Glu-Glu-Glu-Glu[SEQ ID NO: 13]-Hydrocodone

Synthesis of Glu-Glu-Glu-Glu-Glu[SEQ ID NO: 13]-Hydrocodone

Glu-Glu-Glu-Glu-Glu[SEQ ID NO: 13]-Hydrocodone was prepared by a similar method to Example 50 except the amino acid starting material was Boc-Glu(OtBu)-Glu(OtBu)-OSu and the conjugate starting material was Glu-Glu-Glu-Hydrocodone.

Example 52

Glu-Glu-Gly-Gly-Ile[SEQ ID NO: 14]-Hydrocodone

Synthesis of Glu-Glu-Gly-Gly-Ile[SEQ ID NO: 14]-Hydrocodone

Glu-Glu-Gly-Gly-Ile[SEQ ID NO: 14]-Hydrocodone was prepared by a similar method to Example 50 except the amino acid starting material was Boc-Glu(OtBu)-Glu(OtBu)-OSu and the conjugate starting material was Gly-Gly-Ile-Hydrocodone.

Example 53

Glu-Glu-Gly-Gly-Leu[SEQ ID NO: 15]-Hydrocodone

Synthesis of Glu-Glu-Gly-Gly-Leu[SEQ ID NO: 15]-Hydrocodone

Glu-Glu-Gly-Gly[SEQ ID NO: 15]-Leu-Hydrocodone was prepared by a similar method to Example 50 except the amino acid starting material was Boc-Glu(OtBu)-Glu(OtBu)-OSu and the conjugate starting material was Gly-Gly-Leu-Hydrocodone.

Example 54

Gly-Gly-Gly-Gly-Ile[SEQ ID NO: 16]-Hydrocodone

Synthesis of Gly-Gly-Gly-Gly-Ile[SEQ ID NO: 16]-Hydrocodone

Gly-Gly-Gly-Gly-Ile[SEQ ID NO: 16]-Hydrocodone was prepared by a similar method to Example 50 except the amino acid starting material was Boc-Gly-Gly-OSu and the conjugate starting material was Gly-Gly-Ile-Hydrocodone.

Example 55

Glu-Glu-Phe-Phe-Phe[SEQ ID NO: 3]-Hydrocodone

Synthesis of Glu-Glu-Phe-Phe-Phe[SEQ ID NO: 3]-Hydrocodone

Glu-Glu-Phe-Phe-Phe[SEQ ID NO: 3]-Hydrocodone was prepared by a similar method to Example 50 except the amino acid starting material was Boc-Glu(OtBu)-Glu(OtBu)-OSu and the conjugate starting material was Phe-Phe-Phe-Hydrocodone.

Example 56

Lys-Lys-Gly-Gly-Ile[SEQ ID NO: 17]-Hydrocodone

Synthesis of Lys-Lys-Gly-Gly-Ile[SEQ ID NO: 17]-Hydrocodone

Lys-Lys-Gly-Gly-Ile[SEQ ID NO: 17]-Hydrocodone was prepared by a similar method to Example 50 except the amino acid starting material was Boc-Lys(Boc)-Lys(Boc)-OSu and the conjugate starting material was Gly-Gly-Ile-Hydrocodone.

Example 57

Lys-Lys-Pro-Pro-Ile[SEQ ID NO: 18]-Hydrocodone

Synthesis of Lys-Lys-Pro-Pro-Ile[SEQ ID NO: 18]-Hydrocodone

Lys-Lys-Pro-Pro-Ile[SEQ ID NO: 18]-Hydrocodone was prepared by a similar method to Example 50 except the amino acid starting material was Boc-Lys(Boc)-Lys(Boc)-OSu and the conjugate starting material was Pro-Pro-Ile-Hydrocodone.

Example 58

Tyr-Tyr-Gly-Gly-Ile[SEQ ID NO: 19]-Hydrocodone

Synthesis of Tyr-Tyr-Gly-Gly-Ile[SEQ ID NO: 19]-Hydrocodone

Tyr-Tyr-Gly-Gly-Ile-[SEQ ID NO: 19]Hydrocodone was prepared by a similar method to Example 50 except the amino acid starting material was Boc-Tyr(tBu)-Tyr(tBu)-OSu and the conjugate starting material was Gly-Gly-Ile-Hydrocodone.

Example 59

Gly-Gly-Pro-Pro-Ile[SEQ ID NO: 20]-Hydrocodone

Synthesis of Gly-Gly-Pro-Pro-Ile[SEQ ID NO: 20]-Hydrocodone

Gly-Gly-Pro-Pro-Ile[SEQ ID NO: 20]-Hydrocodone was prepared by a similar method to Example 50 except the amino acid starting material was Boc-Gly2-OSu and the conjugate starting material was Pro-Pro-Ile-Hydrocodone.

Example 60

Asp-Asp-Phe-Phe-Ile[SEQ ID NO: 21]-Hydrocodone

Synthesis of Asp-Asp-Phe-Phe-Ile[SEQ ID NO: 21]-Hydrocodone

Asp-Asp-Phe-Phe-Ile[SEQ ID NO: 21]-Hydrocodone was prepared by a similar method to Example 50 except the amino acid starting material was Boc-Asp(OtBu)-Asp(OtBu)-OSu and the conjugate starting material was Phe-Phe-Ile-Hydrocodone.

Example 61

Glu-Glu-Asp-Asp-Ile[SEQ ID NO: 22]-Hydrocodone

Synthesis of Glu-Glu-Asp-Asp-Ile[SEQ ID NO: 22]-Hydrocodone

Glu-Glu-Asp-Asp-Ile[SEQ ID NO: 22]-Hydrocodone was prepared by a similar method to Example 50 except the amino acid starting material was Boc-Glu(OtBu)-Glu(OtBu)-OSu and the conjugate starting material was Asp-Asp-Ile-Hydrocodone.

Example 62

Lys-Lys-Asp-Asp-Ile[SEQ ID NO: 23]-Hydrocodone

Synthesis of Lys-Lys-Asp-Asp-Ile[SEQ ID NO: 23]-Hydrocodone

Lys-Lys-Asp-Asp-Ile[SEQ ID NO: 23]-Hydrocodone was prepared by a similar method to Example 50 except the amino acid starting material was Boc-Lys(Boc)-Lys(Boc)-OSu and the conjugate starting material was Asp-Asp-Ile-Hydrocodone.

Example 63

Tyr-Tyr-Glu-Glu-Ile[SEQ ID NO: 24]-Hydrocodone

Synthesis of Tyr-Tyr-Glu-Glu-Ile[SEQ ID NO: 24]-Hydrocodone

Tyr-Tyr-Glu-Glu-Ile[SEQ ID NO: 24]-Hydrocodone was prepared by a similar method to Example 50 except the amino acid starting material was Boc-Tyr(tBu)-Tyr(tBu)-OSu and the conjugate starting material was Glu-Glu-Ile-Hydrocodone.

Example 64

Asp-Asp-Asp-Asp-Ile[SEQ ID NO: 25]-Hydrocodone

Synthesis of Asp-Asp-Asp-Asp-Ile[SEQ ID NO: 25]-Hydrocodone

Asp-Asp-Asp-Asp-Ile[SEQ ID NO: 25]-Hydrocodone was prepared by a similar method to Example 50 except the amino acid starting material was Boc-Asp(OtBu)-Asp(OtBu)-OSu and the conjugate starting material was Asp-Asp-Asp-Asp-Ile-Hydrocodone.

Example 65

Glu-Glu-Phe-Phe-Ile[SEQ ID NO: 5]-Hydrocodone

Synthesis of Glu-Glu-Phe-Phe-Ile[SEQ ID NO: 5]-Hydrocodone

Glu-Glu-Phe-Phe-Ile[SEQ ID NO: 5]-Hydrocodone was prepared by a similar method to Example 50 except the amino acid starting material was Boc-Glu(OtBu)-Glu(OtBu)-OSu and the conjugate starting material was Phe-Phe-Ile-Hydrocodone.

Example 66

Lys-Lys-Glu-Glu-Ile[SEQ ID NO: 26]-Hydrocodone

Synthesis of Lys-Lys-Glu-Glu-Ile[SEQ ID NO: 26]-Hydrocodone

Lys-Lys-Glu-Glu-Ile[SEQ ID NO: 26]-Hydrocodone was prepared by a similar method to Example 50 except the amino acid starting material was Boc-Lys(Boc)-Lys(Boc)-OSu and the conjugate starting material was Glu-Glu-Ile-Hydrocodone.

Example 67

Tyr-Tyr-Phe-Pro-Ile[SEQ ID NO: 12]-Hydrocodone

Synthesis of Tyr-Tyr-Phe-Pro-Ile[SEQ ID NO: 12]-Hydrocodone

Tyr-Tyr-Phe-Pro-Ile[SEQ ID NO: 12]-Hydrocodone was prepared by a similar method to Example 50 except the amino acid starting material was Boc-Tyr(tBu)-Tyr(tBu)-OSu and the conjugate starting material was Phe-Pro-Ile-Hydrocodone.

YYFFI[SEQ ID NO: 8]-HC

Example 68

Tyr-Tyr-Phe-Phe-Ile[SEQ ID NO: 8]-(6-O)-Hydrocodone

Preparation of Tyr-Tyr-Phe-Phe-Ile[SEQ ID NO: 8]-(6-O)-hydrocodone

Hydrocodone bitartrate (48.38 g) was stirred in 500 ml 1N NaOH for 5 minutes. Suspension was split into 2 batches and extracted using $CHCl_3$ (2×250 ml), organics were dried using $MgSO_4$ and filtered. Solvent was removed and product was obtained as a white powder (29.05 g).

To a solution of hydrocodone freebase (7.12 g) in tetrahydrofuran (THF) (300 ml) was added LiN(TMS)$_2$ in THF (1M, 36.0 ml) via syringe. The solution was stirred at ambient temperatures for 10 minutes then Boc-Ile-OSu (11.7 g) was added. The resulting reaction mixture was stirred at ambient temperatures for 3 hours. Reaction was neutralized to pH 7 with 1M HCl and stirred for 10 minutes. Solvent was removed. Crude material was taken up in diethyl ether (100 ml), washed with sat. NaHCO$_3$ (3×100 ml), dried over MgSO$_4$, filtered, and solvent was removed. Solid was collected as a yellow powder (11.1 g).

To the Boc-Ile-Hydrocodone (11.1 g) was added 125 ml of 4N HCl in dioxane. The resulting mixture was stirred at ambient temperatures for 1 hour. Solvent was removed and final product dried under vacuum. Solid was collected as a slightly yellow powder (10.43 g).

To a suspension of Boc-Phe-Phe-OH (10.0 g) and N-hydroxysuccininiide (NHS) (3.06 g) in acetone (300 ml) was added dicyclohexylcarbodiimide (DCC) (4.99 g). The solution was stirred at ambient temperatures under argon for 18 hrs. Solid dicyclohexylurea (DCU) was filtered away and washed with acetone. Solvent was removed from filtrate. Crude material was recrystallized using a system of acetone and hexane. Solvent was filtered off and the solid was collected as a white powder (12.2 g).

To a solution of Ile-HC-2HCl (6.00 g) in N,N-dimethylformamide (DMF) (150 ml) was added 4-methyl morpholine (NMM) (6.79 ml) followed by Boc-Phe-Phe-OSu (6.93 g). The solution was stirred at ambient temperatures for 18 hours. Solvent was reduced to approximately ¼ total volume, added to sat. NaHCO$_3$ (~100 ml), and stirred for 30 minutes. The precipitate was filtered and washed thoroughly with water. Solid material was dried in vacuum, dissolved in a small amount of ethyl acetate, and filtered. Product was obtained as a slightly yellow powder (8.39 g).

To Boc-Phe-Phe-Ile-HC (2.99 g) was added 50 ml 4N HCl in dioxane. The resulting suspension was stirred at ambient temperatures for 1 hour. Solvent was removed and product was dried. Product was obtained as a yellow solid (2.60 g).

To a solution of Boc-Tyr(tBu)-OH (1.00 g) in 15 ml DMF was added O—(N-succinimidyl)-1,1,3,3-tetramethyluronium tetrafluoroborate (TSTU) (0.892 g) and NMM (0.65 ml). After 10 minutes of activation, H-Tyr(tBu)-OH (0.844 g) in 40 ml DMF:dioxane:water (2:2:1) was added. The resulting suspension was stirred at ambient temperature for 4 hours. After this time, water (15 ml) was added and the resulting solution was stirred at ambient temperature for 30 minutes. The solvent volume was reduced to ¼ and extracted with ethyl acetate (250 ml), washed with 5% acetic acid in water (2×150 ml), water (3×150 ml), and brine (150 ml). The organic layer was dried over MgSO$_4$, filtered, and solvent removed. Crude product was purified using recrystallization with IPAC/hexane solvent system. Final product was isolated as a white solid (1.025 g).

To a suspension of Boc-Tyr(tBu)-Tyr(OtBu)-OH (7.32 g) and NHS (1.54 g) in acetone (150 ml) was added DCC (2.51 g). The solution was stirred at ambient temperatures under argon for 18 hrs. Solid DCU was filtered away and washed with acetone. Solvent was removed from filtrate. Crude material was washed with warm hexane. Solid was collected as a white powder (6.65 g).

To a solution of Phe-Phe-Ile-HC-2HCl (2.63 g) in DMF (100 ml) was added NMM (3.70 ml) followed by Boc-Tyr (tBu)-Tyr(tBu)-OSu (4.41 g). The solution was stirred at ambient temperatures for 18 hours. Solvent was reduced to approximately ¼ total volume, added to sat. NaHCO$_3$ (~100 ml), and stirred for 30 minutes. The precipitate was filtered and washed thoroughly with water. Solid material was dried in vacuum and purified by reverse phase HPLC (2.77 g). Product was deprotected using 4N HCl in dioxane (~50 ml).

To a solution of Phe-Phe-Ile-HC-2HCl (5.00 g) in DMF (250 ml) was added NMM (3.52 ml) followed by Boc-Tyr (tBu)-Tyr(tBu)-OSu (4.61 g). The solution was stirred at ambient temperatures for 6 hours. Solvent was reduced to approximately ¼ total volume, added to sat. NaHCO$_3$ (~500 ml), and stirred for 30 minutes. The precipitate was filtered and washed thoroughly with water. Solid material was dried in vacuum overnight, dissolved in methanol, and any remaining solid material was filtered. The solvent was evaporated from the filtrate and the product was recrystallized using ethanol (~60 ml). The precipitate was filtered and dried in vacuum overnight. Product was collected as a pale brown powder (4.57 g).

Boc-Tyr(OtBu)-Tyr(OtBu)-Phe-Phe-Ile-HC (3.53 g) was deprotected using 4N HCl in dioxane (~100 ml). This material was stirred at ambient temperatures for ~1 hour. The solvent was evaporated and the product was collected as a slightly yellow powder (3.64 g).

FIGS. 60 through 85 demonstrate plasma levels measured by ELISA of various compounds described in Examples 35 through 68.

Glycopeptides

Figure 86:
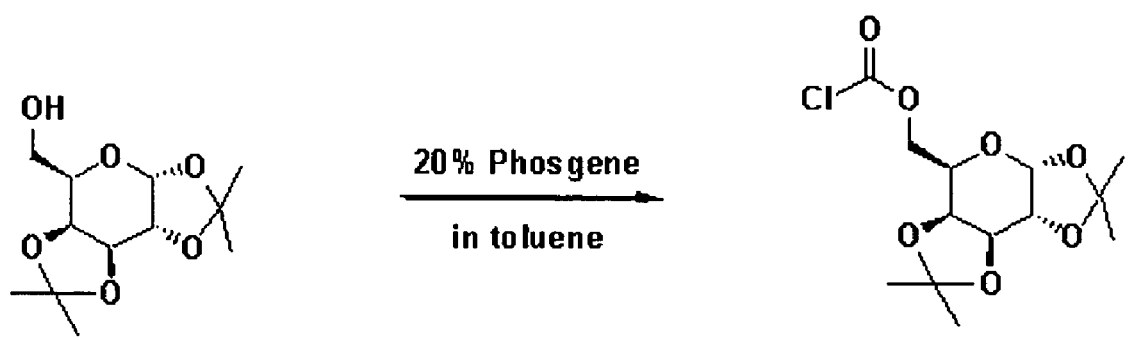
FIG. 86. illustrates preparation of 1,2:3,4-di-O-isopropylidene-D-galactopyranose.

FIG. 86 illustrates preparation of 1,2:3,4-di-O-isopropylidene-D-galactopyranose.

| Reagents | MW | Weight | mmoles | Molar Equivalents |
|---|---|---|---|---|
| 1,2:3,4-di-O-isopropylidene-D-galactopyranose | 260 | 1.00 g | 3.85 | 1 |
| 20% Phosgene in toluene | — | 20 ml | — | — |

Chloroformate of 1,2:3,4-di-O-isopropylidene-D-galactopyranose

To a stirring solution of 20% phosgene in toluene under an inert atmosphere was added 1,2:3,4-di-O-isopropylidene-D-galactopyranose via syringe. The resulting clear, colorless solution was stirred at ambient temperature for 30 minutes. After stirring, Ar(g) was bubbled through the solution for approximately 20 minutes to remove any excess phosgene. Solvent was then removed and product dried under vacuum for 18 hours. Product was used without further purification or characterization.

Example 69

Galactose-CO-Leu-Hydrocodone

Synthesis of Galactose-CO-Leu-Hydrocodone

To the chloroformate of galactose (1.5 eq) in dimethylformamide (DMF) (2 ml/mmol) was added Leu-Hydrocodone (1 eq) and 4-methylmorpholine (NMM) (6 eq). The reaction was stirred at ambient temperatures for 18 hours. Reaction was quenched by the addition of water, solvents were removed and crude product was isolated by purification with reverse-phase HPLC.

Product was deprotected using 1:1 1M HCl:THF (1 ml/0.1 mmol) in 3 hours. Product was re-purified by reverse-phase HPLC.

Example 70

Galactose-CO-Pro-Pro-Ile-Hydrocodone

Synthesis of Galactose-CO-Pro-Pro-Ile-Hydrocodone
Galactose-CO-Pro-Pro-Ile-Hydrocodone was prepared in a manner similar to Example 69 except Pro-Pro-Ile-Hydrocodone was used as the conjugated starting material.

Example 71

Galactose-CO-Pro-Pro-Leu-Hydrocodone

Synthesis of Galactose-CO-Pro-Pro-Leu-Hydrocodone
Galactose-CO-Pro-Pro-Leu-Hydrocodone was prepared in a manner similar to Example 69 Pro-Pro-Leu-Hydrocodone was used as the conjugated starting material.

Figure 87:
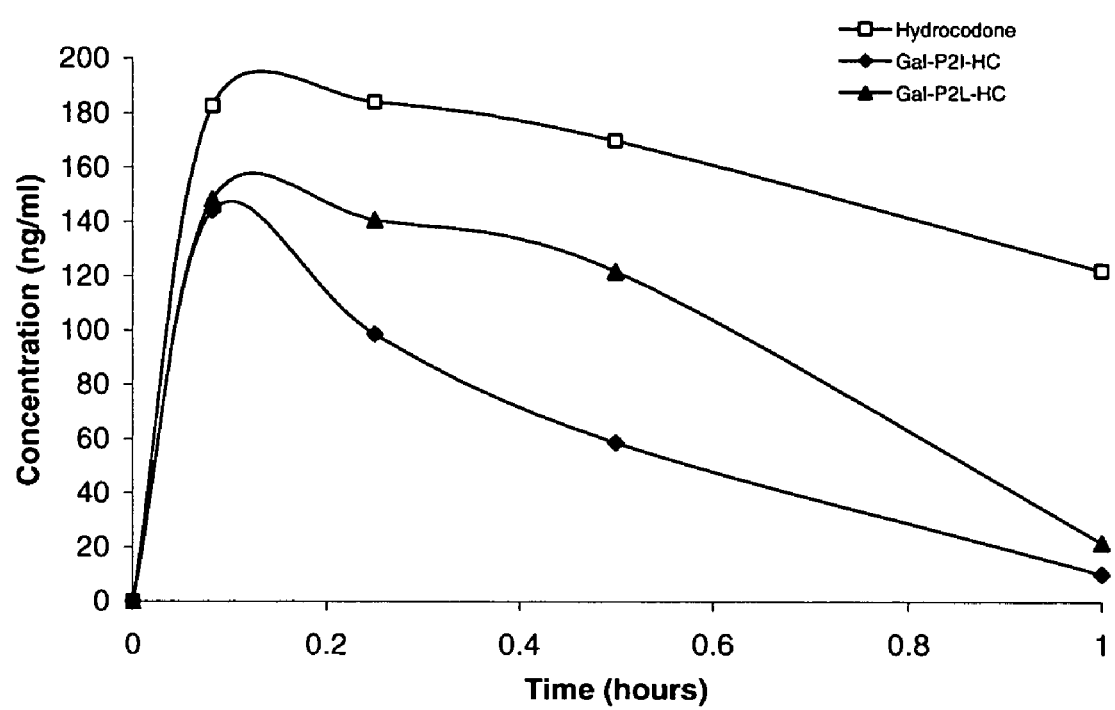
FIG. 87. Oral bioavailability of abuse-resistant hydrocodone glyco-peptide conjugates, measured as free hydrocodone.

FIG. 87 illustrates oral bioavailability of abuse-resistant hydrocodone glyco-peptide conjugates, measured as free hydrocodone.

Example 72

Gulonic Acid-Ile-Hydrocodone

Synthesis of Gulonic Acid-Ile-Hydrocodone
Gulonic acid-Ile-Hydrocodone was prepared in a manner similar to Example 69 except Ile-Hydrocodone was used as the conjugated starting material and Gulonic acid-OSu was used as the carbohydrate starting material.

Figure 88:
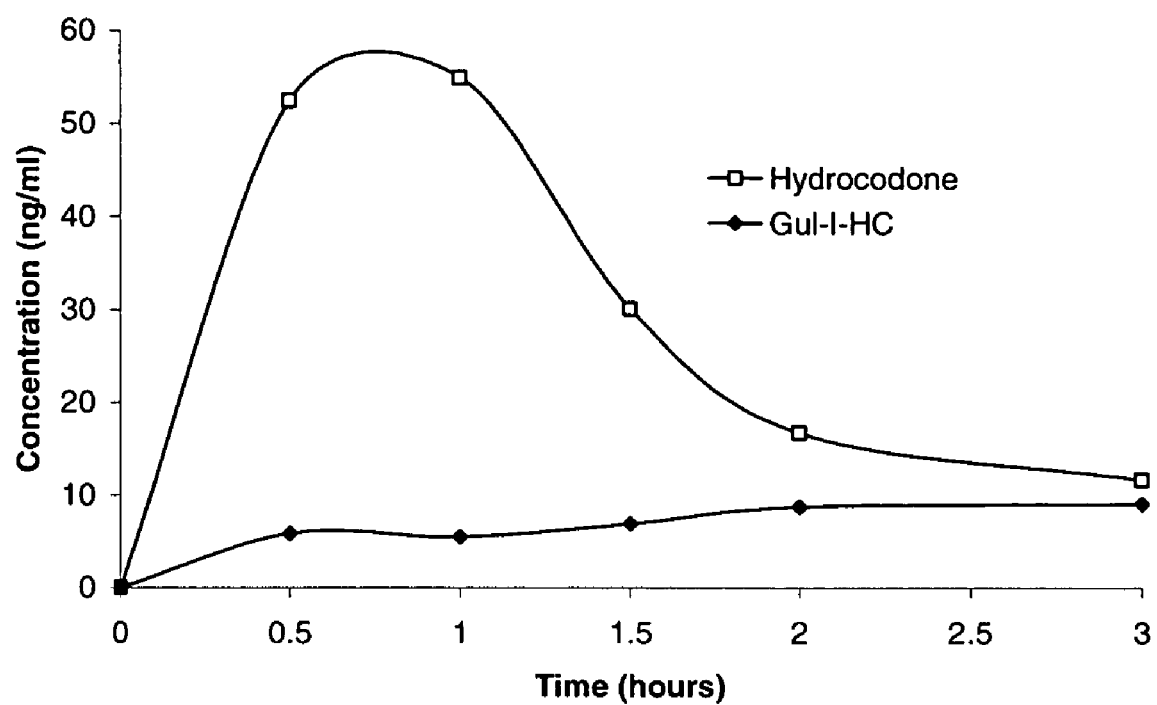
FIG. 88. Oral bioavailability of an abuse-resistant hydrocodone amino acid-crabohydrate conjugate, measured as free hydrocodone.

FIG. 88 illustrates Oral bioavailability of an abuse-resistant hydrocodone amino acid-carbohydrate conjugate, measured as free hydrocodone.

D-Amino Acids

Example 73

(d)-Lys-(l)-Lys-Ile-Hydrocodone

Preparation of (d)-Lys-(l)-Lys-Ile-Hydrocodone
To a solution of Ile-Hydrocodone in DMF was added NMM followed by Boc-(d)-Lys(Boc)-(l)-Lys(Boc)-OSu. The solution was stirred at ambient temperatures for 18 hours. Solvent was removed. Crude material was purified using preparative HPLC (Phenomenex Luna C18, 30×250 mm, 5 µM, 100 Å; Gradient: 90 water/10 0.1% TFA-MeCN→0/100; 30 ml/min.). Solid was collected as a slightly yellow powder. To the Boc-(d)-Lys(Boc)-(l)-Lys (Boc)-Hydrocodone was added 4N HCl in dioxane. The resulting mixture was stirred at ambient temperatures for 18 hours. Solvent was removed and final product dried under vacuum. Solid was collected as a slightly yellow solid.

Nucleosides

Figure 89:
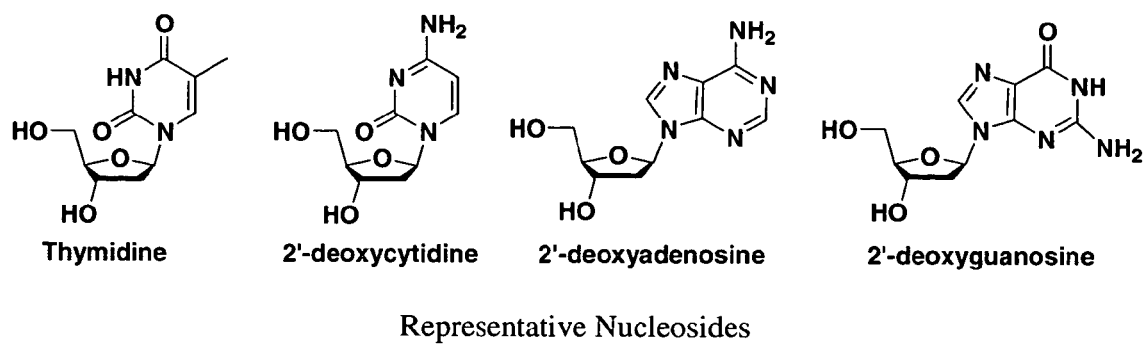
FIG. 89. illustrates nucleosides and conjugation sites.
Figure 89:
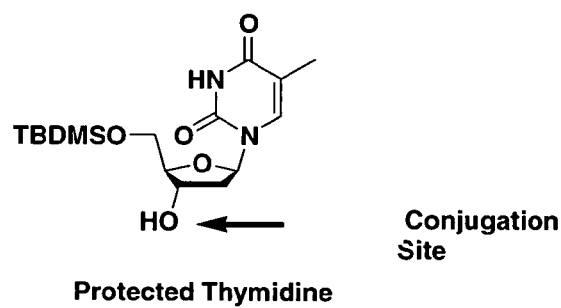
Figure 90:
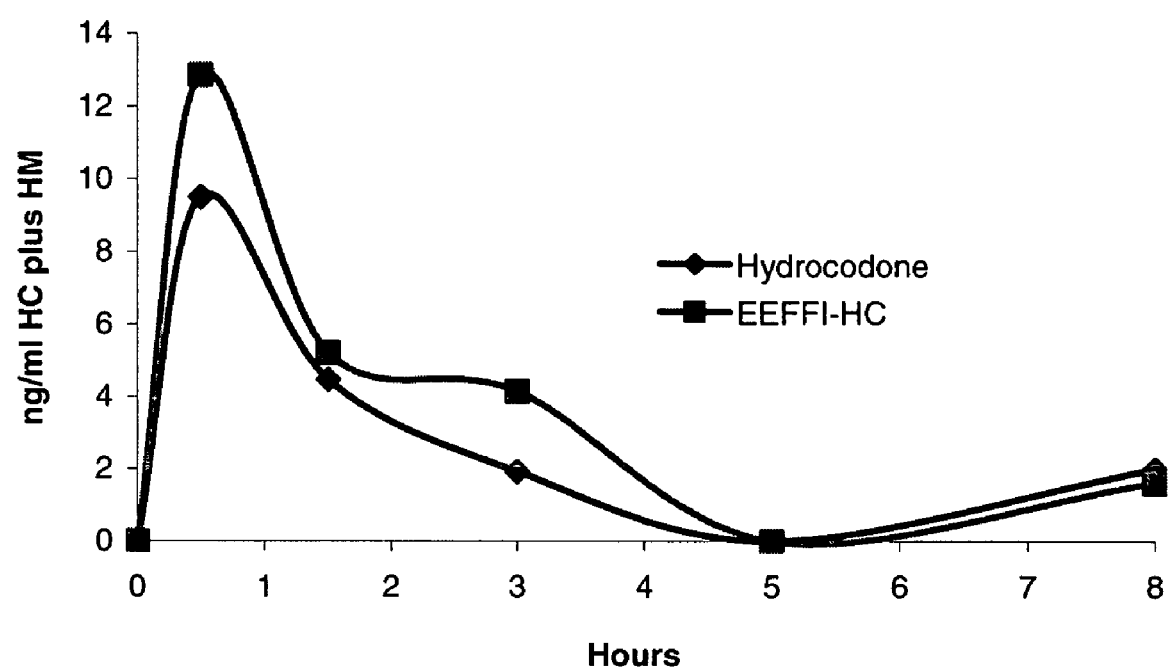
FIG. 90. Oral bioavailability in rats for hydrocodone vs. EEFFFI[SEQ ID NO: 2]-HC at a dose (1 mg/kg) approximating a therapeutic human dose equivalent measured as free hydrocodone.
Figure 91:
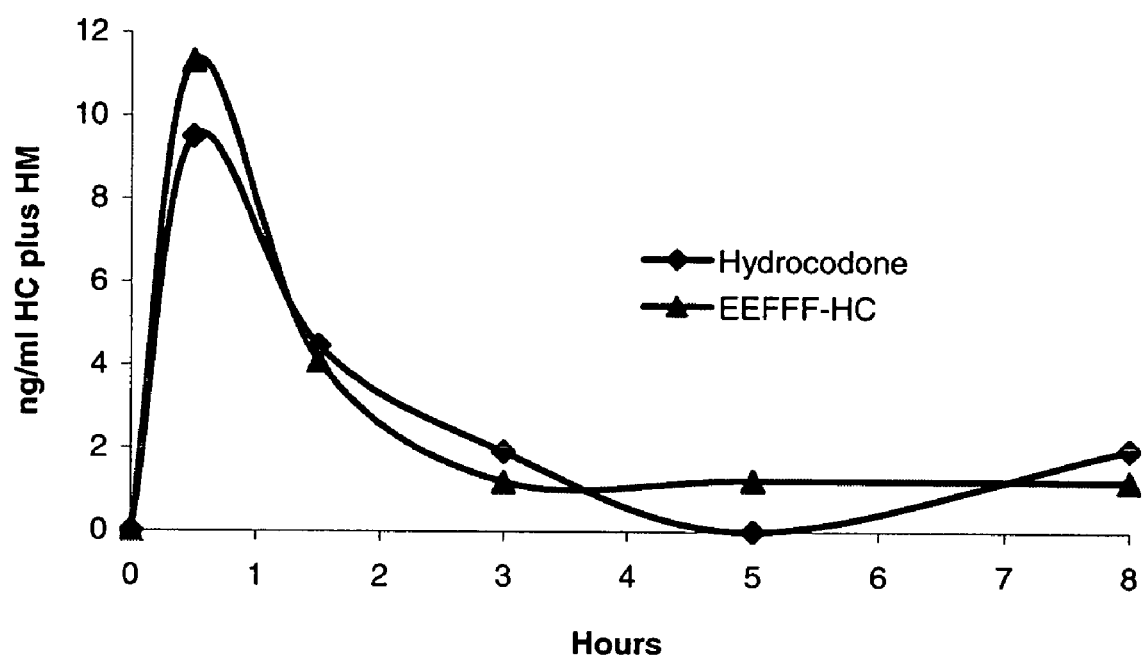
FIG. 91. Oral bioavailability in rats for hydrocodone vs. EEFFF[SEQ ID NO: 3]-HC at a dose (1 mg/kg) approximating a therapeutic human dose equivalent measured as free hydrocodone.
Figure 92:
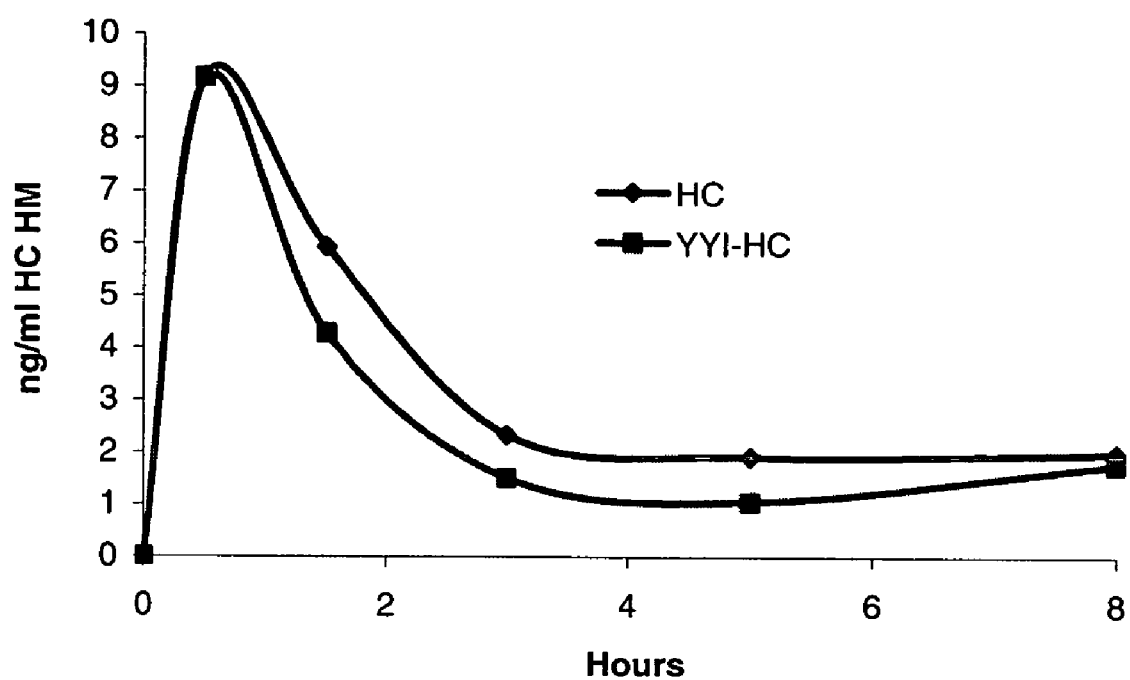
FIG. 92. Oral bioavailability in rats for hydrocodone vs. YYI-HC at a dose (1 mg/kg) approximating a therapeutic human dose equivalent measured as free hydrocodone.
Figure 93:
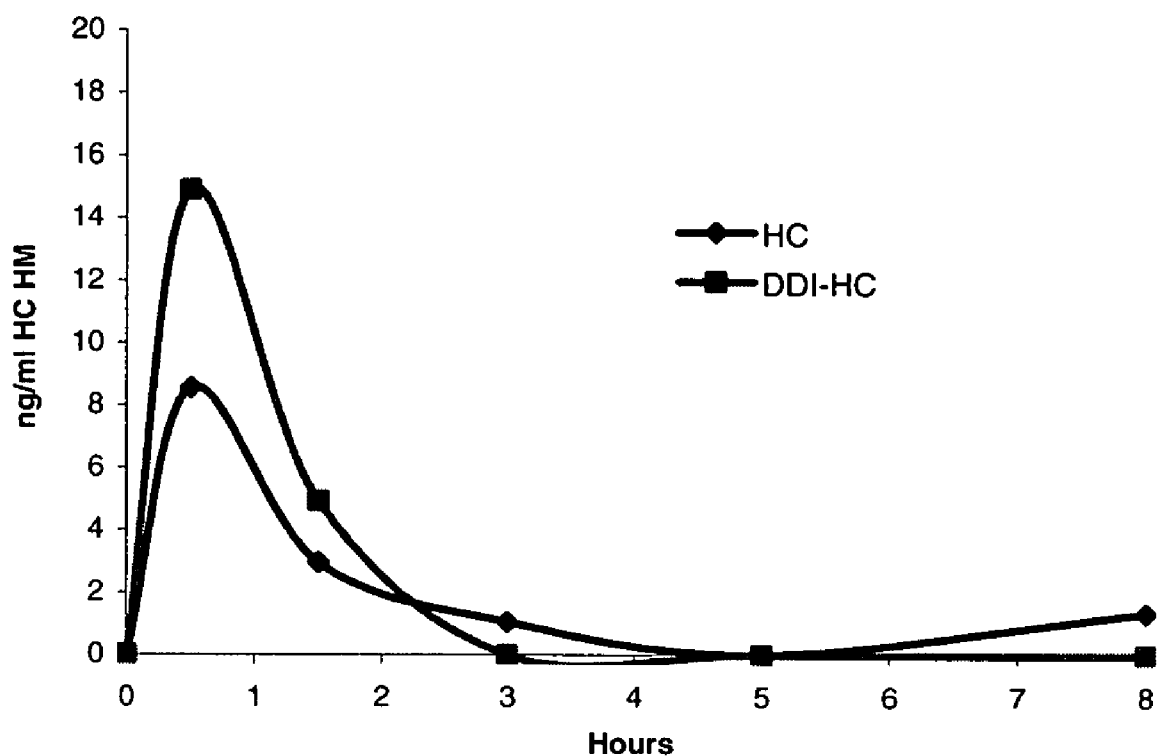
FIG. 93. Oral bioavailability in rats for hydrocodone vs. DDI-HC at a dose (1 mg/kg) approximating a therapeutic human dose equivalent measured as free hydrocodone.
Figure 94:
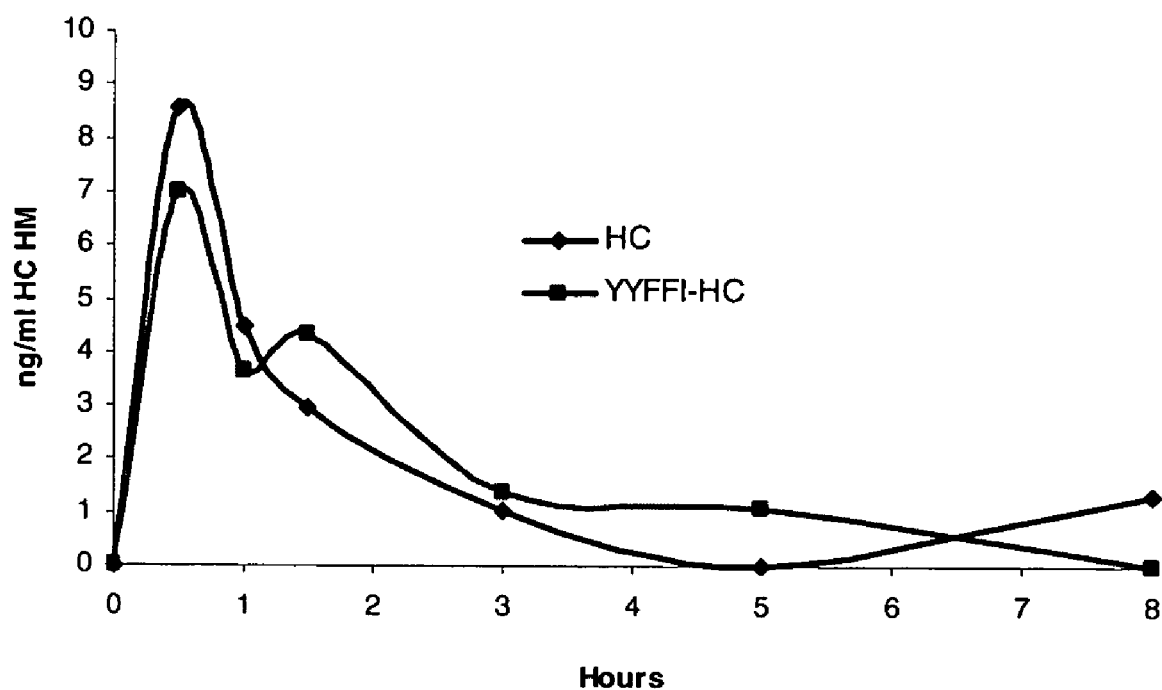
FIG. 94. Oral bioavailability in rats for hydrocodone vs. YYFFI[SEQ ID NO: 8]-HC at a dose (1 mg/kg) approximating a therapeutic human dose equivalent measured as free hydrocodone.
Figure 95:
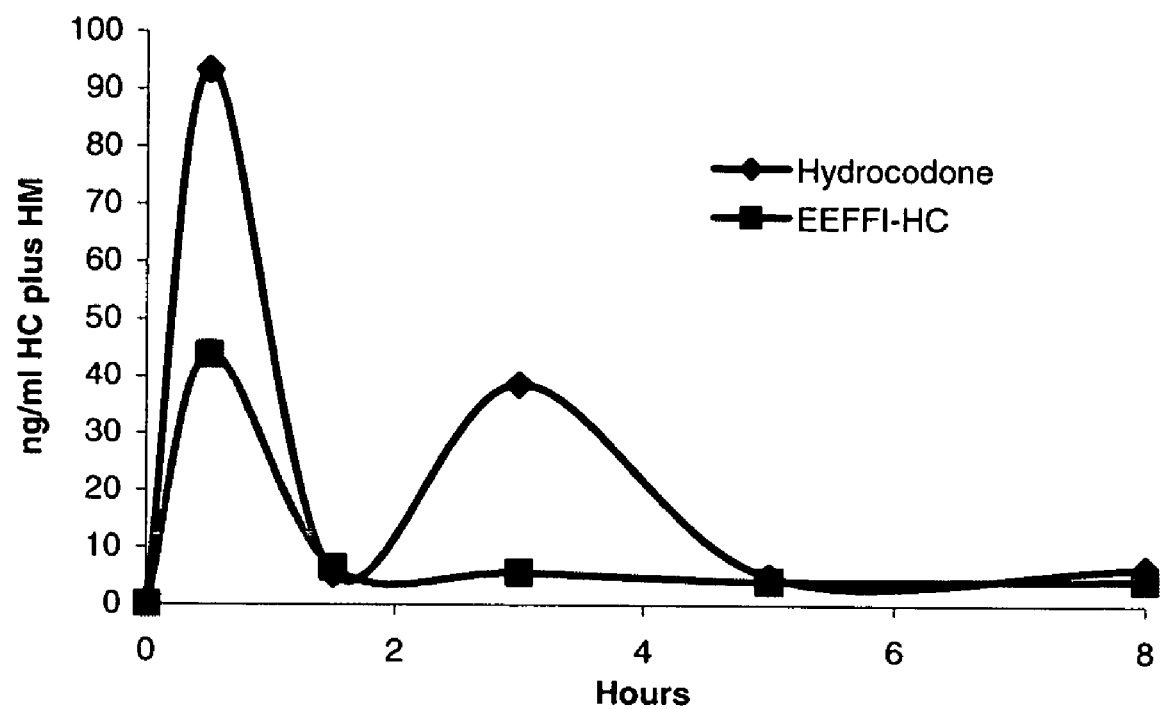
FIG. 95. Oral bioavailability in rats for hydrocodone vs. EEFFI[SEQ ID NO: 5]-HC at a dose (5 mg/kg) approaching a human overdose equivalent measured as free hydrocodone.
Figure 96:
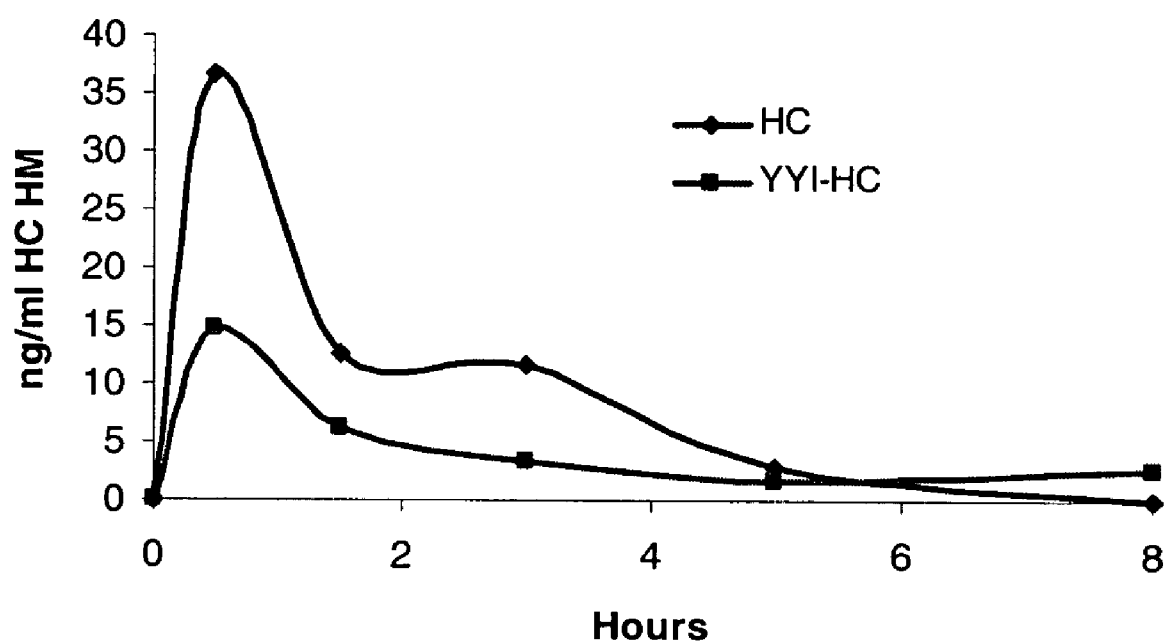
FIG. 96. Oral bioavailability in rats for hydrocodone vs. YYI-HC at a dose (5 mg/kg) approaching a human overdose equivalent measured as free hydrocodone.
Figure 97:
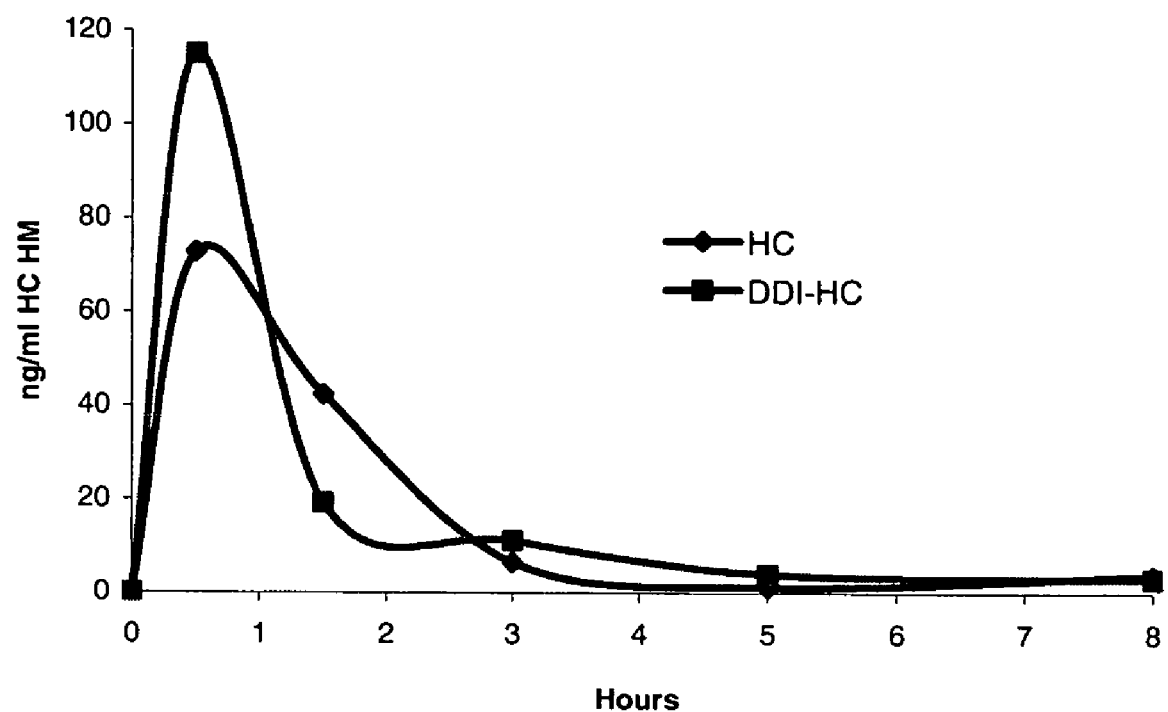
FIG. 97. Oral bioavailability in rats for hydrocodone vs. DDI-HC at a dose (5 mg/kg) approaching a human overdose equivalent measured as free hydrocodone.
Figure 98:
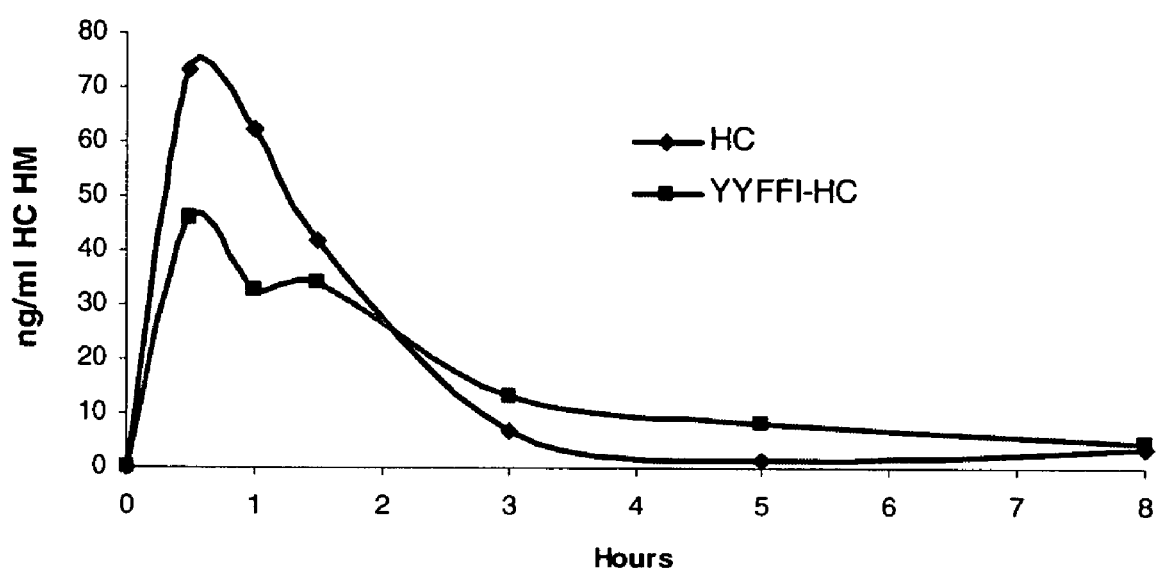
FIG. 98. Oral bioavailability in rats for hydrocodone vs. YYFFI[SEQ ID NO: 8]-HC at a dose (5 mg/kg) approaching a human overdose equivalent measured as free hydrocodone.
Figure 99:
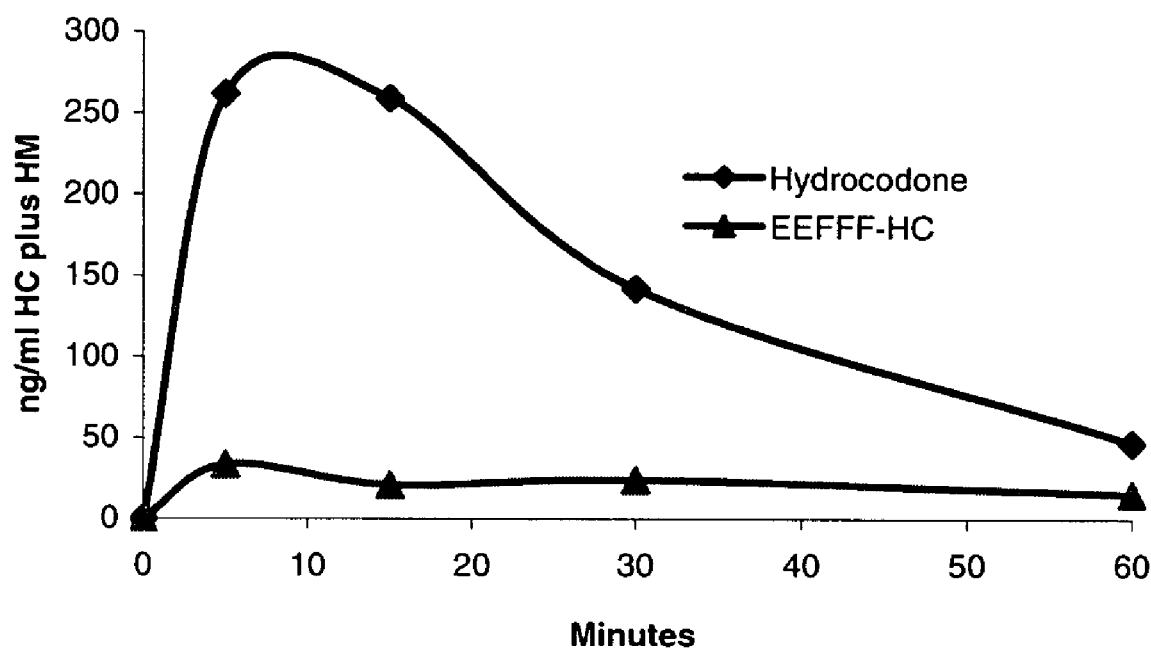
FIG. 99. Decrease in bioavailability of EEFFF[SEQ ID NO: 3]-HC as compared to hydrocodone by the intranasal route of administration measured as free hydrocodone.
Figure 100:
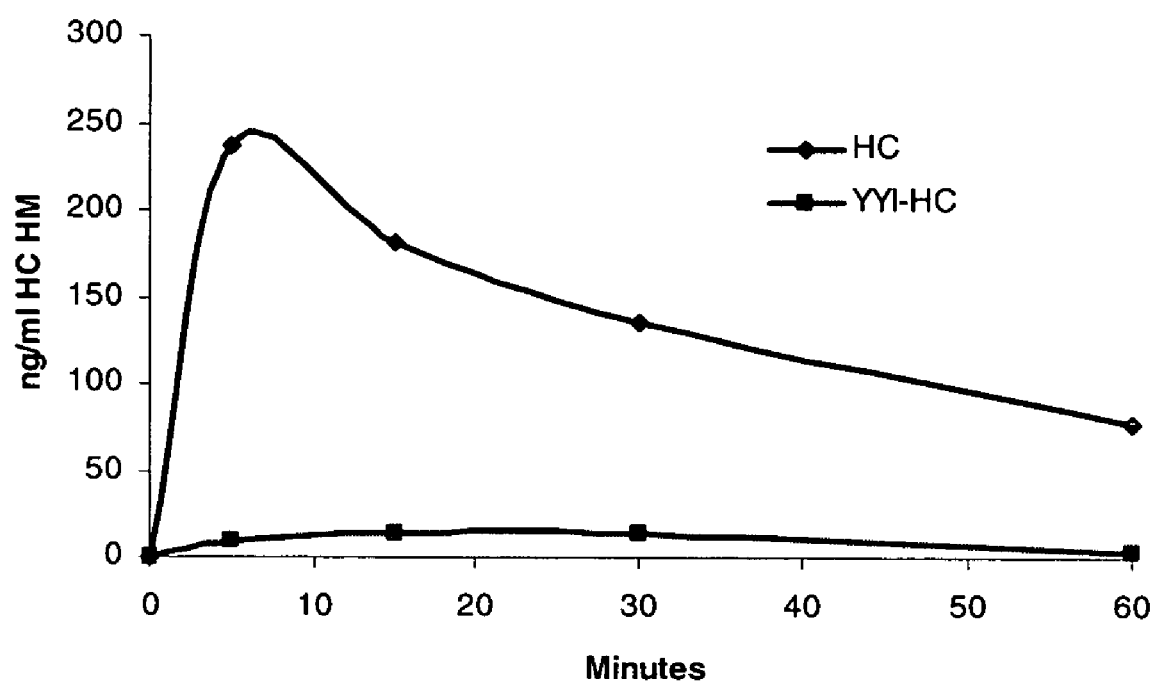
FIG. 100. Decrease in bioavailability of YYI-HC as compared to hydrocodone by the intranasal route of administration measured as free hydrocodone.
Figure 101:
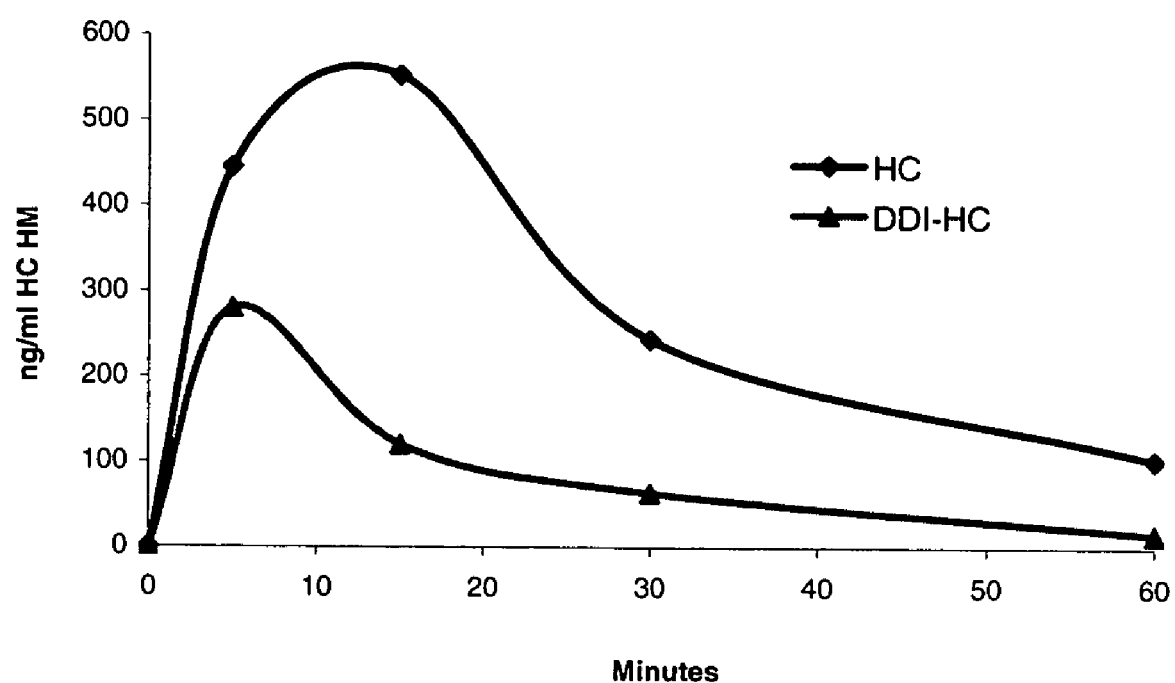
FIG. 101. Decrease in bioavailability of DDI-HC as compared to hydrocodone by the intranasal route of administration measured as free hydrocodone.
Figure 102:
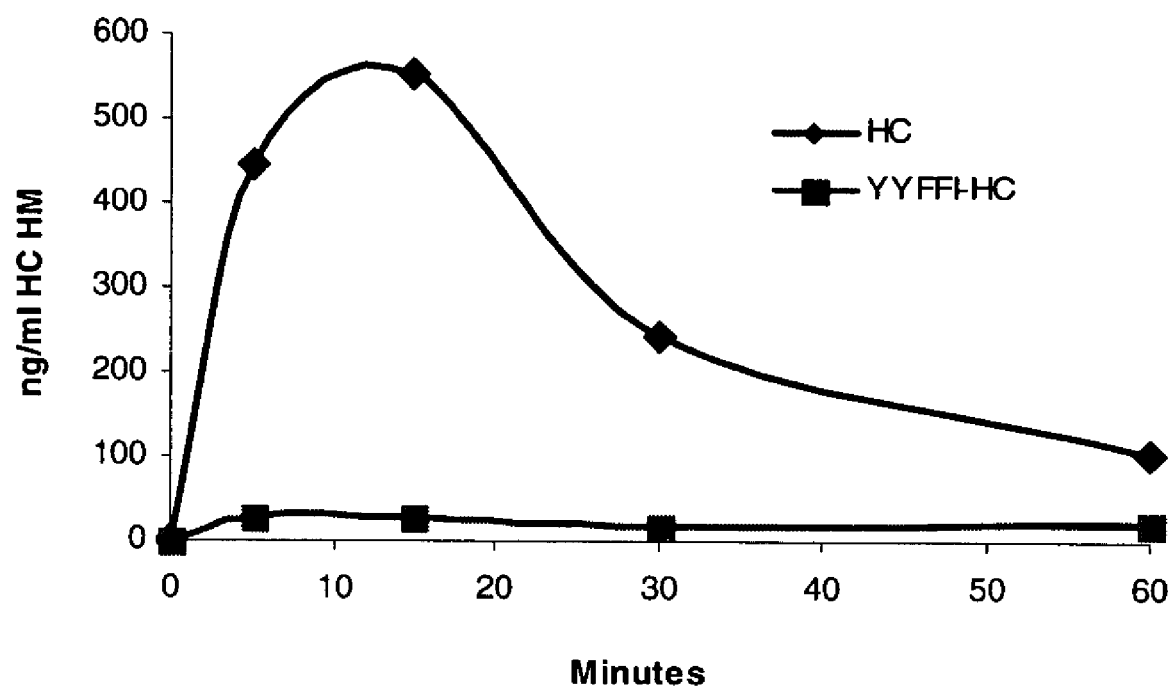
FIG. 102. Decrease in bioavailability of YYFFI[SEQ ID NO: 8]-HC as compared to hydrocodone by the intranasal route of administration measured as free hydrocodone.
Figure 103:
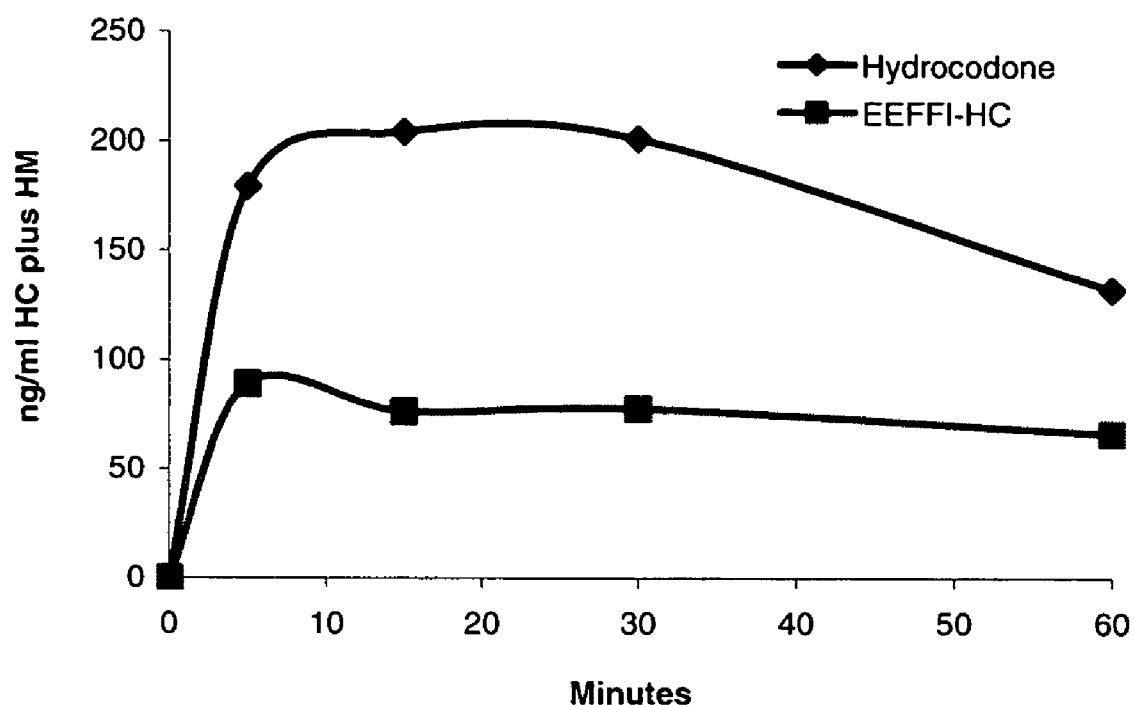
FIG. 103. Decrease in bioavailability of EEFFI[SEQ ID NO: 5]-HC as compared to hydrocodone by the intravenous route of administration measured as free hydrocodone.
Figure 104:
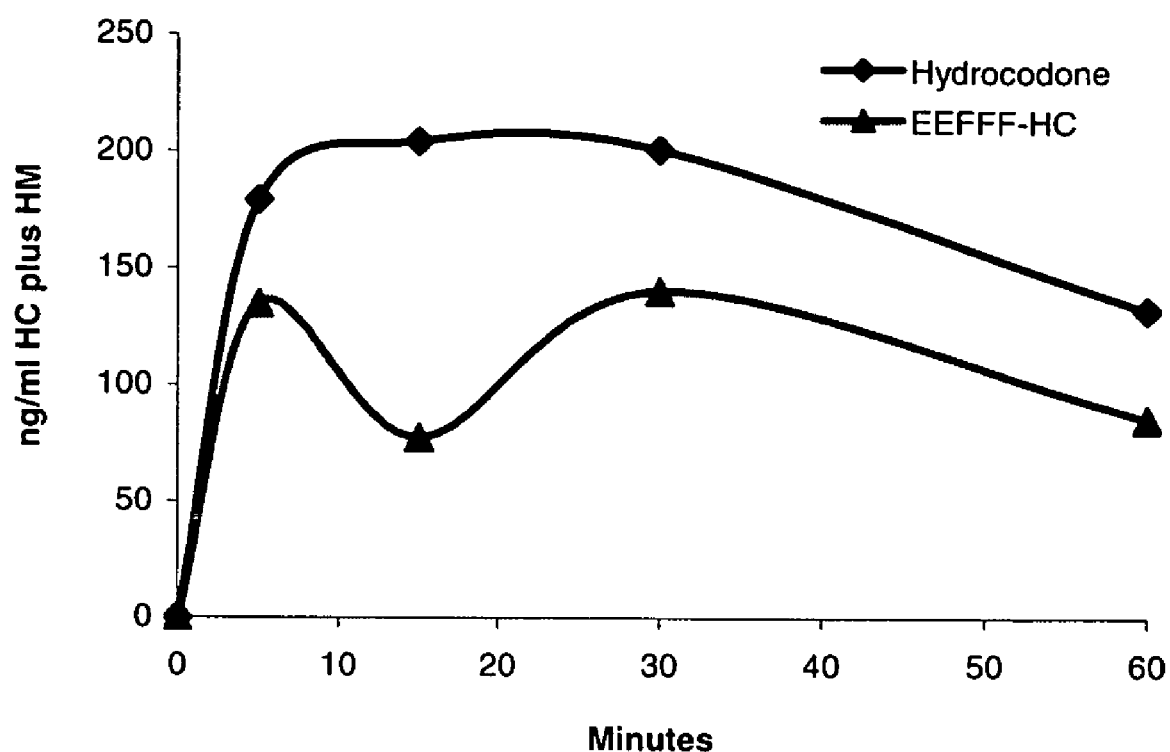
FIG. 104. Decrease in bioavailability of EEFFF[SEQ ID NO: 3]-HC as compared to hydrocodone by the intravenous route of administration measured as free hydrocodone.
Figure 105:
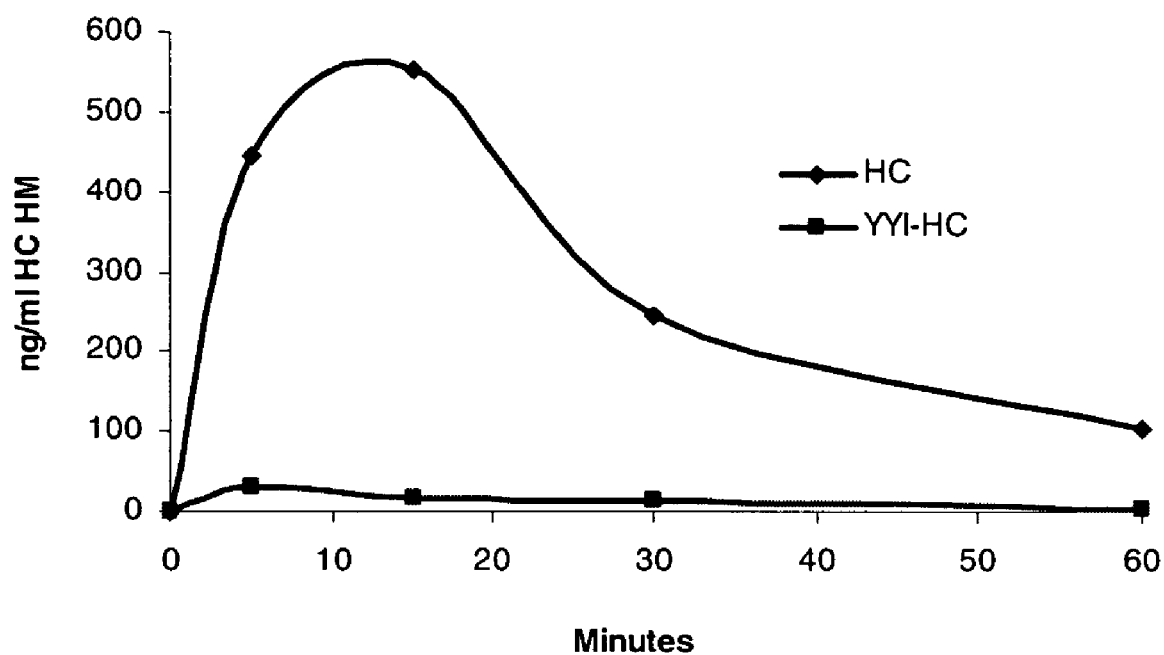
FIG. 105. Decrease in bioavailability of YYI-HC as compared to hydrocodone by the intravenous route of administration measured as free hydrocodone.
Figure 106:
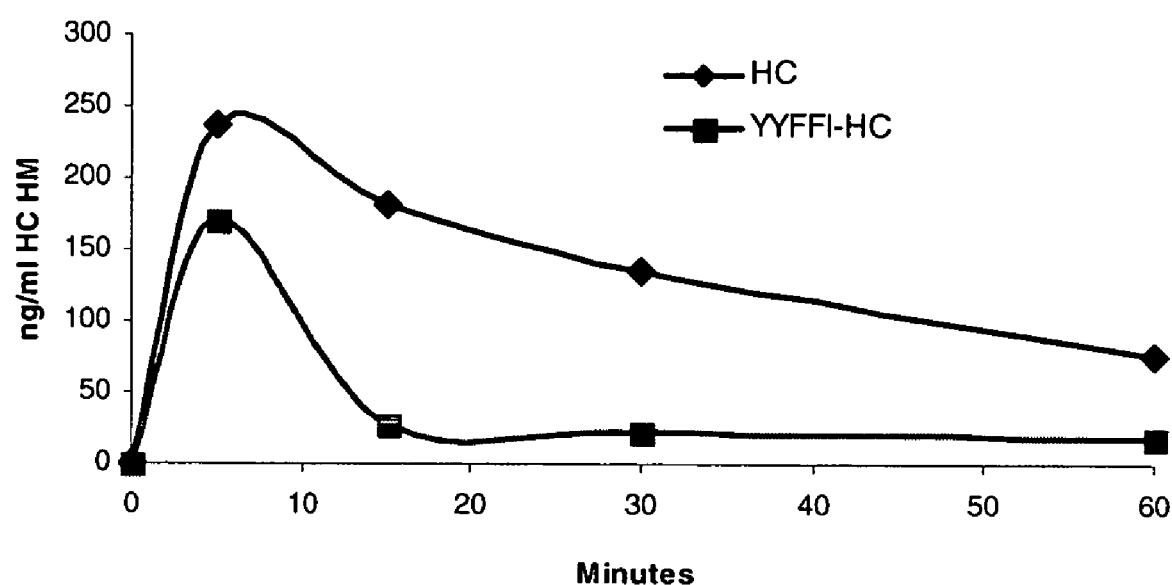
FIG. 106. Decrease in bioavailability of YYFFI[SEQ ID NO: 8]-HC as compared to hydrocodone by the intravenous route of administration measured as free hydrocodone.
Figure 107:
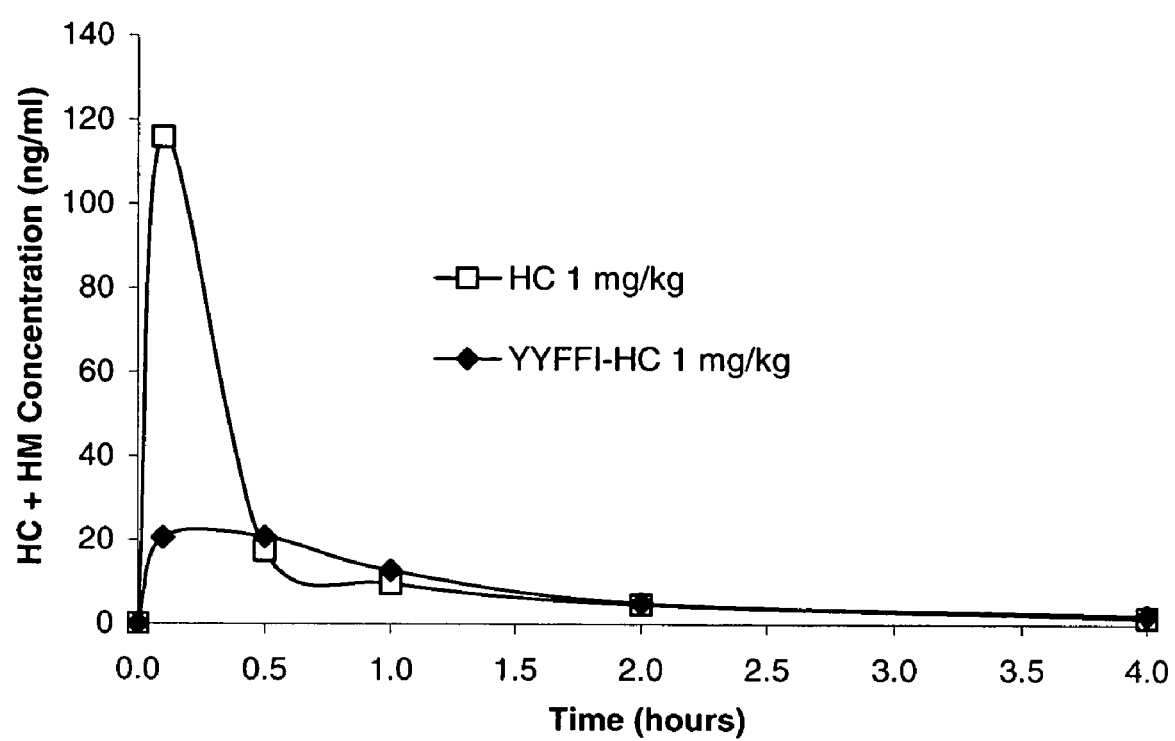
FIG. 107. Oral bioavailability of hydrocodone plus hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.
Figure 108:
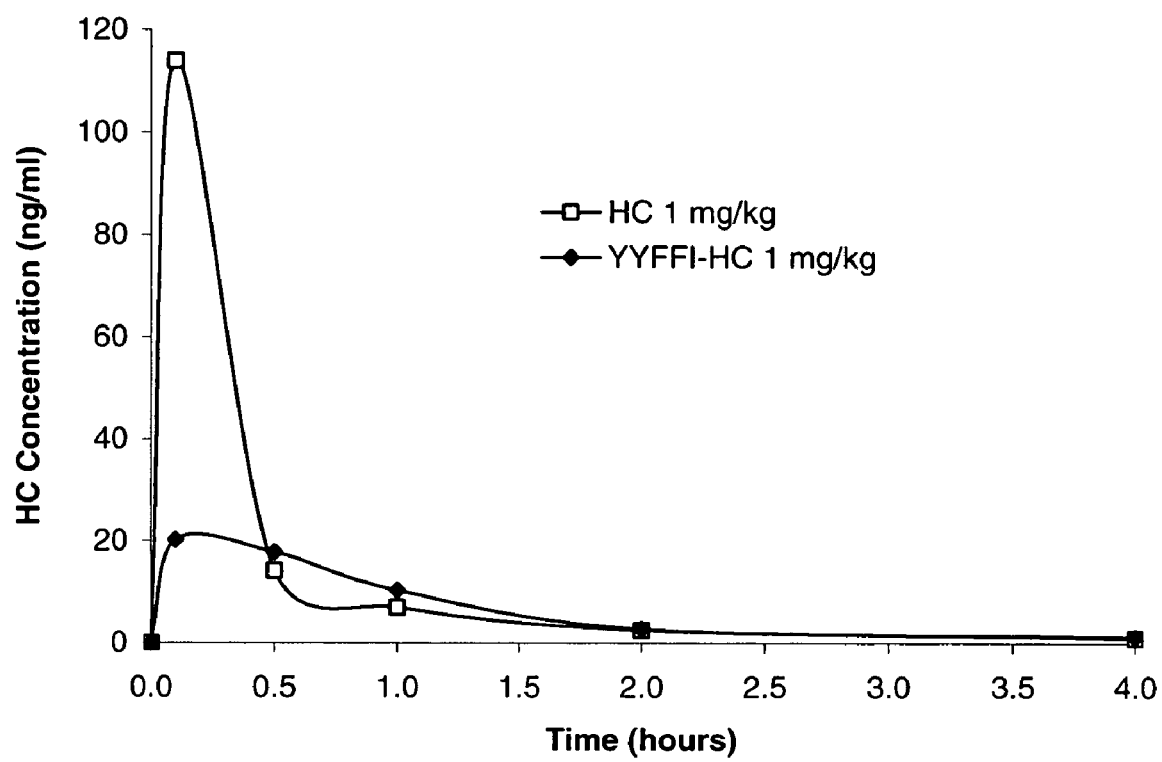
FIG. 108. Oral bioavailability of hydrocodone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.
Figure 109:
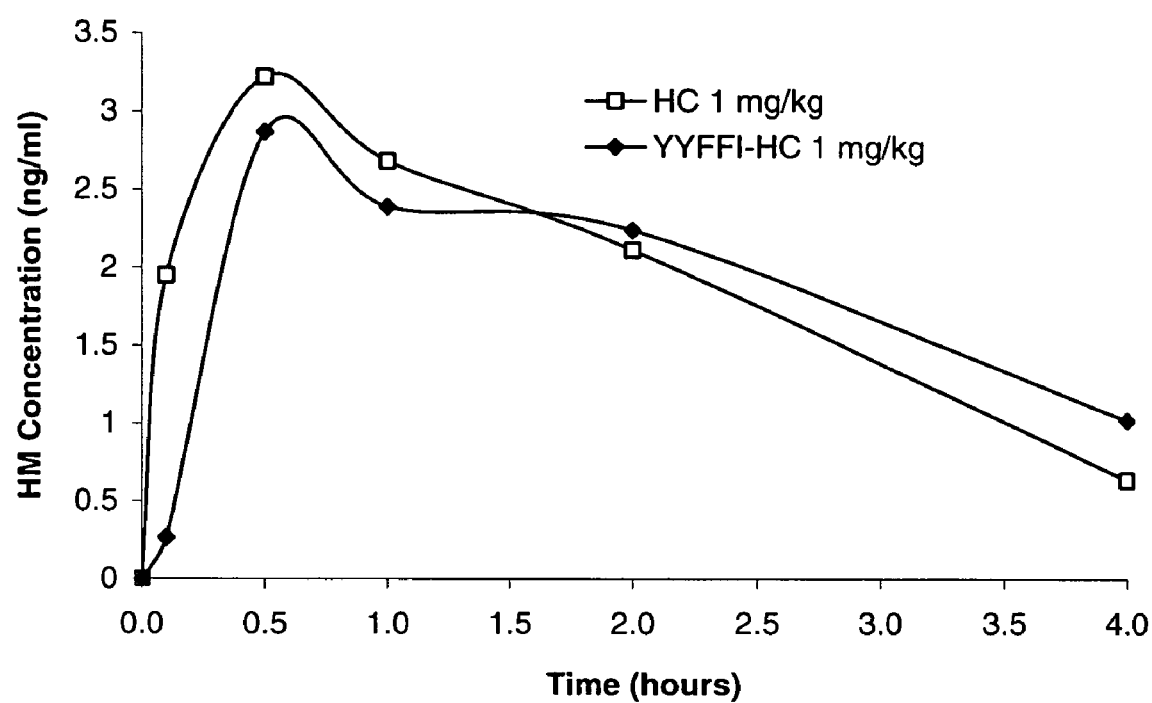
FIG. 109. Oral bioavailability of hydromorphone (concentration vs. time) following administration of hydrocodone bitratrate or YYFFI[SEQ ID NO: 8]-HC at 1 mg/kg (equimolar doses with equivalent content of hydrocodone base) in rats, measured as free hydrocodone.
Figure 110:
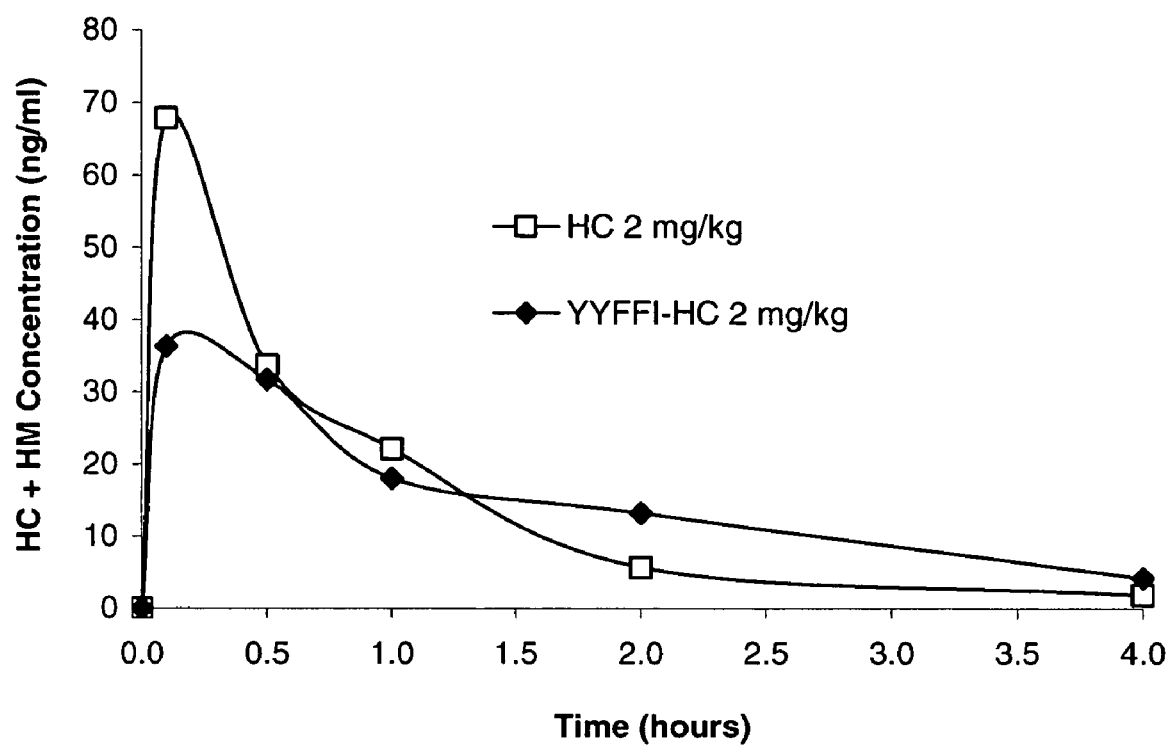
FIG. 110. Oral bioavailability of hydrocodone plus hydromorphone (concentration vs. time) following administration of hydrocodone bitratrate or YYFFI[SEQ ID NO: 8]-HC at 2 mg/kg (equimolar doses with equivalent content of hydrocodone base) in rats, measured as free hydrocodone.
Figure 111:
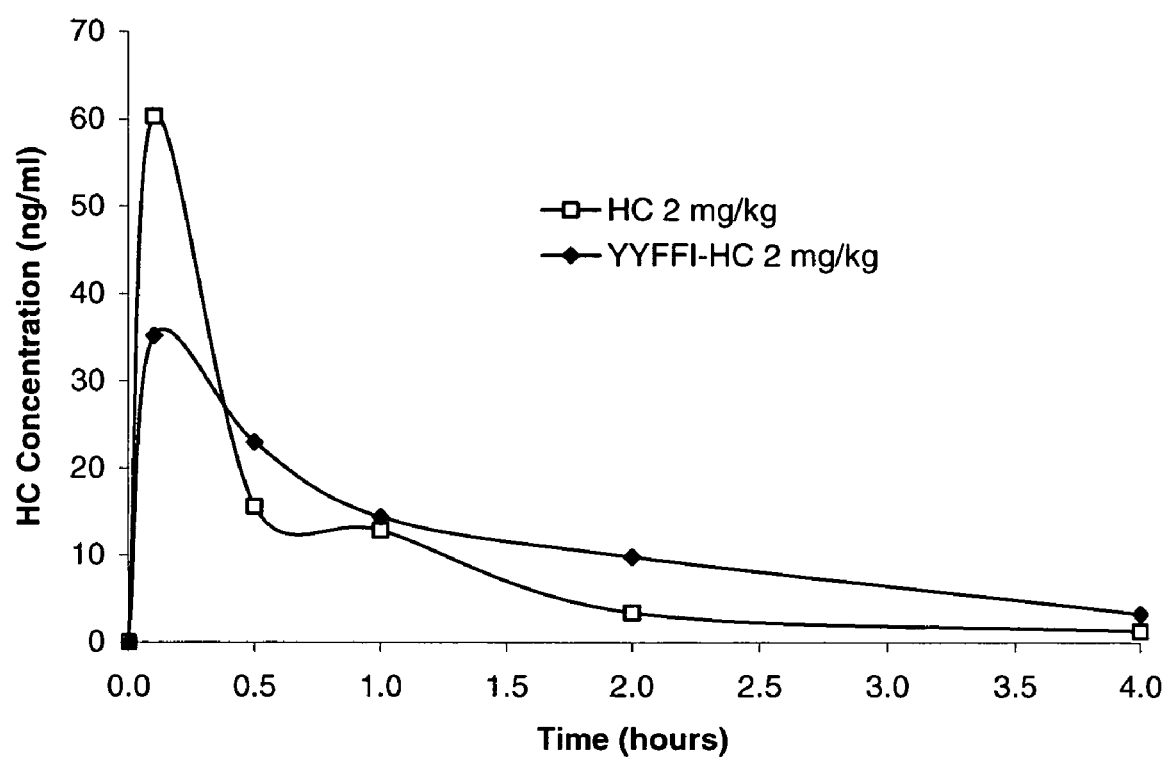
FIG. 111. Oral bioavailability of hydrocodone (concentration vs. time) following administration of hydrocodone bitratrate or YYFFI[SEQ ID NO: 8]-HC at 2 mg/kg (equimolar doses with equivalent content of hydrocodone base) in rats, measured as free hydrocodone.
Figure 112:
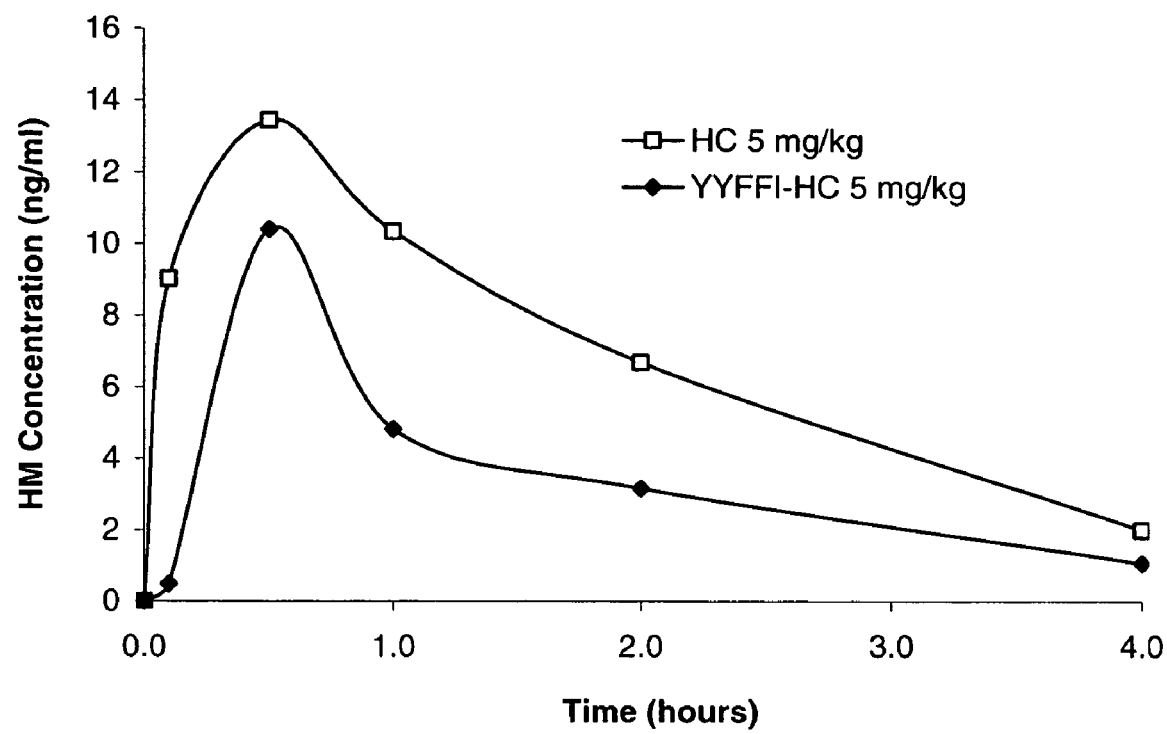
FIG. 112. Oral bioavailability of hydromorphone (concentration vs. time) following administration of hydrocodone bitratrate or YYFFI[SEQ ID NO: 8]-HC at 2 mg/kg (equimolar doses with equivalent content of hydrocodone base) in rats, measured as free hydrocodone.
Figure 113:
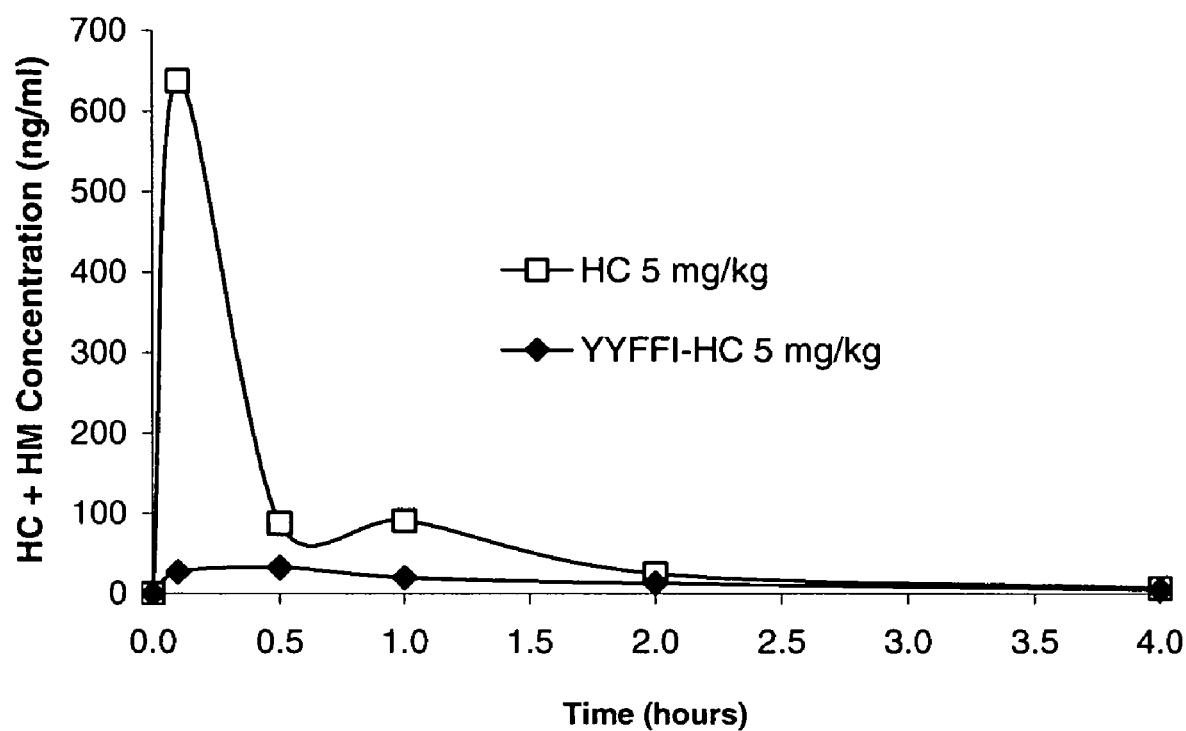
FIG. 113. Oral bioavailability of hydrocodone plus hydromorphone (concentration vs. time) following administration of hydrocodone bitratrate or YYFFI[SEQ ID NO: 8]-HC at 5 mg/kg (equimolar doses with equivalent content of hydrocodone base) in rats, measured as free hydrocodone.
Figure 114:
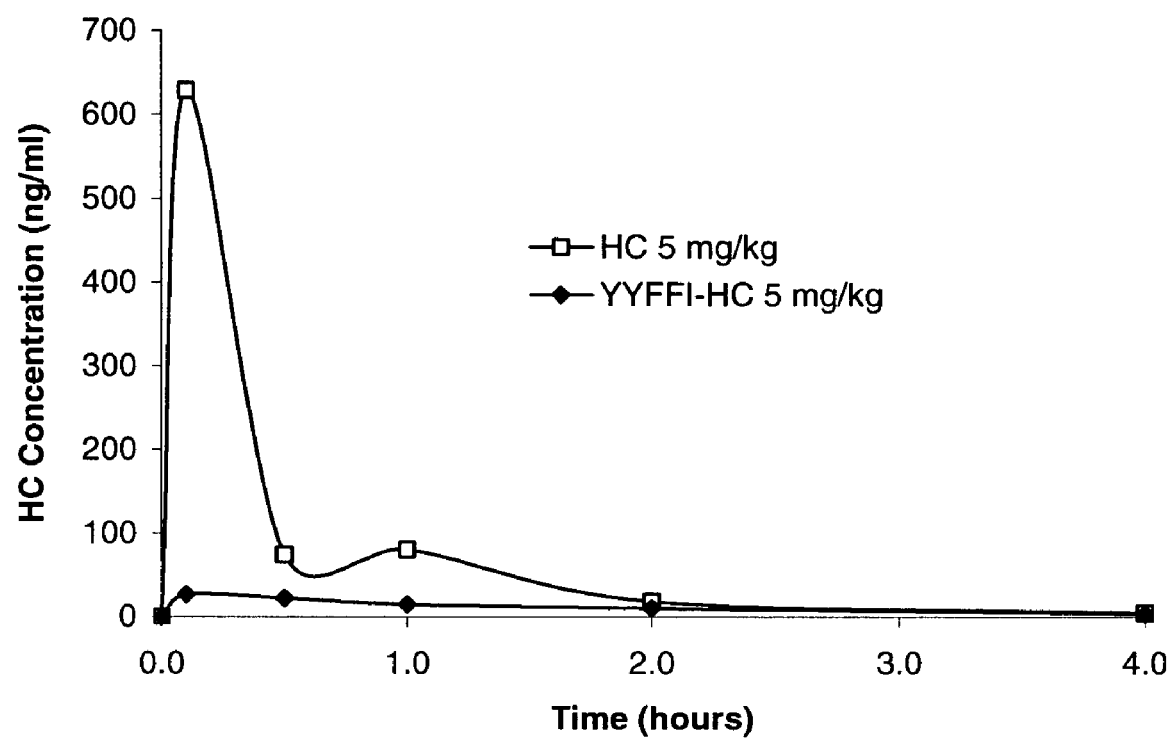
FIG. 114. Oral bioavailability of hydrocodone (concentration vs. time) following administration of hydrocodone bitratrate or YYFFI[SEQ ID NO: 8]-HC at 5 mg/kg (equimolar doses with equivalent content of hydrocodone base) in rats, measured as free hydrocodone.
Figure 115:
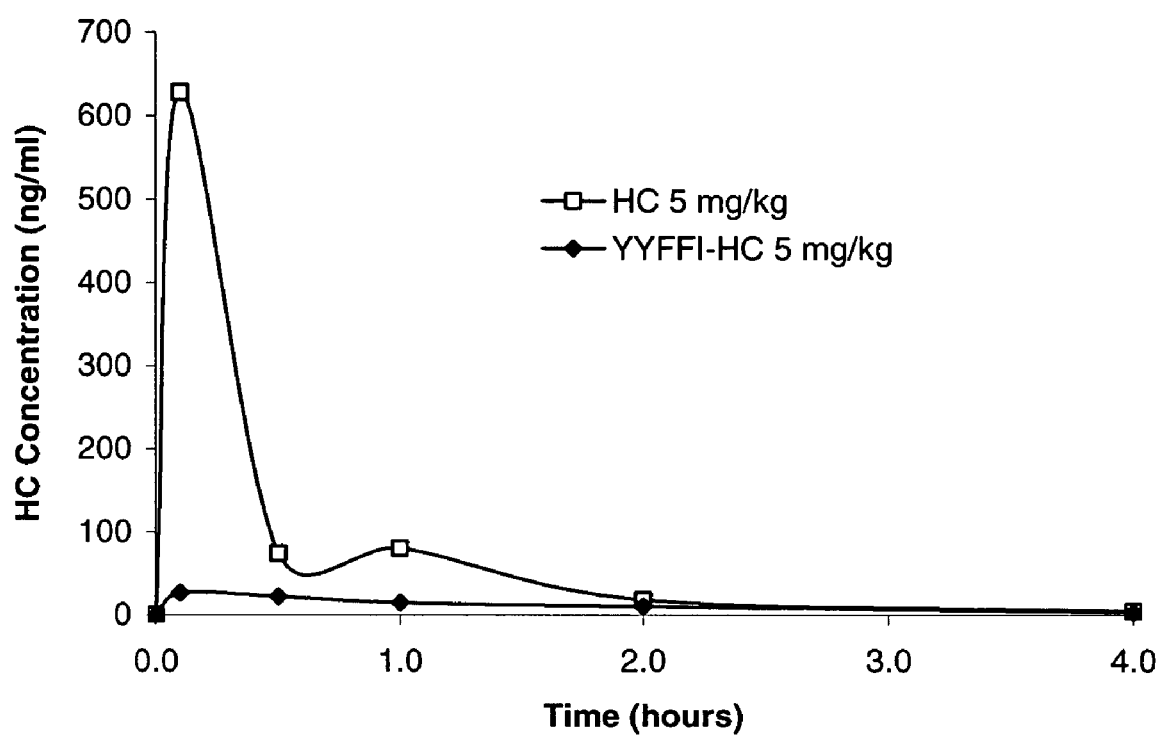
FIG. 115. Oral bioavailability of hydromorphone (concentration vs. time) following administration of hydrocodone bitratrate or YYFFI[SEQ ID NO: 8]-HC at 5 mg/kg (equimolar doses with equivalent content of hydrocodone base) in rats, measured as free hydrocodone.
Figure 116:
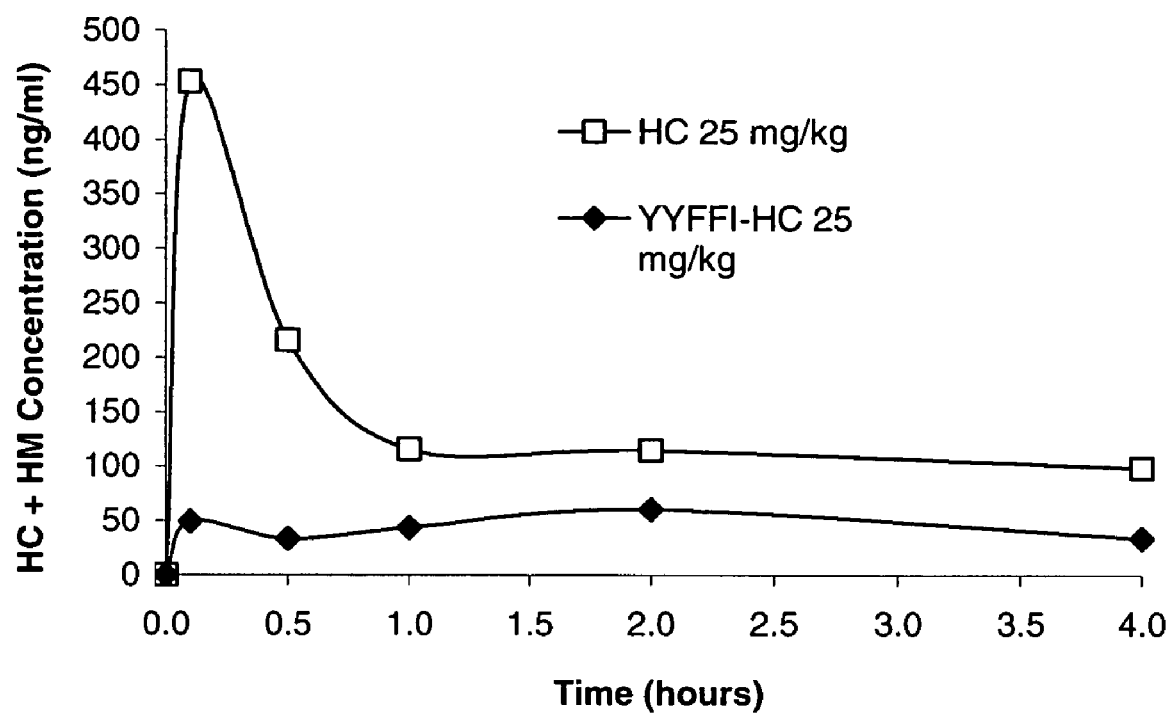
FIG. 116. Oral bioavailability of hydrocodone plus hydromorphone (concentration vs. time) following administration of hydrocodone bitratrate or YYFFI[SEQ ID NO: 8]-HC at 25 mg/kg (equimolar doses with equivalent content of hydrocodone base) in rats, measured as free hydrocodone.
Figure 117:
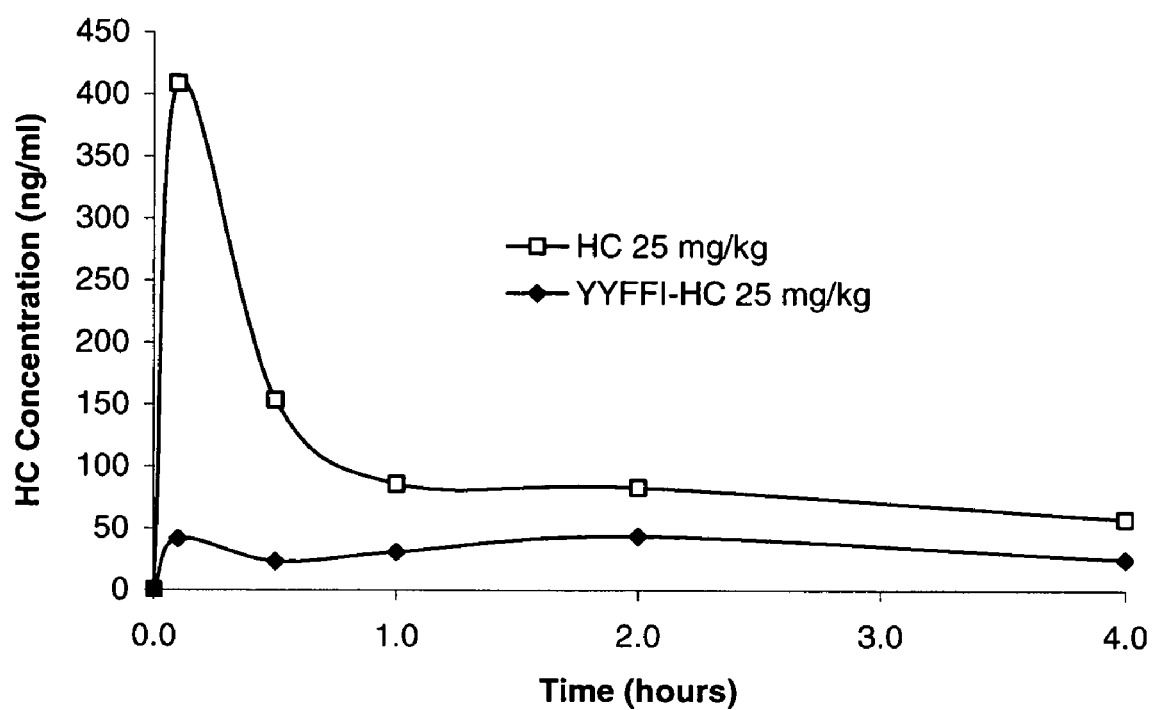
FIG. 117. Oral bioavailability of hydrocodone (concentration vs. time) following administration of hydrocodone bitratrate or YYFFI[SEQ ID NO: 8]-HC at 25 mg/kg (equimolar doses with equivalent content of hydrocodone base) in rats, measured as free hydrocodone.
Figure 118:
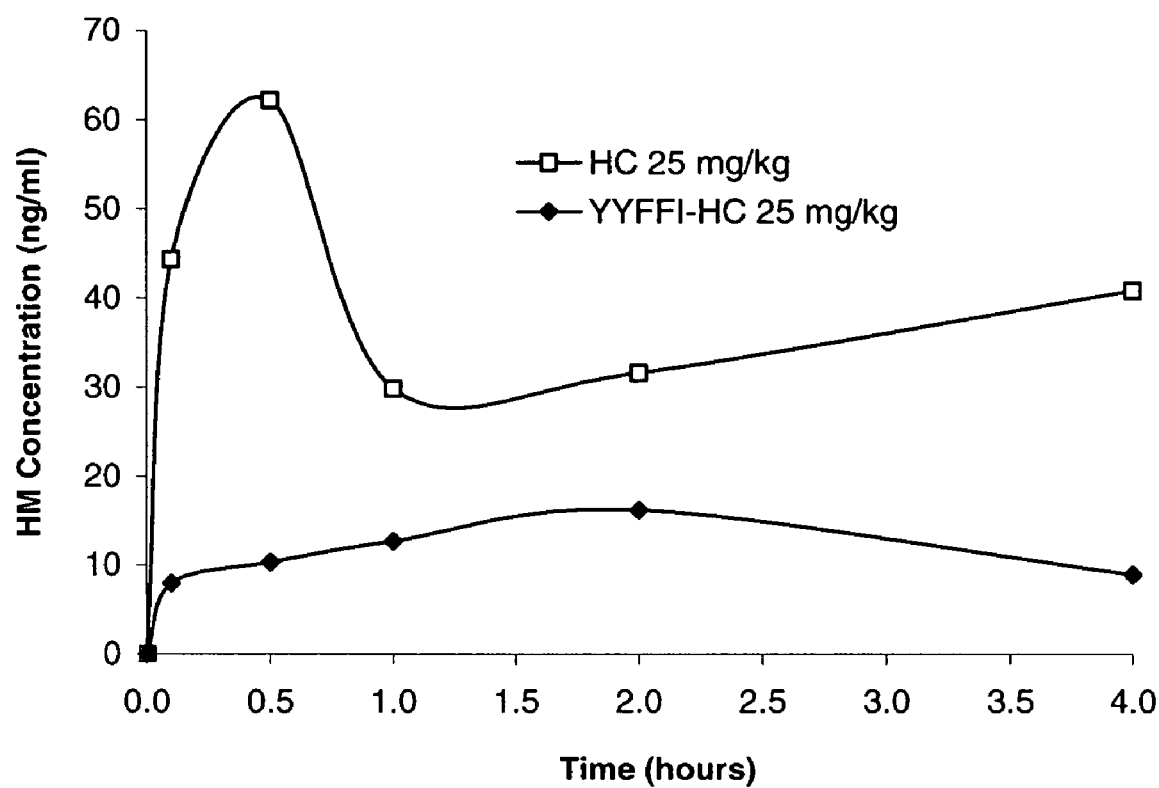
FIG. 118. Oral bioavailability of hydromorphone (concentration vs. time) following administration of hydrocodone bitratrate or YYFFI[SEQ ID NO: 8]-HC at 25 mg/kg (equimolar doses with equivalent content of hydrocodone base) in rats, measured as free hydrocodone.
Figure 119:
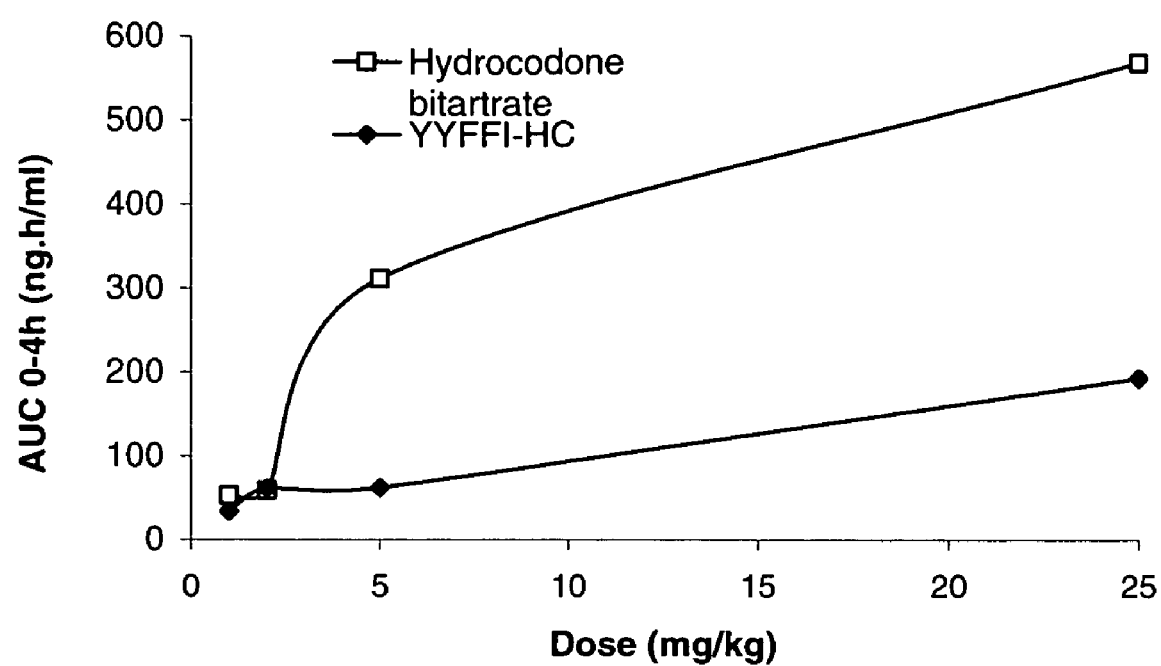
FIG. 119. Oral bioavailability (AUC0-4h) of hydrocodone plus hydromorphone (concentration vs. dose) in proportion to dose following administration of hydrocodone bitratrate or YYFFI[SEQ ID NO: 8]-HC at escalating doses (1, 2, 5, and 25 mg/kg—equimolar doses with equivalent content of hydrocodone base) in rats, measured as free hydrocodone.

FIG. 89 illustrates nucleosides and conjugation sites. Examples 74 through 83 are also described through FIGS. 90 through 128 (with plasma levels measured by LC/MS/MS).

Example 74

Oral Bioavailability of Peptide-Hydrocodone Conjugates at a Dose (1 mg/kg) Approximating a Therapeutic Human Dose and at an Elevated Dose Example 74 illustrates that when the peptides EEFFI[SEQ ID NO: 6] (Table 46, FIG. 90), EEFFF[SEQ ID NO: 7] (Table 47, FIG. 91), YYI (Table 48, FIG. 92), DDI (Table 49, FIG. 93), and YYFFI[SEQ ID NO: 8] (Table 50, FIG. 94) are conjugated to the active agent hydrocodone oral bioavailability is maintained or increased over an equivalent hydrocodone dose when the dose is administered as 1 mg/kg. This dose is the equivalent of a human dose of 10 to 14 mg for an individual weighing 70 kg (148 lbs) according to Chou et al. However, when administered orally at 5 mg/kg peak levels and bioavailability of EEFFI[SEQ ID NO: 5]-HC (Table 51, FIG. 95), YYI-HC (Table 52, FIG. 96), DDI-HC (Table 53, FIG. 97) and YYFFI[SEQ ID NO: 8]-HC (Table 54, FIG. 98) are substantially decreased. A 5 mg/kg dose in rats approximates an 80 mg human equivalent dose (HED) of hydrocodone bitartrate; a dose that would be likely to be harmful to a naïve patient in immediate release form with the potential for fatal overdose. Human equivalent doses are defined as the equivalent dose for a 60 kg person adjusted for the body surface area of the animal model. The adjustment factor for rats is 6.2. The HED for a rat dose of 5 mg/kg of hydrocodone base, for example, is equivalent to 48.39 mg (5/6.2×60) hydrocodne base; which is equivalent to 79.98 (48.39/0.605) mg hydrocodone bitartrate, when adjusted for the salt content.

Thus the peptide-hydrocodone conjugates maintain their therapeutic value at the lower dose (1 mg/kg), whereas when given at a dose above a safe level (5 mg/kg) bioavailability is decreased as compared to hydrocodone, thus diminishing the potential for overdose by oral ingestion. The decrease in bioavailability of hydrocodone from peptide hydrocodone conjugates relative to hydrocodone ranged from 9 to 70 percent (Table 55).

TABLE 46

Oral Pharmacokinetics of Hydrocodone vs. EEFFI[SEQ ID NO: 5]-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 9.5 | 4.5 | 1.9 | 0 | 2 | 19.1 | 100 | 9.5 | 100 |
| EEFFI[SEQ ID NO: 5]-HC | 12.9 | 5.2 | 4.2 | 0 | 1.6 | 25.8 | 135 | 12.9 | 136 | hydrocodone plus hydromorphone (ng/ml)

TABLE 47

Oral Pharmacokinetics of Hydrocodone vs. EEFFF[SEQ ID NO: 3]-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 9.5 | 4.5 | 1.9 | 0 | 2 | 19.1 | 100 | 9.5 | 100 |
| EEFFF[SEQ ID NO: 3]-HC | 11.3 | 4.1 | 1.2 | 1.2 | 1.2 | 20.7 | 108 | 11.3 | 119 | hydrocodone plus hydromorphone (ng/ml)[SEQ ID NO: 3]

TABLE 48

Oral Pharmacokinetics of Hydrocodone vs. YYI-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 9.2 | 5.9 | 2.3 | 1.9 | 2 | 26.1 | 100 | 9.2 | 100 |
| YYI-HC | 9.2 | 4.3 | 1.5 | 1.1 | 1.8 | 20.4 | 78 | 9.2 | 100 | hydrocodone plus hydromorphone (ng/ml)

Table 49

Oral Pharmacokinetics of Hydrocodone vs. DDI-HC (1 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 8.6 | 3 | 1.1 | 0 | 1.4 | 14 | 100 | 8.6 | 100 |
| DDI-HC | 14.9 | 5 | 0 | 0 | 0 | 17.4 | 124 | 14.9 | 173 | hydrocodone plus hydromorphone (ng/ml)

TABLE 50

Oral Pharmacokinetics of Hydrocodone vs. YYFFI[SEQ ID NO: 8]-HC (1 mg/kg dose).

| Drug | Hours | | | | | | AUC (ng/ml h) 0-8h | Percent HC | Cmax ng/ml | Percent HC |
| --- | --- | --- | --- | --- | --- | --- | --- | --- | --- | --- |
| | 0.5 | 1.0 | 1.5 | 3 | 5 | 8 | | | | |
| Hydrocodone Bitartrate | 8.6 | 4.5 | 3 | 1.1 | 0 | 1.4 | 13.6 | 100 | 8.6 | 100 |
| YYFFI[SEQ ID NO: 8]-HC | 7 | 3.7 | 4.3 | 1.4 | 1.1 | 0 | 14.9 | 110 | 7 | 81 | hydrocodone plus hydromorphone (ng/ml)

TABLE 51

Oral Pharmacokinetics of Hydrocodone vs. EEFFI[SEQ ID NO: 5]-HC (5 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 93 | 5.3 | 39 | 5 | 6.5 | 167 | 100 | 93 | 100 |
| EEFFI[SEQ ID NO: 5]-HC | 44 | 6.5 | 5.7 | 4.2 | 4.5 | 68 | 41 | 44 | 47 | hydrocodone plus hydromorphone (ng/ml)

TABLE 52

Oral Pharmacokinetics of Hydrocodone vs. YYI-HC (5 mg/kg dose).

| Drug | Hours | | | | | AUC (ng/ml h) 0-8 h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 37 | 13 | 12 | 3 | 0 | 71 | 100 | 37 | 100 |
| YYI-HC | 15 | 6.3 | 3.3 | 1.6 | 2.7 | 33 | 46 | 15 | 41 | hydrocodone plus hydromorphone (ng/ml)

TABLE 53

Oral Pharmacokinetics of Hydrocodone vs. DDI-HC (5 mg/kg dose).

| Drug | Hours | | | | | AUC (ng/ml h) 0-8h | Percent HC | Cmax ng/ml | Percent HC |
| --- | --- | --- | --- | --- | --- | --- | --- | --- | --- |
| | 0.5 | 1.5 | 3 | 5 | 8 | | | | |
| Hydrocodone Bitartrate | 73 | 42 | 6.7 | 1.2 | 3.8 | 128 | 100 | 73 | 100 |
| DDI-HC | 115 | 19 | 11 | 4 | 3.1 | 145 | 113 | 115 | 158 | hydrocodone plus hydromorphone (ng/ml)

TABLE 54

Oral Pharmacokinetics of Hydrocodone vs. YYFFI[SEQ ID NO: 8]-HC (5 mg/kg dose).

| Drug | Hours | | | | | | AUC (ng/ml h) 0-8 h | Percent HC | Cmax ng/ml | Percent HC |
| --- | --- | --- | --- | --- | --- | --- | --- | --- | --- | --- |
| | 0.5 | 1.0 | 1.5 | 3 | 5 | 8 | | | | |
| Hydrocodone Bitartrate | 73 | 62 | 42 | 6.7 | 1.2 | 3.8 | 123 | 100 | 73 | 100 |
| YYFFI[SEQ ID NO: 8]-HC | 46 | 33 | 34 | 13 | 8.3 | 4.5 | 105 | 86 | 46 | 63 | hydrocodone plus hydromorphone (ng/ml)

TABLE 55

Decrease in Oral Bioavailability at 5 mg/kg vs. Therapeutic Dose of 1 mg/kg.

| Drug | Bioavailability 1 mg/kg | | Bioavailability 5 mg/kg | | Percent Decrease 1 mg/kg vs. 5 mg/kg | |
| --- | --- | --- | --- | --- | --- | --- |
| | AUC | Cmax | AUC | Cmax | AUC | Cmax |
| YYI-HC | 78 | 100 | 46 | 40 | 41 | 60 |
| DDI-HC | 124 | 174 | 113 | 158 | 9 | 9 |
| YYFFI[SEQ ID NO: 8]-HC | 109 | 81 | 86 | 62 | 15 | 23 |
| EEFFI[SEQ ID NO: 5]-HC | 135 | 136 | 41 | 47 | 70 | 65 |

Example 75

Bioavailability of Peptide-HC Conjugates by the Intranasal Route

Example 75 illustrates that when the peptides EEFFF [SEQ ID NO: 7] (Table 56, FIG. 99), YYI (Table 57, FIG. 100), DDI (Table 58, FIG. 101) and YYFFI[SEQ ID NO: 8] (Table 59, FIG. 102) are conjugated to the active agent hydrocodone the bioavailability by the intravenous route is substantially decreased thereby diminishing the possibility of overdose when the drug is administered by snorting.

TABLE 56

Intranasal Pharmacokinetics of Hydrocodone vs. EEFFF[SEQ ID NO: 3]-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 262 | 259 | 142 | 47 | 152 | 100 | 262 | 100 |
| EEFFF[SEQ ID NO: 3]-HC | 34 | 21 | 24 | 15 | 21 | 14 | 34 | 13 | hydrocodone plus hydromorphone (ng/ml)

TABLE 57

Intranasal Pharmacokinetics of Hydrocodone vs. YYI-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 446 | 553 | 244 | 103 | 288 | 100 | 553 | 100 |
| YYI-HC | 31 | 17 | 12 | 2 | 12 | 4 | 31 | 6 | hydrocodone plus hydromorphone (ng/ml)

TABLE 58

Intranasal Pharmacokinetics of Hydrocodone vs. DDI-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 446 | 553 | 244 | 103 | 288 | 100 | 553 | 100 |
| DDI-HC | 281 | 121 | 64 | 16 | 88 | 31 | 281 | 51 | hydrocodone plus hydromorphone (ng/ml)

TABLE 59

Intranasal Pharmacokinetics of Hydrocodone vs. YYFFI[SEQ ID NO: 3]-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 446 | 553 | 244 | 103 | 288 | 100 | 553 | 100 |
| YYFFI[SEQ ID NO: 3]-HC | 28 | 27 | 16 | 21 | 20 | 100 | 28 | 5 | hydrocodone plus hydromorphone (ng/ml)

Example 76

Bioavailability of Peptide-HC Conjugates by the Intravenous Route

Example 76 illustrates that when the peptides EEFFI[SEQ ID NO: 6] (Table 60, FIG. 103), EEFFF[SEQ ID NO: 7] (Table 61, FIG. 104), YYI (Table 62, FIG. 105) and YYFFI [SEQ ID NO: 8] (Table 63, FIG. 106) are conjugated to the active agent hydrocodone the bioavailability by the intravenous route is substantially decreased thereby diminishing the possibility of overdose when the drug is administered by this unintended route.

TABLE 60

Intravenous Pharmacokinetics of Hydrocodone vs. EEFFI[SEQ ID NO: 5]-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 179 | 204 | 201 | 132 | 173 | 100 | 179 | 100 |
| EEFFI[SEQ ID NO: 5]-HC | 89 | 76 | 78 | 66 | 66 | 38 | 89 | 44 | hydrocodone plus hydromorphone (ng/ml)

TABLE 61

Intravenous Pharmacokinetics of Hydrocodone vs. EEFFF[SEQ ID NO: 3]-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 179 | 204 | 201 | 132 | 173 | 100 | 179 | 100 |
| EEFFF[SEQ ID NO: 3]-HC | 135 | 77 | 140 | 85 | 107 | 62 | 135 | 75 | hydrocodone plus hydromorphone (ng/ml)

TABLE 62

Intravenous Pharmacokinetics of Hydrocodone vs. YYI-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 238 | 182 | 136 | 77 | 138 | 100 | 238 | 100 |
| YYI-HC | 9 | 13 | 13 | 3 | 10 | 7 | 13 | 6 | hydrocodone plus hydromorphone (ng/ml)

TABLE 63

Intravenous Pharmacokinetics of Hydrocodone vs. YYFFI[SEQ ID NO: 8]-HC (1 mg/kg dose).

| Drug | Minutes | | | | AUC (ng/ml h) | Percent | Cmax | Percent |
| --- | --- | --- | --- | --- | --- | --- | --- | --- |
| | 5 | 15 | 30 | 60 | 0-1 h | HC | ng/ml | HC |
| Hydrocodone Bitartrate | 238 | 182 | 136 | 77 | 138 | 100 | 238 | 100 |
| YYFFI[SEQ ID NO: 8]-HC | 171 | 28 | 22 | 18 | 40 | 29 | 171 | 72 | hydrocodone plus hydromorphone (ng/ml)

Example 77

Hydrocodone Conjugates

Bioavailability (AUC and Cmax) of various peptide-hydrocodone conjugates relative to that of hydrocodone bitartrate are shown in Table 64. The invention is well illustrated by the in vivo performance of YYFFI[SEQ ID NO: 8]-HC (FIGS. 107 through 128). At the relatively low doses of 1 and 2 mg/kg (human equivalent doses (HEDs) of 16 and 32 mg hydrocodone bitartrate) YYFFI[SEQ ID NO: 8]-HC showed comparable bioavailability to that of hydrocodone bitartrate (Table 65, FIGS. 129 through 134). At the elevated doses of 5 and 25 mg/kg bioavailability of hydrocodone and hydromorphone were substantially decreased as compared to that of hydrocodone (Table 66, FIGS. 135 through 150). These doses (HED of 80 and 400 mg hydrocodne bitartrate) are equivalent to amounts well above the available prescription doses of hydrocodone bitartrate which range from 2.5 to 10 mg. When delivered by the parentaral routes of intravenous and intranasal administration a substantial decrease in bioavailability of hydrocodone and hydromorphone from YYFFI[SEQ ID NO: 8]-HC as compared to hydrocodone bitratrate was observed. These examples establish that covalent modification of an opiod via attachment of a peptide provides a method of delivering bioequivalent doses when given at doses approximating a normal prescribed dose. When administered by parenteral routes or at oral doses in excess of the intended prescription the bioavailability is substantially decreased. Collectively, the examples clearly illustrate the utility of the invention for decreasing the abuse potential of opiods.

TABLE 64

Mean hydrocodone concentrations following oral administration of hydrocodone bitartrate or YYFFI[SEQ ID NO: 8]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] |
| 0 | 0 | 0 | 0 | 0 | 0 | 0 | 0 | 0 |
| 0.1 | 114.0 | 20.3 | 60.3 | 35.2 | 628.7 | 26.6 | 408.9 | 41.4 |
| 0.5 | 14.3 | 17.9 | 15.6 | 23 | 74.3 | 22.5 | 153.9 | 23.3 |
| 1.0 | 7.0 | 10.4 | 12.9 | 14.4 | 80.8 | 15.1 | 86.2 | 31.0 |
| 2.0 | 2.6 | 2.8 | 3.4 | 9.8 | 18.4 | 10.3 | 83.3 | 43.9 |
| 4.0 | 1.0 | 1.2 | 1.3 | 3.3 | 4.9 | 3.6 | 57.8 | 25.0 |

[1]hydrocodone base content
[2]hydrocodone bitartrate
[3]YYFFI[SEQ ID NO: 8]-HC HCl

TABLE 65

Hydrocodone pharmacokinetic parameters following oral administration of hydrocodone bitartrate or YYFFI[SEQ ID NO: 8]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] |
| AUC | 45.1 | 26.3 | 38.2 | 48 | 234 | 47 | 419.0 | 135.0 |
| Percent HC + HM[4] | 100 | 58 | 100 | 126 | 100 | 20 | 100 | 32 |
| Cmax | 114.0 | 20.3 | 60.3 | 35.2 | 628.7 | 26.6 | 408.9 | 41.4 |
| Percent HC + HM[4] | 100 | 18 | 100 | 58 | 100 | 4 | 100 | 10 |

[1]hydrocodone base content
[2]hydrocodone bitartrate
[3]YYFFI[SEQ ID NO: 8]-HC HCl
[4]percent relative to parameter following administration of hydrocodone bitartrate

TABLE 66

Mean hydromorphone concentrations following oral administration of hydrocodone bitartrate or YYFFI[SEQ ID NO: 8]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] |
| 0 | 0 | 0 | 0 | 0 | 0 | 0 | 0 | 0 |
| 0.1 | 1.95 | 0.27 | 7.61 | 1.13 | 9.03 | 0.49 | 44.36 | 8.00 |
| 0.5 | 3.22 | 2.87 | 18.10 | 8.74 | 13.46 | 10.41 | 62.24 | 10.35 |
| 1.0 | 2.69 | 2.39 | 9.23 | 3.63 | 10.36 | 4.82 | 29.89 | 12.70 |
| 2.0 | 2.11 | 2.24 | 2.31 | 3.41 | 6.68 | 3.17 | 31.62 | 16.22 |
| 4.0 | 0.64 | 1.02 | 0.59 | 0.88 | 2.00 | 1.07 | 40.86 | 8.98 |

[1]hydrocodone base content
[2]hydrocodone bitartrate
[3]YYFFI[SEQ ID NO: 8]-HC HCl

TABLE 67

Hydromorphone pharmacokinetic parameters following oral administration of hydrocodone bitartrate or YYFFI[SEQ ID NO: 8]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] |
| AUC | 7.8 | 7.5 | 21.0 | 12.9 | 28.1 | 14.3 | 149 | 49 |
| Percent HM[4] | 100 | 97 | 100 | 61 | 100 | 51 | 100 | 33 |
| Cmax | 3.2 | 2.9 | 18.1 | 8.7 | 13.5 | 10.4 | 44.4 | 16.2 |
| Percent HM[4] | 100 | 89 | 100 | 48 | 100 | 77 | 100 | 37 |

[1]hydrocodone base content
[2]hydrocodone bitartrate
[3]YYFFI[SEQ ID NO: 8]-HC HCl
[4]percent relative to parameter following administration of hydrocodone bitartrate

TABLE 68

Mean hydrocodone plus hydromorphone concentrations following oral administration of hydrocodone bitartrate or YYFFI[SEQ ID NO: 8]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Hours | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] |
| 0 | 0 | 0 | 0 | 0 | 0 | 0 | 0 | 0 |
| 0.1 | 116 | 20.6 | 67.9 | 36.3 | 637.7 | 27.1 | 453.3 | 49.4 |
| 0.5 | 17.5 | 20.;8 | 33.7 | 31.7 | 87.8 | 32.9 | 216.1 | 33.7 |
| 1.0 | 9.7 | 12.8 | 22.1 | 18.0 | 91.2 | 19.9 | 116.1 | 43.7 |
| 2.0 | 4.7 | 5.0 | 5.7 | 13.2 | 25.1 | 13.5 | 114.9 | 60.1 |
| 4.0 | 1.6 | 2.2 | 1.9 | 4.2 | 6.9 | 4.7 | 98.7 | 34.0 |

[1]hydrocodone base content
[2]hydrocodone bitartrate
[3]YYFFI[SEQ ID NO: 8]-HC HCl

TABLE 69

Hydrocodone plus hydromorphone pharmacokinetic parameters following oral administration of hydrocodone bitartrate or YYFFI[SEQ ID NO: 8]-HC at escalating doses.

| | Dose[1]/Concentration (ng/ml) | | | | | | | |
|---|---|---|---|---|---|---|---|---|
| | 1 mg/kg | | 2 mg/kg | | 5 mg/kg | | 25 mg/kg | |
| Parameter | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] | HC[2] | YYFFI [SEQ ID NO: 8]-HC[3] |
| AUC | 53 | 34 | 59 | 61 | 312 | 62 | 569 | 193 |
| Percent HC[4] | 100 | 64 | 100 | 103 | 100 | 20 | 100 | 34 |
| Cmax | 116 | 20.8 | 67.9 | 36.3 | 638 | 32.9 | 453 | 49.4 |
| Percent HC[4] | 100 | 18 | 100 | 53 | 100 | 5 | 100 | 11 |

[1]hydrocodone base content
[2]hydrocodone bitartrate
[3]YYFFI[SEQ ID NO: 8]-HC HCl
[4]percent relative to parameter following administration of hydrocodone bitartrate

TABLE 70

Mean hydrocodone plus hydromorphone, hydrocodone, and hydromorphone, concentrations following intravenous administration of hydrocodone bitartrate or YYFFI[SEQ ID NO: 8]-HC at 1 mg/kg (hydrocodone base content).

| | Concentration (ng/ml) | | | | | |
|---|---|---|---|---|---|---|
| | HC + HM | | HC | | HM | |
| Hours | HC[1] | YYFFI [SEQ ID NO: 8]-HC[2] | HC[1] | YYFFI [SEQ ID NO: 8]-HC[2] | HC[1] | YYFFI [SEQ ID NO: 8]-HC[2] |
| 0 | 0 | 0 | 0 | 0 | 0 | 0 |
| 0.1 | 208.9 | 22.6 | 42.97 | 8.75 | 251.9 | 31.3 |
| 0.5 | 83.7 | 13.5 | 16.09 | 1.44 | 99.8 | 14.9 |
| 1.0 | 38.4 | 13.0 | 3.65 | 0.92 | 42.1 | 13.9 |
| 2.0 | 12.4 | 13.1 | 1.77 | 0.41 | 14.2 | 13.5 |
| 4.0 | 2.9 | 8.5 | 0.70 | 0.33 | 3.6 | 8.8 |

[1]hydrocodone bitartrate
[2]YYFFI[SEQ ID NO: 8]-HC HCl

TABLE 71

Hydrocodone plus hydromorphone, hydrocodone, and hydromorphone pharmacokinetic parameters following intravenous administration of hydrocodone bitartrate or YYFFI[SEQ ID NO: 8]-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI [SEQ ID NO: 8]-HC[2] | HC[1] | YYFFI [SEQ ID NO: 8]-HC[2] | HC[1] | YYFFI [SEQ ID NO: 8]-HC[2] |
| AUC | 140.0 | 50.0 | 24.10 | 4.50 | 164 | 54 |
| Percent[1] | 100 | 36 | 100 | 19 | 100 | 33 |
| Cmax | 208.9 | 22.6 | 43.0 | 8.7 | 252 | 31.3 |
| Percent[1] | 100 | 10.8 | 100 | 20.2 | 100 | 12.4 |

[1]hydrocodone bitartrate
[2]YYFFI[SEQ ID NO: 8]-HC HCl
[3]percent relative to parameter following administration of hydrocodone bitartrate

TABLE 72

Mean hydrocodone plus hydromorphone, hydrocodone, and hydromorphone, concentrations following intranasal administration of hydrocodone bitartrate or YYFFI[SEQ ID NO: 8]-HC at 1 mg/kg.

| | Concentration (ng/ml) | | | | | |
|---|---|---|---|---|---|---|
| | HC + HM | | HC | | HM | |
| Minutes | HC[1] | YYFFI [SEQ ID NO: 8]-HC[2] | HC[1] | YYFFI [SEQ ID NO: 8]-HC[2] | HC[1] | YYFFI [SEQ ID NO: 8]-HC[2] |
| 0 | 0 | 0 | 0 | 0 | 0 | 0 |
| 5 | 446 | 28 | 441 | 28 | 4.4 | bql[3] |
| 15 | 553 | 27 | 543 | 27 | 10.6 | bql[4] |
| 30 | 244 | 16 | 227 | 16 | 17.1 | bql[5] |
| 60 | 103 | 21 | 96 | 21 | 7.2 | bql[6] |

[1]hydrocodone bitartrate
[2]YYFFI[SEQ ID NO: 8]-HC HCl

TABLE 73

Hydrocodone plus hydromorphone, hydrocodone, and hydromorphone pharmacokinetic parameters following intravenous administration of hydrocodone bitartrate or YYFFI[SEQ ID NO: 8]-HC at 1 mg/kg (hydrocodone base content).

| | Concentration (ng/ml) | | | | | |
|---|---|---|---|---|---|---|
| | HC + HM | | HC | | HM | |
| Parameter | HC[1] | YYFFI [SEQ ID NO: 8]-HC[2] | HC[1] | YYFFI [SEQ ID NO: 8]-HC[2] | HC[1] | YYFFI [SEQ ID NO: 8]-HC[2] |
| AUC | 288.0 | 20.0 | 74.70 | 10.30 | 7.0 | NA |
| Percent[3] | 100 | 6.9 | 100 | 13.8 | 100 | NA |
| Cmax | 553.0 | 28.0 | 543.0 | 28.0 | 17 | NA |
| Percent[3] | 100 | 5.1 | 100 | 5.2 | 100 | NA |

[1]hydrocodone bitartrate
[2]YYFFI[SEQ ID NO: 8]-HC HCl
[3]percent relative to parameter following administration of hydrocodone bitartrate Summary of in vivo testing of abuse resistant hydrocodone conjugates. In vivo testing of hydrocodone conjugates demonstrates for instance decreased intranasal analgesic response, decreased intravenous analgesic response, decreased subcutaneous analgesic response, decreased oral $C_{max}$, decreased intranasal bioavailability (AUC and $C_{max}$),

Example 78

Decreased Intranasal Analgesic Response to Hydrocodone Conjugates

Male Sprague-Dawley rats were dosed by placing 0.02 ml of water containing hydrocodone conjugate or hydrocodone bitartrate into the nasal flares. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curves shown in FIGS. 112 and 114 indicate the decrease in analgesia produced by the hydrocodone conjugates as compared to an equimolar (hydrocodone base) dose of hydrocodone bitartrate. The analgesic response as determined by the hot plate test is a pharmacodynanmic measurement of the pharmacological effect of hydrocodone. These examples illustrate that hydrocodone conjugates decrease the analgesic effect by the intranasal route of administration as compared to hydrodone bitartrate.

Example 79

Decreased Intravenous Analgesic Response to Hydrocodone Conjugates

Male Sprague-Dawley rats were dosed by tail vein injection of 0.1 ml of water containing hydrocodone conjugates or hydrocodone bitartrate. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curve shown in FIG. 67 indicates the decrease in analgesia produced by a hydrocodone conjugate as compared to an equimolar (hydrocodone base) dose of hydrocodone bitartrate. The analgesic response as determined by the hot plate test is a pharmacodynamic measurement of the pharmacological effect of hydrocodone. This example illustrates that a hydrocodone conjugate decreased the analgesic effect by the intravenous route of administration as compared to hydrocodone bitartrate.

Example 80

Decreased Subcutaneous Analgesic Response to Hydrocodone Conjugates

Male Sprague-Dawley rats were dosed by subcutatenous injection of 0.1 ml of water containing hydrocodone conjugates or hydrocodone bitartrate. All doses contained equivalent amounts of hydrocodone base. The time (seconds) until paw lick latency was used a measure of the analgesic effect. Rats were habituated to determine baseline response. Hot plate tests were conducted at 55° C. A limit of 45 seconds was used in all testing to avoid tissue damage. All animals were humanely sacrificed following the end of testing. The paw lick latency (analgesic effect)-time curve shown in FIG. 62 indicates the decrease in analgesia produced by a hydrocodone conjugate as compared to an equimolar (hydrocodone base) dose of hydrocodone bitartrate. The analgesic response as determined by the hot plate test is a pharmacodynamic measurement of the pharmacological effect of hydrocodone. This example illustrates that a hydrocodone conjugate decreased the analgesic effect by the subcutaneous route of administration as compared to hydrodone bitartrate.

Example 81

Decreased Oral $C_{max}$ of Hydrocodone Conjugates

Male Sprague-Dawley rats were provided water ad libitum, fasted overnight and dosed by oral gavage with hydrocodone conjugates or hydrocodone bitartrate. All doses contained equivalent amounts of hydrocodone base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of various hydrocodone conjugates vs. hydrocodone bitratrate are shown in FIGS. 53, 76, 84, and 85. These examples illustrate that hydrocodone conjugates decrease the peak level ($C_{max}$) of hydrocodone plus hydromorphone as compared to that produced by equimolar (hydrocodone base) doses of hydrocodone bitartrate when given by the oral route of administration.

Example 82

Decreased Intranasal Bioavailability (AUC and $C_{max}$) Hydrocodone Conjugates Male Sprague-Dawley rats were provided water ad libitum and doses were administered by placing 0.02 ml of water containing hydrocodone conjugates or hydrocodne bitartrate into the nasal flares. All doses contained equivalent amounts of hydrocodone base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of various hydrocodone conjugates vs. hydrocodone bitartrate are shown in FIGS. 55, 60, 64-66, 69-73, 75, 77-85. These examples illustrate that hydrocodone conjugates decrease the peak level ($C_{max}$) and total absorption (AUC) of hydrocodone plus hydromorphone as compared to those produced by equimolar (hydrocodone base) doses of hydrocodone bitartrate when given by the intranasal route of administration.

Example 83

Figure 74:
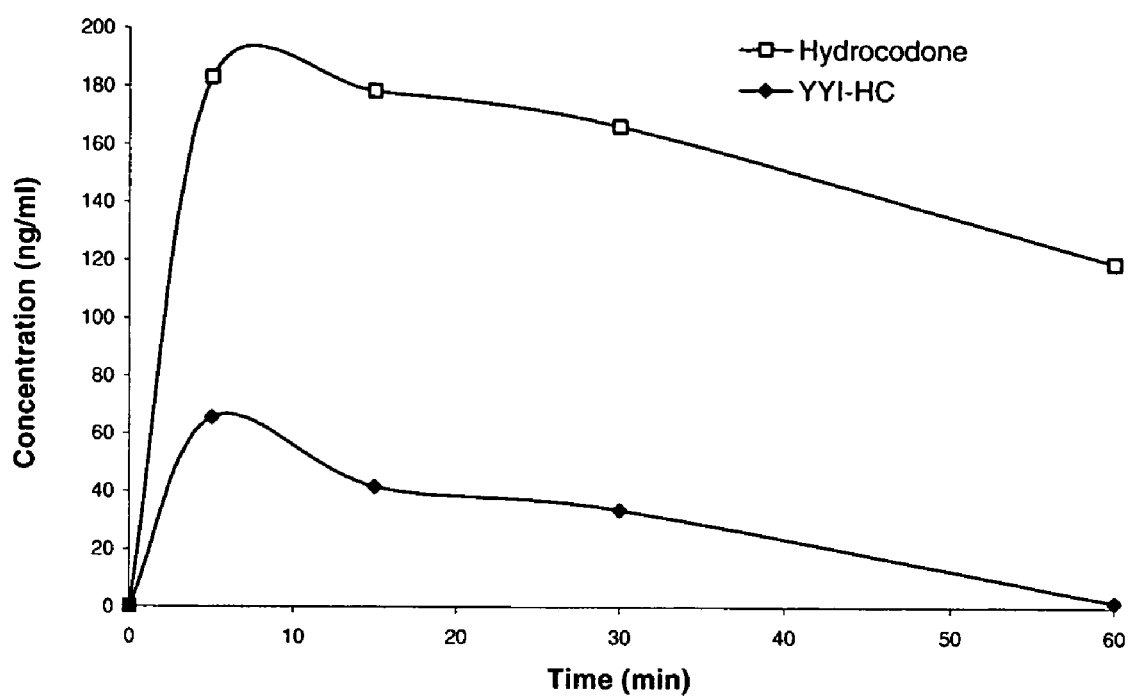
FIG. 74. Intravenous bioavailability of an abuse-resistant hydrocodone tri-peptide conjugate, measured as free hydrocodone.
Figure 75:
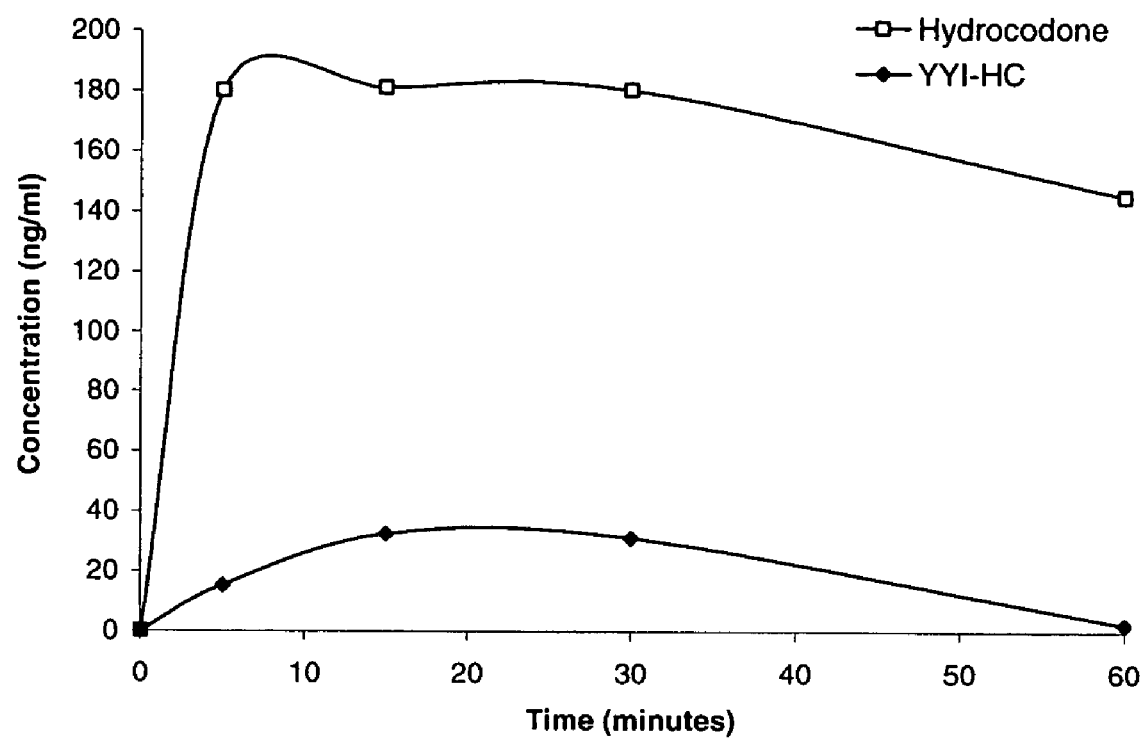
FIG. 75. Intranasal bioavailability of an abuse-resistant hydrocodone tri-peptide conjugate, measured as free hydrocodone.
Figure 76:
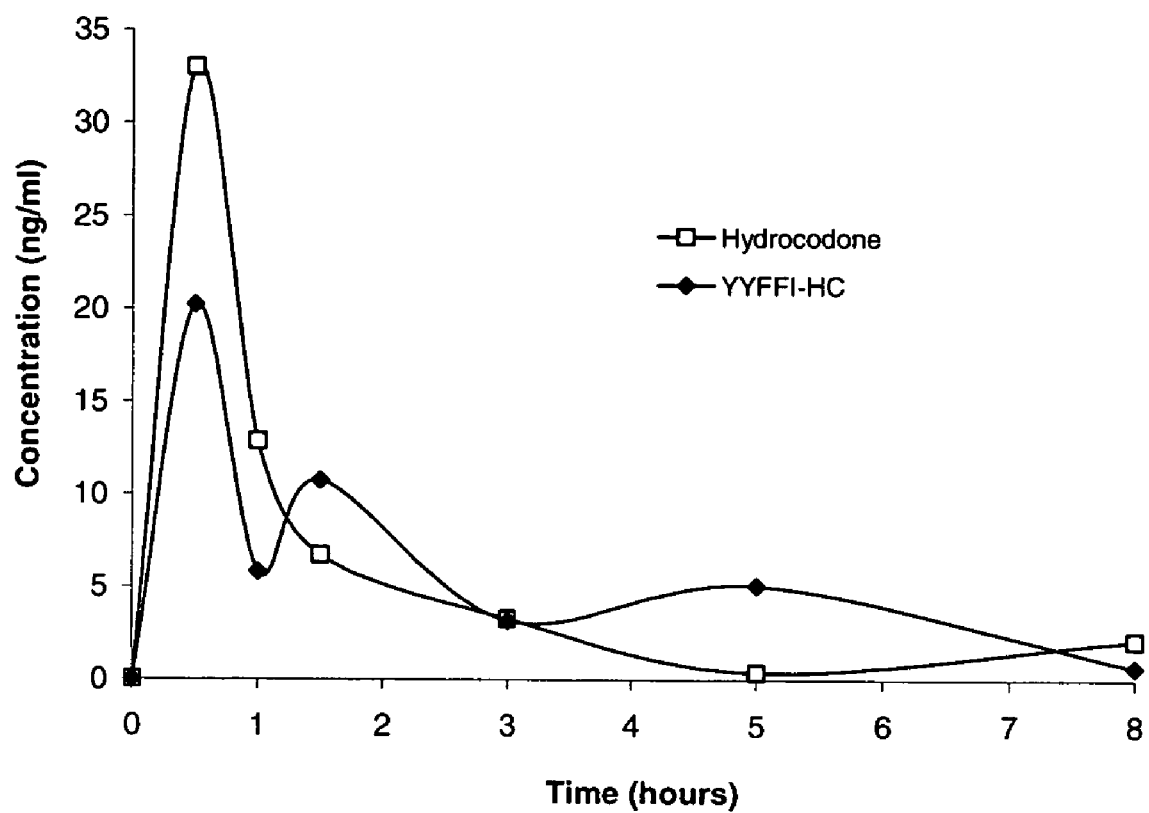
FIG. 76. Oral bioavailability of an abuse-resistant hydrocodone penta-peptide conjugate, measured as free hydrocodone.
Figure 77:
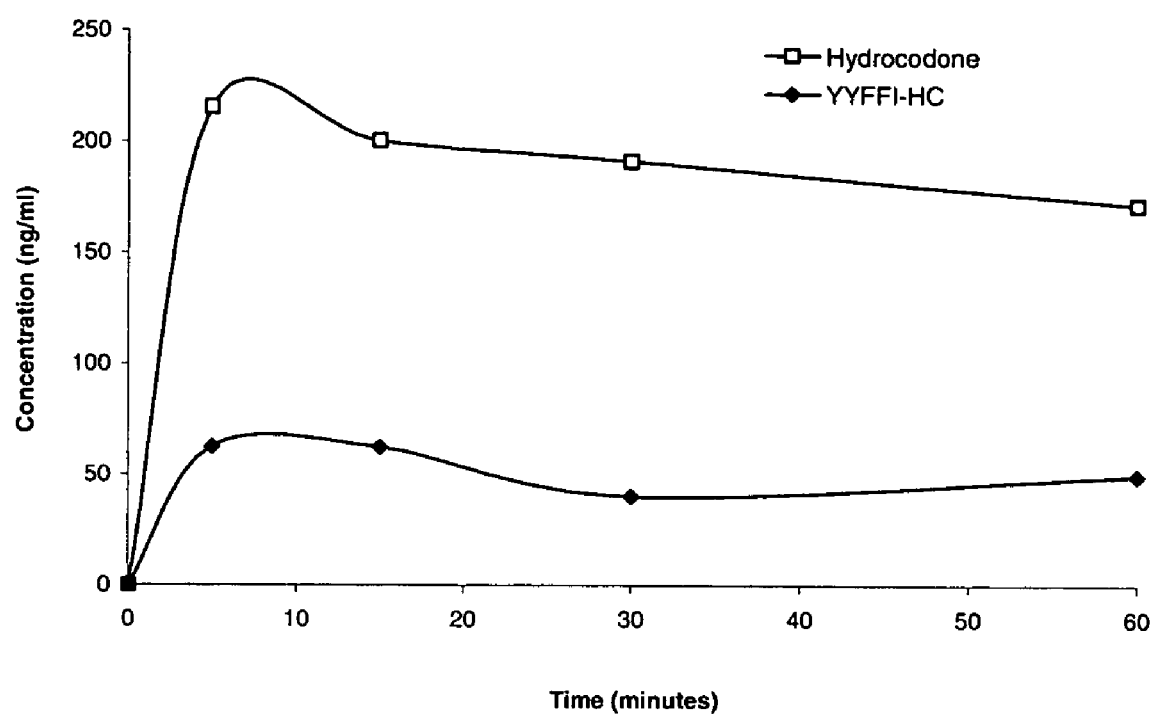
FIG. 77. Intranasal bioavailability of an abuse-resistant hydrocodone tri-penta-peptide conjugate, measured as free hydrocodone.
Figure 78:
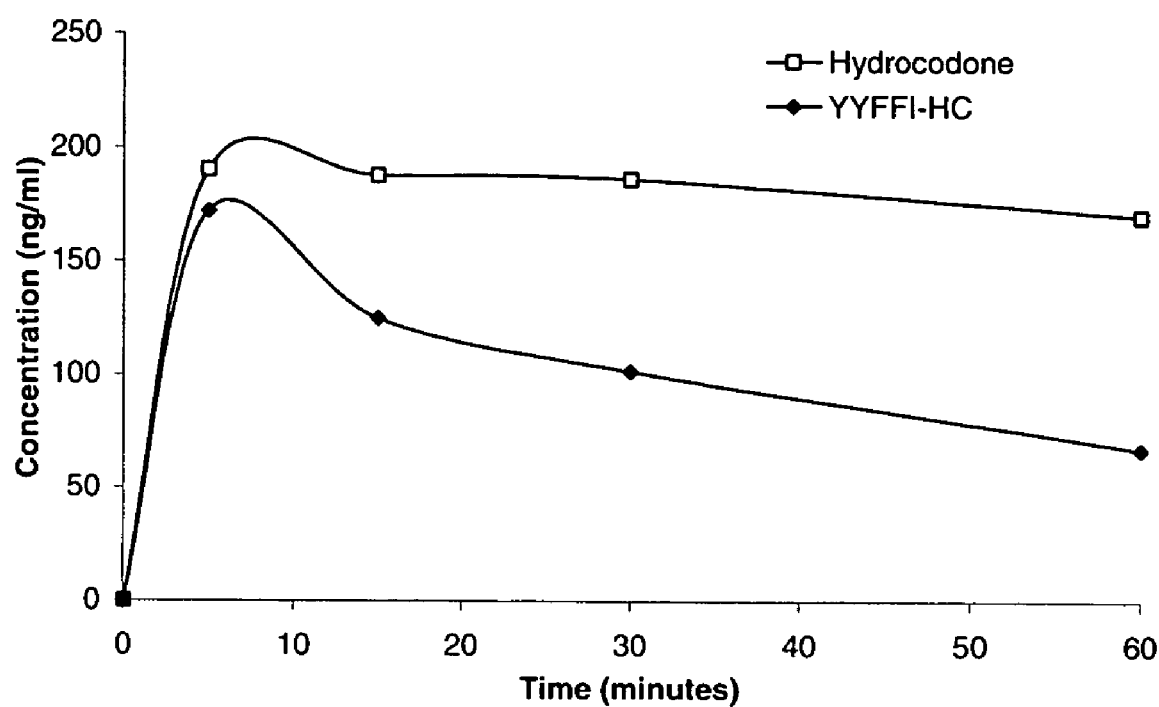
FIG. 78. Intranasal bioavailability of an abuse-resistant hydrocodone penta-peptide conjugate, measured as free hydrocodone.
Figure 79:
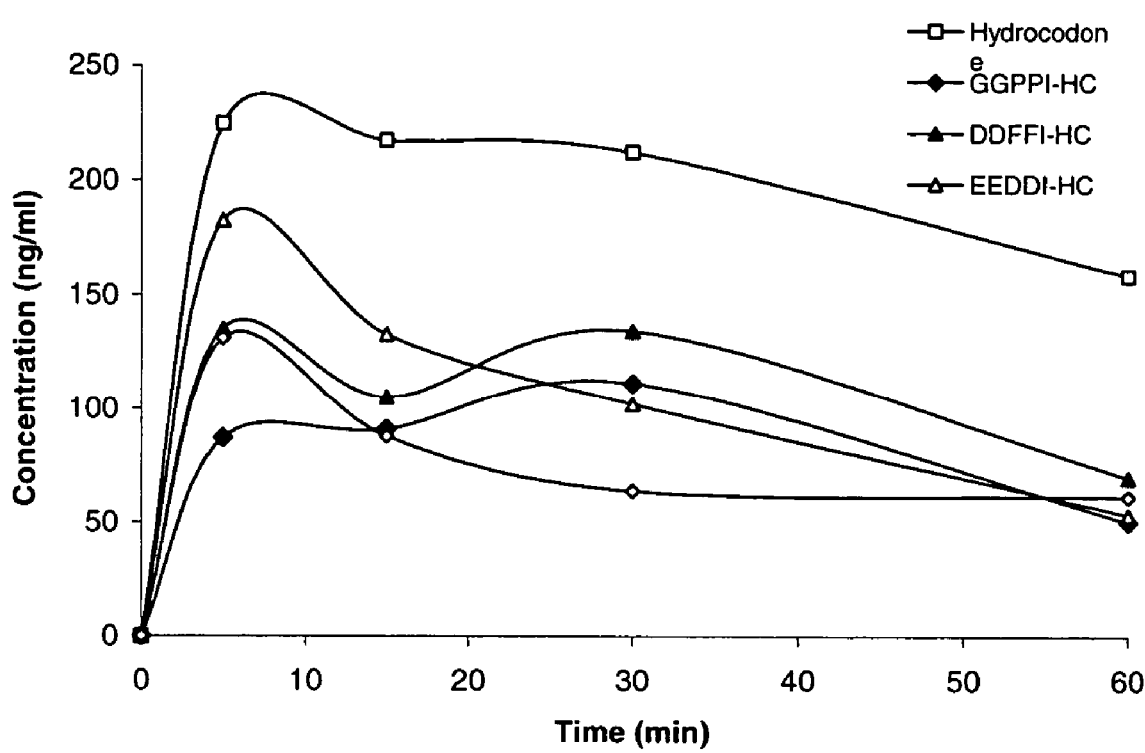
FIG. 79. Intranasal bioavailability of abuse-resistant hydrocodone penta-peptide conjugates, measured as free hydrocodone.
Figure 80:
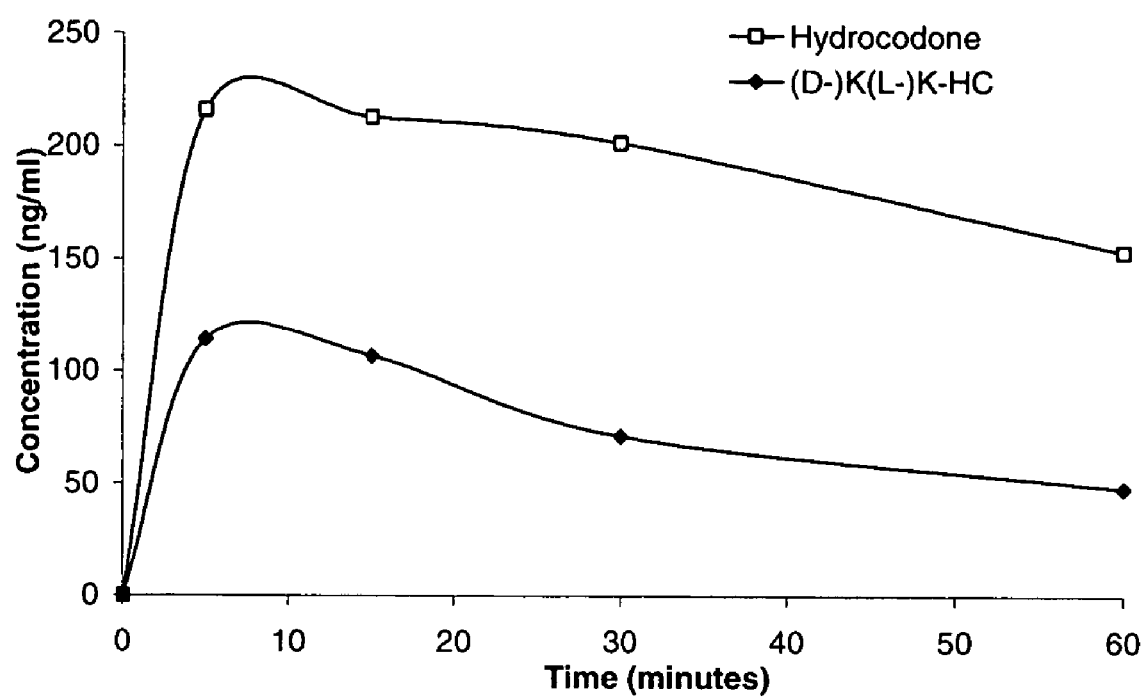
FIG. 80. Intranasal bioavailability of an abuse-resistant hydrocodone tri-peptide conjugate containing D- and L-isomers, measured as free hydrocodone.
Figure 81:
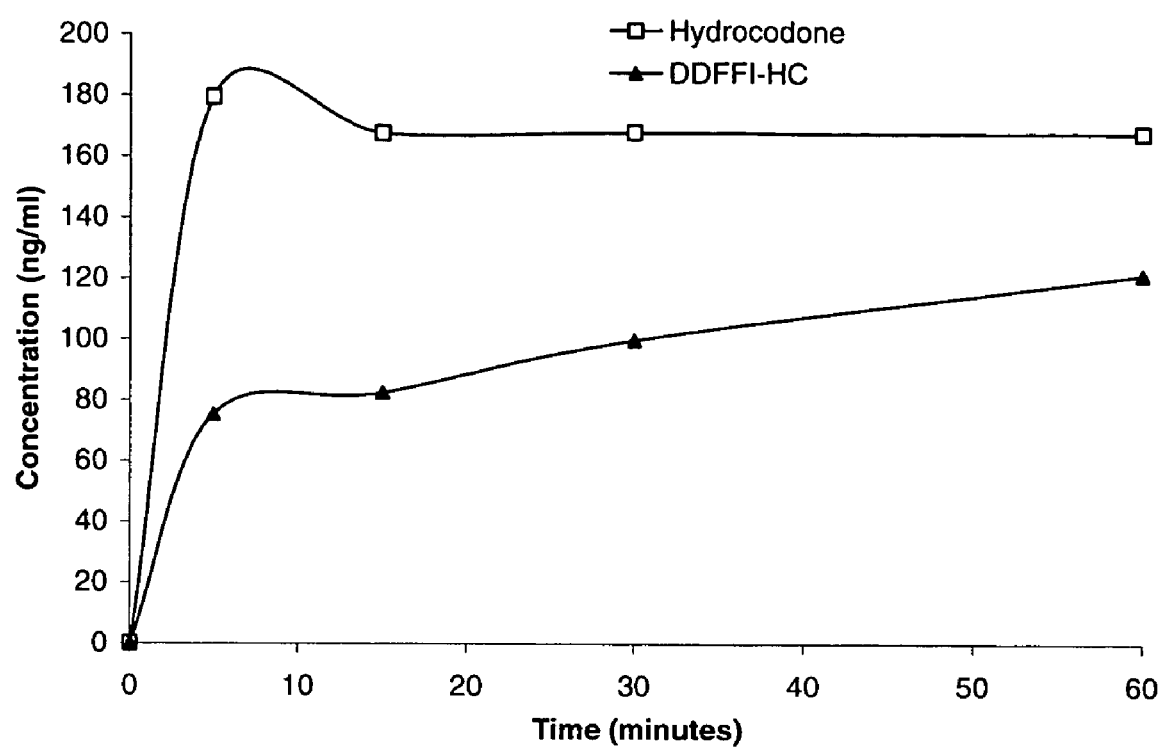
FIG. 81. Intranasal bioavailability of an abuse-resistant hydrocodone penta-peptide conjugate, measured as free hydrocodone.
Figure 82:
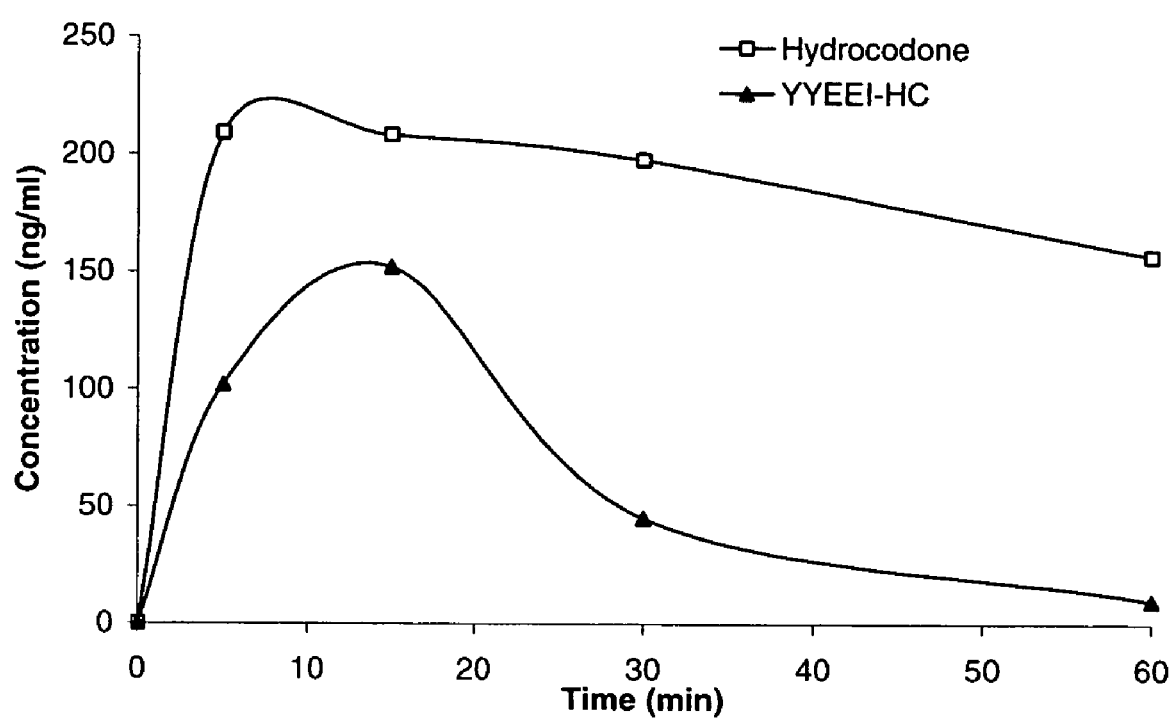
FIG. 82. Intranasal bioavailability of an abuse-resistant hydrocodone penta-peptide conjugate, measured as free hydrocodone.
Figure 83:
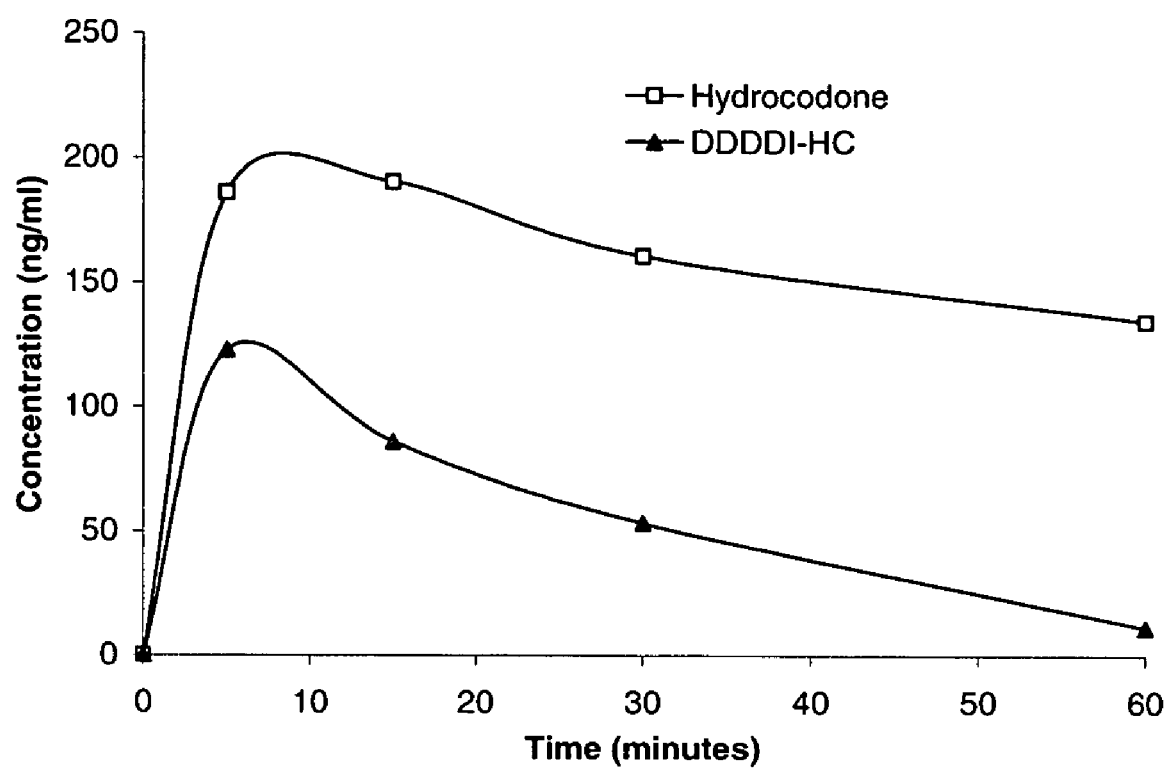
FIG. 83. Intranasal bioavailability of an abuse-resistant hydrocodone penta-peptide conjugate, measured as free hydrocodone.
Figure 84:
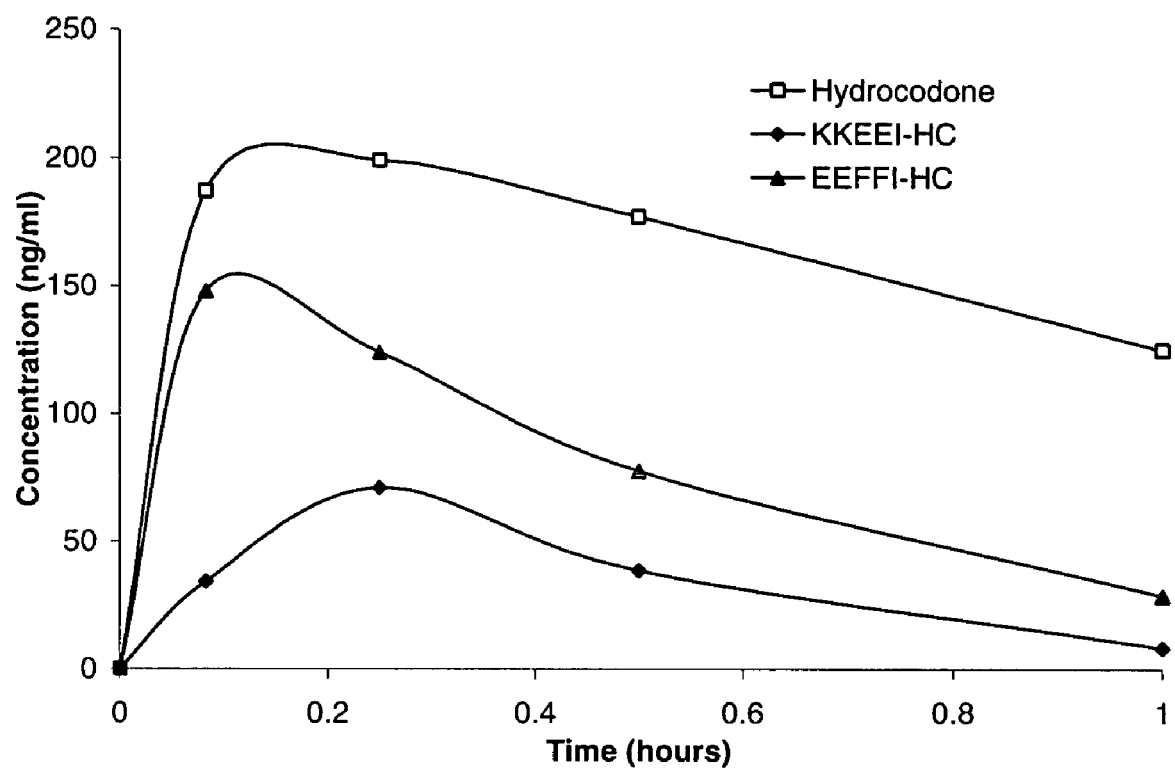
FIG. 84. Intranasal bioavailability of abuse-resistant hydrocodone penta-peptide conjugates, measured as free hydrocodone.
Figure 85:
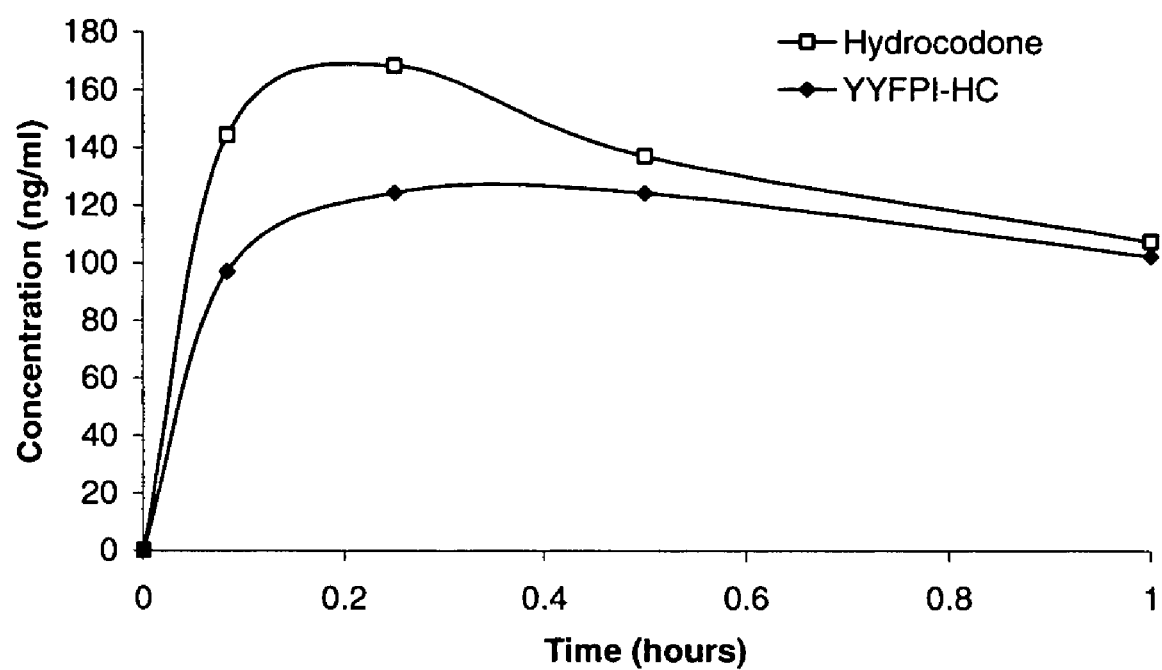
FIG. 85. Intranasal bioavailability of an abuse-resistant hydrocodone penta-peptide conjugate, measured as free hydrocodone.

Decreased Intravenous Bioavailability (AUC and $C_{max}$) Hydrocodone Conjugates Male Sprague-Dawley rats were provided water ad libitum and doses were administered by intravenous tail vein injection of 0.1 ml of water containing hydrocodone conjugates or hydrocodone bitartrate. All doses contained equivalent amounts of d-amphetamine base. Plasma hydrocodone concentrations were measured by ELISA (Hydromorphone, 106619-1, Neogen, Corporation, Lexington, Ky.). The assay is specific for hydromorphone (the major hydrocodone metabolite, 100% reactive) and hydrocodone (62.5% reactive). The plasma concentration-time curves of a hydrocodone conjugate vs. hydrocodone bitartrate is shown in FIG. 74. This example illustrates that a dose of hydrocodone conjugate decreases the peak level ($C_{max}$) and total absorption (AUC) of hydrocodone plus hydromorphone as compared to those produced by an equimolar (hydrocodone base) dose of hydrocodone bitartrate when given by the intranasal route of administration.

Examples 84 through 118 Oxycodone

Examples 84 through 118 illustrate the compounds and compositions for reducing the potential for overdose and abuse while maintaining therapeutic value wherein the active agent oxycodone (OC) is covalently attached to a chemical moiety. The compound which is di-substituted at the 6 and 14 position of oxycodone is termed [PPL]$_2$-OC.

Oral, intranasal, and intravenous bioavailability studies of oxycodone and oxycodone conjugates were conducted in male Sprague-Dawley rats. Doses of oxycodone hydrochloride and oxycodone conjugates containing equivalent amounts of oxycodone were administered in deionized water. Oral administration was in 0.5 ml by gavage needle. Intranasal doses were administered by placing 20 microliters into the nasal flares of rats anesthetized with isoflurane. Intravenous administration was in 0.1 ml by tail vein injection. Plasma was collected by retroorbital sinus puncture under isoflurane anesthesia. Oxycodone and oxymorphone (major active metabolite) concentrations were determined by LC/MS/MS.

The below examples are illustrative only and [PPL]$_2$-OC is not meant to be limiting. As such, synthesis and attachment of oxycodone may be accomplished for instance view the following exemplary methods. Additionally, Examples 84 through 96 describe methods for attaching amino acid or various length peptides to oxycodone.

Oxycodone Synthetic Examples

Example 84

Synthesis of [Boc-X]$_2$-Oxycodone

To a solution of oxycodone free base (2.04 g, 6.47 mmol) in THF (~35 ml) was added LiN(TMS)$_2$ (19.41 ml, 19.41 mmol) and stirred for ~30 mins. To this was added solid Boc-X—OSu (X=amino acid, 21 mmol) at one time and the reaction mixture was stirred at room temperature overnight. The solution was neutralized with 1N HCl and the THF was removed under reduced pressure. The residue was diluted with EtOAc (200 mL), satd. NaHCO$_3$ (150 mL) was added and stirred for 1 h. EtOAc part was washed with NaHCO3 and brine. Dried over Na$_2$SO$_4$ and evaporated to dryness. Compound was obtained by purification over silica gel column (30% EtOAc/Hexane).

Deprotection of [Boc-X]$_2$-Oxycodone:

General method of deprotection: The above compound was reacted with 4N HCl/dioxane (25 mL/gm) at room temperature for 4 h. Solvent was evaporated and dried over vacuum to give X$_2$-Oxycodone-3HCl.

EXAMPLES

1. [Val]$_2$-Oxycodone
2. [Ile]$_2$-Oxycodone
3. [Leu]$_2$-Oxycodone
4. [Lys]$_2$-Oxycodone
5. [Phe]$_2$-Oxycodone
6. [Glu]$_2$-Oxycodone Example 85

Synthesis of [Boc-Z-Y—X]$_2$-Oxycodone [X, Y and Z are Amino Acids]

To a solution of X$_2$-Oxycodone.3HCl (1 mmol) in DMF (15-20 mL) were added NMM (10-12 eqv) and Boc-Z-Y—OSu (2.6 eqv). The reaction mixture was stirred at RT overnight. Solvent was evaporated under reduced pressure. To the residue was added satd. NaHCO$_3$ (~30 mL) and stir for 1-2 h. The white/pale yellow residue was filtered, thoroughly washed with water and dried in the vacuum oven at room temperature.

Deprotection of [Boc-X—Y-Z]$_2$-Oxycodone:

Deprotection is same as general method mentioned above. For 100-200 mg of tripeptide derivative 10-15 ml 4N HCl/dioxane is used. Deprotection is done overnight to give [X—Y-Z]$_2$-Oxycodone.3HCl.

Deprotection of Tripeptide Derivatives Containing Threonine and Serine:

First the tripeptide derivatives are dissolved 95% TFA (5% water) and stirred for 4 h at room temperature. Solvent is evaporated, the residue is co-evaporated with toluene twice and dried over vacuum. 4N HCl/dioxane is added and stirred overnight. Residue was evaporated to dryness and dried over vacuum.

EXAMPLES

1. [Glu-Asp-Val]$_2$-Oxycodone
2. [Ile-Tyr-Val]$_2$-Oxycodone
3. [Tyr-Pro-Val]$_2$-Oxycodone
4. [Gly-Leu-Val]$_2$-Oxycodone
5. [Phe-Val-Val]$_2$-Oxycodone
6. [Ser-Thr-Val]$_2$-Oxycodone
7. [Lys-Ser-Val]$_2$-Oxycodone Example 86

Synthesis of [Boc-X]—$O^6$-Oxycodone:

To a solution of oxycodone (10 mmol) in THF (50 mL) was added LiN(TMS)$_2$ (10.5 mmol) at 0° C. After 20 mins was added Boc-X—OSu (11 mmol) and then the reaction mixture was stirred at room temperature overnight. The solution was cooled down to 0° C. and neutralized with 1N HCl. The organic solvent was evaporated and to the residue were added EtOAc (200 mL) and saturated aq. NaHCO$_3$ (150 mL) and stirred for 1 h. The EtOAc portion was washed with water, brine, dried over Na$_2$SO$_4$ and evaporated to dryness. The residue was purified over silica gel (70% EtOAc-Hexane) to give the title compound.

Deprotection of Boc-X—$O^6$-Oxycodone:

A solution of [Boc-X]-Oxycodone in 4N HCl/dioxane (10 ml/mmol) was stirred at room temperature 4 h. Solvent was evaporated under reduced pressure and the residue was dried under vacuum to give X—O$^6$-Oxycodone.2HCl.

EXAMPLES

1. Val-Oxycodone
2. Ile-Oxycodone
3. Leu-Oxycodone

Example 87

Synthesis of Boc-Z-Y—X—O$^6$-Oxycodone

To a solution of X—O$^6$-Oxycodone.2HCl (1 mmol) in DMF were added NMM (10 mmol) and Boc-Z-Y—OSu (1.2 mamol). The reaction mixture was stirred at room temperature overnight. Solvent was evaporated to the residue was added saturated NaHCO$_3$ solution and stirred for 1 h. The precipitate was filtered, thoroughly washed with water and dried to give the title compound.

Deprotection of Boc-Z-Y—X—O$^6$-Oxycodone:

Deprotection is same as general method mentioned above to give Z-Y—X—O$^6$-Oxycodone.2HCl.

EXAMPLES

1. Pro-Glu-Val-Oxycodone
2. Glu-Leu-Val-Oxycodone
3. Glu-Tyr-Val-Oxycodone

Example 88

Synthesis of Boc-X—O$^6$-Oxycodone-O$^{14}$—Ac

To a solution of [Boc-X]-O$^6$-Oxycodone (1 mmol) in pyridine (15 mL) were added DMAP (75 mg), triethyl amine (1.5 mmol) and Ac$_2$O (8 mmol). The reaction mixture was heated at 65° C. for 3 days. The dark brown solution was cooled down to room temperature and MeOH (5 mL) was added and stirred for 1 h. The solvent was evaporated, co-evaporated with toluene. The residue was taken in EtOAc (50 mL), washed with satd. NaHCO$_3$, brine, dried over Na$_2$SO$_4$ and evaporated to dryness. The residue was purified over silila gel to give the title compound.

Example 89

Synthesis of Boc-X—O$^6$-Oxycodone-O$^{14}$—CO$_2$Et

To a solution of [Boc-X]—O$^6$-Oxycodone (1 mmol) in THF (10 mL) was added LiN(TMS)$_2$ (1.05 mmol) at 0° C. After 20 mins, ethyl chloroformate (1.1 mmol) was added and reaction mixture was slowly brought to room temperature and stirred at room temperature for 1 h. The solution was poured into 2% aqueous acetic acid (ice cold) and extracted with EtOAc. The EtOAc part was washed with water, aq. NaHCO$_3$, brine, dried over Na$_2$SO$_4$ and evaporated to dryness. The residue was purified over silica gel to give the title compound.

Deprotection of Boc-X—O$^6$-Oxycodone-O$^{14}$—R (R=Ac, CO$_2$Et):

Deprotection is same as general method mentioned above to give X—O$^6$-Oxycodone-O$^{14}$—R.2HCl (R=Ac, CO$_2$Et).

EXAMPLES 1. (Val)-Oxycodone-(CO$_2$Et)
2. (Val)-Oxycodone-(OAc)

Example 90

Synthesis of Boc-Z-Y—X—O$^6$-Oxycodone-O$^{14}$—R (R=Ac, CO,Et)

To a solution of X—O$^6$-Oxycodone-O$^{14}$—R.2HCl (1 mmol, R=Ac, CO$_2$Et) in DMF were added NMM (10 mmol) and Boc-Z-Y—OSu (1.2 mmol). The reaction mixture was stirred at room temperature overnight. Solvent was evaporated to the residue was added saturated NaHCO$_3$ solution and stirred for 1 h. The precipitate was filtered, thoroughly washed with water and dried to give the title compound.

Deprotection of Boc-Z-Y—X—O$^6$-Oxycodone-O$^{14}$—R (R=Ac, CO$_2$Et):

Deprotection is same as general method mentioned above. Deprotection is done overnight to give Z-Y—X—O$^6$-Oxycodone-O$^{14}$—R.2HCl.

EXAMPLES 1. (Ile-Tyr-Val)-Oxycodone-(CO$_2$Et)
2. (Ile-Tyr-Val)-Oxycodone-(OAc)

Example 91

Synthesis of Boc-X—O$^6$-Oxycodone-O$^{14}$—Y-Boc

To a solution of Boc-X-Oxycodone (1 mmol) in THF (10 mL) was added LiN(TMS)$_2$ (1.1 mmol) at 0° C. and the solution was stirred for 30 mins then Boc-Y—OSu (1.25 mmol) was added. The reaction mixture was stirred at room temperature overnight. The solution was cooled down to 0° C., neutralized with 1N HCl and the organic part was evaporated. To the residue were added EtOAc (50 mL) and satd. NaHCO$_3$ (50 ml), stirred for 1 h. The organic part was washed with water, brine, dried over Na$_2$SO$_4$ and evaporated to dryness. The residue was purified over silica gel to give the title compound.

Deprotection of Boc-X—O$^6$-Oxycodone-O$^{14}$—Y-Boc:

Boc-X—O$^6$-Oxycodone-O$^{14}$—Y-Boc was deprotected following the general method for deprotection mentioned above to give X—O$^6$-Oxycodone-O$^{14}$—Y.3HCl.

EXAMPLE

Val-Oxycodone-Gly

Example 92

Synthesis of Boc-A-B-X—O$^6$-Oxycodone-O$^{14}$—Y-B-A-Boc (A,B,X,Y=Amino Acids)

To a solution of X—O$^6$-Oxycodone-O$^{14}$—Y.3HCl (1 mmol) and NMM (10 mmol) in DMF (10 mL) was added Boc-A-B—OSu (2.5 mmol) and the reaction mixture was stirred at room temperature overnight. Solvent was evaporated under reduced pressure and to the residue satd. NaHCO$_3$ (15 mL) was added and stirred for 1 h. The precipitate was filtered off and the residue was washed thoroughly with water and dried.

Deprotection of Boc-A-B—X—O$^6$-Oxycodone-O$^{14}$—Y—B-A-Boc:

Deprotection is same as general method mentioned above. Deprotection is done overnight to give A-B—X—O$^6$-Oxycodone-O 4-Y—B-A-3HCl.

EXAMPLES 1. (Ile-Tyr-Val)-Oxycodone-(Gly-Tyr-Ile)
2. (Leu-Tyr-Val)-Oxycodone-(Gly-Tyr-Leu)

Example 93

Synthesis of Boc-X—O$^6$-Oxycodone-O$^{14}$—Y-Cbz

To a solution of Boc-X-Oxycodone (1 mmol) in THF (10 mL) was added LiN(TMS)$_2$ (1.1 mmol) at 0° C. and the solution was stirred for 30 mins then Cbz-Y—OSu (1.25 mmol) was added. The reaction mixture was stirred at room temperature overnight. The solution was cooled down to 0° C., neutralized with 1N HCl and the organic part was evaporated. To the residue were added EtOAc (50 mL) and satd. NaHCO$_3$ (50 ml), stirred for 1 h. The organic part was washed with water, brine, dried over Na$_2$SO$_4$ and evaporated to dryness. The residue was purified over silica gel to give the title compound.

Deprotection of Boc-X—O$^6$-Oxycodone-O$^{14}$—Y-Cbz-2HCl:

Boc-X—O$^6$-Oxycodone-O$^{14}$—Y-Cbz was deprotected following the general method for deprotection mentioned above to give X—O$^6$-Oxycodone-O$^{14}$—Y-Cbz,2HCl.

Example 94

Synthesis of Boc-A-B—X—O$^6$-Oxycodone-O$^{14}$—Y-Cbz

To a solution of X—O$^6$-Oxycodone-O$^{14}$—Y-Cbz.2HCl (1 mmol) and NMM (10 mmol) in DMF (10 mL) was added Boc-A-B—OSu (1.1 mmol) and the reaction mixture was stirred at room temperature overnight. Solvent was evaporated under reduced pressure and to the residue satd. NaHCO$_3$ (20 mL) was added and stirred vigorously for 2-3 h. The precipitate was filtered off and the residue was washed thoroughly with water and dried.

Example 95

Synthesis of Boc-A-B—X—O$^6$-Oxycodone-O$^{14}$—Y—NH2

To a suspension of Boc-A-B—X—O$^6$-Oxycodone-O$^{14}$—Y-Cbz and Pd/C (25 Wt %) in EtOH (20 ml/gm) and cyclohexene (10 ml/gm) was heated under reflux for 30 mins. The reaction mixture was cooled down to room temperature and filtered. The filtrate was evaporated to dryness to give the title compound.

Example 96

Synthesis of Boc-A-B—X—O$^6$-Oxycodone-O$^{14}$—Y—C-D-Boc (A,B,C,D,X,Y=Amino Acids)

To a solution of Boc-A-B—X—O6-Oxycodone-O$^{14}$—Y—NH$_2$ (1 mmol) in DMF (10 mL) were added NMM (5 mmol) and Boc-D-C—OSu (1.1 mmol) and the reaction mixture was stirred at room temperature overnight. Solvent was evaporated under reduced pressure and to the residue satd. NaHCO$_3$ was added and stirred for 1 h. The white precipitate was filtered, washed with water and dried.

Deprotection of Boc-A-B—X—O$^6$-Oxycodone-O$^{14}$—Y—C-D-Boc

Deprotection is same as general method mentioned above. Deprotection is done overnight to give A-B—X—O$^6$-Oxycodone-O$^{14}$—Y—C-D.3HCl.

EXAMPLES 1. (Ile-Tyr-Val)-Oxycodone-(Val-Glu-Gly)
2. (Leu-Tyr-Val)-Oxycodone-(Val-Glu-Gly)

Mono-Substituted Single Amino Acids (Enol Ester)

FIG. 151 depicts oxycodone.

Example 97

Phe-Oxycodone

To a solution of oxycodone-freebase (1.0 eq) in tetrahydrofuran (THF) (10 ml/mmol) was added LiN(TMS)$_2$ (3.5 eq). After 5 minutes, Boc-Phe-OSu (3.5 eq) was added. The reaction was stirred at ambient temperatures for 18 hours, quenched with water and solvents removed. Crude protected product was purified using reverse-phase HPLC. Deprotection occurred with 4N HCl in dioxane (20 ml/mmol) to obtain Phe-Oxycodone.

Example 98

Synthesis of Ile-Oxycodone

Ile-Oxycodone was prepared in a similar manner to Example 97 except Boc-Ile-OSu was used as the amino acid starting material.

Mono-Substituted Tripeptides (Enol Ester)

Example 99

Pro-Pro-Leu-Oxycodone

To a solution of Leu-Oxycodone (1.0 eq) in dimethylformamide (10 ml/0.1 mmol) was added 4-methylmorpholine (10 eq) and Boc-Pro-Pro-OSu (2 eq). The reaction was stirred at ambient temperatures for 18 hours, quenched with water, and solvents removed. Crude protected product was purified using reverse phase HPLC. Deprotection occurred using 4N HCl in dioxane (20 ml/mmol) to obtain Pro-Pro-Leu-Oxycodone.

Example 100

Synthesis of Pro-Pro-Ile-Oxycodone

Pro-Pro-Ile-Oxycodone was prepared in a similar manner to Example 99 except Ile-Oxycodone was used as the conjugated starting material.

Example 101

Oxycodone Disubstituted Tripeptides

General Synthetic Procedure

Synthesis of [Boc-Val]$_2$-OC:

To a solution of OC (2.04 g, 6.47 mmol) in tetrahydrofuran (THF) (~35 ml) was added LiN(TMS)$_2$ (19.41 ml, 19.41 mmol) and stirred for ~30 mins. To this was added solid Boc-Val-OSu (6.72 g, 21 mmol) at one time and the reaction mixture was stirred at room temperature overnight. The solution was neutralized with 1N HCl and the THF was removed under reduced pressure. The residue was diluted with ethyl acetate (EtOAc) (200 mL), satd. NaHCO$_3$ (150 mL) was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Deprotection: For the deprotection of 2.5 g of [Boc-Val]$_2$-OC, 75-80 mL of 4N HCl/dioxane was used. Reaction was complete within 3-4 hours. Evaporate dioxane and dry over vacuum at lease for 24 h.

Coupling: To a solution of Val$_2$-OC.3HCl (250 mg, 0.4 mmol) in DMF (10-12 ml) were added NMM (10-12 eqv) and Boc-X—Y—OSu (2.6 eqv). The reaction mixture was stirred at RT overnight. Solvents were evaporated under reduced pressure. To the residue was added satd. NaHCO$_3$ (~30 mL) and stirred for 1 h. The white/pale yellow residue was filtered, thoroughly washed with water and dried in the vacuum oven at RT.

Deprotection: Deprotection was same as above method. For 100-200 mg of tripeptide derivative 10-15 ml 4N HCl/dioxane was used. Deprotection lasts 18 hours.

Deprotection of tripeptide derivatives containing Threonine and Serine: Tripeptide derivatives were dissolved in 95% TFA (5% water) and stirred for 4 h at room temperature. Solvent was evaporated and the residue was co-evaporated with toluene twice and dried over vacuum. 4N HCl/dioxane was added and stirred overnight. Product was evaporated to dryness and dried over vacuum

Example 102

Oxycodone Branched Amino Acid Chains

General Synthesis

FIG. 152 depicts oxycodone with lysine branched peptides.

Example 103

[Lys]$_2$-Oxycodone

Method was similar to other single amino acid derivatives except Boc-Lys(Boc)-OSu was used as the amino acid starting material.

Example 104

XX-Lys(XX)-Oxycodone

To a solution of [Lys]$_2$-Oxycodone (1.0 eq) in dimethylformamide (1 ml/mmol) was added 4-methylmorpholine (5.5 eq) followed by Boc-XX$_2$—OSu (4.1). Reaction was stirred at ambient temperature for 24 hours. Solvents were removed and crude product was purified by reverse phase HPLC.

Example 105

Synthesis of [Gly-Gly-Lys(-Gly-Gly)]$_2$[SEQ ID NO: 4]-Oxycodone

[Gly-Gly-Lys(-Gly-Gly)]$_2$[SEQ ID NO: 4]-Oxycodone was prepared in a manner similar to Example 104 except Boc-Gly2-OSu was used as the amino acid starting material.

Example 106

Oxycodone D-Amino Acids

General Synthesis

Disubstituted D-amino acid tripeptides were prepared in a manner similar to disubstituted tripeptide conjugates except the amino acid starting material used the unnatural D-amino acids.

[(l)-Lys-(d)-Lys-Leu]$_2$-Oxycodone

To a solution of [Leu]$_2$-Oxycodone (1.0 eq) in dimethylformamide (1 ml/mmol) was added 4-methylmorpholine (10 eq) followed by Boc-(l)-Lys(Boc)-(d)-Lys(Boc)-OSu (3 eq). Reaction was stirred at ambient temperature for 24 hours. Solvents were removed and crude product was purified by reverse phase HPLC.

Example 107

Synthetic Amino Acids

Synthesis of [Boc-Z]$_2$-OC [where Z can equal cyclohexylalanine (Cha), dipropylglycine (Dpg), tert-Leucine (Tle) or any other synthetic amino acid] To a solution of OC (6.47 mmol) in THF was added LiN(TMS)$_2$ (19.41 mmol) and stirred for ~30 mins. To this was added solid Boc-Z-OSu (21 mmol) at one time and the reaction mixture was stirred at room temperature overnight. The solution was neutralized with 1N HCl and the THF was removed under reduced pressure. The residue was diluted with ethyl acetate (EtOAc), satd. NaHCO$_3$ was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Example 108

Non-Standard Amino Acids (Naturally Occurring, Not the Standard 20)

Synthesis of [Boc-N]$_2$—OC [where N can equal norleucine (Nle), homophenylalanine (hPhe) or any other non-standard amino acid]

To a solution of OC (6.47 mmol) in THF was added LiN(TMS)$_2$ (19.41 mmol) and stirred for ~30 mins. To this was added solid Boc-N—OSu (21 mmol) at one time and the reaction mixture was stirred at room temperature overnight. The solution was neutralized with 1N HCl and the THF was removed under reduced pressure. The residue was diluted with ethyl acetate (EtOAc), satd. NaHCO$_3$ was added and stirred for 1 h. EtOAc part was washed with NaHCO$_3$ and brine. Dried over Na$_2$SO$_4$ and evaporated to dryness. Crude product was purified with either silica gel column. (30% EtOAc/Hexane).

Other Oxycodone Conjugates

Example 109

Glycopeptides

Using galactose and a number of tripeptides, glycopeptides will be produced.

Initial Glycopeptides to be Produced
1. [Gal-Gly$_2$-Ile]$_2$-OC
2. [Gal-Pro$_2$-Ile]$_2$-OC
3. [Gal-Gly$_2$-Leu]$_2$-OC
4. [Gal-Pro$_2$-Leu]$_2$-OC

Example 110

Glycosylation of Oxycodone

FIG. 153 depicts a glycosylated oxycodone.

A glycosylation reaction of Oxycodone with a carbohydrate will be attempted. The linkage produced would essentially be an enol ether which are difficult to cleave chemically yet glycosidic bonds are commonly broken down in vivo. Either site or both may be conjugated.

Example 111

Formation of an Enol Ether with Serine

FIG. 154 depicts formation of an enol ether with serine.

Using serine and OC, an enol ether conjugate will be produced. This conjugate would be stable to most hydrolysis conditions. Only the enol ether would be formed in this reaction.

Example 112

Vitamins

FIG. 155 depicts niacin and biotin.

Vitamins can be used to cap or further functionalize the peptide chain. Niacin and biotin will be conjugated to four different dipeptides.

Conjugates to Prepare
1. [Nia-Gly$_2$-Ile]$_2$-OC
2. [Nia-Gly$_2$-Leu]$_2$-OC
3. [Bio-Gly$_2$-Ile]$_2$-OC
4. [Bio-Gly$_2$-Leu]$_2$-OC FIGS. 156-192 demonstrate plasma levels of oxycodone measured by ELISA.

Example 113

Decreased Oral C$_{max}$ of Oxycodone Conjugates

Male Sprague-Dawley rats were provided water ad libitum, fasted overnight and dosed by oral gavage with oxycodone conjugates or oxycodone HCl. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves are shown in FIGS. 156-174. These examples illustrate that doses of oxycodone conjugates decrease the peak level ($C_{max}$) of oxycodone plus oxymorphone as compared to that produced by equimolar (oxycodone base) doses of oxycodone HCl when given by the oral route of administration.

Example 114

Oral Bioavailability of a Peptide-Oxycodone Conjugates at a Dose (2.5 mg/kg) Approximating a Therapeutic Human Dose This example illustrates that when the peptide PPL (Table 74, FIG. 193) is conjugated (disubstituted at the 6 and 14 positions) to the active agent oxycodone oral bioavailability is maintained as compared to an equimolar oxycodone dose when the dose administered is 1 mg/kg. This dose is the equivalent of a human dose of 25 to 35 mg for an individual weighing 70 kg (148 lbs) according to Chou et al.

TABLE 74

Oral Pharmacokinetics of Oxycodone vs. [PPL]$_2$OC (2.5 mg/kg dose).

| | Hours | | | | | AUC (ng/ml h) | Percent | Cmax | Percent |
|---|---|---|---|---|---|---|---|---|---|
| Drug | 0.5 | 1.5 | 3 | 5 | 8 | 0-8 h | OC | ng/ml | OC |
| Oxycodone Bitartrate | 145 | 27 | 11 | 2 | 1 | 168 | 100 | 145 | 100 |
| [PPL]$_2$OC | 124 | 78 | 46 | 1 | 3 | 278 | 165 | 124 | 86 | oxycodone plus oxymorphone

Example 115

Bioavailability of [PPL]$_2$-oxycodone by the Intranasal Route

This example illustrates that when [PPL]$_2$ is conjugated to the active agent oxycodone the bioavailability by the intranasal route is substantially decreased thereby diminishing the possibility of overdose (Table 75, FIG. 194).

TABLE 75

Intranasal Pharmacokinetics of Oxyocodone vs. [PPL]$_2$OC (1 mg/kg dose).

| Drug | Minutes | | | | AUC (ng/ml h) 0-1 h | Percent OC | Cmax ng/ml | Percent OC |
|---|---|---|---|---|---|---|---|---|
| | 5 | 15 | 30 | 60 | | | | |
| Oxycodone Bitartrate | 2128 | 1003 | 688 | 278 | 428 | 100 | 2128 | 100 |
| [PPL]$_2$OC | 1380 | 499 | 390 | 98 | 261 | 61 | 1380 | 65 | oxycodone plus oxymorphone

Example 116

Bioavailability of [PPL]$_2$-oxycodone by the Intravenous Route

This example illustrates that when [PPL]$_2$ is conjugated to the active agent oxycodone the bioavailability by the intravenous route is substantially decreased thereby diminishing the possibility of overdose (Table 76, FIG. 195).

TABLE 76

Intravenous Pharmacokinetics of Oxycodone vs. [PPL]$_2$OC (1 mg/kg dose).

| Drug | Minutes | | | | AUC (ng/ml h) 0-1 h | Percent OC | Cmax ng/ml | Percent OC |
|---|---|---|---|---|---|---|---|---|
| | 5 | 15 | 30 | 60 | | | | |
| Oxycodone Bitartrate | 99 | 104 | 94 | 51 | 82 | 100 | 99 | 100 |
| [PPL]$_2$OC | 22 | 19 | 19 | 43 | 24 | 29 | 43 | 43 | oxycodone plus oxymorphone

Summary of in vivo Testing of Abuse Resistant Oxycodone Conjugates.

In vivo testing of oxycodone conjugates demonstrates for instance decreased oral $C_{max}$, decreased intranasal bioavailability (AUC and $C_{max}$), and decreased intravenous bioavailability (AUC and $C_{max}$) and is described in further detail below.

Example 117

Decreased Intranasal Bioavailability (AUC and $C_{max}$) of Oxycodone Conjugates Male Sprague-Dawley rats were provided water ad libitum and doses were administered by placing 0.02 ml of water containing oxycodone conjugates or oxycodone bitartrate into the nasal flares. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves of various oxycodone conjugates vs. oxycodone HCl are shown in FIGS. 175-192. These examples illustrate that oxycodone conjugates decrease the peak level ($C_{max}$) and total absorption (AUC) of oxycodone plus oxymorphone as compared to those produced by equimolar (oxycodone base) doses of oxycodone HCl when given by the intranasal route of administration.

Example 118

Decreased Intravenous Bioavailability (AUC and $C_{max}$) of Oxycodone Conjugates Male Sprague-Dawley rats were provided water ad libitum and doses were administered by intravenous tail vein injection of 0.1 ml of water containing oxycodone conjugates or oxycodone HCl. All doses contained equivalent amounts of oxycodone base. Plasma oxycodone concentrations were measured by ELISA (Oxymorphone, 102919, Neogen, Corporation, Lexington, Ky.). The assay is specific for oxymorphone (the major oxycodone metabolite) and oxycodone. Plasma concentration-time curves of an oxycodone conjugate vs. oxycodone HCl is shown in FIG. 195. This example illustrates that an oxycodone conjugate decreases the peak level ($C_{max}$) and total absorption (AUC) of oxycodone plus oxymorphone as compared to those produced by an equimolar (oxycodone base) dose of oxycodone HCl when given by the intravenous route of administration.

| | oral 2 mg/kg | | intranasal 2 mg/kg | |
|---|---|---|---|---|
| | % AUC | % Cmax | % AUC | % Cmax |
| [Gly-Glu-Val]$_2$-OC | 93 | 61 | 29 | 48 |
| [Pro-Glu-Val]$_2$-OC | 90 | 82 | 34 | 46 |
| [Glu-Pro-Val]$_2$-OC | 142 | 134 | 56 | 65 |
| [Ser-Gly-Val]$_2$-OC | 90 | 92 | 64 | 73 |
| [Glu-Tyr-Val]$_2$-OC | 115 | 103 | 18 | 20 |
| [Gly-Tyr-Val]$_2$-OC | 92 | 99 | 56 | 54 |
| [Ile-Tyr-Val]$_2$-OC | 71 | 82 | 3 | 4 |
| [Leu-Tyr-Val]$_2$-OC | 131 | 120 | 4 | 5 |

OC = Oxycodone

Collectively, examples 33 through 118 illustrate the application of the invention for reducing the overdose potential of narcotic analgesics. These examples establish that an active agent can be covalently modified by attachment of a chemical moiety in a manner that maintains therapeutic value over a normal dosing range, while substantially decreasing if not eliminating the possibility of overdose by oral, intranasal, or intravenous routes of administration with the active agent.

The invention claimed is:

1. A method for altering the short term bioavailability of an oral dosage form of a hydromorphone composition comprising:

covalently bonding hydromorphone or a pharmaceutically acceptable salt thereof through the 2' or 6' position to the C-terminus of a single amino acid or an oligopeptide of 15 or fewer amino acids such that the hydromorphone does not release into a patient's bloodstream at levels that give rise to a euphoric or overdose level.

2. A method for altering the short term bioavailability of an oral dosage form of a hydromorphone composition in a patient comprising providing to said patient hydromorphone, or a pharmaceutically acceptable salt thereof, covalently bound through the 2' or 6' position to the C-terminus of a single amino acid or an oligopeptide of 15 or fewer amino acids wherein said bound hydromorphone maintains a serum release curve which provides therapeutically effective bioavailability but prevents spiking or an increase in blood serum concentrations compared to unbound hydromorphone when taken at doses exceeding the therapeutically effective range.

3. The method of claim 1 or 2 wherein the oligopeptide is selected from a single amino acid, a dipeptide, a tripeptide, a tetrapeptide, a pentapeptide and a hexapeptide.

4. The method of claim 1 or 2 wherein hydromorphone is bound to a single amino acid and the single amino acid is selected from Ala, Glu, Ile, Leu, Lys, Phe, Ser, or Val.

5. The method of claim 3 wherein said oligopeptide is a dipeptide selected from Val-Val, Val-Gly, Ser-Amp, Phe-Amp, Lys-Lys, Gly-Gly, Glu-Glu, Glu-Amp, or Ala-Pro.

6. The method of claim 3 wherein said oiigopeptide is a tripeptide selected from Tyr-Tyr-Val, Tyr-Tyr-Phe, Tyr-Tyr-Ile, Thr-Thr-Val, Pro-Glu-Val, Pro2-Leu, Pro2-Ile, Phe-Phe-Leu, Phe-Phe-Ile, Lys-Lys-Val, Lys-Lys-Ile, Leu-Pro-Leu, Leu-Leu-Leu, Gly-Gly-Leu, Gly-Gly-Ile, Glu-Tyr-Val, Glu-Leu-Val, Glu-Glu-Val, Glu-Glu-Ile, Glu-Glu-Glu, Glu-Glu-Phe, Asp-Asp-Val, Asp-Asp-Ile, His-Gly-Gly, Ile-Tyr-Val, Gly-Gly-Gly, Val-Glu-Gly, Leu-Tyr-Val, Gly-Tyr-Leu, Gly-Tyr-Ile, Lys-Ser-Val, Ser-Gly-Val, Gly-Tyr-Val, Gly-Glu-Val, Glu-Pro-Val, Tyr-Pro-Val, Ser-Thr-Val, Phe-Val-Val, Gly-Leu-Val, Glu-Asp-Val, or Gly-Lys-Gly.

7. The method of claim 3 wherein said oligopeptide is a pentapeptide selected from Tyr-Tyr-Phe-Phe-Ile [SEQ ID NO: 8], Tyr-Tyr-Lys-Tyr-Tyr [SEQ ID NO: 9], Tyr-Tyr-Phe-Pro-Ile [SEQ ID NO: 12], Tyr-Tyr-Gly-Gly-Ile [SEQ ID NO: 19], Tyr-Tyr-Glu-Glu-Ile [SEQ ID NO: 24], Phe-Phe-Lys-Phe-Phe [SEQ ID NO: 10], Lys-Lys-Gly-Gly-Ile [SEQ ID NO: 17], Lys-Lys-Glu-Glu-Ile [SEQ ID NO: 26], Lys-Lys-Asp-Asp-Ile [SEQ ID NO: 23], Gly-Gly-Gly-Gly-Leu [SEQ ID NO: 1], Gly-Gly-Gly-Gly-Ile [SEQ ID NO: 16], Gly-Gly-Pro-Pro-Ile [SEQ ID NO: 20], Glu-Glu-Phe-Phe-Phe [SEQ ID NO: 3], Glu-Glu-Phe-Phe-Ile [SEQ ID NO: 5], Glu-Glu-Glu-Glu-Glu [SEQ ID NO: 13], Glu-Glu-Gly-Gly-Leu [SEQ ID NO: 15], Glu-Glu-Gly-Gly-Ile [SEQ ID NO: 14], Glu-Glu-Asp-Asp-Ile[SEQ ID NO: 22], Asp-Asp-Asp-Asp-Ile [SEQ ID NO: 25], Asp-Asp-Phe-Phe-Ile [SEQ ID NO: 21], or Lys-Lys-Pro-Pro-Ile [SEQ ID NO: 18].

8. The method of claim 3 wherein said oligopeptide is a hexapeptide that is Glu-Glu-Phe-Phe-Phe-Ile [SEQ ID NO: 2].

9. The method of claim 3 wherein said oligopeptide is a tetrapeptide that is Lys-Lys-Gly-Gly [SEQ ID NO: 11].

10. The method of claim 1 or 2, wherein said oral dosage form is a tablet, a capsule, an oral solution, or an oral suspension.

* * * * *